US011951010B2

(12) United States Patent
Greenhalgh et al.

(10) Patent No.: US 11,951,010 B2
(45) Date of Patent: Apr. 9, 2024

(54) SACROILIAC JOINT STABILIZATION SYSTEM

(71) Applicant: SurGenTec, LLC, Boca Raton, FL (US)

(72) Inventors: Travis Greenhalgh, Boca Raton, FL (US); Andrew Shoup, Boca Raton, FL (US); John Souza, Monroe, NC (US); Bryan Hellriegel, Boynton Beach, FL (US); Richard Sharp, Tamarac, FL (US)

(73) Assignee: SurGenTec, LLC, Boca Raton, FL (US)

( * ) Notice: Subject to any disclaimer, the term of this patent is extended or adjusted under 35 U.S.C. 154(b) by 0 days.

(21) Appl. No.: 18/095,981

(22) Filed: Jan. 11, 2023

(65) Prior Publication Data

US 2023/0181323 A1   Jun. 15, 2023

Related U.S. Application Data

(63) Continuation of application No. 18/079,710, filed on Dec. 12, 2022.

(60) Provisional application No. 63/342,518, filed on May 16, 2022, provisional application No. 63/288,495, filed on Dec. 10, 2021.

(51) Int. Cl.
*A61F 2/30* (2006.01)
*A61F 2/46* (2006.01)

(52) U.S. Cl.
CPC ...... *A61F 2/30988* (2013.01); *A61F 2002/30299* (2013.01); *A61F 2002/30433* (2013.01); *A61F 2002/30518* (2013.01); *A61F 2002/30593* (2013.01); *A61F 2002/30845* (2013.01); *A61F 2002/3085* (2013.01); *A61F 2002/3092* (2013.01); *A61F 2002/30995* (2013.01); *A61F 2002/4627* (2013.01)

(58) Field of Classification Search
CPC .............................................. A61F 2002/30995
See application file for complete search history.

(56) References Cited

U.S. PATENT DOCUMENTS

| | | | |
|---|---|---|---|
| 7,648,509 B2 | 1/2010 | Stark | |
| 9,492,284 B2 | 11/2016 | Ginn et al. | |
| 9,615,856 B2 | 4/2017 | Arnett et al. | |
| 9,668,781 B2 | 6/2017 | Stark | |
| 10,596,003 B2 | 3/2020 | Donner et al. | |
| 10,646,236 B2 | 5/2020 | Donner et al. | |
| 11,045,231 B2 | 6/2021 | Stark | |
| 11,147,675 B2 | 10/2021 | Ginn et al. | |
| 2016/0100870 A1* | 4/2016 | Lavigne | A61B 17/0642 606/304 |
| 2019/0083271 A1 | 3/2019 | Donner et al. | |
| 2020/0268518 A1* | 8/2020 | Suh | A61B 17/7055 |

* cited by examiner

*Primary Examiner* — Javier G Blanco

(74) *Attorney, Agent, or Firm* — Knobbe, Martens, Olson & Bear, LLP

(57) ABSTRACT

A sacroiliac joint implant system includes a primary implant configured to be received in a sacroiliac joint of a patient and a secondary implant configured to couple with the primary implant. The primary implant includes a body extending from a proximal end to a distal end and a plurality of threads extending from the body. The secondary implant includes a first anchor configured to anchor within a sacrum of the patient and a second anchor configured to anchor within an ilium of the patient.

12 Claims, 102 Drawing Sheets

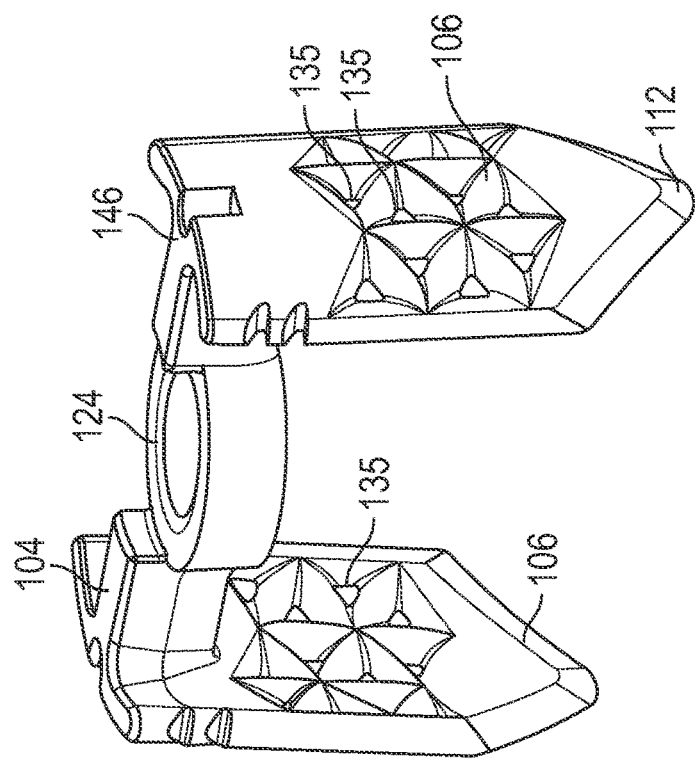
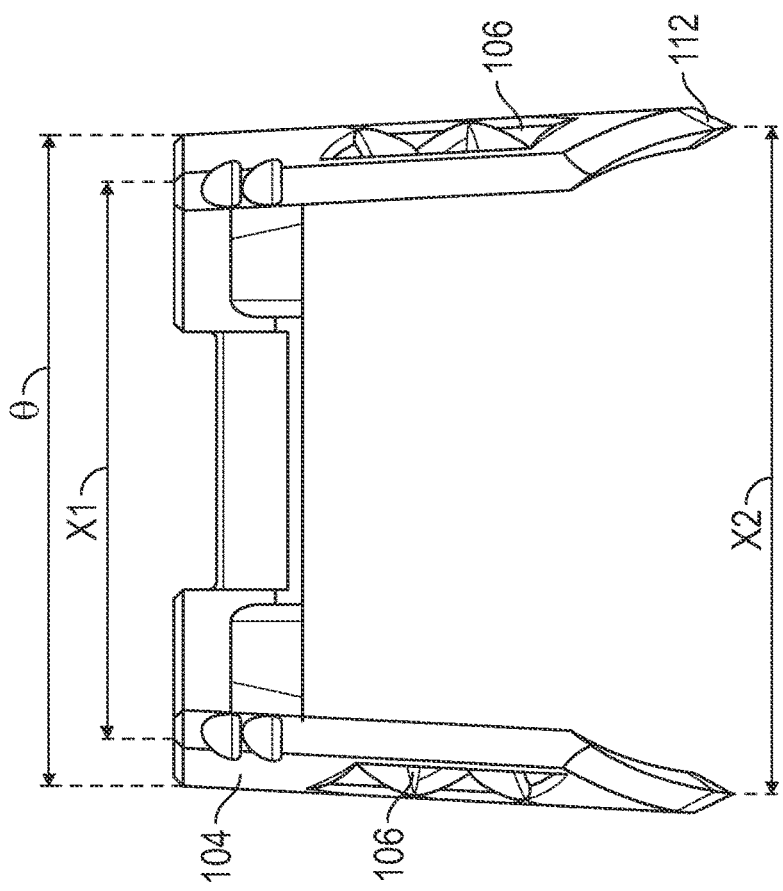
FIG. 63B
FIG. 63A

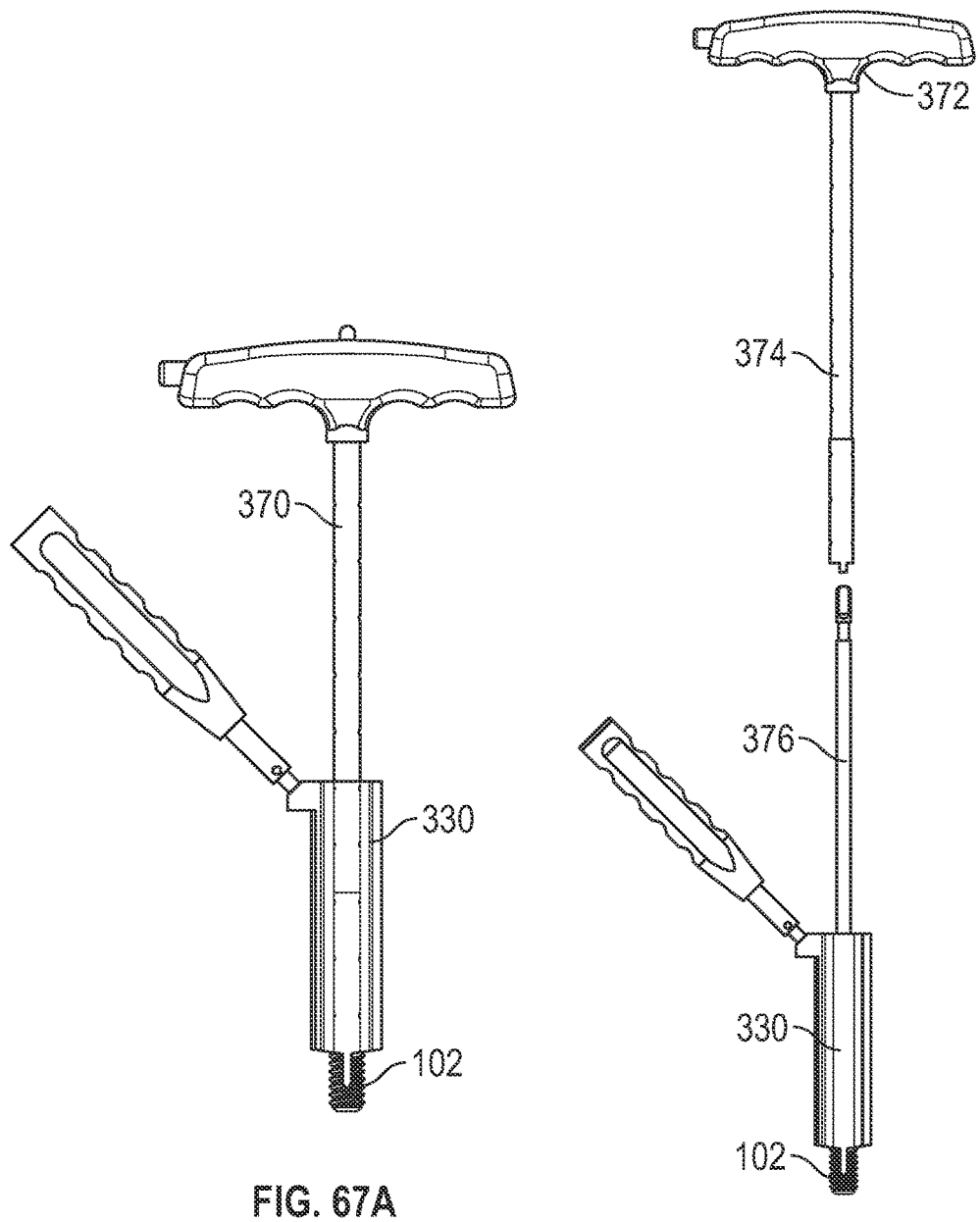
FIG. 67A
FIG. 67B
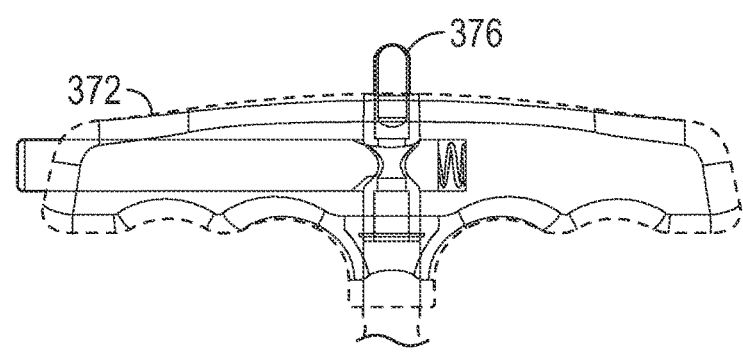
FIG. 67C

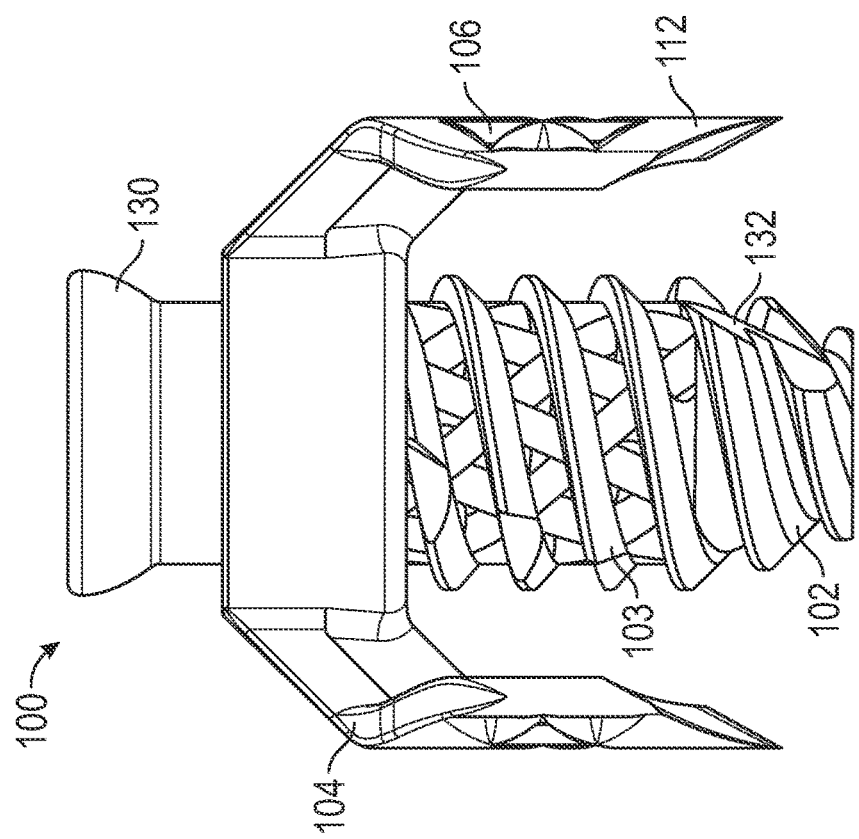
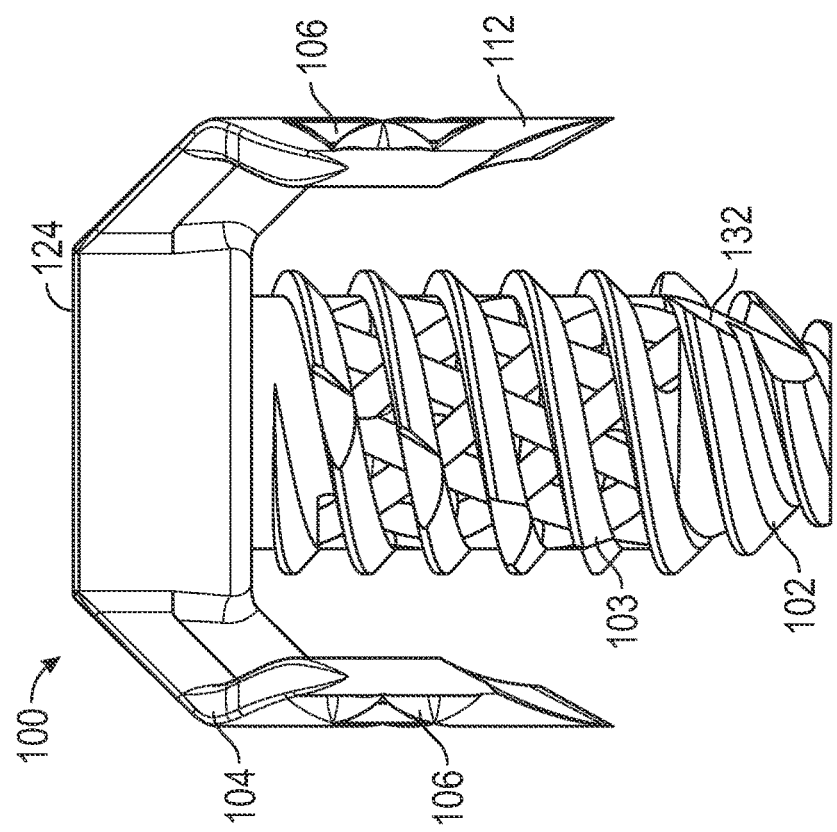
FIG. 72B
FIG. 72A

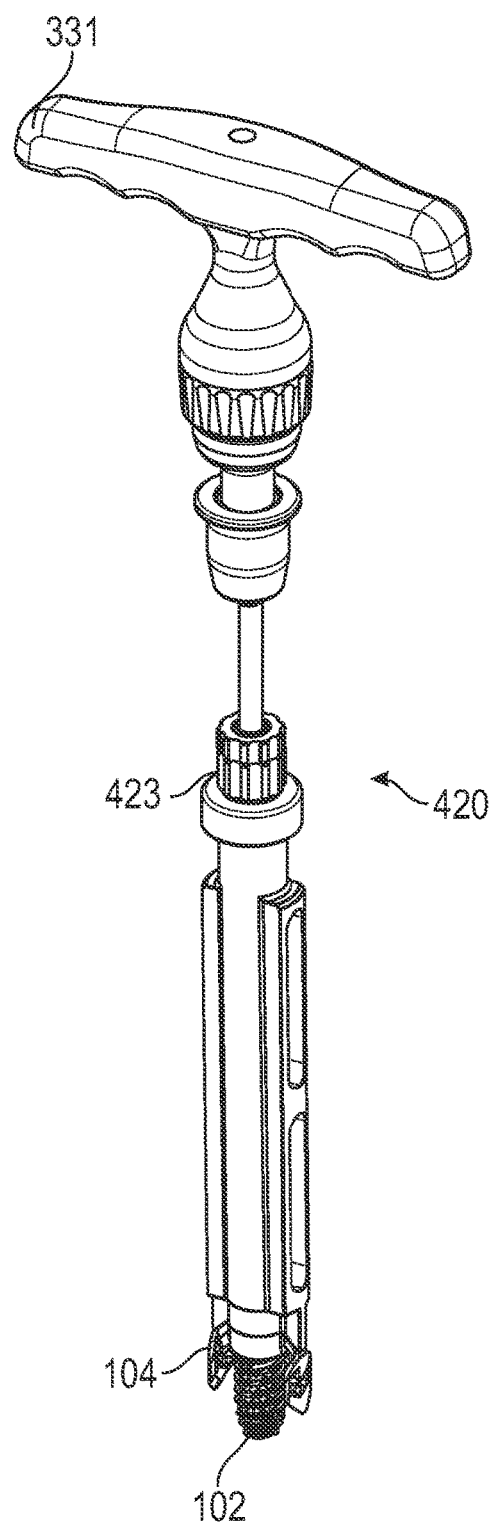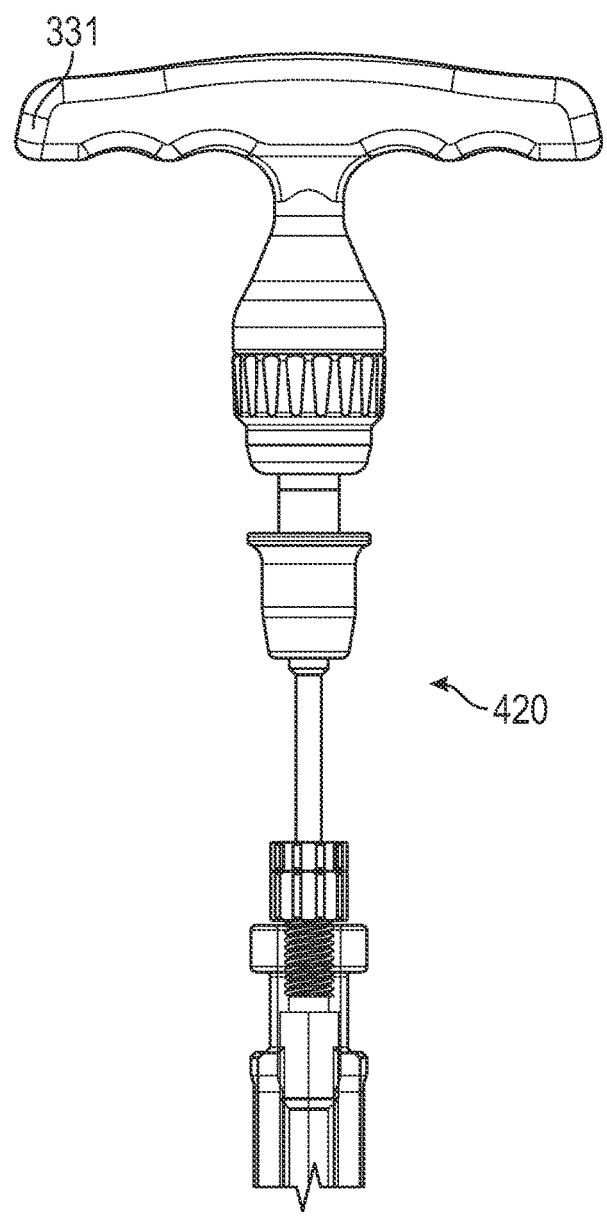
FIG. 75A
FIG. 75B

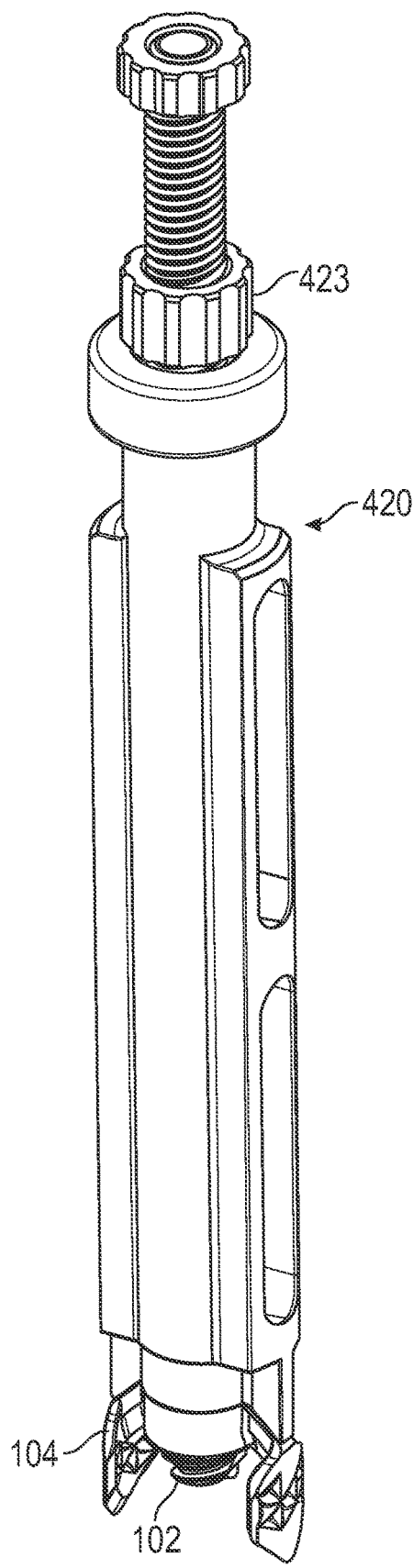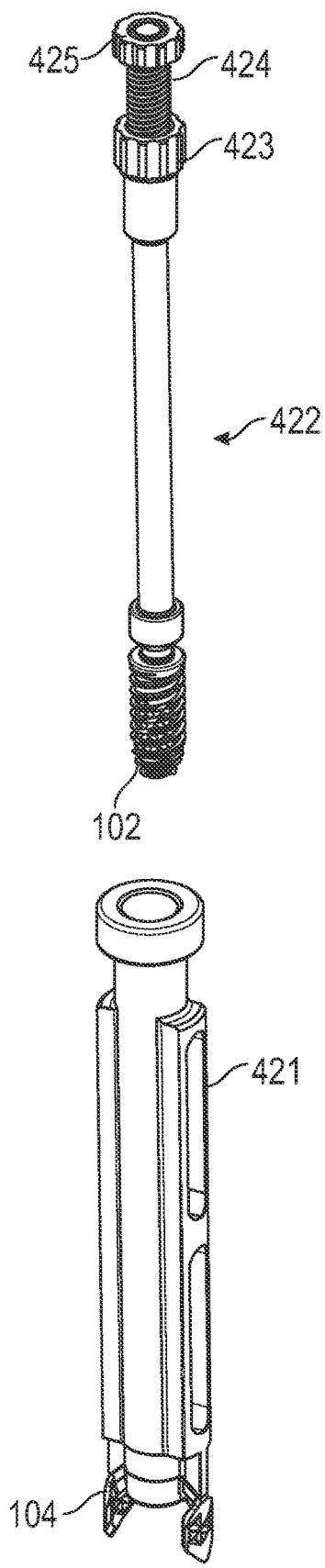
FIG. 75C
FIG. 75D

SACROILIAC JOINT STABILIZATION SYSTEM

CROSS-REFERENCE TO RELATED APPLICATIONS

The present application is a continuation of U.S. application Ser. No. 18/079,710, entitled "SACROILIAC JOINT STABILIZATION SYSTEM," filed Dec. 12, 2022, which claims priority benefit of U.S. Provisional Application Ser. No. 63/288,495, entitled "SACROILIAC JOINT STABILIZATION SYSTEM", filed Dec. 10, 2021, and U.S. Provisional Application Ser. No. 63/342,518, entitled "SACROILIAC JOINT STABILIZATION SYSTEM," filed May 16, 2022, the entire contents of which are incorporated by reference herein in their entirety and for all purposes.

BACKGROUND

Field

The present application relates to orthopedic surgery in general, and more particularly, to methods, systems, and apparatuses for sacroiliac joint stabilization.

Description of the Related Art

The sacroiliac ("SI") joint is formed between the ilium and sacrum, connecting the spine and hips. The SI joints are considered true diarthrodial joints which contain hyaline cartilage on the sacral side and fibrocartilage on the iliac side. The two SI joints provide stability and support while also playing a role in absorbing impact with movement. The joint is re-enforced with thick ligaments surrounding it, some of which extend across the joint in the back of the pelvis. Too much movement may cause the joint to become unstable and lead to pain. Too little movement can cause muscle tension or pain and limit mobility Inflammation of the joint can lead to chronic pain and the need for treatments ranging from conservative care to surgery.

BRIEF DESCRIPTION OF THE DRAWINGS

FIG. 58E illustrates a top view of an embodiment of the joint implant from FIG. 58C.

FIG. 58F illustrates a cross sectional side view of an embodiment of the joint implant from FIG. 58C.

FIG. 59A illustrates a side view of an embodiment of the joint implant.

FIG. 59B illustrates a perspective view of an embodiment of the joint implant from FIG. 59A.

FIG. 59C illustrates a perspective view of an embodiment of the joint implant from FIG. 59A.

FIG. 59D illustrates a perspective view of an embodiment of the joint implant from FIG. 59A.

FIG. 60 illustrates a top view of an embodiment of the implant within the SI joint.

FIG. 61 illustrates a top view of a rotated embodiment of the implant within the SI joint.

FIG. 62 illustrates a top view of a rotated embodiment of the implant within the SI joint.

FIG. 63A illustrates a side view of an embodiment of the secondary implant.

FIG. 63B illustrates a perspective view of an embodiment of the secondary implant from FIG. 63A.

FIG. 64A illustrates a side view of the guide, dilator, and joint locator of an embodiment of the implant system.

Figure 64B:
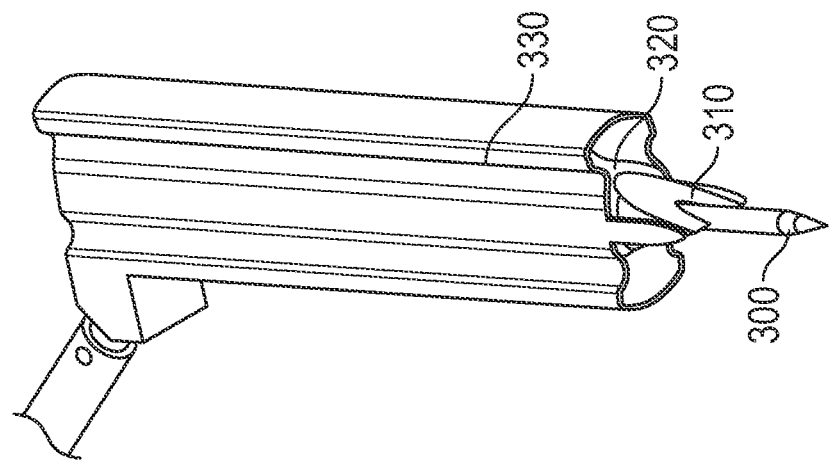
Figure 64A:
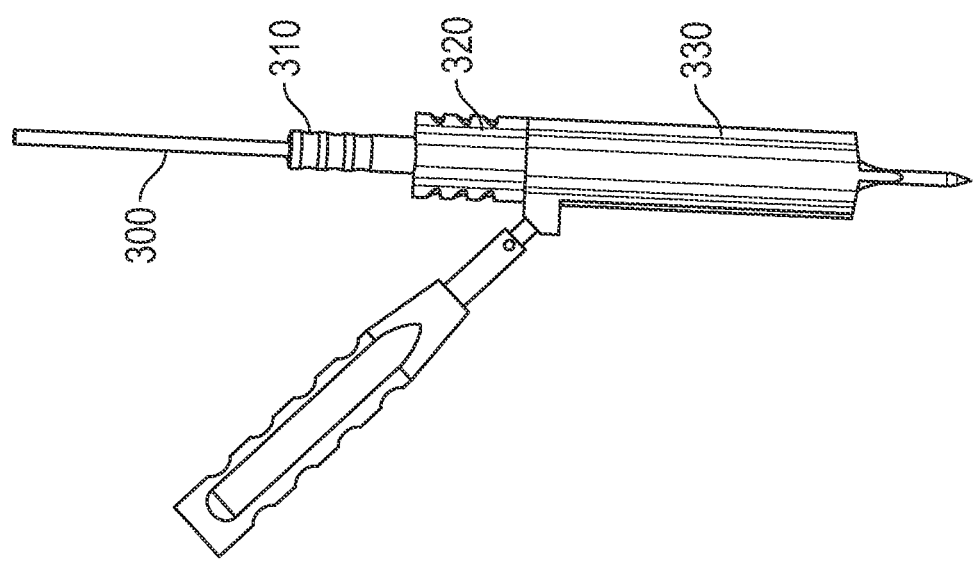

FIG. 64B illustrates an enlarged perspective view of the end of the implant system from FIG. 64A.

Figure 65B:
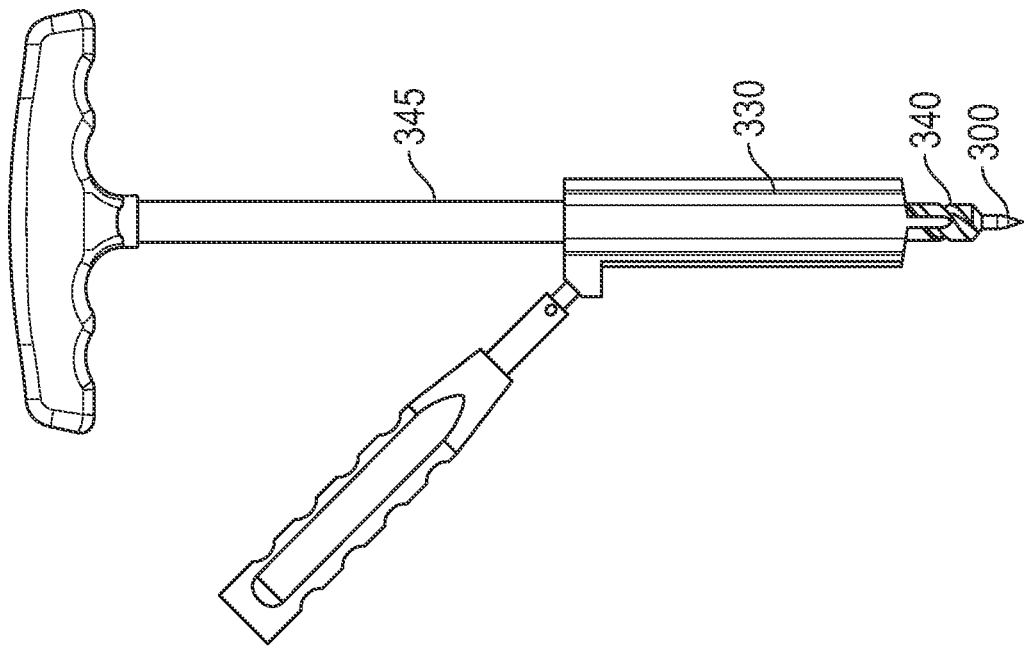
Figure 65A:
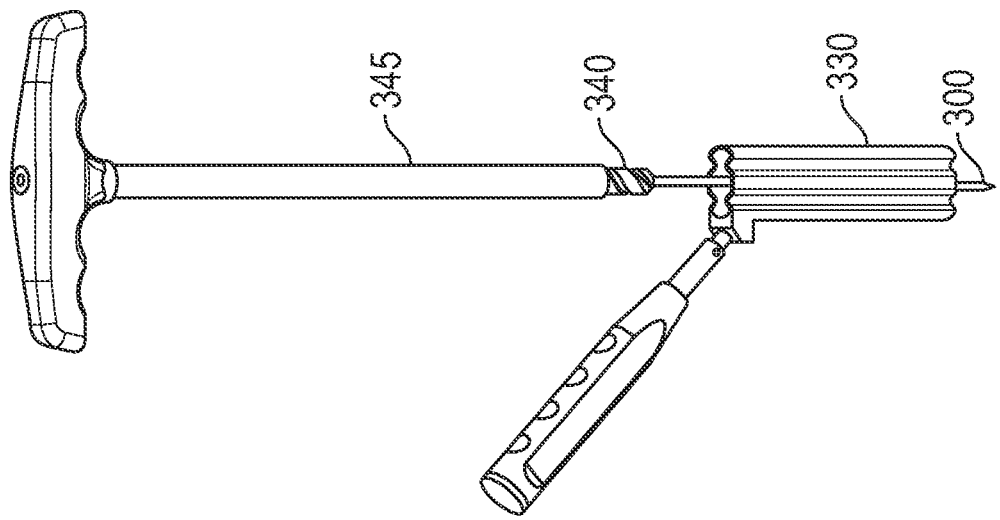

FIG. 65A illustrates a perspective view of the drill, drill bit, guide, and guidewire of an embodiment of the implant system.

FIG. 65B illustrates a side view of the drill, drill bit, guide, and guidewire of an embodiment of the implant system from FIG. 65A.

Figure 66C:
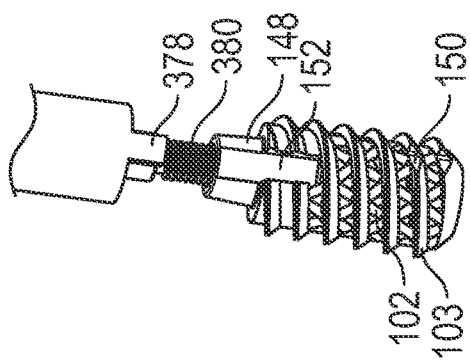
Figure 66D:
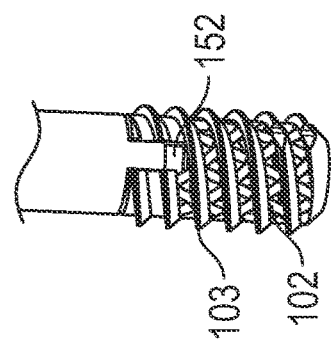
Figure 66B:
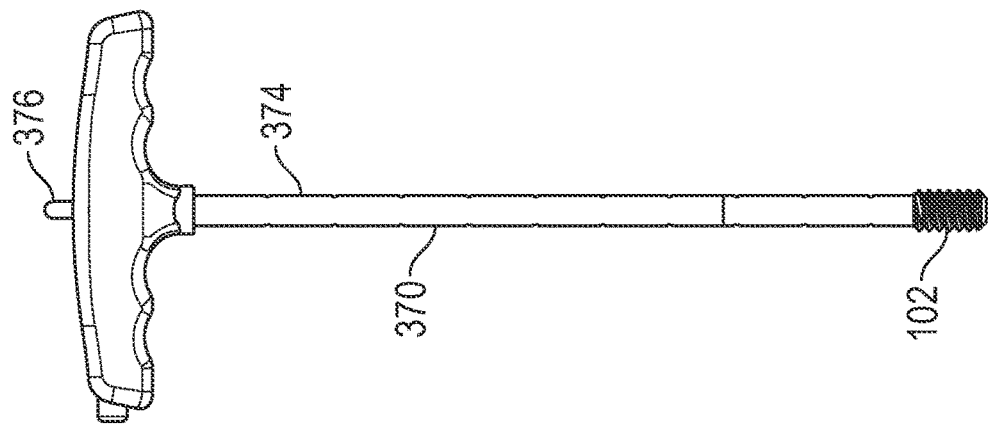
Figure 66A:
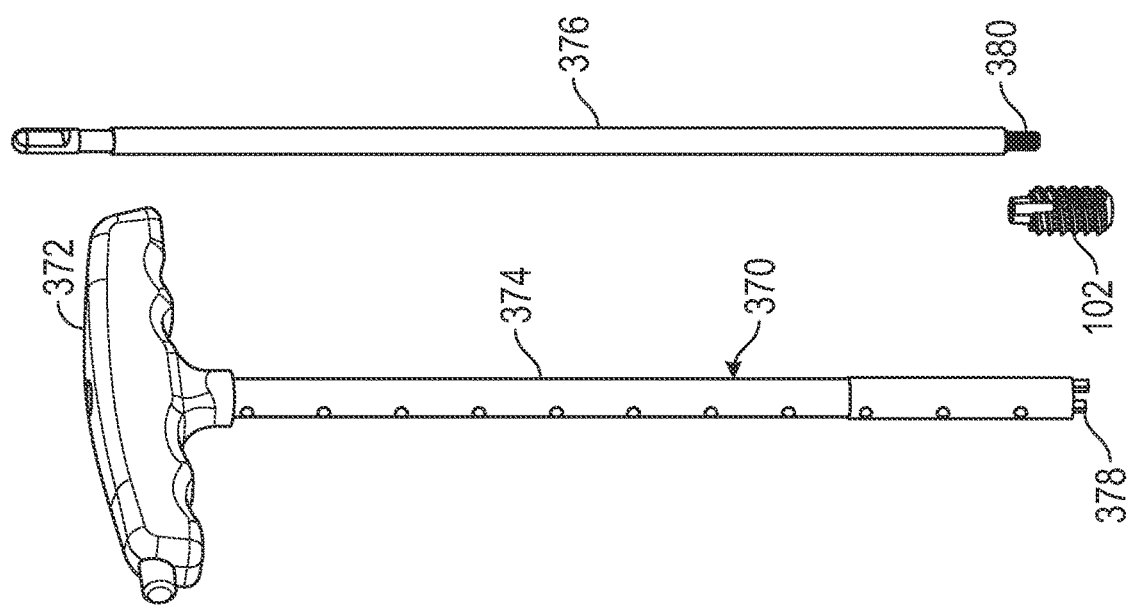

FIG. 66A illustrates a shaft, threaded rod, and implant of an embodiment of the implant system.

FIG. 66B illustrates a side view of the shaft, threaded rod, and implant as an embodiment of a system.

FIG. 66C illustrates an enlarged perspective view of the end of the implant system from FIG. 66B.

FIG. 66D illustrates an alternative enlarged perspective view of the end of the implant system from FIG. 66B.

FIG. 67A illustrates a side view of an implant inserter, guide, and implant of an embodiment of the implant system.

FIG. 67A illustrates an exploded side view of an implant inserter, guide, and implant of an embodiment of the implant system from FIG. 67B.

FIG. 67C illustrates an enlarged side view of the threaded rod and handle of an embodiment of the implant system from FIG. 67A.

Figure 68C:
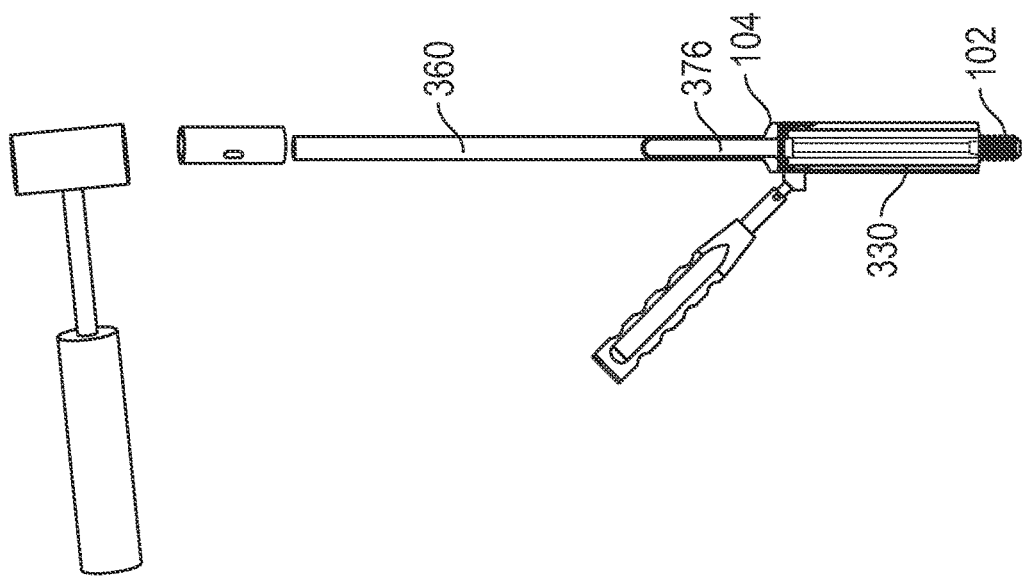
Figure 68B:
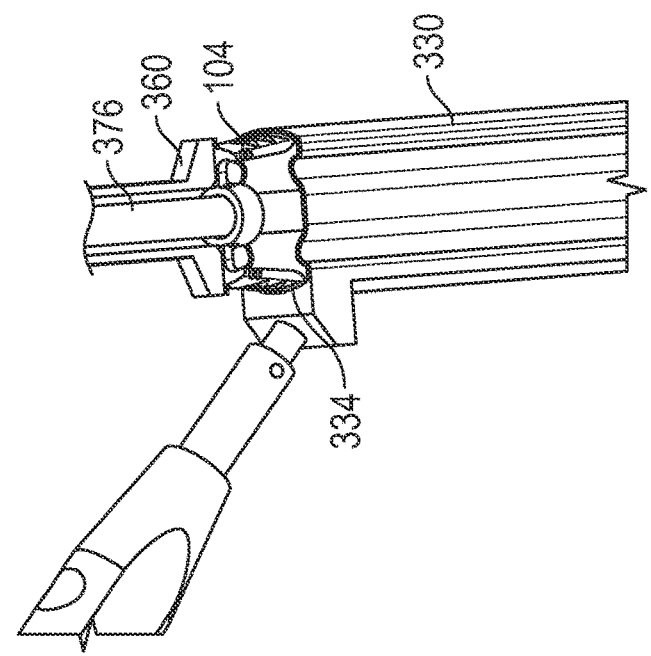
Figure 68A:
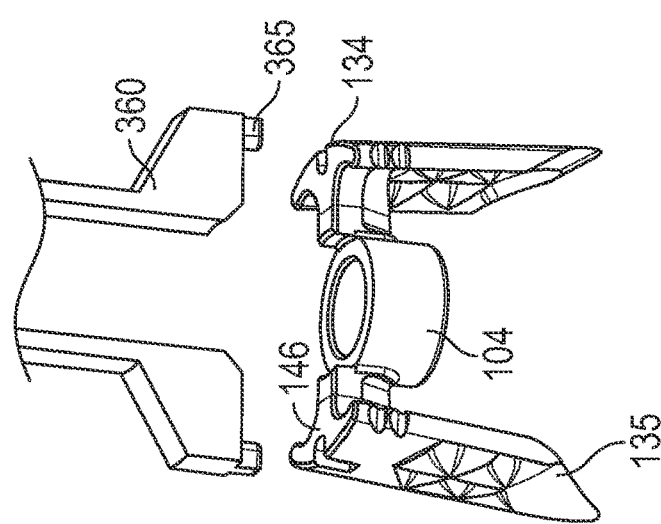

FIG. 68A illustrates an enlarged perspective view of the end of an inserter and a secondary implant of an embodiment of the implant system.

FIG. 68B illustrates an enlarged perspective view of a threaded rod, inserter, and guide of an embodiment of the implant system.

FIG. 68C illustrates a perspective view of an inserter, threaded rod, guide, and implant of an embodiment of the implant system.

Figure 69C:
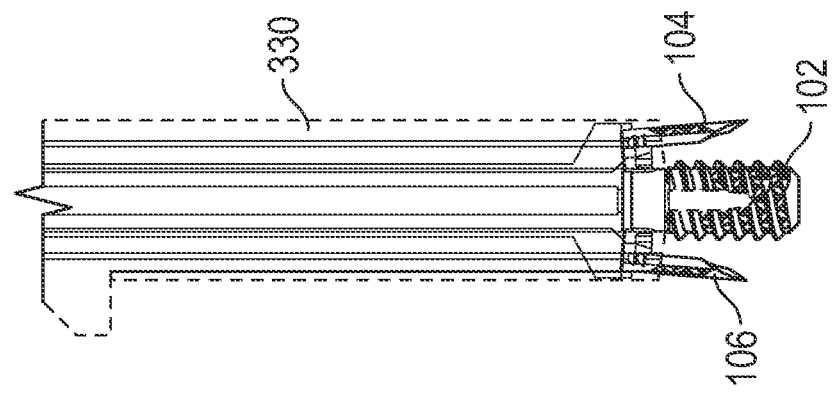
Figure 69B:
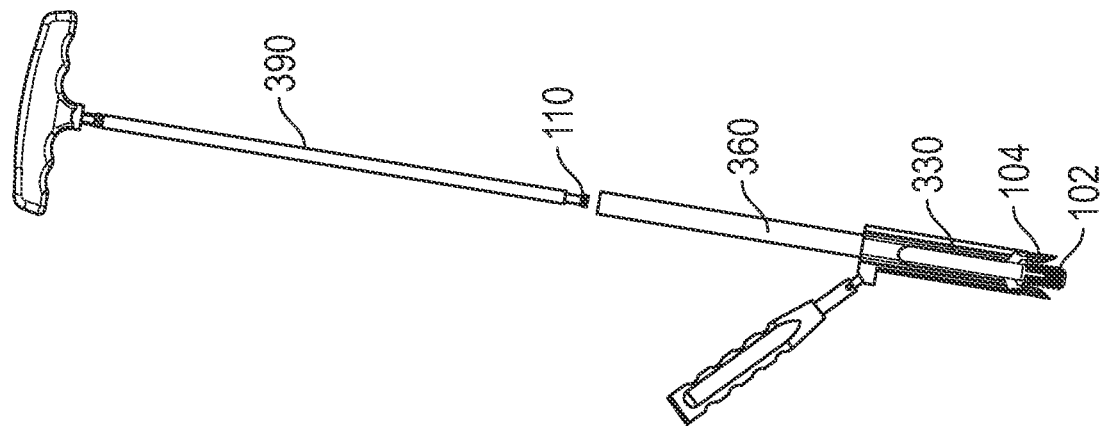
Figure 69A:
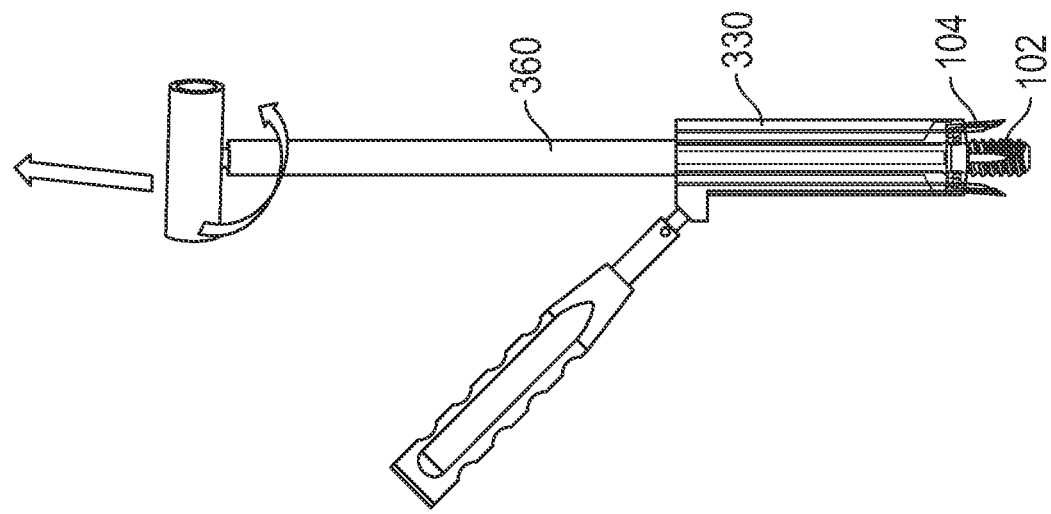

FIG. 69A illustrates a perspective view of an alternative embodiment of the implant system.

FIG. 69B illustrates a perspective view of an alternative embodiment of the implant system.

FIG. 69C illustrates an enlarged side view of the end of an embodiment of the implant system.

Figure 70B:
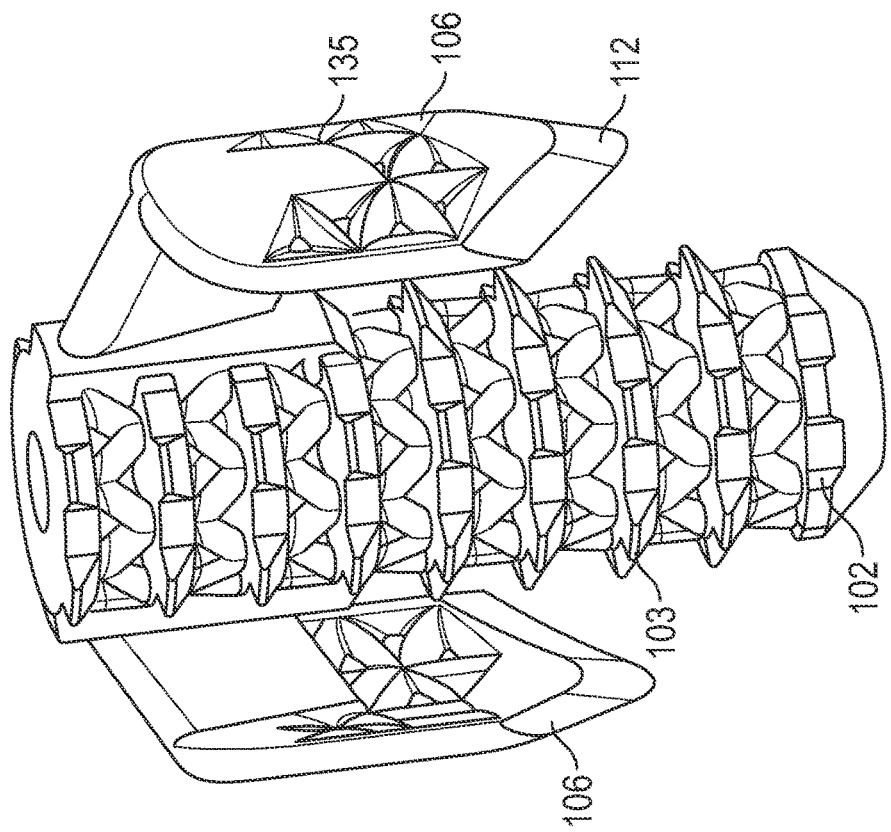
Figure 70A:
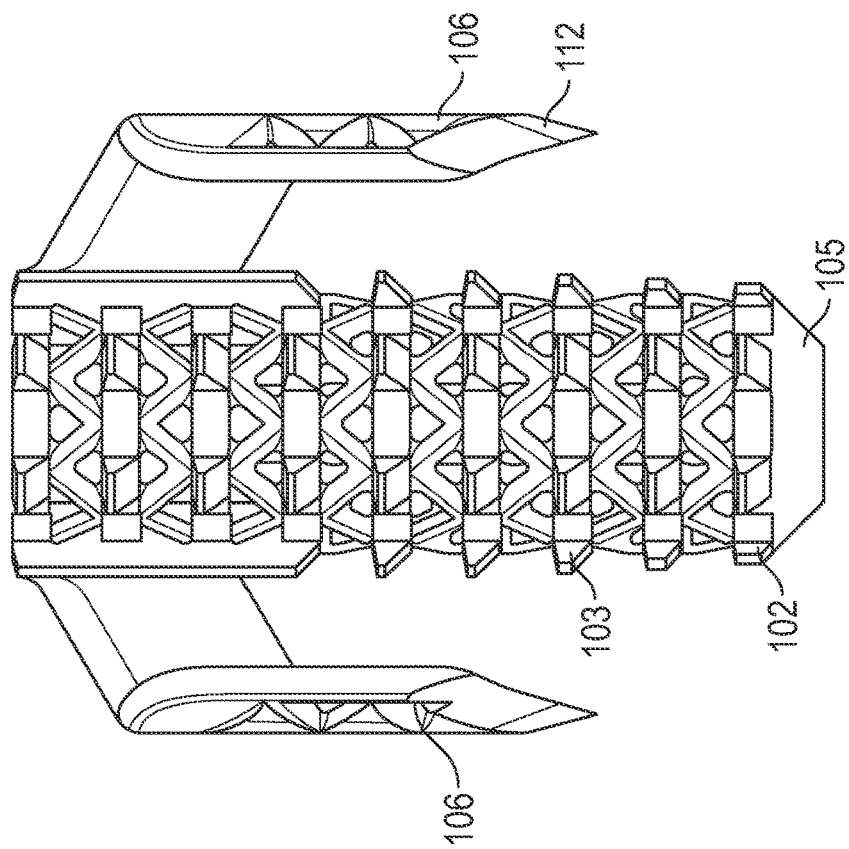

FIG. 70A illustrates a side view of an embodiment of a joint implant.

FIG. 70B illustrates a perspective view of an embodiment of the joint implant from FIG. 70A.

Figure 70C:
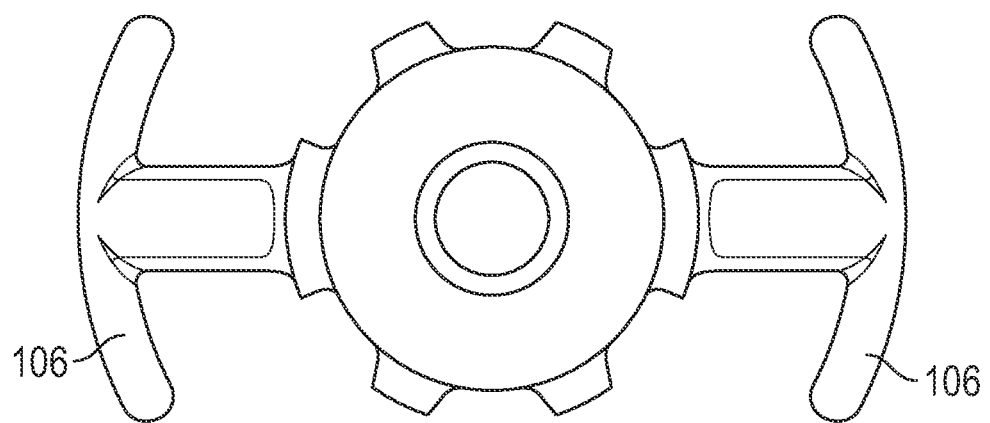

FIG. 70C illustrates a top view of an embodiment of the joint implant from FIG. 70A.

Figure 71B:
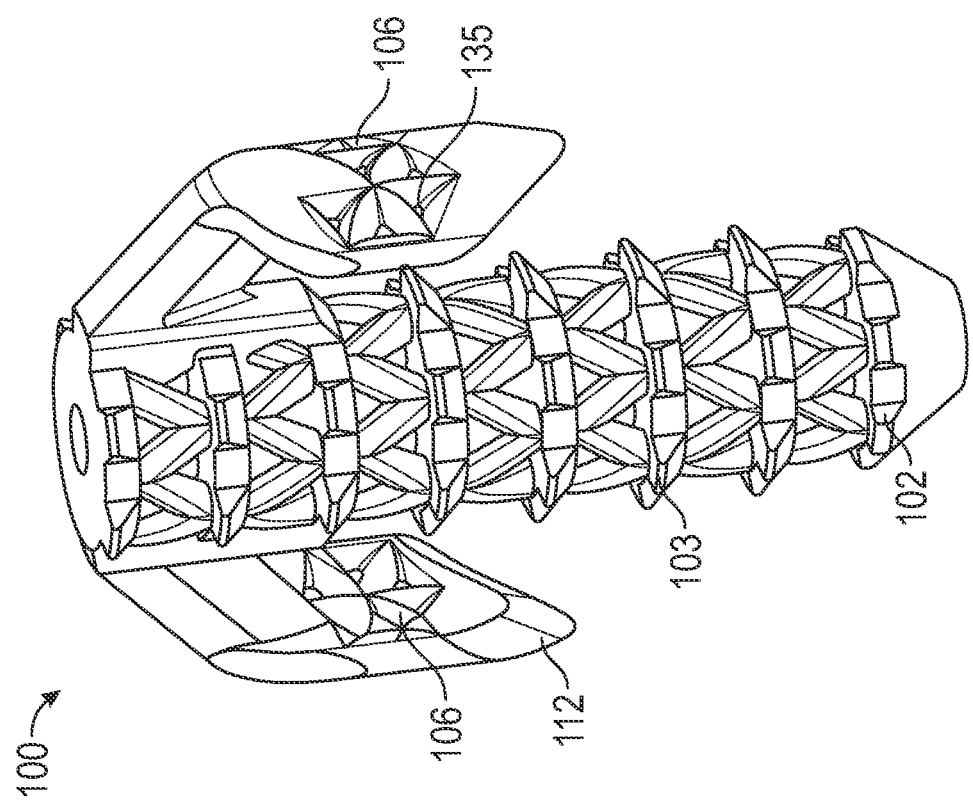
Figure 71A:
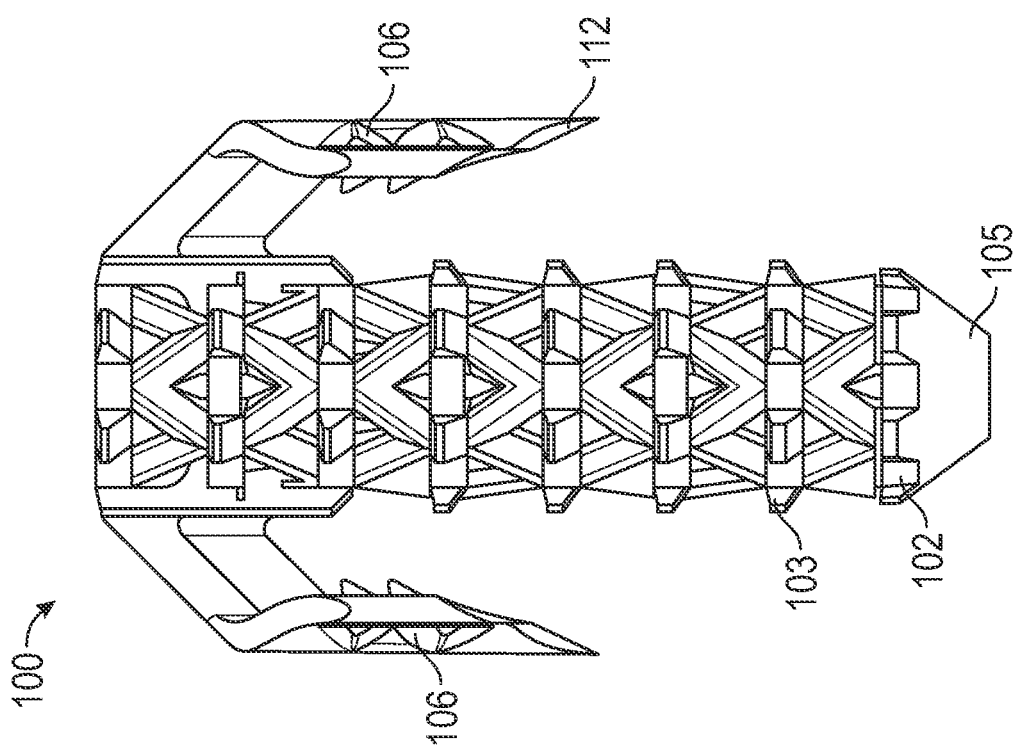

FIG. 71A illustrates a side view of an embodiment of a joint implant.

FIG. 71B illustrates a perspective view of an embodiment of the joint implant from FIG. 71A.

FIG. 72A illustrates a side view of an embodiment of a joint implant.

FIG. 72B illustrates an altered side view of an embodiment of the joint implant from FIG. 72A.

Figure 72D:
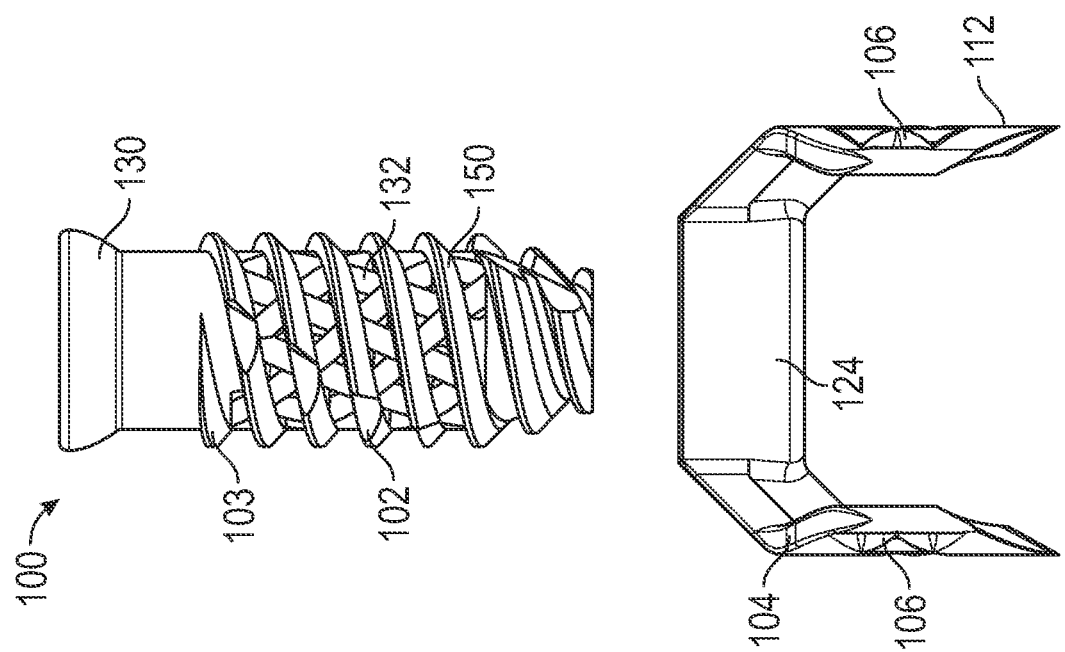
Figure 72C:
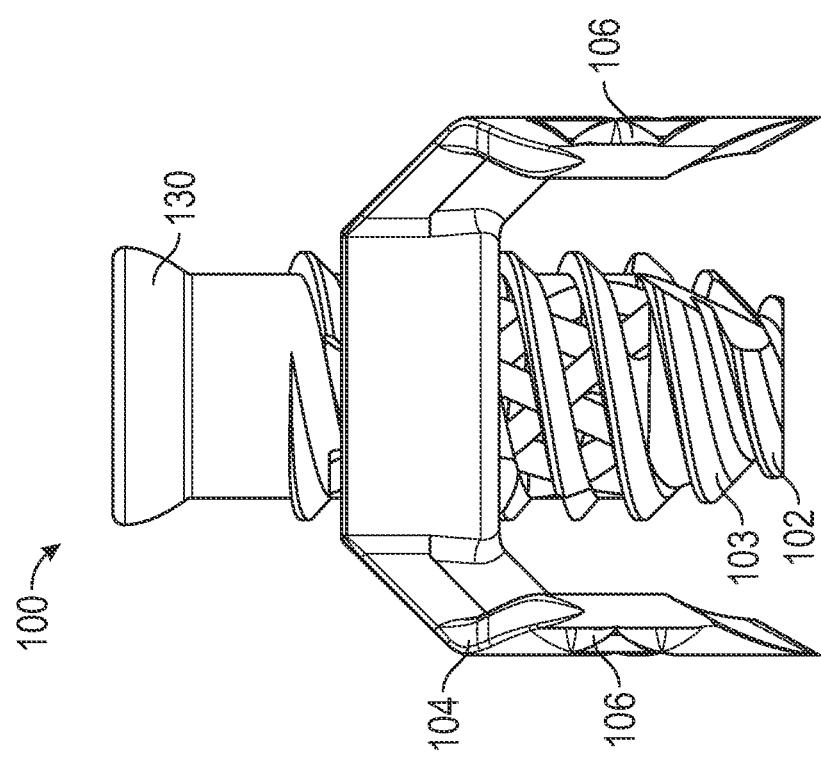

FIG. 72C illustrates an altered side view of an embodiment of the joint implant from FIG. 72A.

FIG. 72D illustrates an exploded side view of an embodiment of the joint implant from FIG. 72A.

Figure 72E:
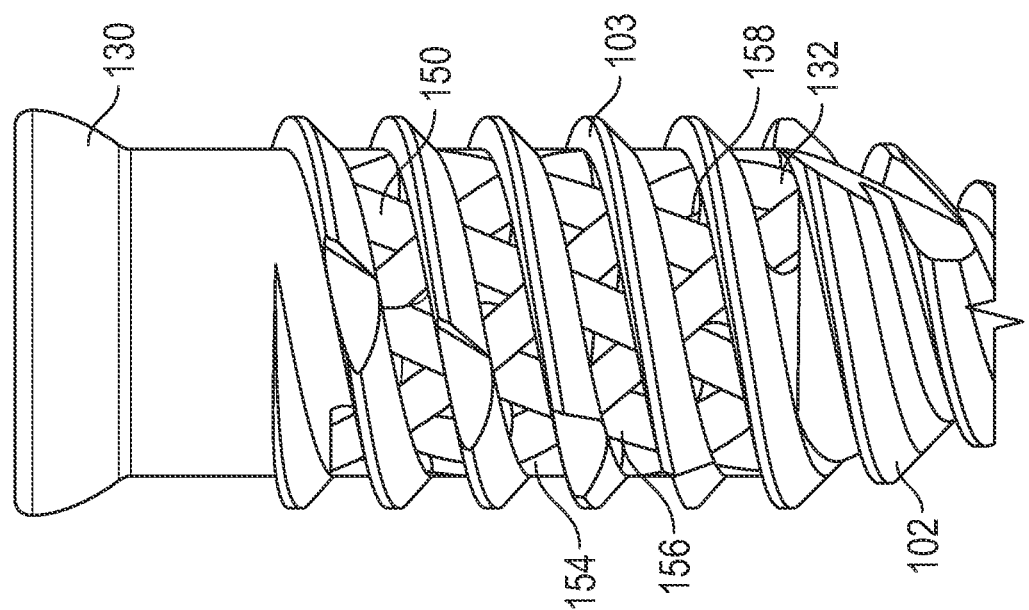
Figure 72E:
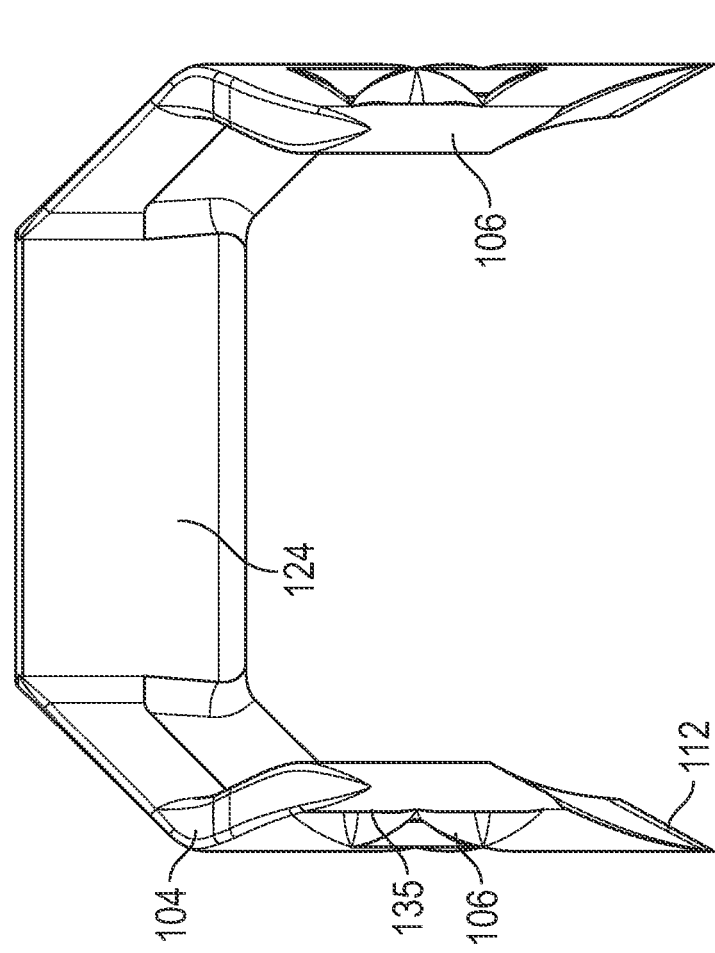

FIG. 72E illustrates an alternative exploded side view of an embodiment of the joint implant from FIG. 72A.

Figure 72F:
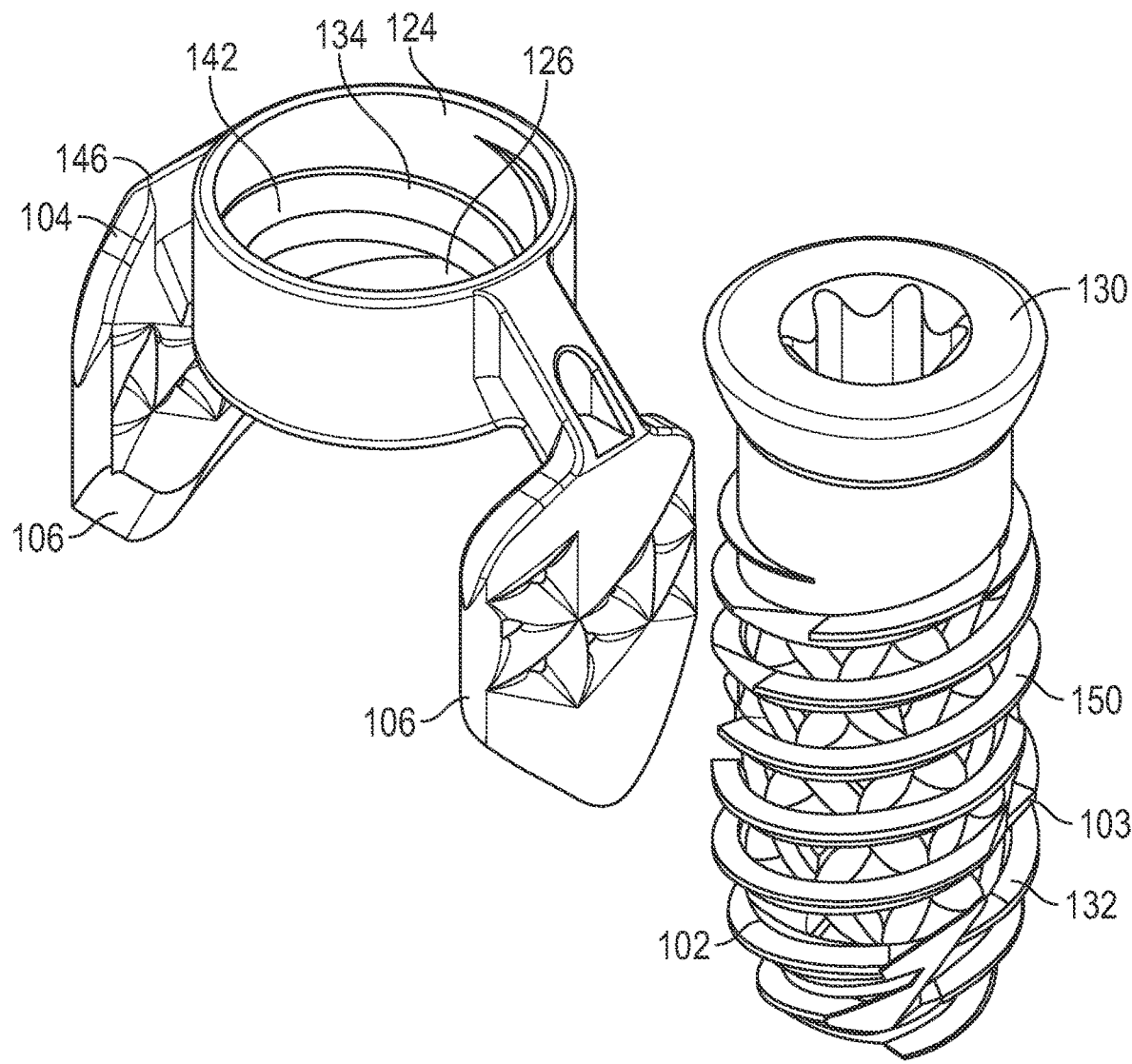

FIG. 72F illustrates an exploded perspective view of an embodiment of the joint implant from FIG. 72A.

Figure 73A:
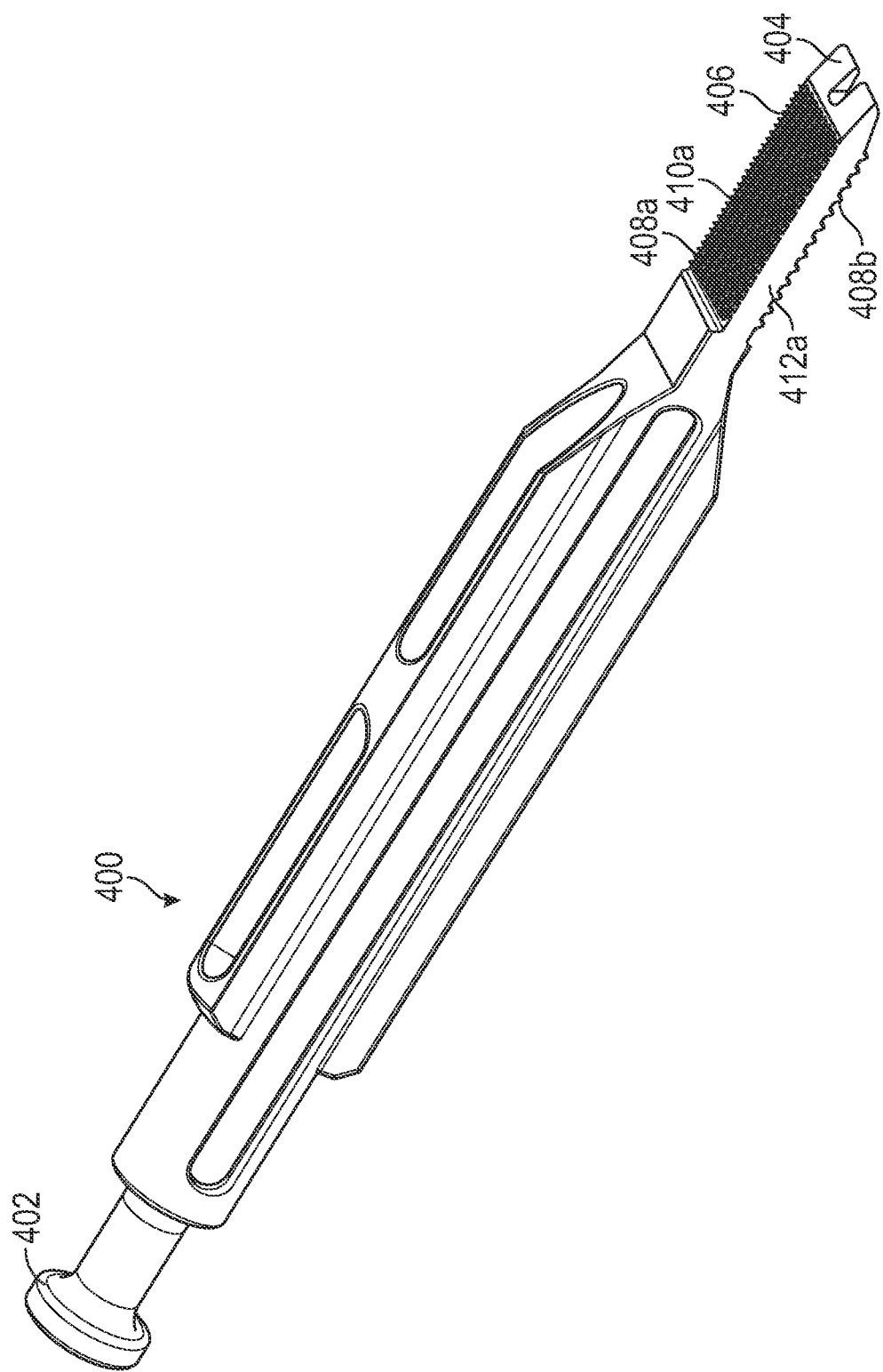

FIG. 73A illustrates a perspective view of a rasp as an embodiment of the implant system.

Figure 73B:
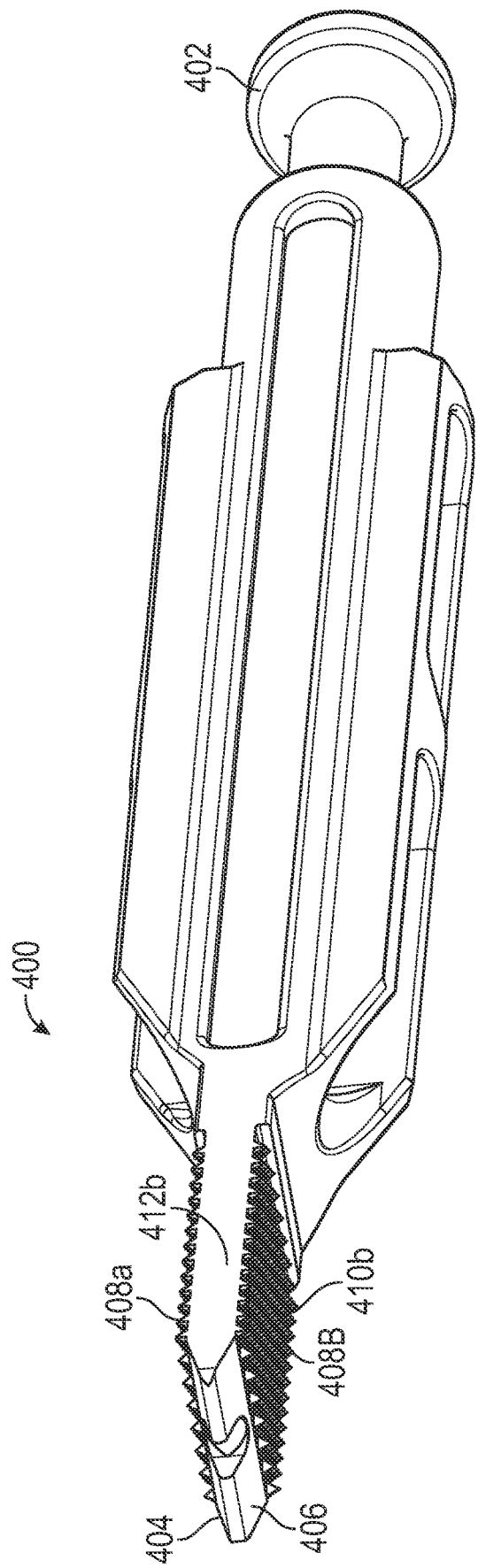

FIG. 73B illustrates an alternative perspective view of a rasp as an embodiment of the implant system from FIG. 73A.

Figure 73C:
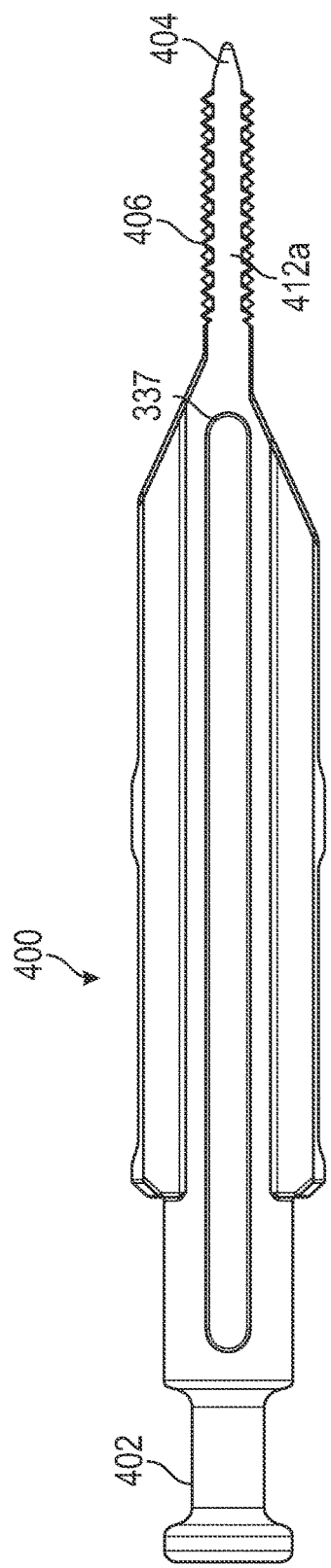

FIG. 73C illustrates a side view of the rasp from FIG. 73A.

Figure 73D:
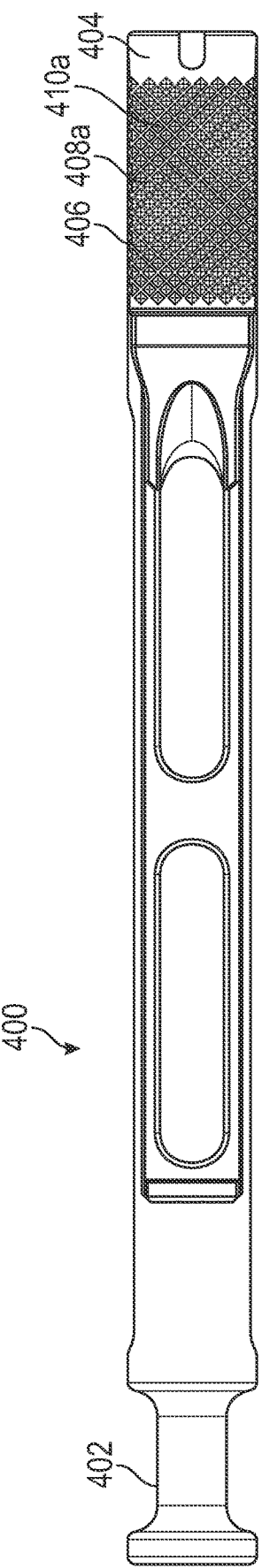

FIG. 73D illustrates an alternative side view of the rasp from FIG. 73A.

Figure 73E:
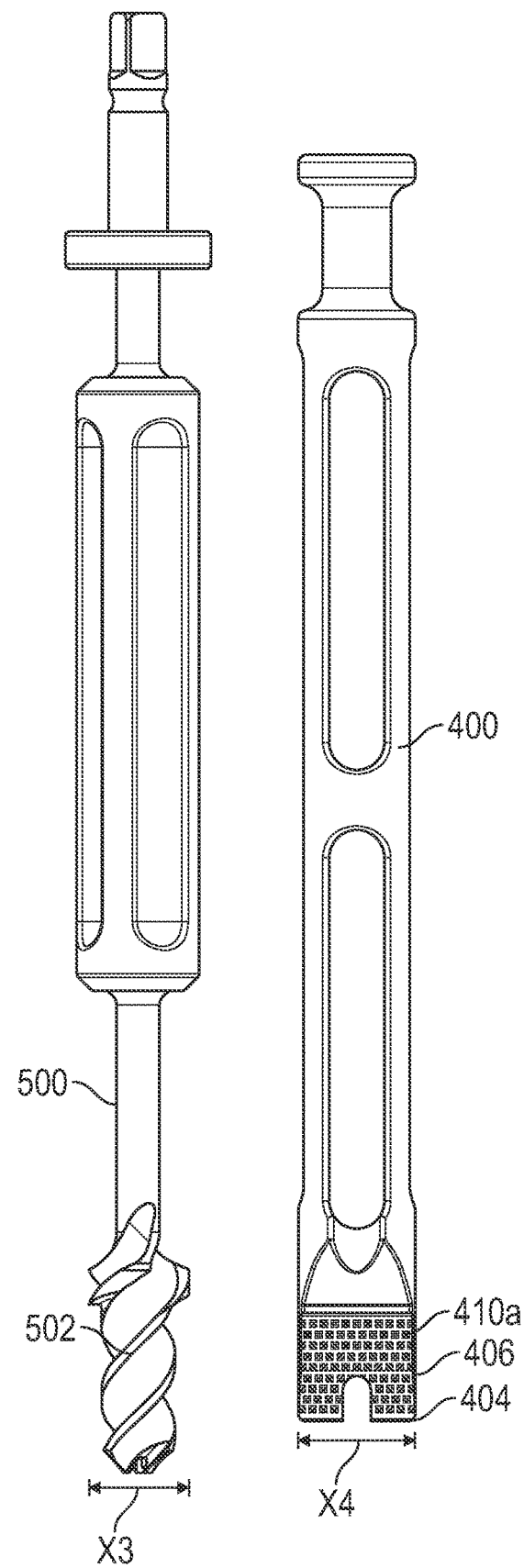

FIG. 73E illustrates the side view of some alternative embodiments of the implant system.

Figure 74B:
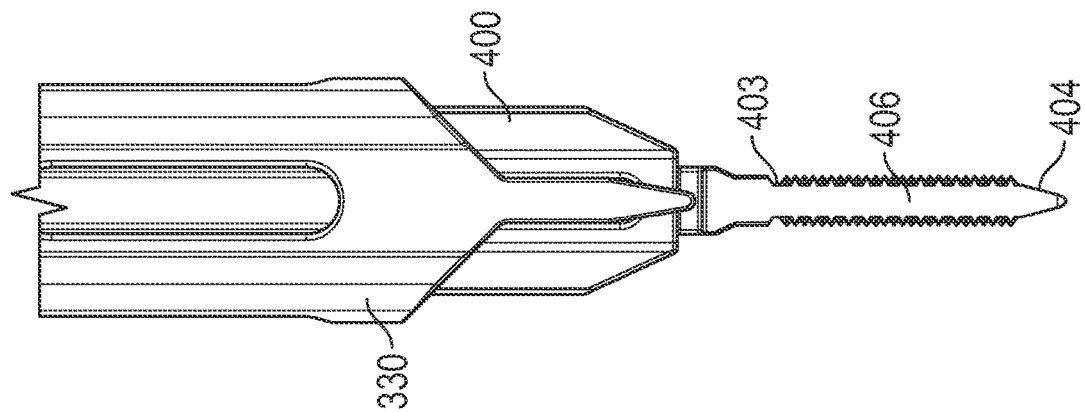
Figure 74A:
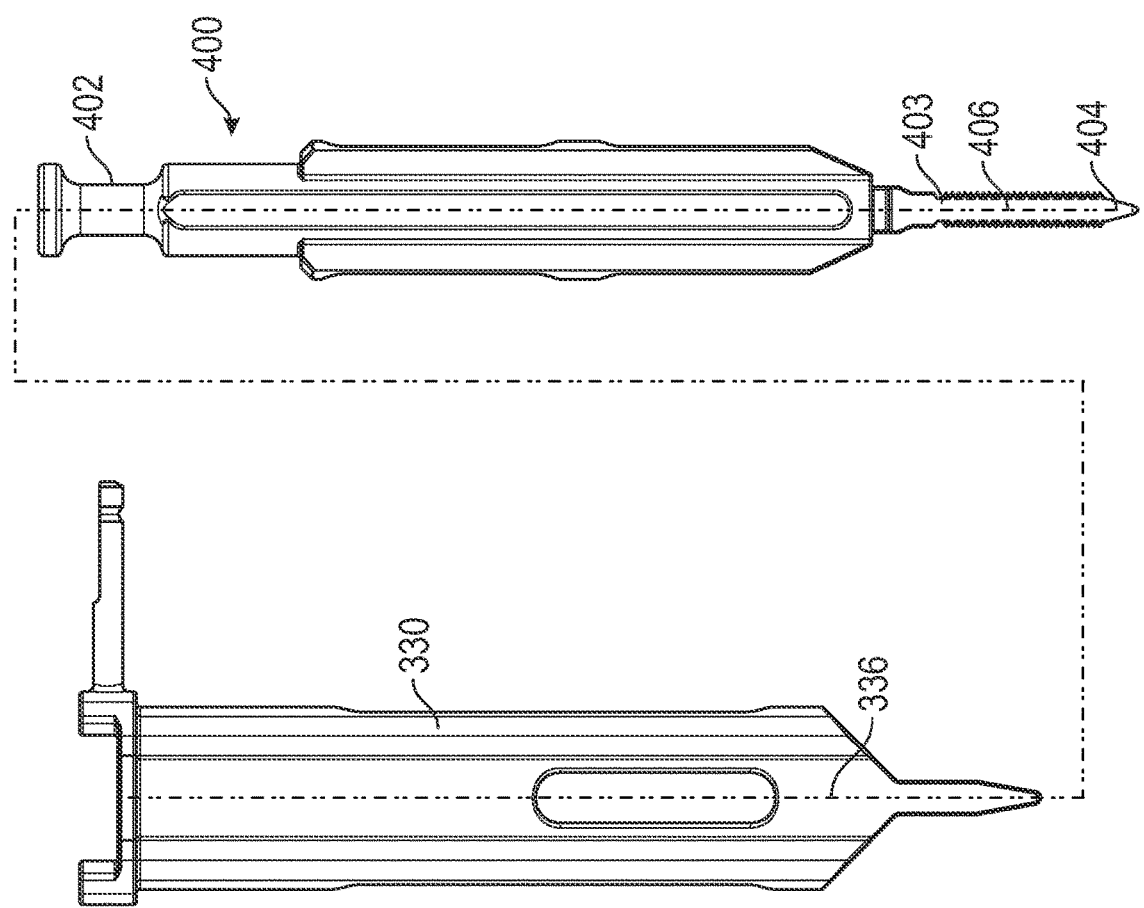

FIG. 74A illustrates a side view of a drill guide with a rasp in an embodiment of the implant system.

FIG. 74B illustrates a side view of a rasp and drill guide coupled in an embodiment.

Figure 74D:
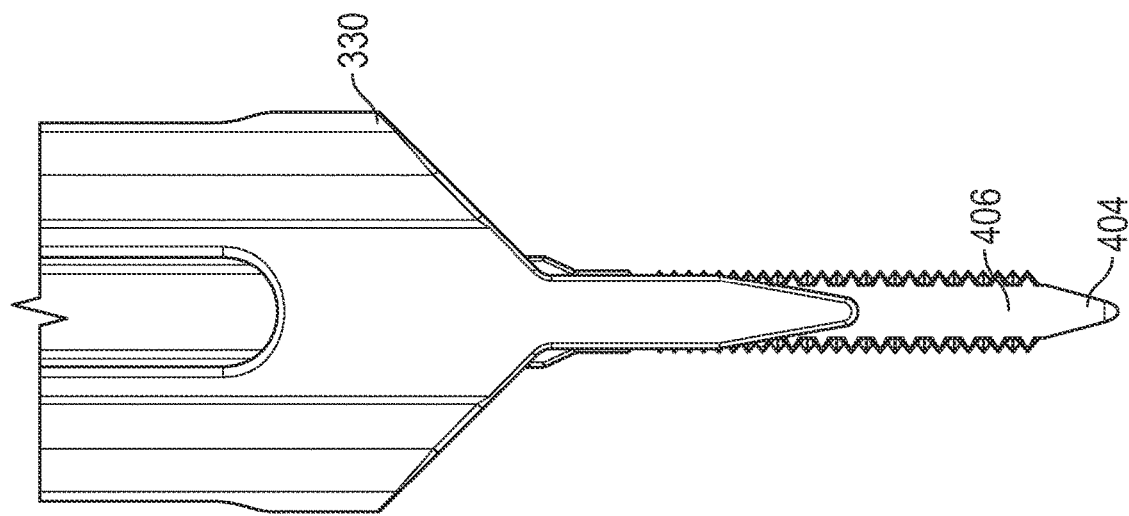
Figure 74C:
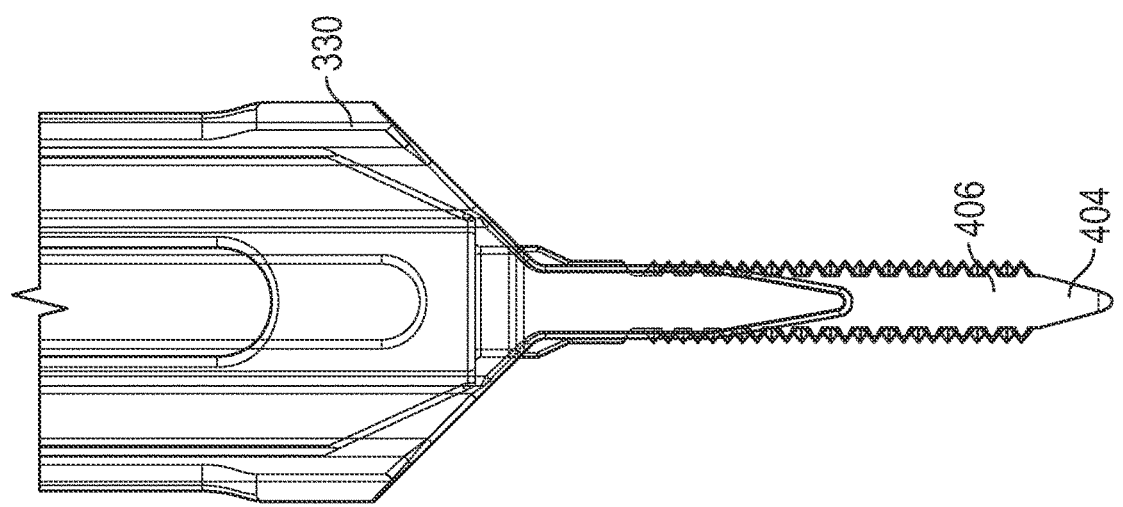

FIG. 74C illustrates a side view of a rasp placed through a drill guide in an embodiment.

FIG. 74D illustrates a side view of a rasp placed through a drill guide in an embodiment.

FIG. 75A illustrates a perspective view of an inserter in an embodiment.

FIG. 75B illustrates a side view of an inserter with a handle in an embodiment.

FIG. 75C illustrates a perspective view of an inserter with an engaged implant in an embodiment.

FIG. 75D illustrates a perspective view of an inserter engaging with an implant in an embodiment.

SUMMARY

Embodiments of the present application are directed to intrasacroiliac implants, implant components, implant inserters, rasps, drill bits, and related systems, devices, and methods.

In some embodiments, a sacroiliac joint implant system is provided, the sacroiliac joint implant system comprises a primary implant configured to be received in a sacroiliac joint of a patient. The primary implant comprising a body extending from a proximal end to a distal end and a plurality of threads extending from the body. The secondary implant configured to couple with the primary implant wherein the secondary implant comprises a plurality of anchors. The plurality of anchors comprises a first anchor configured to anchor within a sacrum of the patient and a second anchor configured to anchor within an ilium of the patient. The primary implant of the joint implant system may comprise a plurality of tabs defining a plurality of recesses, wherein the plurality of recesses are configured to receive the secondary implant. The secondary implant comprises a ring configured to receive a head of the primary implant. In some embodiments, the ring is configured to couple with the head of the primary implant to facilitate polyaxial movement of the primary implant relative to the secondary implant. The secondary implant comprises a plurality of arms extending laterally from the ring, wherein each of the plurality of anchors is coupled to one of the plurality of arms.

In some embodiments, the joint implant system may further comprise a fastener configured to couple the primary implant and the secondary implant. The primary implant comprises a channel configured to receive bone graft material. The primary implant comprises a plurality of openings between the channel and an exterior of the primary implant. Each of the plurality of anchors comprises a plurality of openings configured to facilitate bony ingrowth. Each of the plurality of anchors comprises a leading edge configured to cut bone.

In some embodiments, a method for implanting a sacroiliac joint implant system is provided. The method includes making an incision, advancing a primary implant through the incision and into a sacroiliac joint of a patient, the primary implant including a body extending from a proximal end to a distal end a plurality of threads extending from the body, advancing a secondary implant through the incision towards the sacroiliac joint, the secondary implant comprising a plurality of anchors, anchoring a first anchor of the plurality of anchors into a sacrum of the patient; and anchoring a second anchor of the plurality of anchors in the ilium of the patient.

The method can further include advancing the secondary implant through the incision towards the sacroiliac joint after advancing the primary implant through the incision and into the sacroiliac joint of the patient. Advancing the secondary implant through the incision towards the sacroiliac joint can be performed after advancing the primary implant through the incision and into the sacroiliac joint of the patient. The primary implant and the secondary implant may be coupled to one another. The primary implant and the second implant may be coupled to one another within the patient. The instrument assembly may comprise a guide with a plurality of slots extending therethrough, wherein advancing a secondary implant through the incision towards the sacroiliac joint comprises advancing each of the plurality of anchors along one of the plurality of slots of the guide. The primary implant may be advanced through a central lumen of the guide. The central lumen can be in communication with the plurality of slots. The method can include advancing a bone punch along the plurality of slots prior to advancing each of the plurality of anchors along one of the plurality of slots of the guide. The method can further include coupling the primary implant to an inserter and advancing the secondary implant along channels of the inserter to couple the secondary implant with the primary implant.

DETAILED DESCRIPTION

Embodiments of the present application are directed to a posterior SI joint implant system for SI joint fusion. Fusion of the SI joint can fix the sacrum and ilium relative to one another, which may reduce pain due to instability or inflammation. The embodiments described herein provide fixation of the SI joint in different planes by combining fixation points using a single implant system.

FIGS. 1A-1D depict an embodiment of an SI joint implant system 100. The SI joint implant system 100 can provide fixation of the SI joint (e.g., for SI joint fusion). In certain embodiments, the SI joint implant system 100 can prevent or resist shearing forces at the SI joint. Alternatively or additionally, in certain embodiments, the SI joint implant system 100 can prevent or resist rotational movement at the SI joint. Alternatively or additionally, in certain embodiments, the SI joint implant system 100 can prevent or resist forces that compress and/or distract the SI joint.

In certain embodiments, the SI joint implant system 100 can include a primary implant 102. As described in further detail herein, in certain embodiments, the primary implant can be positioned within the SI joint to engage both the ilium and the sacrum. In certain embodiments, the primary implant can resist shearing forces, such as for example, shearing forces of the sacrum, when positioned within the SI joint. In certain embodiments, the primary implant can resist rotational movement.

In certain embodiments, the SI joint implant system 100 can include a secondary implant 104. As described in further detail herein, in certain embodiments, the secondary implant 104 may anchor within both the ilium and the sacrum on opposing sides of the SI joint. In certain embodiments, the secondary implant 104 may extend across the SI joint.

In certain embodiments, the primary implant 102 and secondary implant 104 can be used in combination to provide fixation to an SI joint. In other embodiments, only one of the primary implant 102 and secondary implant 104 may be used. In combination, the primary implant 102 and secondary implant 104 can act as one system to achieve multiple points of fixation and resist multiple forces. For example, in certain embodiments, the primary implant 102 and second implant 104 can act as one system to resist all of the forces acting on the SI joint. As described herein, in certain embodiments, the primary implant 102 and the secondary implant 104 may be coupled together when implanted. In other embodiments, the primary implant 102 and the secondary implant 104 may be uncoupled when implanted.

As described herein, the primary implant 102 can be configured to be inserted into the SI joint. For example, in some embodiments, the primary implant 102 can be inserted into a defect created in the SI joint as described herein. The primary implant 102 can have a proximal end 101 and a distal end 105. In certain embodiments, the primary implant 102 is configured so that the distal end 105 can be inserted within the SI joint without creating joint distraction.

In some embodiments, the primary implant can be configured to engage the ilium and the sacrum to secure the SI joint with the implant. For example, in certain embodiments, the primary implant 102 can include one or more engagement features 103. As shown in FIGS. 1A-1D, the engagement features 103 may bite into each side of the ilium and sacrum for fixation and to prevent back out. The engagement features 103 may be in the form of threads (e.g., helical threads). For example, in certain embodiments, the primary implant 102 can be in the form of a screw.

In certain embodiments, the threads of the primary implant 102 may extend from the proximal end 101 to the distal end 105 of the primary implant or may extend over any portion thereof. In certain embodiments, the threads do not extend from the proximal end to distal end, for example, to provide a space for anchoring of the secondary implant 104 (as shown for example, in the embodiments of FIGS. 7A-8D and 10A-11D). In certain embodiments, the threads may be placed with different pitches and widths depending the size of the primary implant 102 and the amount of bone needed to capture to prevent back out.

In certain embodiments, the primary implant can be configured to facilitate bony ingrowth. Bony ingrowth can help for a rigid fusion and prevent implant migration. For example, in certain embodiments, the material of primary implant 102 can be porous to allow for bony ingrowth. In certain embodiments, the design of the primary implant 102 may include lattices, planar trusses, non-planar trusses, cancellous or trabecular bone patterns, webs, pin holes, circles, and/or any other design that suitable to allow for bone to permeate and grow into the material. For example, as shown in FIGS. 1A-1D, the primary implant 102 can include a truss or beam system 154. The truss or beam system 154 can act as a scaffolding to provide increased biomechanical strength to the implant 102 and to facilitate bone growth. The truss or beam system 154 can facilitate fusion with surrounding bone. The truss or beam system 154 can also provide stability as the implant 102 fuses with the surrounding bone.

The truss or beam system 154 can be formed of a plurality of truss elements or beams 156. In some embodiments, the plurality of truss elements or beams 156 can extend between at least some of the engagement features 103. A number of windows or openings 158 can be formed between the truss elements of beams 156 of the truss or beam system 154 to facilitate fusion of the implant with surrounding bone. The openings 158 can be positioned so that at least some of the openings 158 will contact the bone of the sacrum and the ilium regardless of the orientation of the primary implant 102 when fully seated within the SI joint to promote bony ingrowth.

In certain embodiments, the primary implant 102 can be cannulated from the proximal end 101 to the distal end 105, having a channel 160 extending between the proximal end 101 and the distal end 105. In some embodiments, as described in further detail herein, the channel 160 can allow for a guidewire or guide rod to extend through the implant 102.

In some embodiments, the primary implant 102 can be loaded with demineralized bone matrix (DBM), cortical fibers, synthetic bone matrix, BMP2 or BMP7, peptide graft, autograft or any combination thereof. In some embodiments, the channel 160 can be packed and/or filled with bone graft material. In some embodiments, the openings 158 and/or alternative openings may be in communication with the channel 160. When the channel 160 is packed and/or filled with bone graft material, the bone graft material can flow through the openings 158 for introduction of bone graft material within the channel 160 to the SI joint.

The truss or beam system 154 can allow for larger volumes of bone graft material to be packed into the implant 102 while maintaining the biomechanical strength of the implant in comparison to implants without a truss or beam system 154.

The openings 158 can be positioned so that at least some of the bone graft flowing through the openings 158 will contact the bone of the sacrum and the ilium regardless of the orientation of the primary implant 102 when fully seated within the SI joint.

In some embodiments, the primary implant 102 can include a plurality of openings 168 in communication with the channel 160. The openings 168 may be positioned along an interior surface of the primary implant 102 that defines the channel 160. The openings 168 may be in communication with the openings 158 of the truss or beam system 154.

In some embodiments it may be desirable for the channel 160 to have a diameter large enough to receive bone graft, but small enough to avoid or inhibit deformation of breakage due to fragility. The diameter can also be sufficiently small for the implant to fit in a desired anatomic location, such as the SI joint.

In certain embodiments, acid etching, bead blasting, surface coating such as HA (Hydroxyapatite), or any other suitable surface technology may be utilized to enhance the surface finish to create an optimal area for bone to grow to in the primary implant 102. In certain embodiments, 3D printing may be utilized to create surfaces structures and features for bone to grow to. In certain embodiments, the surface structures may be on the nanometer or micrometer scale which can be optimal or desirable for bone to grow to.

In certain embodiments, the primary implant 102 may be CNC machined, 3D printed, or manufactured by any other suitable means. In certain embodiments, the primary implant 102 can be made of stainless steel, titanium, poly-etherether-ketone (PEEK), ceramic, human allograft or any other suitable implantable material strong enough to resist the forces described herein and pass biomechanical testing. In certain embodiments, the implant material can be important to achieve bony ingrowth.

In certain embodiments, the implant can be configured to be inserted with a driver, such as a hex driver, a star driver, a square driver, a torx driver, or any other suitable driver for driving the implant into bone. The proximal end 101 of the implant 102 can include an engagement feature 162 for coupling with an inserter such as in FIG. 5, as described herein. The engagement feature 162 may be a recess configured to couple with an inserter. The engagement feature 162 can be shaped to couple with a hex driver, a star driver, a square driver, a torx driver, or any other suitable driver for driving the implant 102 into bone.

Figure 1B:
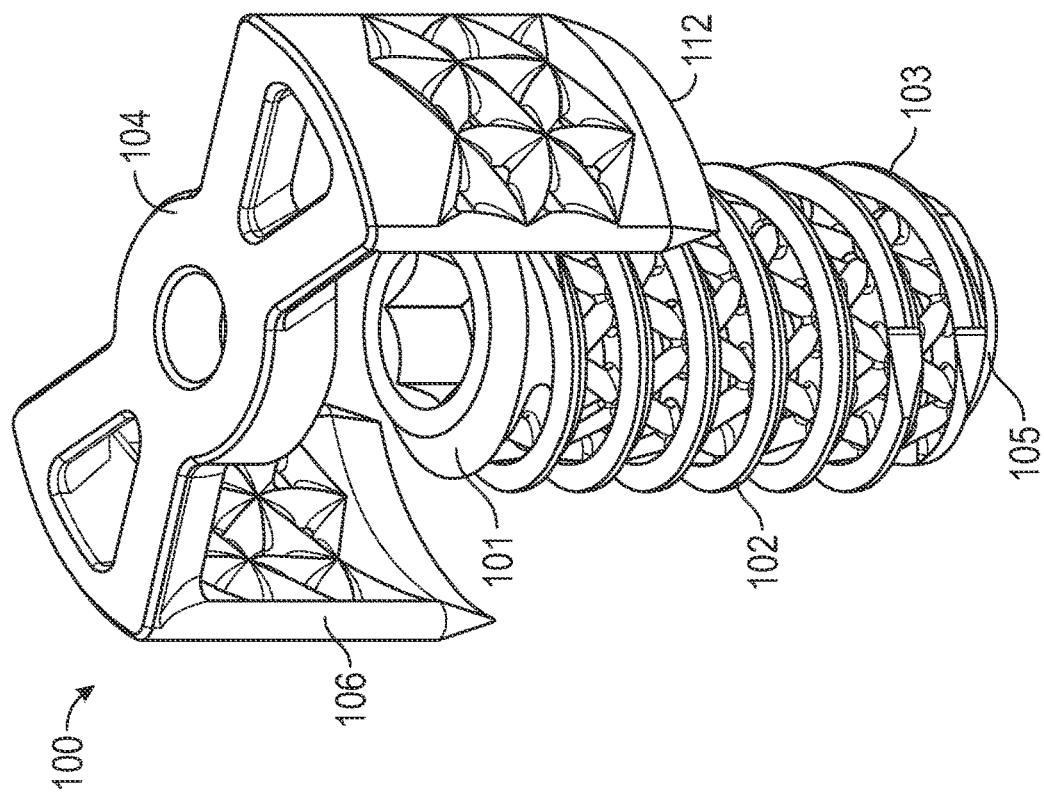
FIG. 1B illustrates an exploded view of the embodiment of the joint implant of FIG. 1A.
Figure 1A:
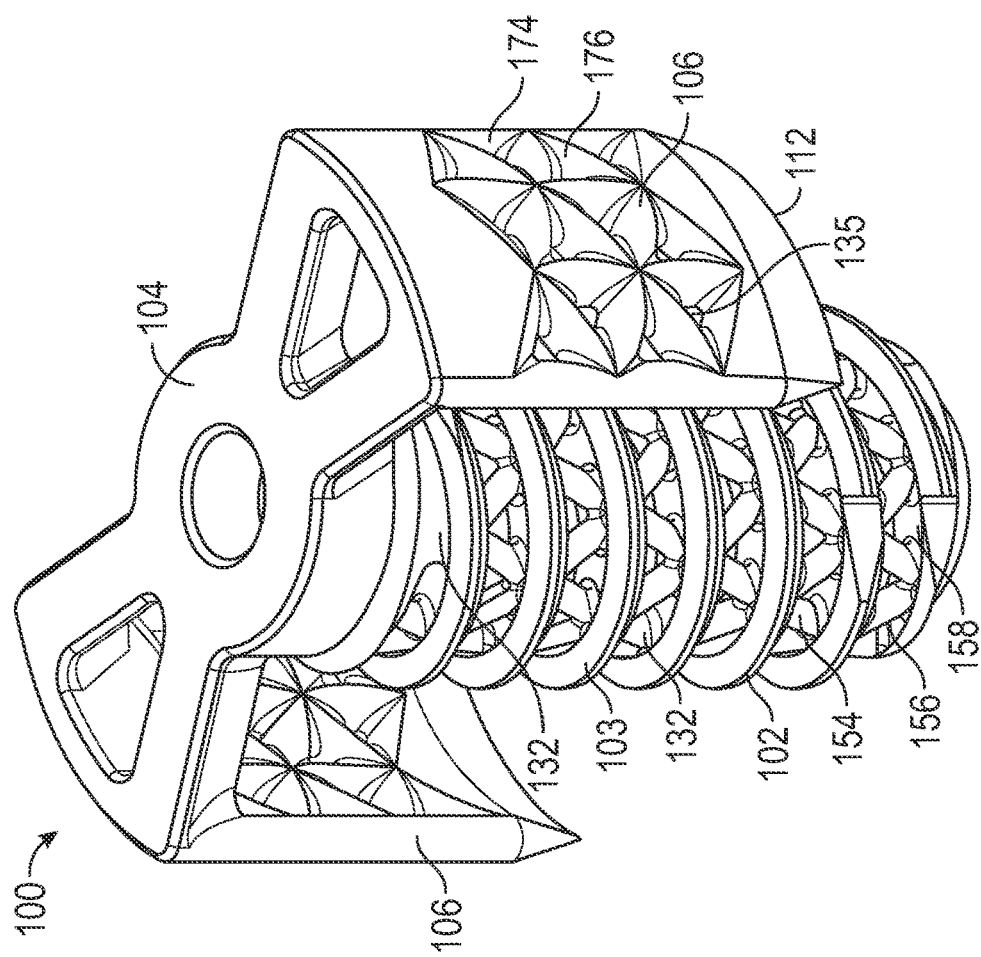
FIG. 1A illustrates a perspective view of an embodiment of a joint implant.
Figure 1D:
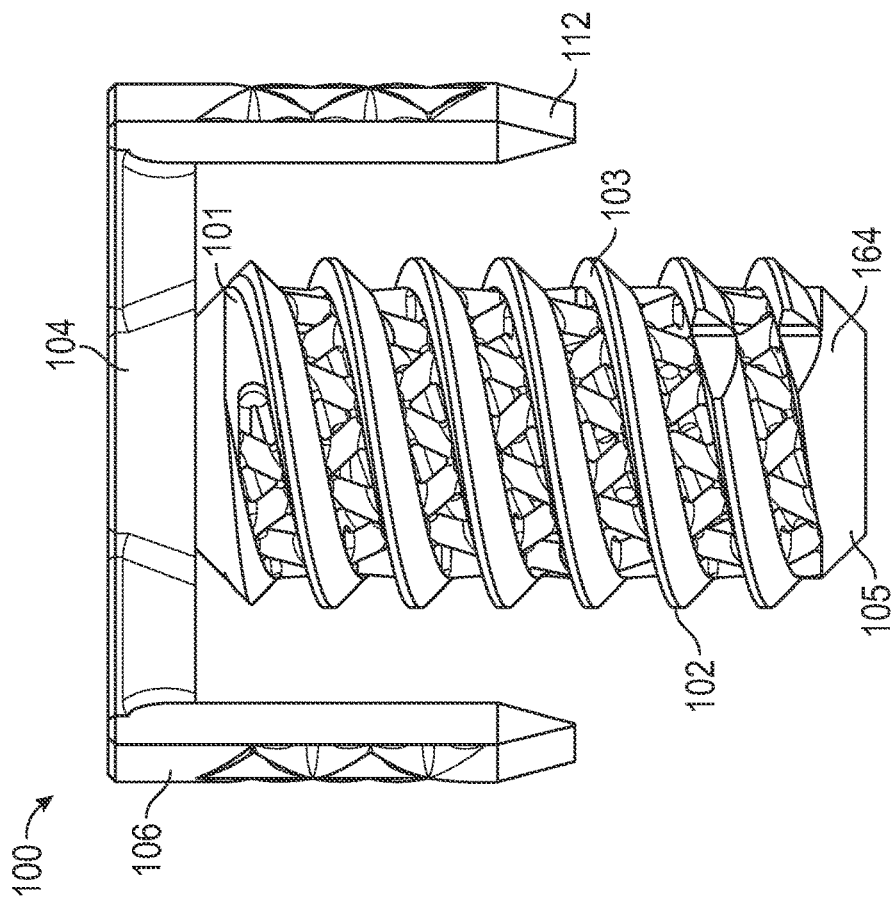
FIG. 1D illustrates a side vide of the embodiment of the joint implant of FIG. 1A.
Figure 1C:
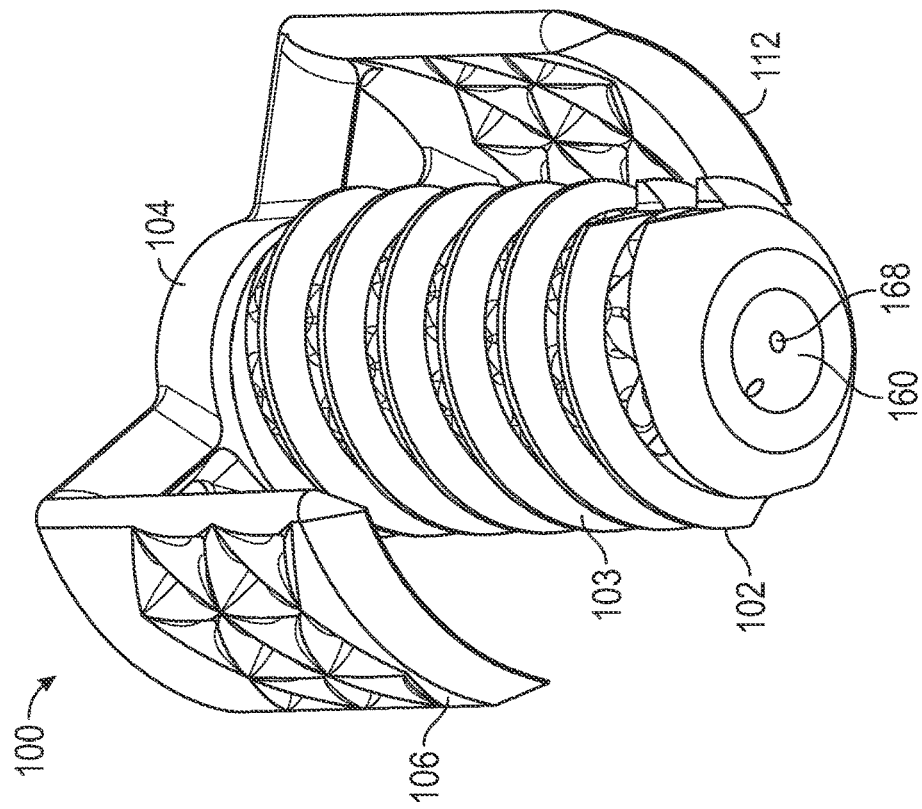
FIG. 1C illustrates a perspective view of the embodiment of the joint implant of FIG. 1A.
Figure 2B:
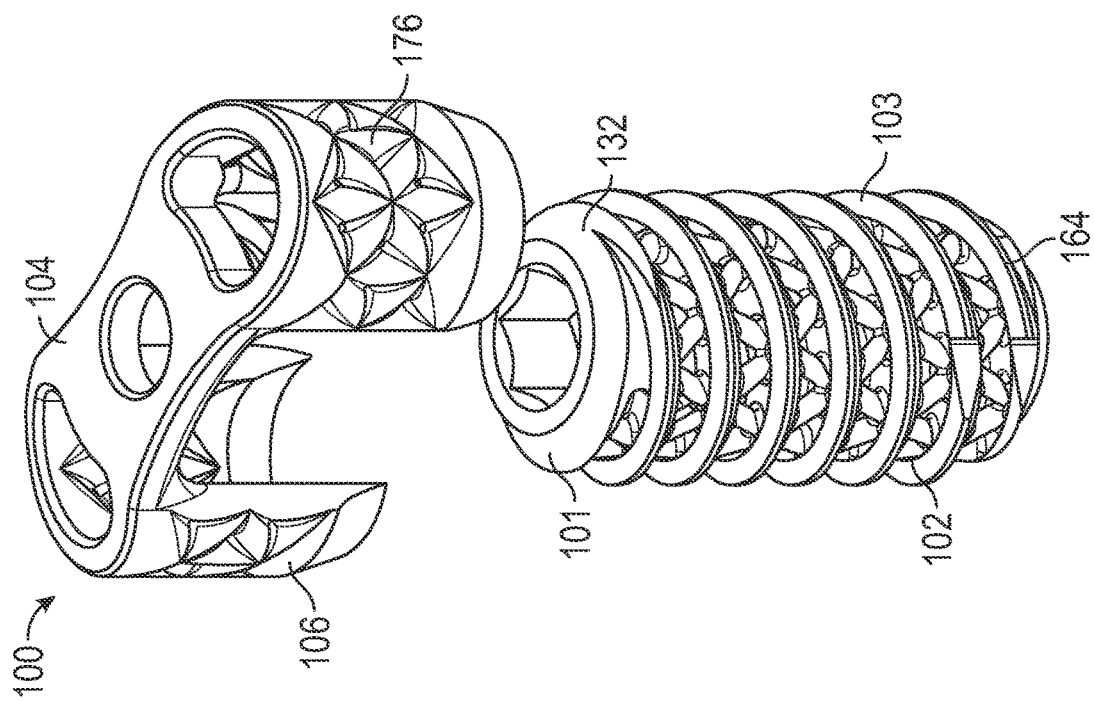
FIG. 2B illustrates an exploded view of the embodiment of the joint implant of FIG. 2A.
Figure 2A:
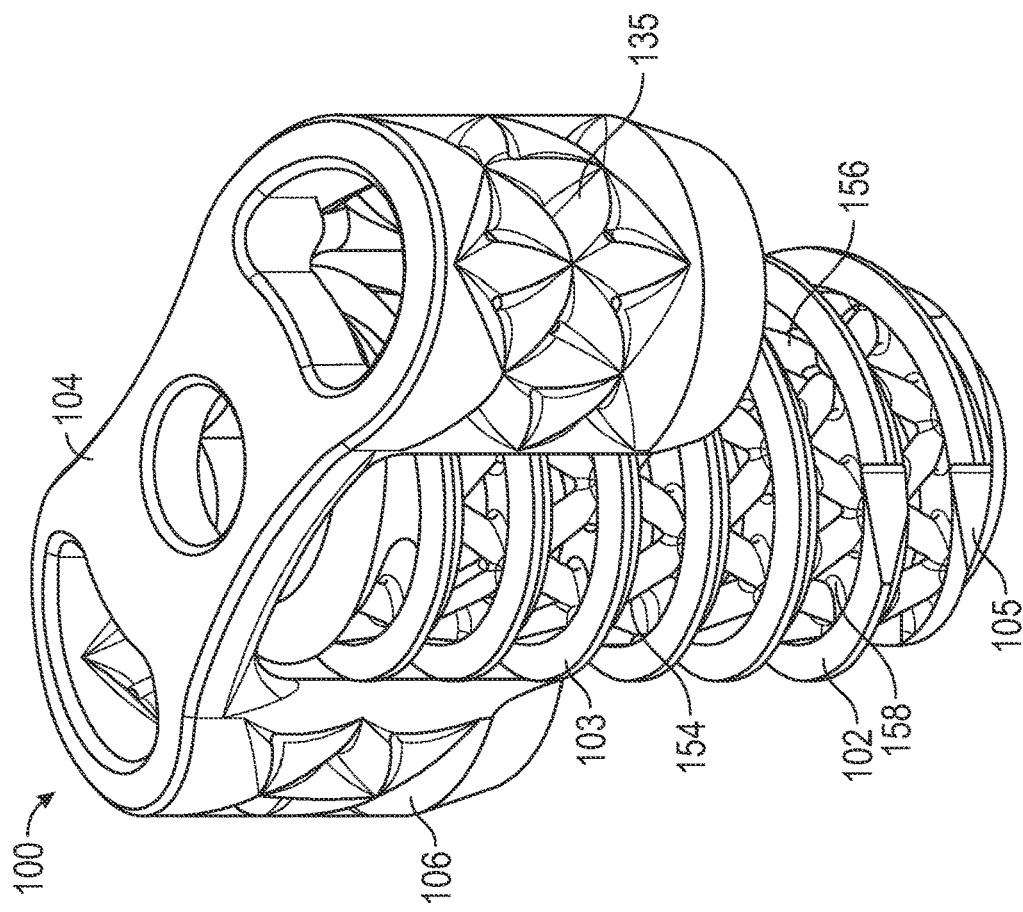
FIG. 2A illustrates a perspective view of an embodiment of a joint implant.
Figure 2C:
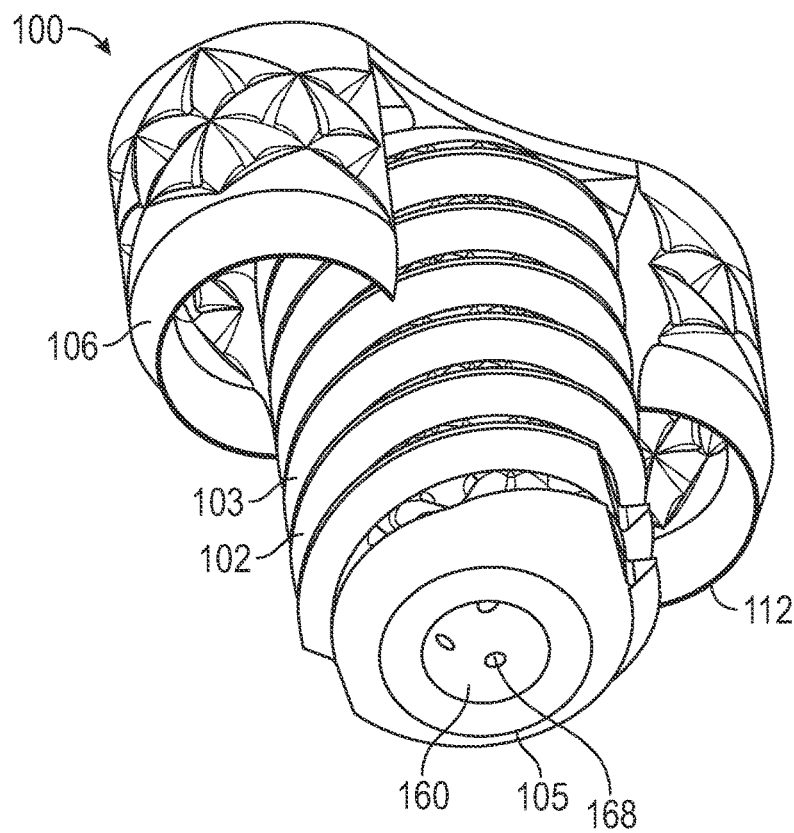
FIG. 2C illustrates a perspective view of the embodiment of the joint implant of FIG. 2A.
Figure 2D:
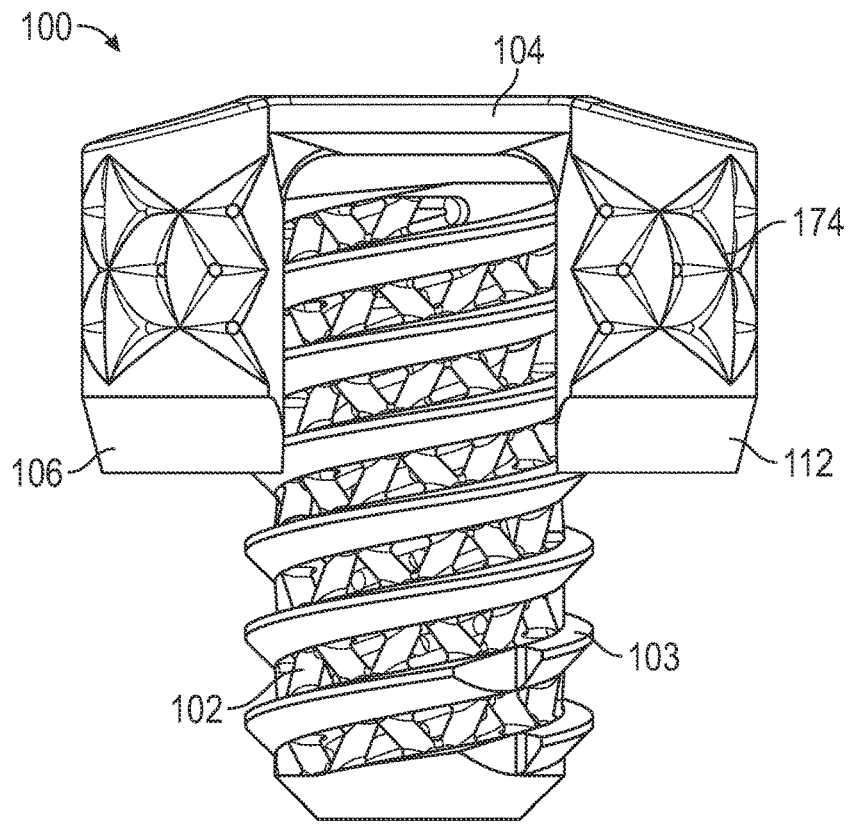
FIG. 2D illustrates a side vide of the embodiment of the joint implant of FIG. 2A.
Figure 3A:
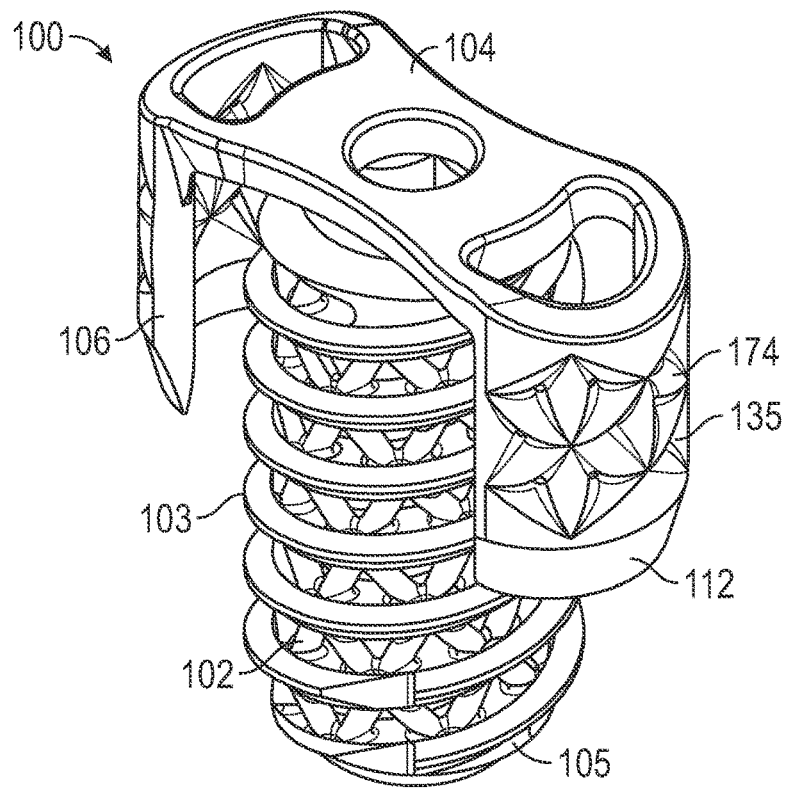
FIG. 3A illustrates a perspective view of an embodiment of a joint implant.
Figure 3B:
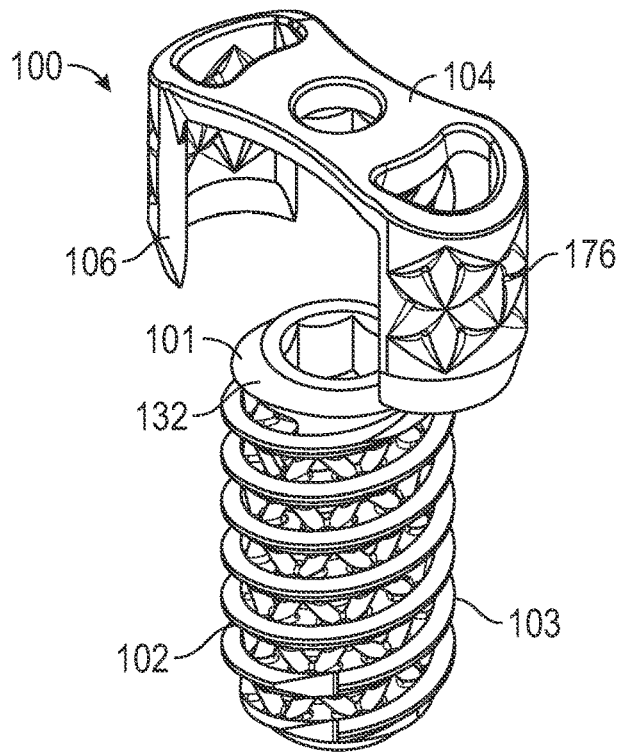
FIG. 3B illustrates an exploded view of the embodiment of the joint implant of FIG. 3A.
Figure 3C:
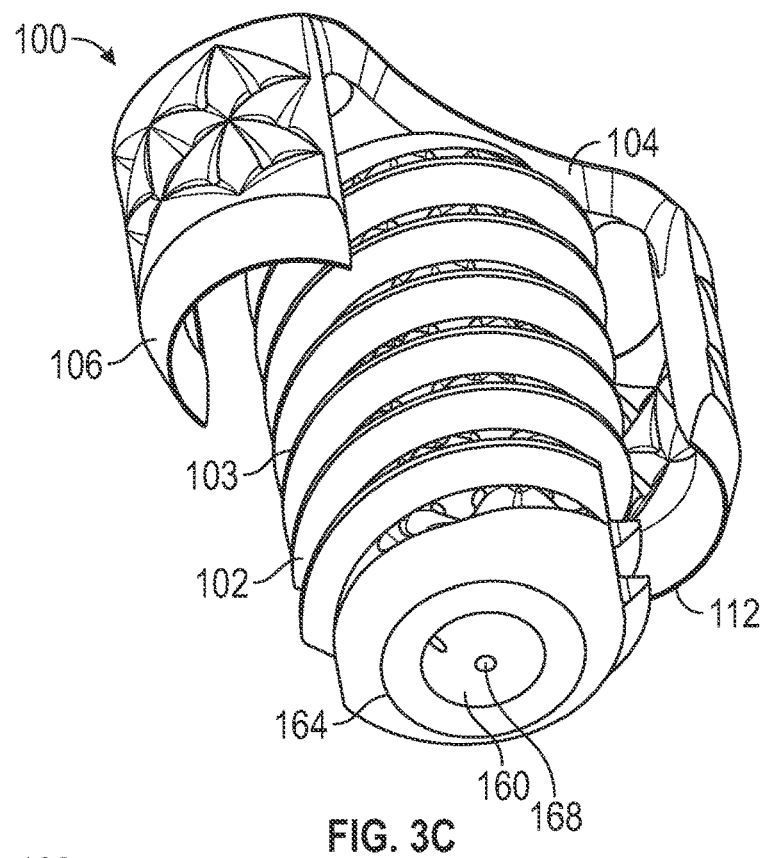
FIG. 3C illustrates a perspective view of the embodiment of the joint implant of FIG. 3A.
Figure 3D:
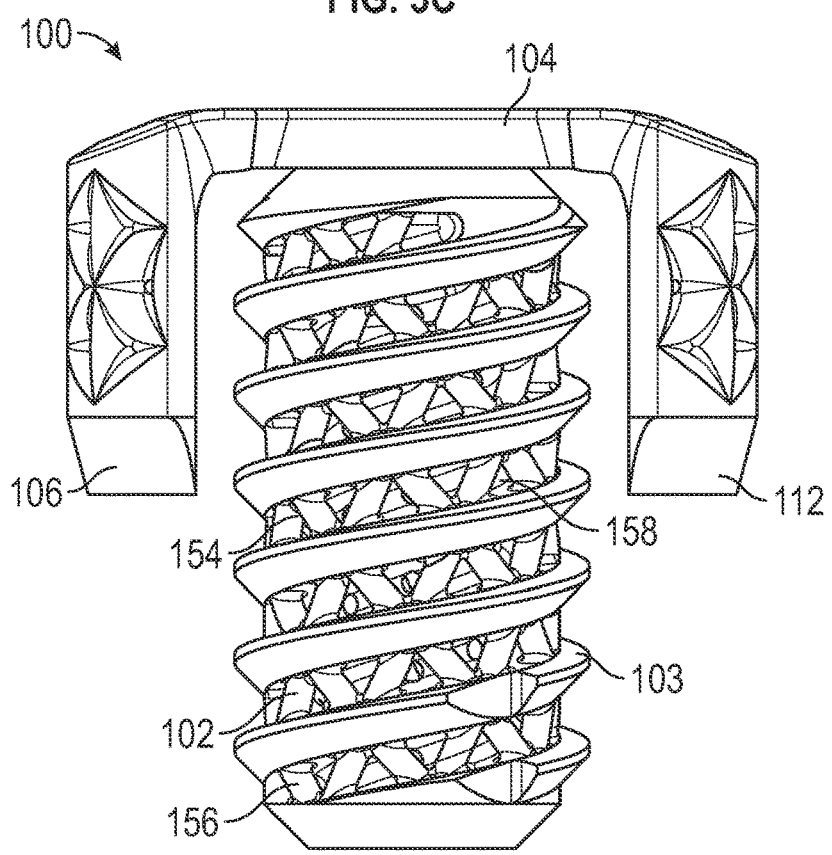
FIG. 3D illustrates a side vide of the embodiment of the joint implant of FIG. 3A.
Figure 4A:
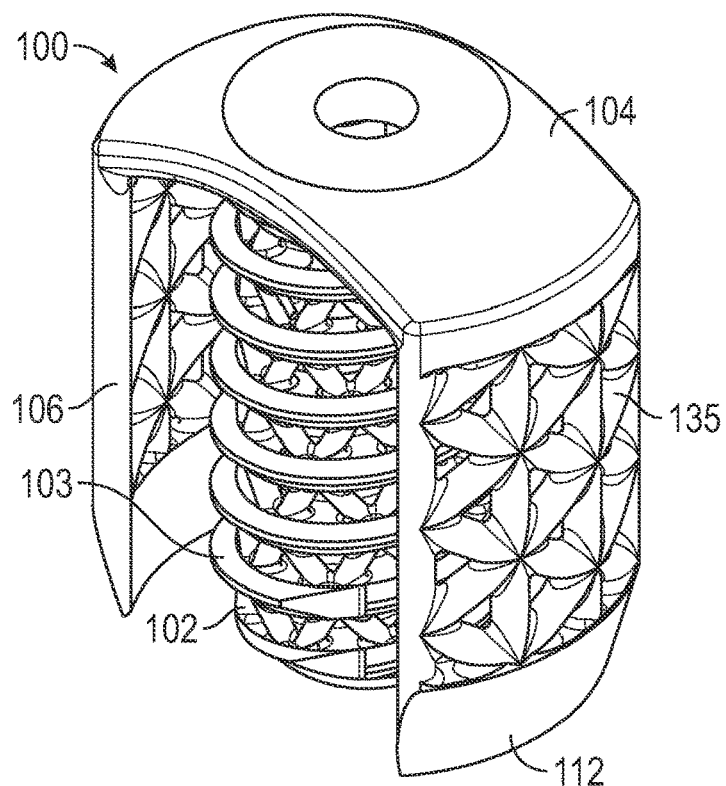
FIG. 4A illustrates a perspective view of an embodiment of a joint implant.
Figure 4B:
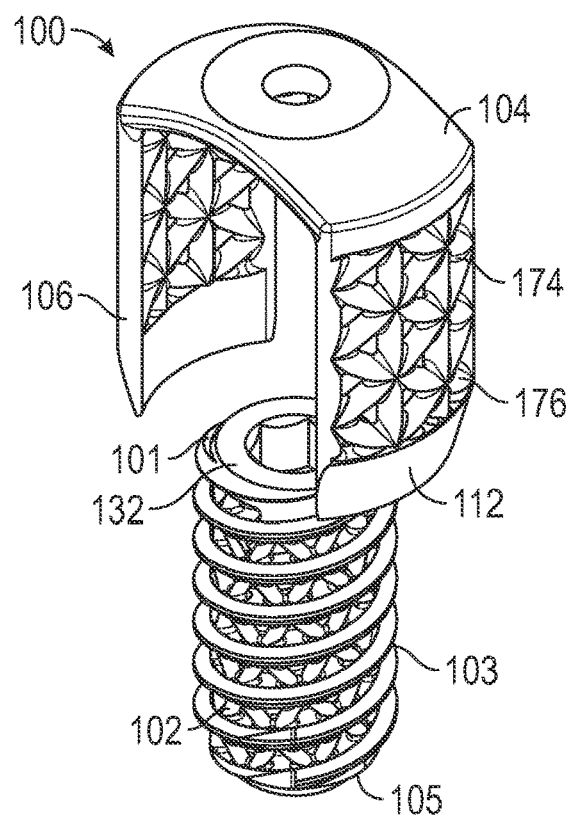
FIG. 4B illustrates an exploded view of the embodiment of the joint implant of FIG. 4A.
Figure 4C:
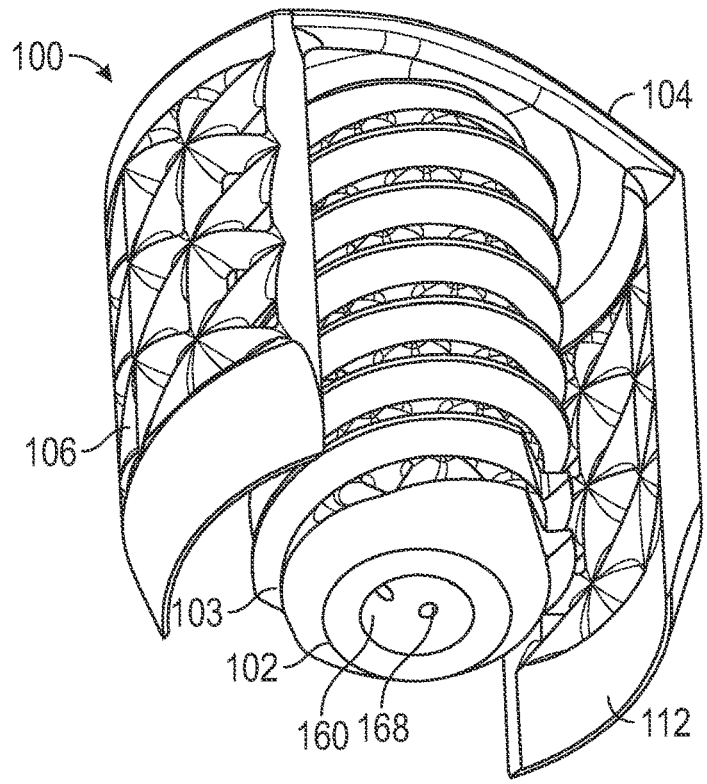
FIG. 4C illustrates a perspective view of the embodiment of the joint implant of FIG. 4A.
Figure 4D:
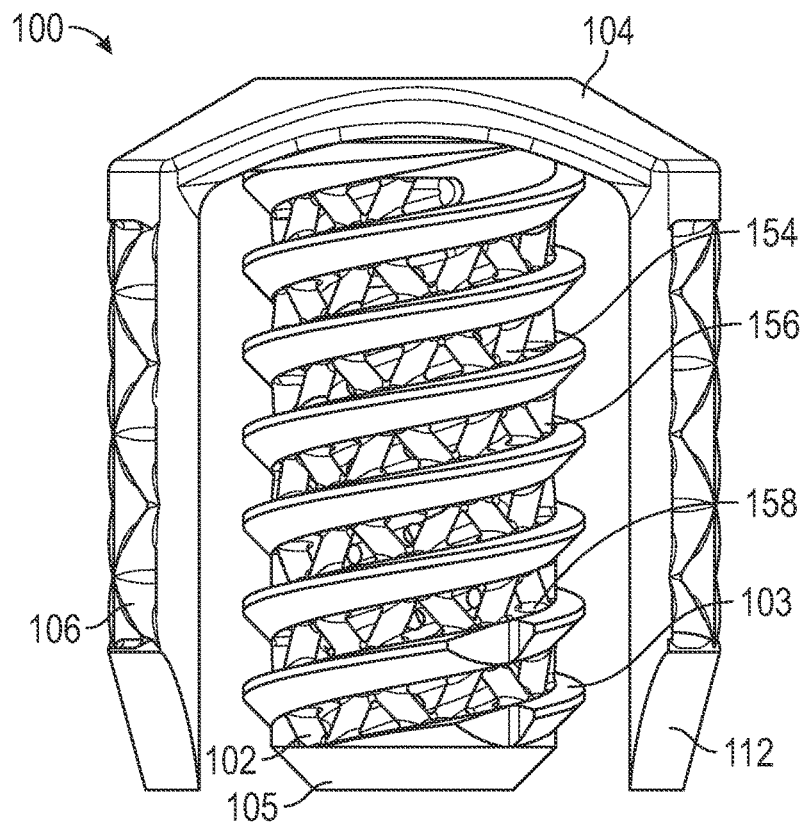
FIG. 4D illustrates a side vide of the embodiment of the joint implant of FIG. 4A.
Figure 5A:
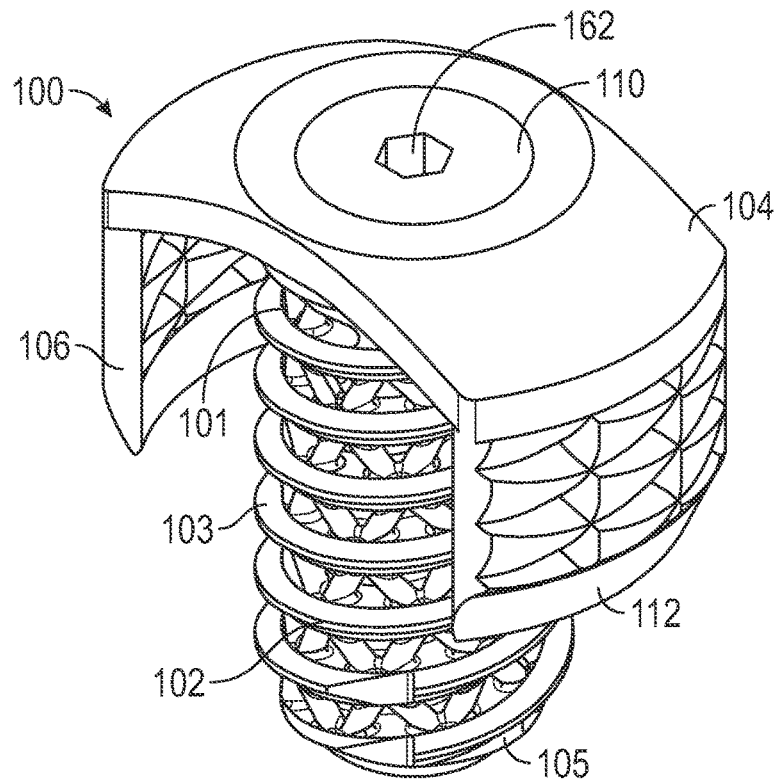
FIG. 5A illustrates a perspective view of an embodiment of a joint implant.
Figure 5B:
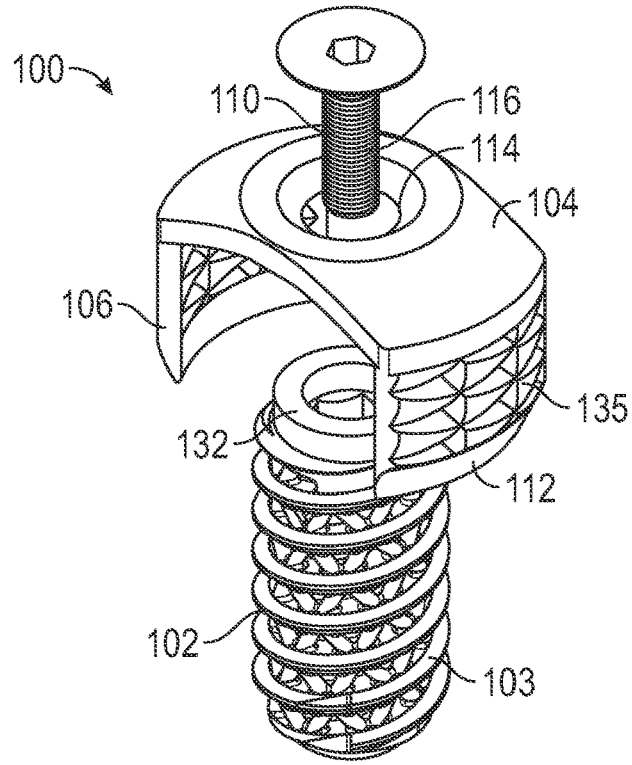
FIG. 5B illustrates an exploded view of the embodiment of the joint implant of FIG. 5A.
Figure 5C:
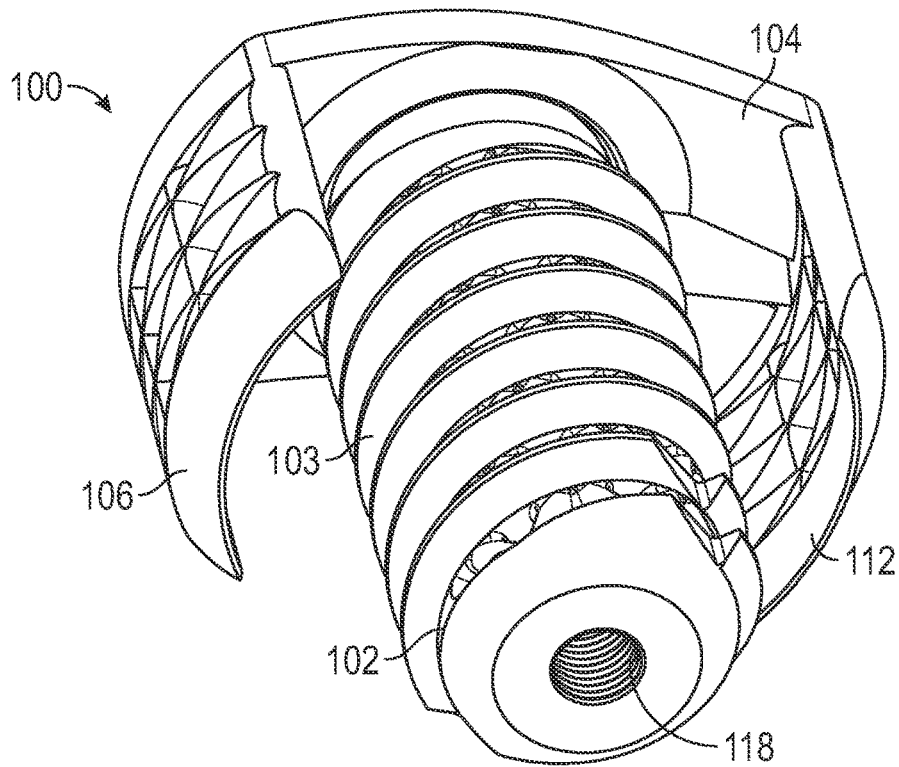
FIG. 5C illustrates a perspective view of the embodiment of the joint implant of FIG. 5A.
Figure 5D:
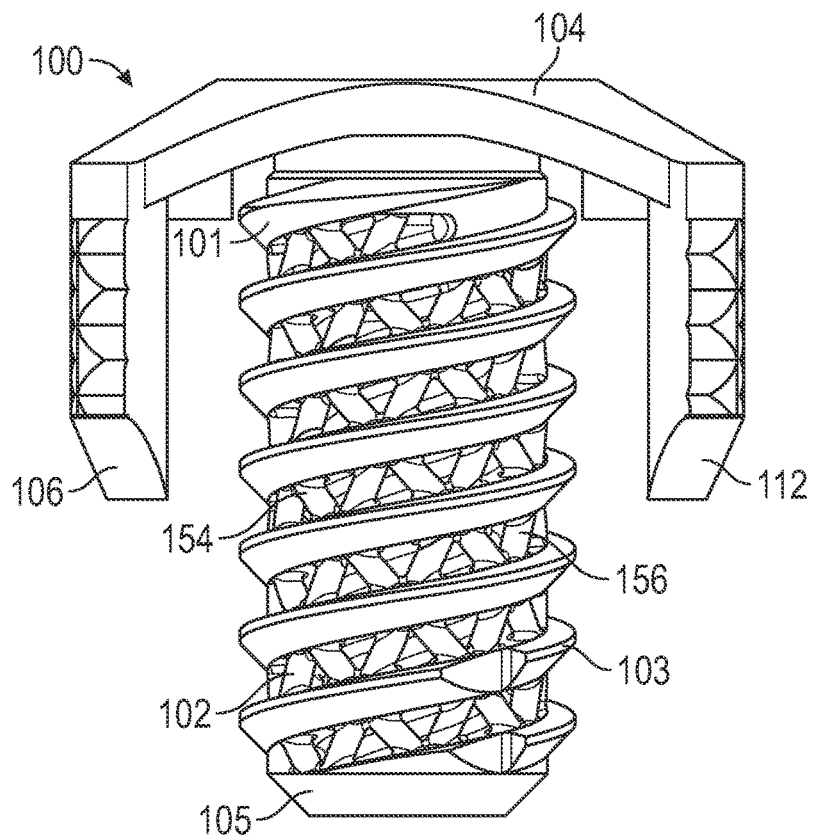
FIG. 5D illustrates a side vide of the embodiment of the joint implant of FIG. 5A.
Figure 6A:
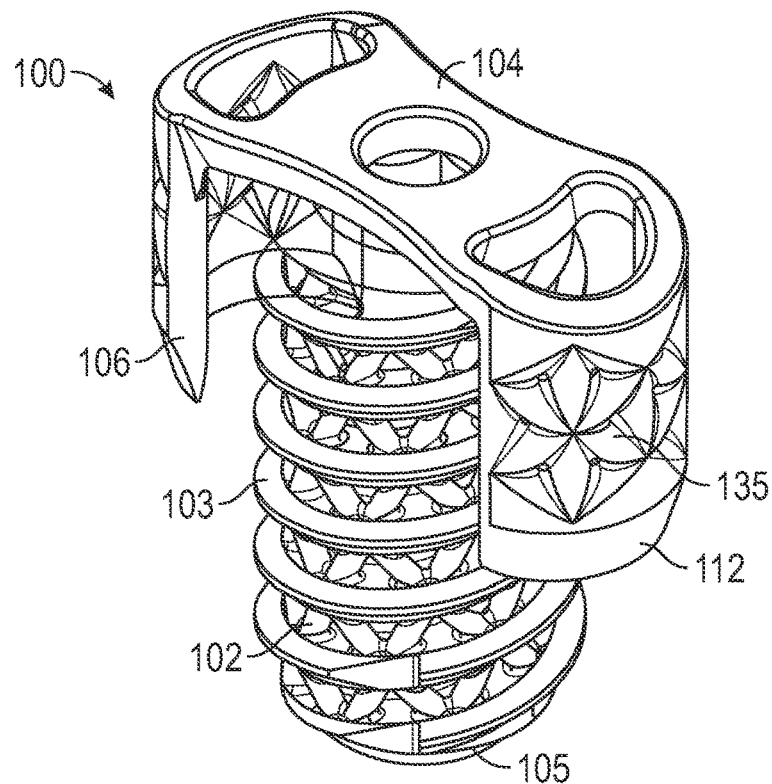
FIG. 6A illustrates a perspective view of an embodiment of a joint implant.
Figure 6B:
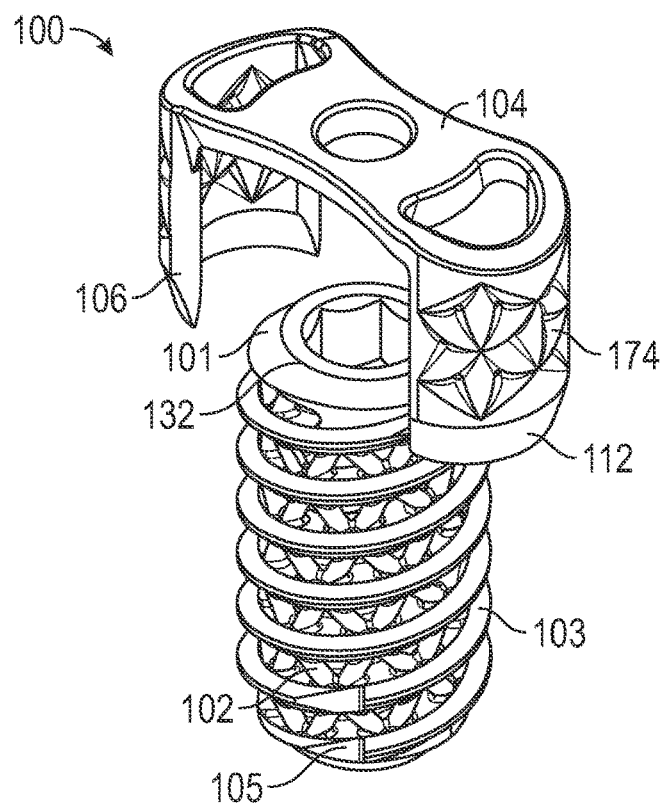
FIG. 6B illustrates an exploded view of the embodiment of the joint implant of FIG. 6A.
Figure 6C:
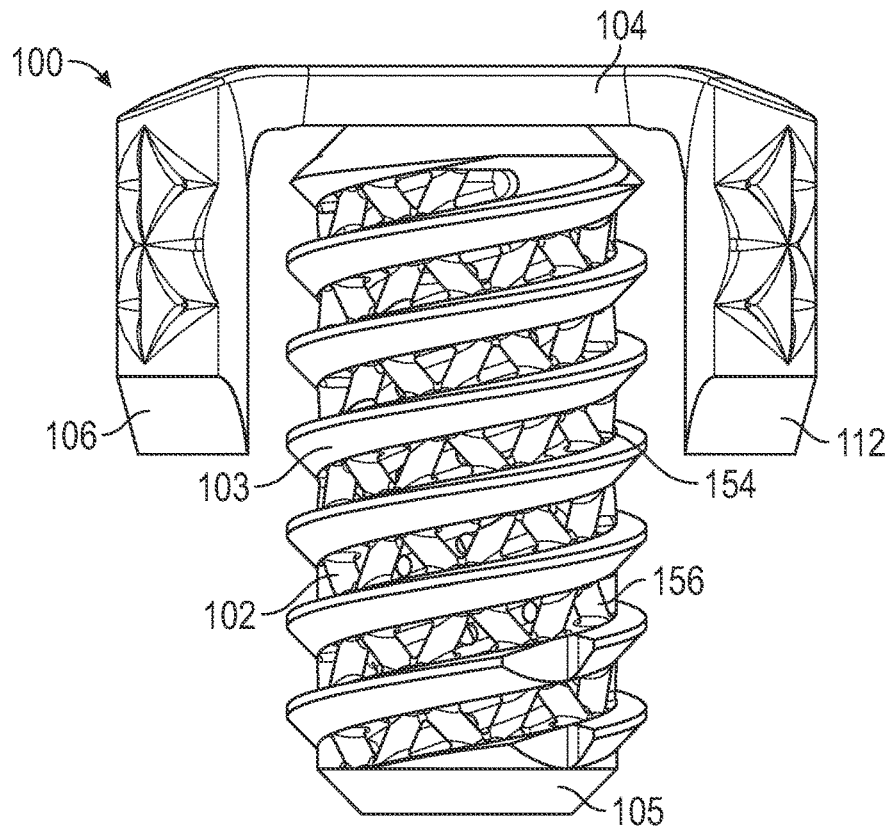
FIG. 6C illustrates a perspective view of the embodiment of the joint implant of FIG. 6A.
Figure 6D:
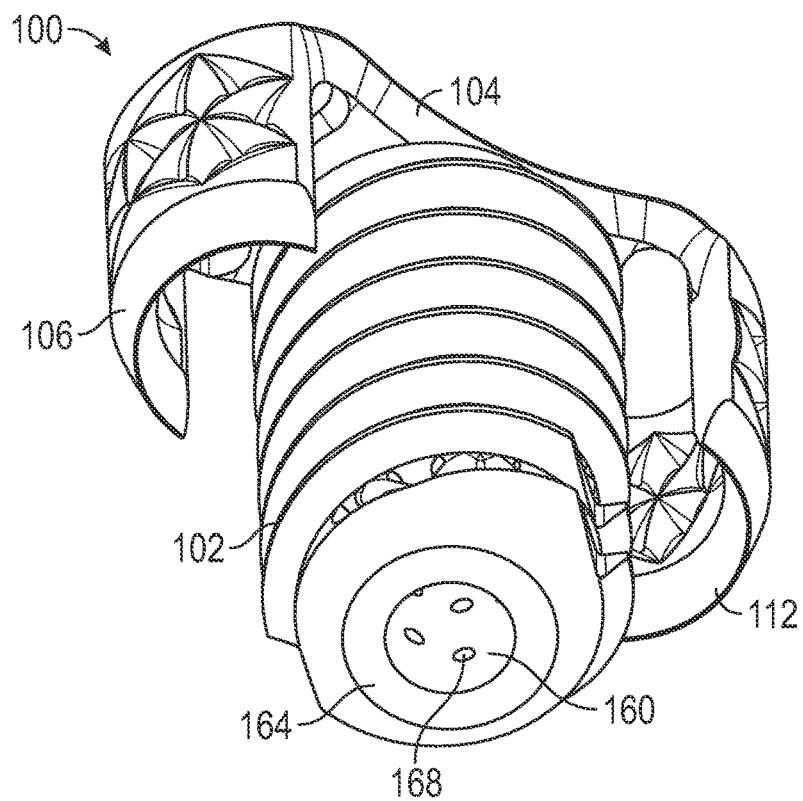
FIG. 6D illustrates a side vide of the embodiment of the joint implant of FIG. 6A.
Figure 7B:
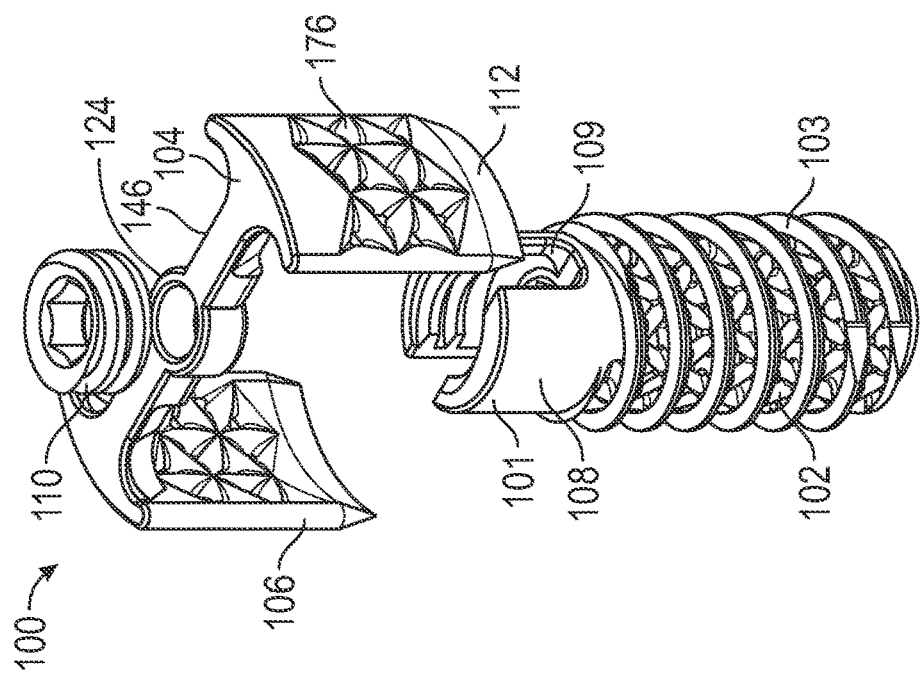
FIG. 7B illustrates an exploded view of the embodiment of the joint implant of FIG. 7A.
Figure 7A:
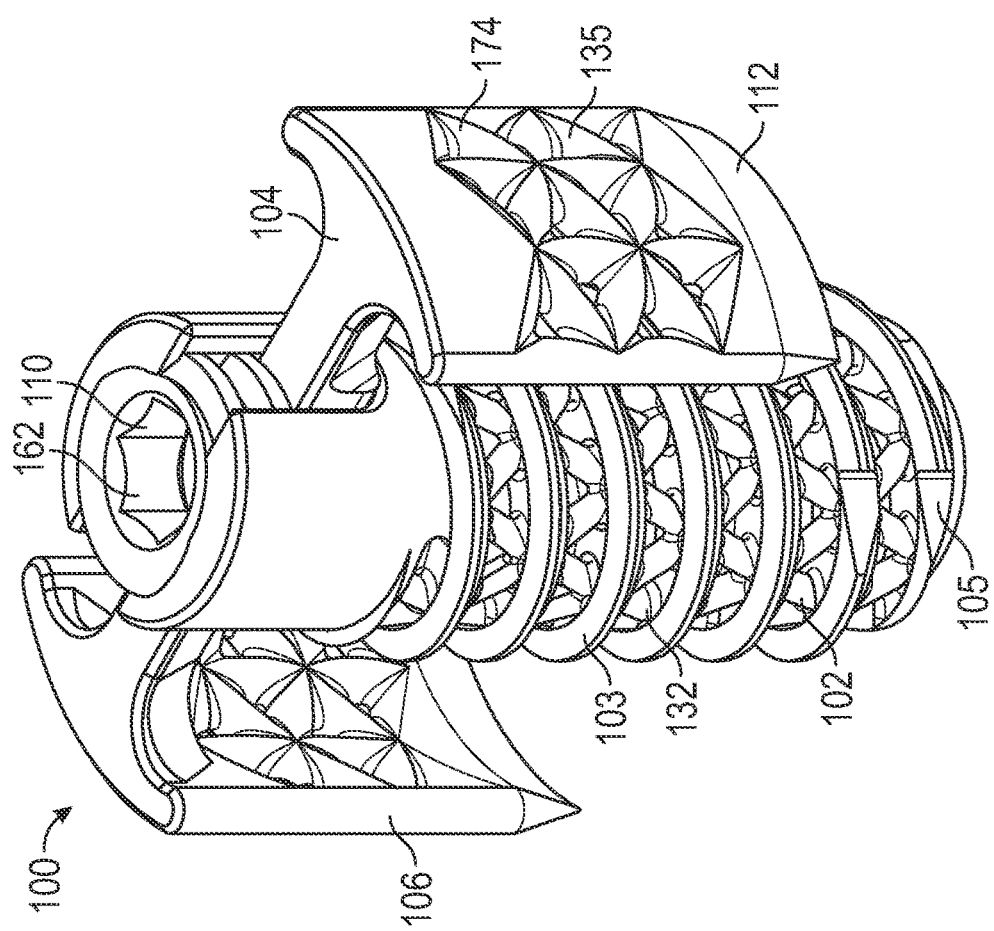
FIG. 7A illustrates a perspective view of an embodiment of a joint implant.
Figure 7D:
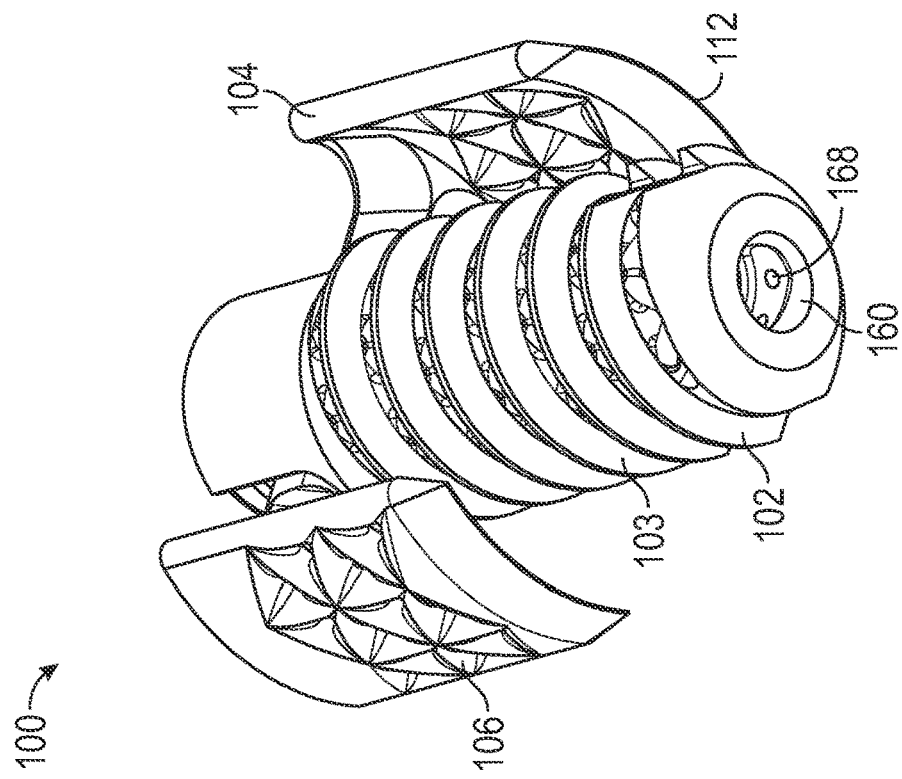
FIG. 7D illustrates a side vide of the embodiment of the joint implant of FIG. 7A.
Figure 7C:
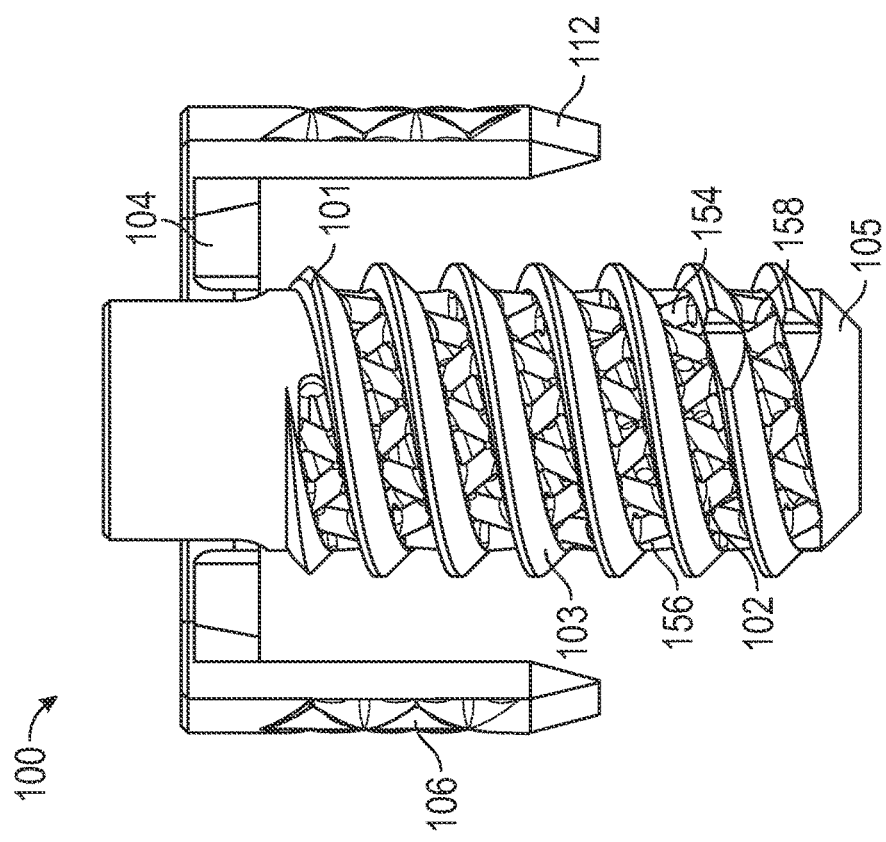
FIG. 7C illustrates a perspective view of the embodiment of the joint implant of FIG. 7A.
Figure 8A:
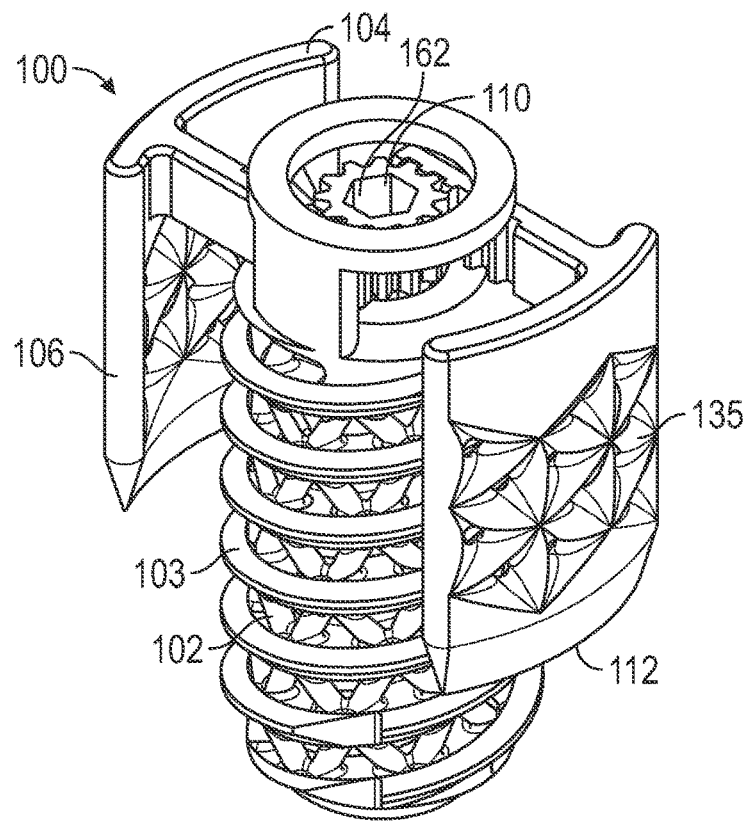
FIG. 8A illustrates a perspective view of an embodiment of a joint implant.
Figure 8B:
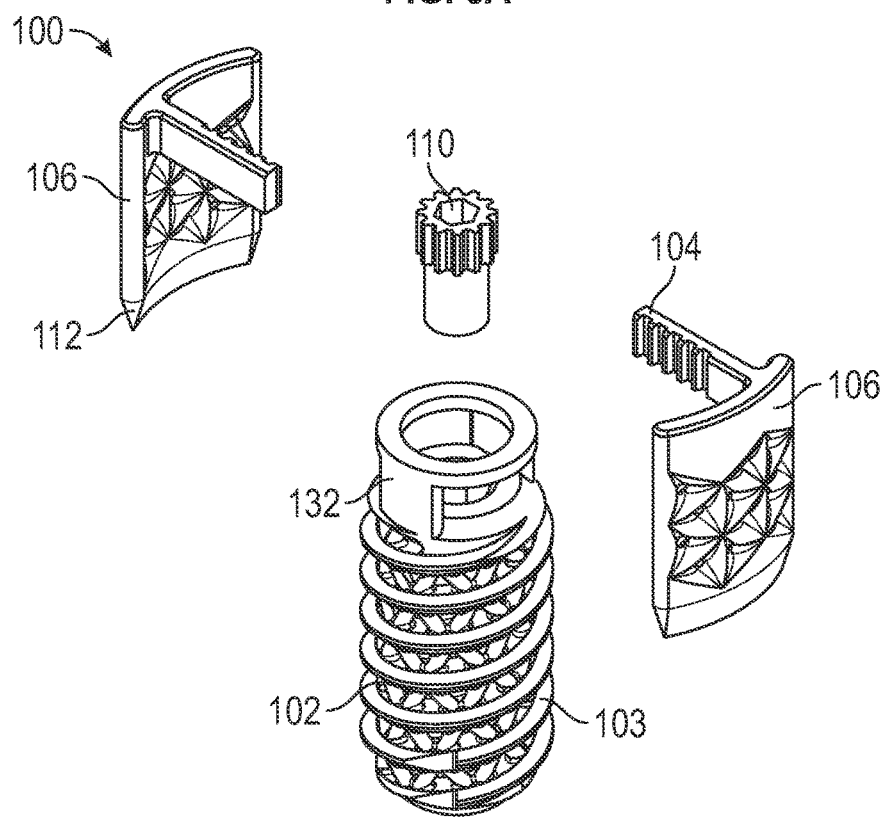
FIG. 8B illustrates an exploded view of the embodiment of the joint implant of FIG. 8A.
Figure 8D:
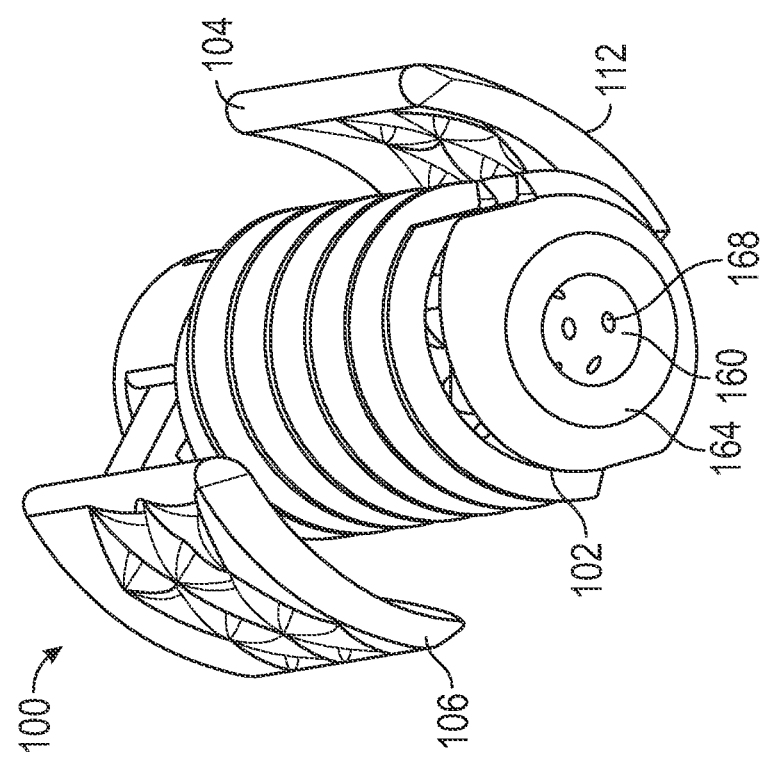
FIG. 8D illustrates a side vide of the embodiment of the joint implant of FIG. 8A.
Figure 8C:
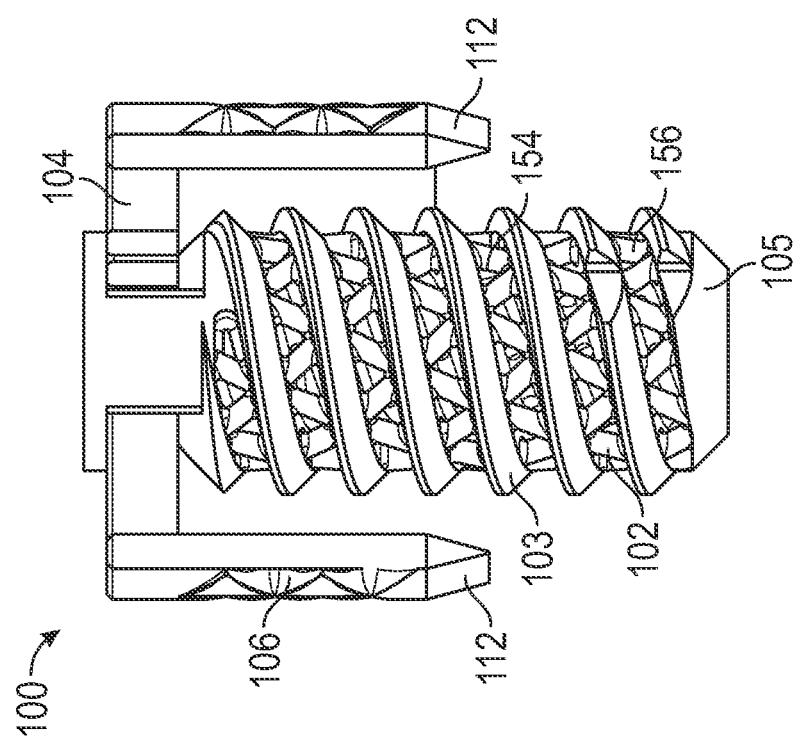
FIG. 8C illustrates a perspective view of the embodiment of the joint implant of FIG. 8A.
Figure 9B:
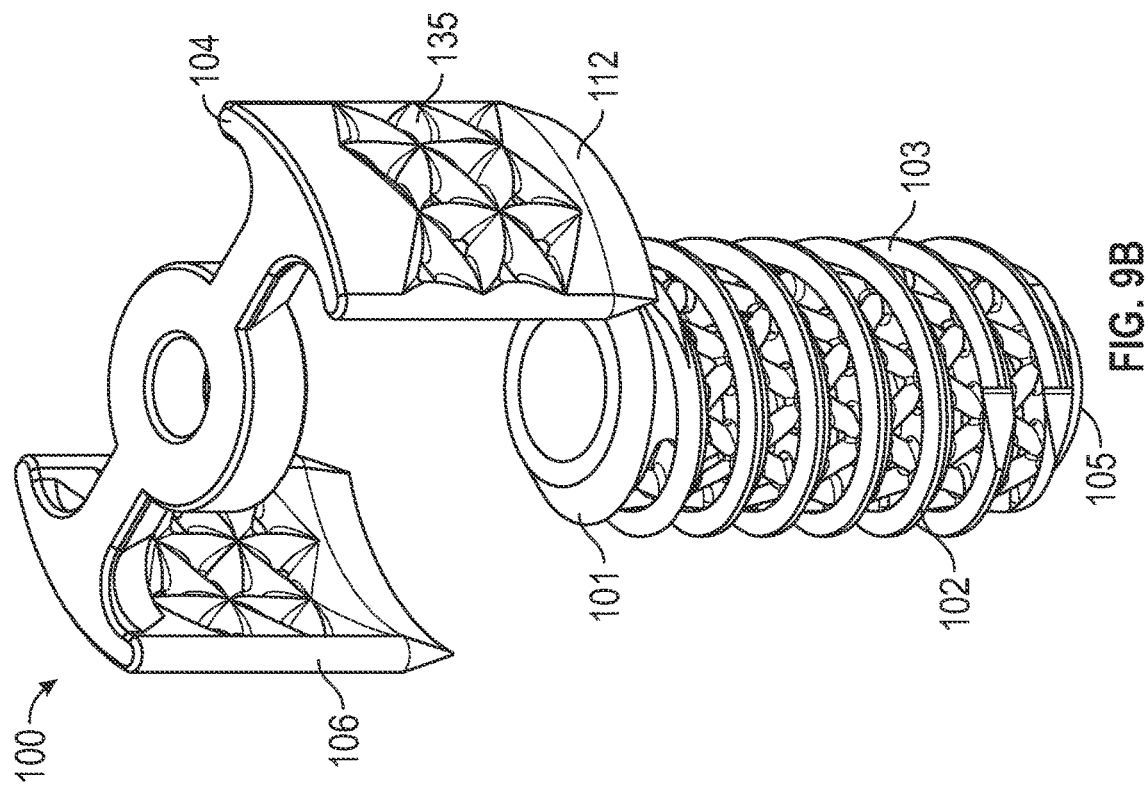
FIG. 9B illustrates an exploded view of the embodiment of the joint implant of FIG. 9A.
Figure 9A:
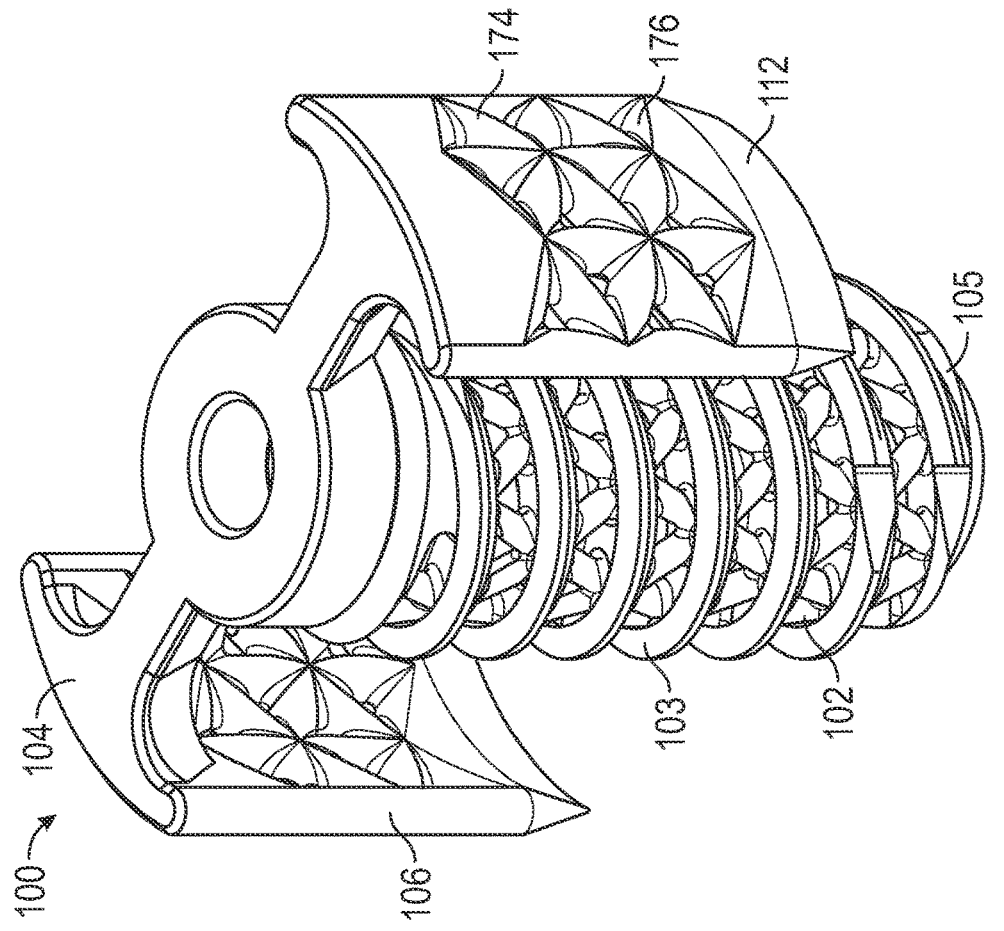
FIG. 9A illustrates a perspective view of an embodiment of a joint implant.
Figure 9D:
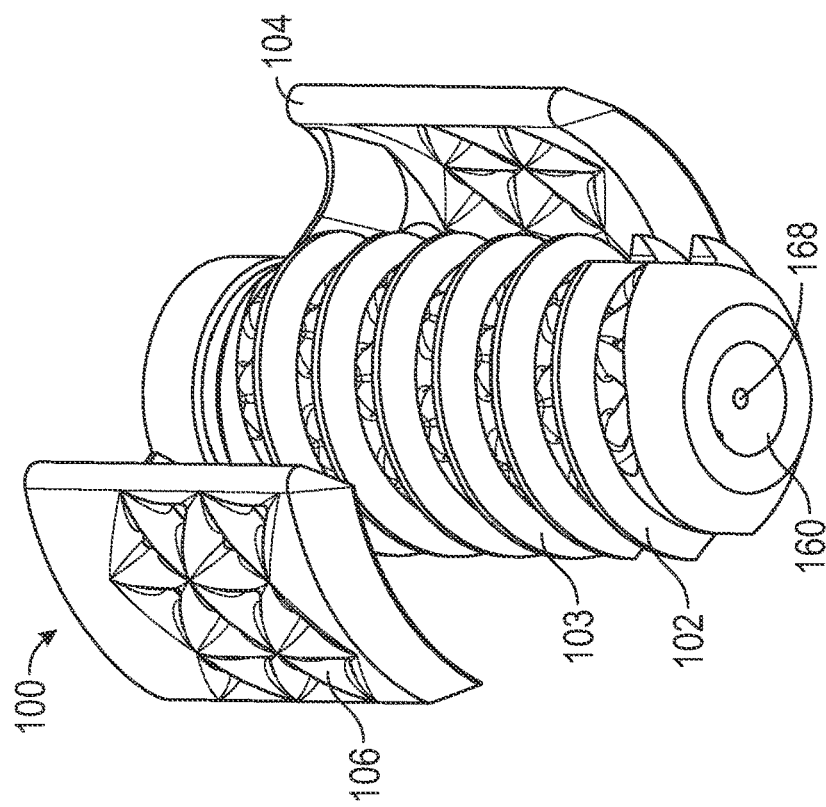
FIG. 9D illustrates a side vide of the embodiment of the joint implant of FIG. 9A.
Figure 9C:
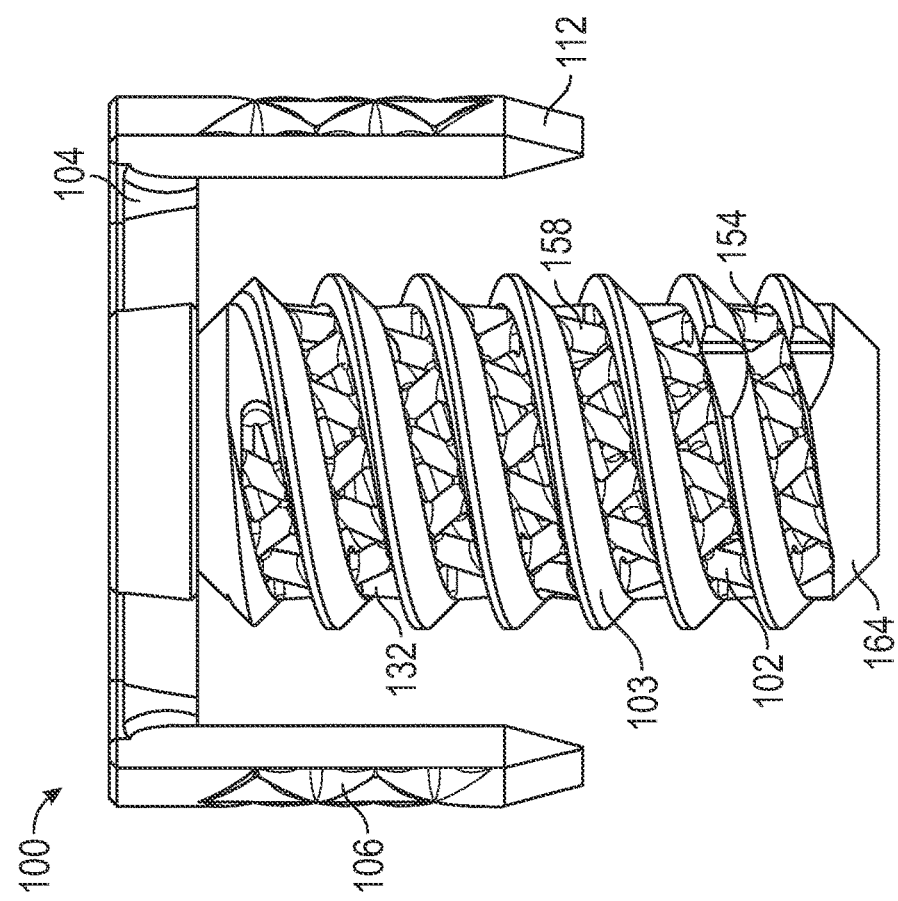
FIG. 9C illustrates a perspective view of the embodiment of the joint implant of FIG. 9A.
Figure 10B:
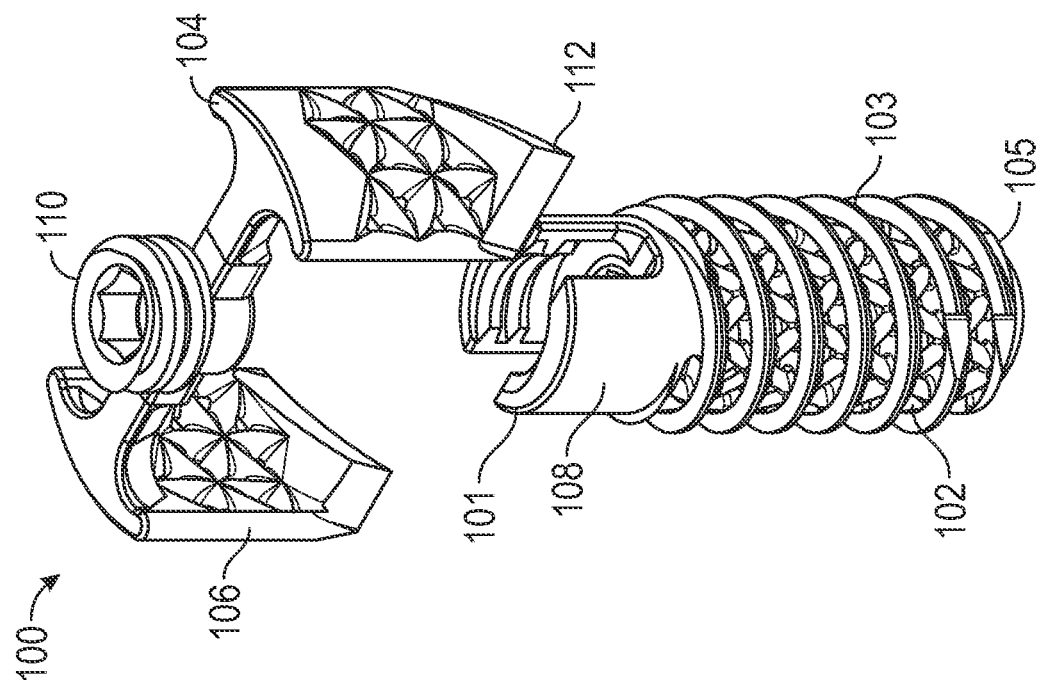
FIG. 10B illustrates an exploded view of the embodiment of the joint implant of FIG. 10A.
Figure 10A:
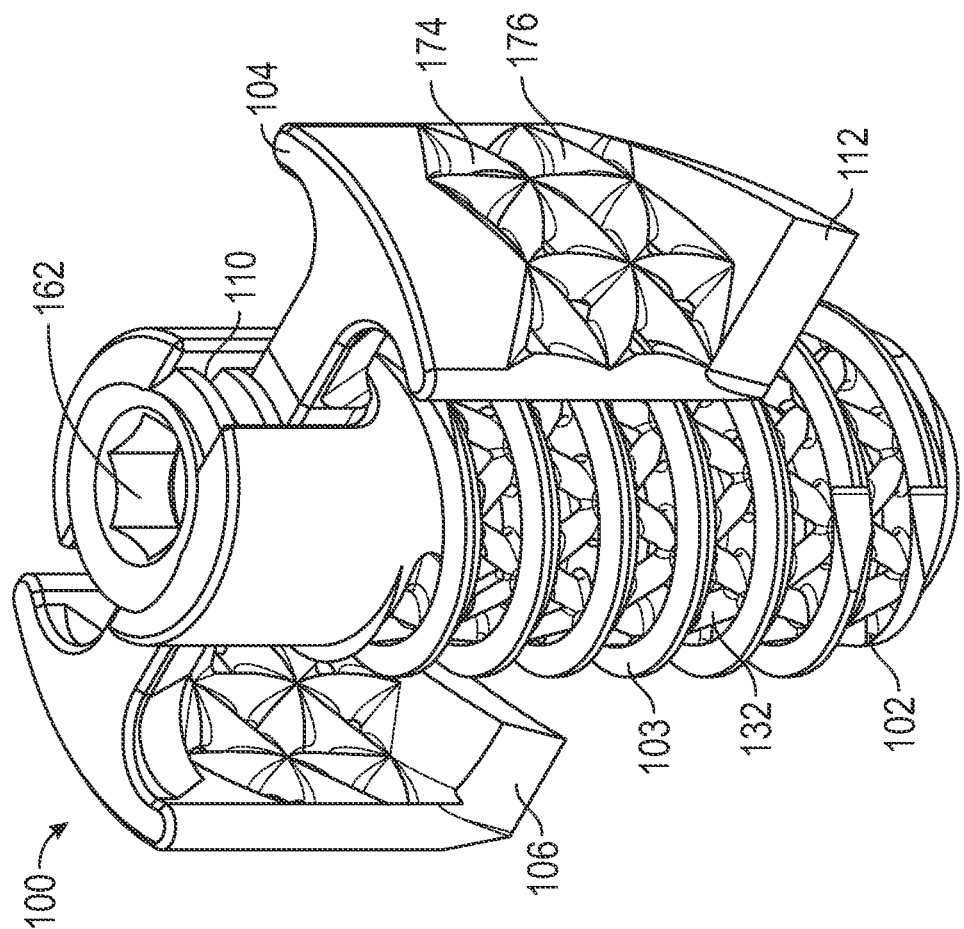
FIG. 10A illustrates a perspective view of an embodiment of a joint implant.
Figure 10D:
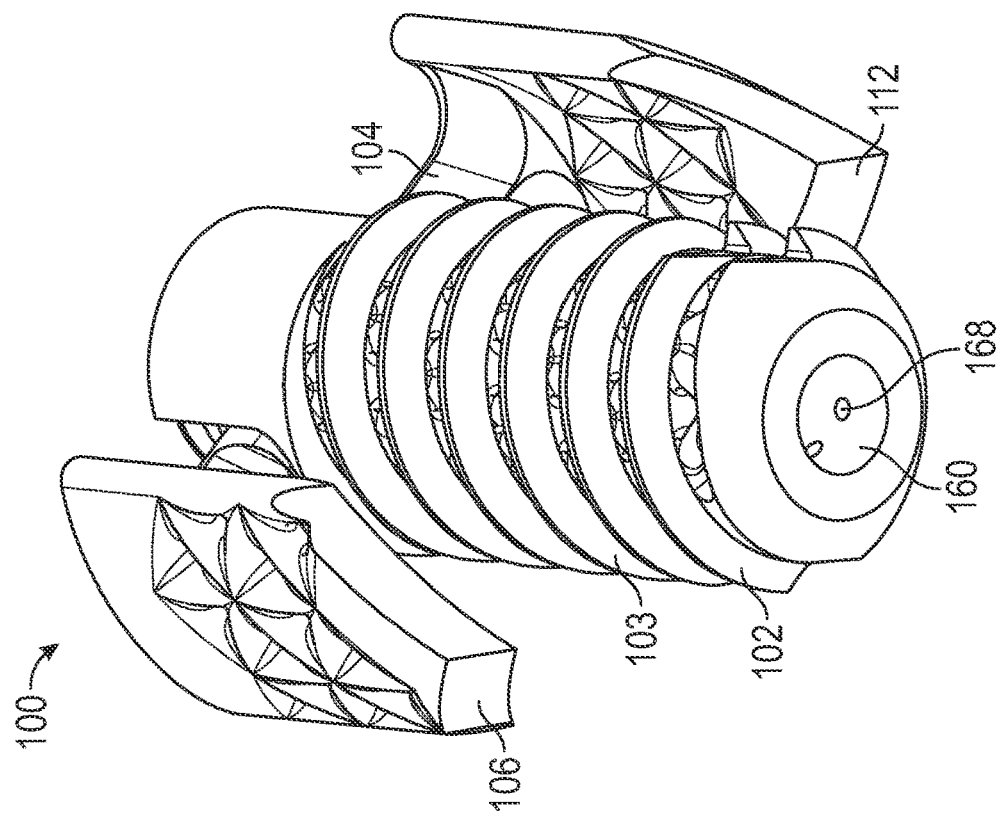
FIG. 10D illustrates a side vide of the embodiment of the joint implant of FIG. 10A.
Figure 10C:
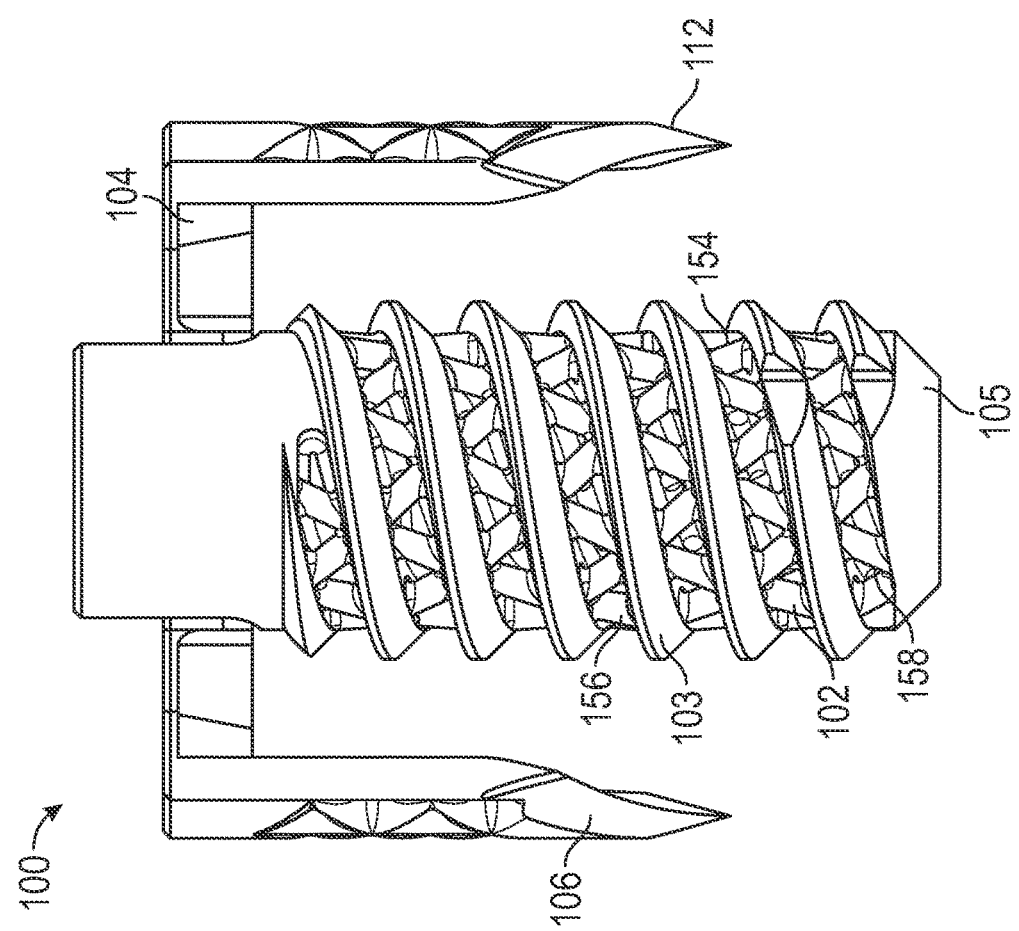
FIG. 10C illustrates a perspective view of the embodiment of the joint implant of FIG. 10A.
Figure 11B:
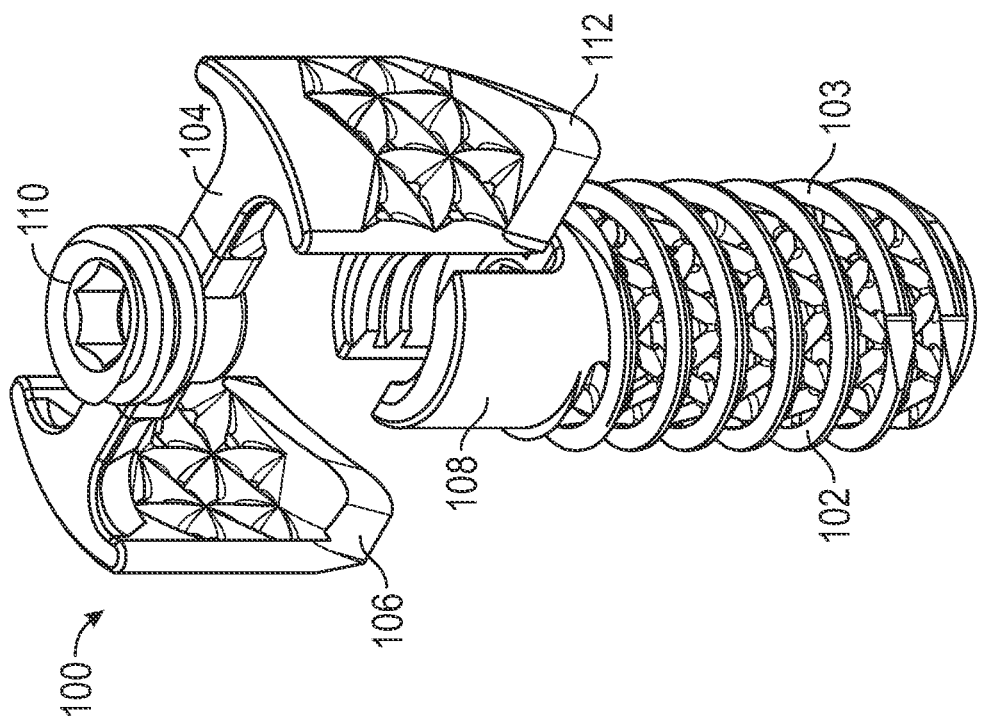
FIG. 11B illustrates an exploded view of the embodiment of the joint implant of FIG. 11A.
Figure 11A:
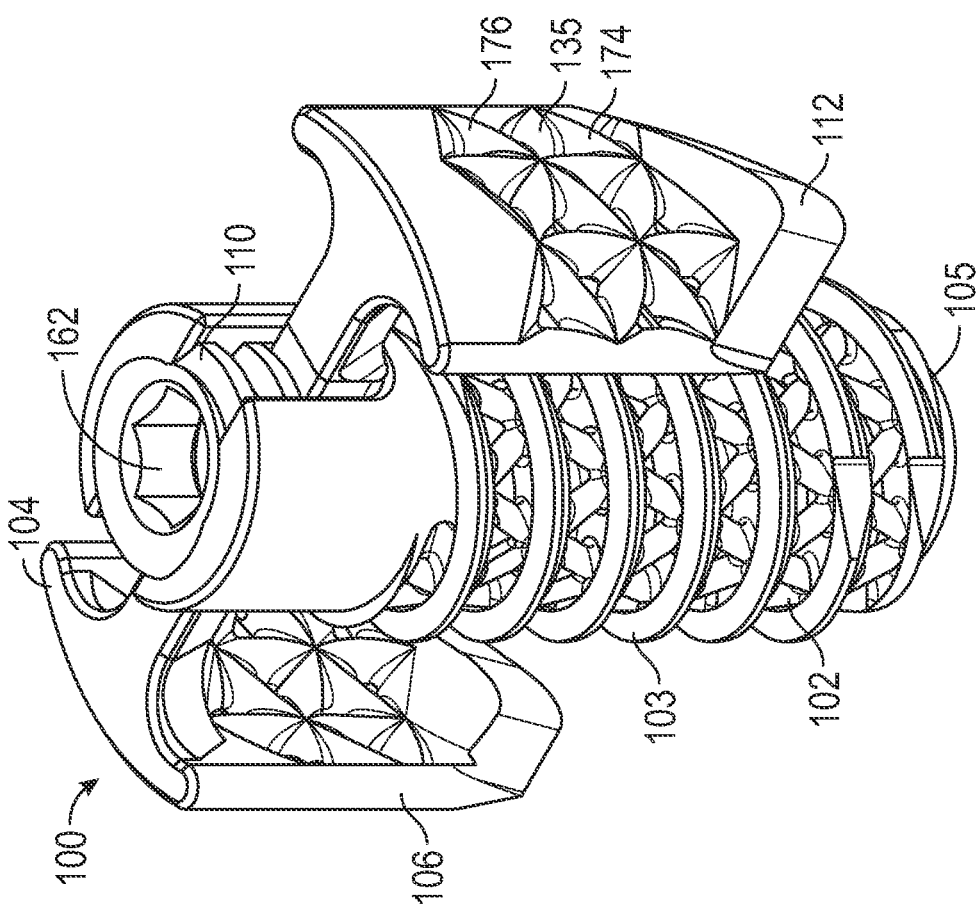
FIG. 11A illustrates a perspective view of an embodiment of a joint implant.
Figure 11D:
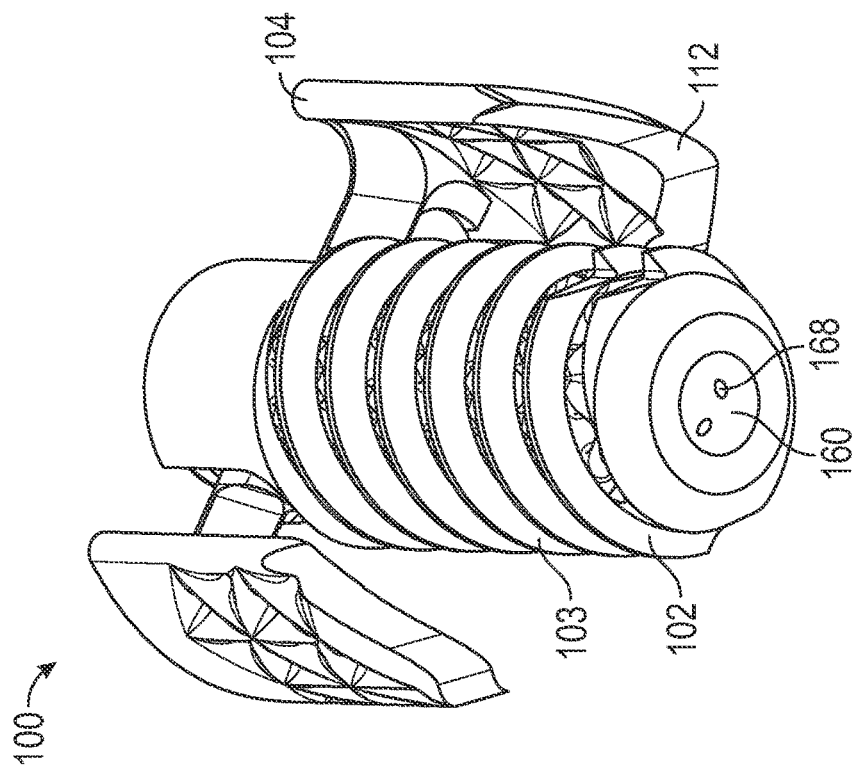
FIG. 11D illustrates a side vide of the embodiment of the joint implant of FIG. 11A.
Figure 11C:
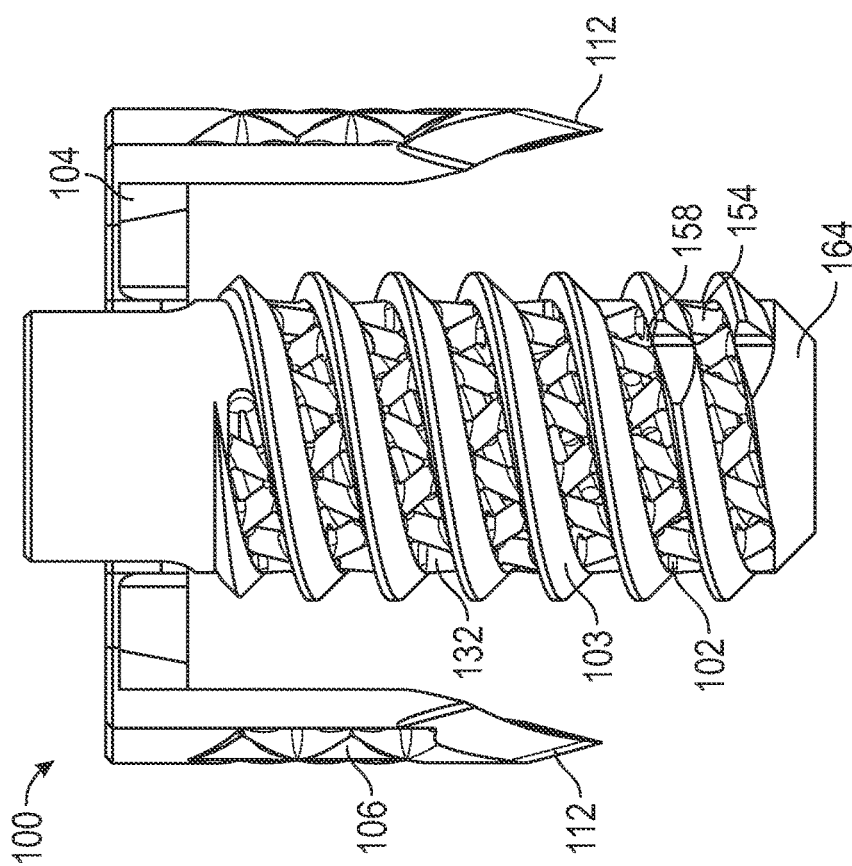
FIG. 11C illustrates a perspective view of the embodiment of the joint implant of FIG. 11A.

As shown in FIG. 1D, a tip 164 of the implant can be flat. In certain embodiments, the primary implant 102, or a shank 132 of the primary implant 102, may be conical. In certain embodiments, the primary implant 102 or the shank 132 can be tapered. In certain embodiments, the primary implant 102 or shank 132 can be symmetrical about a central axis with no taper. In some embodiments, the primary implant 102 or the shank 132 can be untapered throughout the entire length of the implant or a portion of the length. For example, the shank 132 can have a uniform cross-section or a generally uniform cross-section. In some embodiments, the engagement features 103 (e.g., threads) can extend a uniform distance or generally uniform distance from the shank 132 throughout the length of the primary implant 102. Such untapered embodiments may further prevent or reduce migration or back out of the primary implant 102 from the SI joint in comparison to tapered implants. In some embodiments, the primary implant 102 can be self tapping or self drilling.

In some embodiments, the primary implant 102 may be only partially cannulated. For example, the channel 160 may extend from the proximal end 101 only partially along the length of the primary implant 102 towards the distal end 105. In other embodiments, the primary implant 102 may not be cannulated. In other words, the implant 102 may have a solid core. A primary implant 102 that is only partially cannulated may have a higher biomechanical strength than an implant that is cannulated through its entire length. An implant that is not cannulated may have a higher biomechanical strength than a partially or fully cannulated implant.

As described herein, in certain embodiments, the secondary implant 104 can be configured to anchor within both the ilium and the sacrum on opposing sides of the SI joint. In certain embodiments, the secondary implant 104 can include a plurality of anchors 106. The anchors 106 can be a set of tangs, circles, half circles, wedges, triangles, squares, or other three-dimensional shaped anchors. The anchors 106 can have a curvature, for example in a half circle shape, to prevent or restrict movement of the anchors 106 in response to shear stresses (e.g., when the secondary implant is maleated into bone). In contrast, in some embodiments, a flat or planar anchor 106 may slide back and forth in response to shear stresses. Each of the anchors 106 of the secondary implant 104 may contain a blade or sharp edge 112 at the distal leading edge to cut bone during implantation of the secondary implant 104 (e.g., while the secondary implant is maleated into the bone). The edge 112 may converge or taper to a sharp distal point. For example, the edge may converge or taper laterally inwards (e.g., from one lateral direction inwards and the opposite lateral direction inwards, wherein the lateral directions refer to left and right directions of the page with respect to FIG. 1D).

At least one of the anchors 106 can be implanted in the ilium and at least one of the anchors 106 can be implanted into sacrum. For example, as shown in FIGS. 1A-1D, the secondary implant 104 can include two anchors 106. A first anchor 106 can be configured to be implanted in the ilium and a second anchor 106 can be configured to be implanted in the sacrum.

When the anchors 106 are positioned within the ilium and the sacrum, the secondary implant 104 can act as a tension band. The secondary implant 104 can resist forces that compress/distract and forces that rotate the SI joint.

The secondary implant 104 may come in different shapes and patterns. In certain embodiments, different options for secondary implants 104 having different shapes and patterns can be made available at surgeon preference, for example, for different patient anatomies.

In certain embodiments, the secondary implant 104 can be configured to facilitate bony ingrowth. Bony ingrowth can help for a rigid fusion and prevent implant migration. For example, in certain embodiments, the material of secondary implant 104 can be porous to allow for bony ingrowth. In certain embodiments, the design of the secondary implant 104 may include lattices, planar trusses, non-planar trusses, cancellous or trabecular bone patters, webs, pin holes, circles, and/or any other design that suitable to allow for bone to permeate and grow into the material. For example, as shown in FIGS. 1A-1D, the secondary implant 104 can include a truss or beam system 174. The truss or beam system 174 can act as a scaffolding to provide increased biomechanical strength to the implant 104 and to facilitate bone growth. The truss or beam system 174 can facilitate fusion with surrounding bone. The truss or beam system 174 can also provide stability as the implant 104 fuses with the surrounding bone.

The truss or beam system 174 can be formed of a plurality of truss elements or beams 176. In some embodiments, the plurality of truss elements or beams 176 can extend between at least some of the engagement features 103. A number of windows or openings 135 can be formed between the truss elements of beams 176 of the truss or beam system 174 to facilitate fusion of the implant with surrounding bone. The openings 135 can be positioned so that at least some of the openings 135 will contact the bone of the sacrum and the ilium regardless of the orientation of the secondary implant 104 when fully seated within the SI joint to promote bony ingrowth.

In certain embodiments, acid etching, bead blasting, surface coating such as HA (Hydroxyapatite), or any other suitable surface technology may be utilized to enhance the surface finish to create an optimal area for bone to grow to in the secondary implant 104. In certain embodiments, 3D printing may be utilized to create surfaces structures and features for bone to grow to. In certain embodiments, the surface structures may be on the nanometer or micrometer scale which can be optimal or desirable for bone to grow to.

In certain embodiments, the secondary implant 104 may be CNC machined, 3D printed, or manufactured by any other suitable means. In certain embodiments, the secondary implant 104 can be made of stainless steel, titanium, poly-ether-ether-ketone (PEEK), ceramic, human allograft or any other suitable implantable material strong enough to resist the forces described herein and pass biomechanical testing. In certain embodiments, the implant material can be important to achieve bony ingrowth.

In certain embodiments, the secondary implant 104 can couple to the primary implant 102 (or otherwise be in contact with or align with the primary implant 102 when implanted). For example, the secondary implant 104 can be coupled to a proximal end 101 of the primary implant 102. In certain embodiments, interconnected porosity can be attainable within both implants.

In combination, the primary implant 102 and secondary implant 104 can act as one system to achieve multiple points of fixation and resist multiple forces. For example, in certain embodiments, the primary implant 102 and second implant 104 can act as one system to resist all of the forces acting on the SI joint.

In certain embodiments, the secondary implant 104 can extend superiorly from the center of the primary implant 102. In certain embodiments, the secondary implant 104 can extend laterally beyond an outer edge of the primary implant 102 so that the anchors 106 are positioned laterally to the outer edge of the primary implant 102. In certain embodiments, the secondary implant 104 can extends laterally outwards from the primary implant 102 to a distance sufficient for capturing enough bone from both the sacrum and ilium to prevent compression and distraction. In certain embodiments, the length of the secondary implant 104 may match the length of the primary implant 102, may be half or three quarters of the length of the primary implant 102, or may be any other suitable length relative to the primary implant 102. Each anchor 106 may extend the full length of the primary implant 102, may be half or three quarters of the length of the primary implant 102, or may be any other suitable length relative to the primary implant 102. In certain embodiments, a distal end of each anchor 106 can be coplanar with the distal end 105 of the primary implant 102. The length the secondary implant 104 and/or the length of the anchors 106 may be determined by the amount of fixation needed and can be patient dependent.

FIGS. 2A-2D depict another embodiment of the SI joint implant system 100. The embodiment of FIGS. 2A-2D may include any of the same or similar features or functions as any of the other embodiments described herein and vice versa. In comparison to the embodiment of FIGS. 1A-1D, each of the anchors 106 of the embodiment of FIGS. 2A-2D may have a greater degree of curvature.

FIGS. 3A-3D depict another embodiment of the SI joint implant system 100. The embodiment of FIGS. 3A-3D may include any of the same or similar features or functions as any of the other embodiments described herein and vice versa. In comparison to the embodiment of FIGS. 1A-1D, each of the anchors 106 of the embodiment of FIGS. 3A-3D may have a greater degree of curvature. In comparison to the embodiment of FIGS. 2A-2D, each of the anchors 106 of the embodiment of FIGS. 3A-3D may have a smaller degree of curvature.

In some embodiments, a degree of curvature of each anchor 106 can be between 15 degrees and 270 degrees, between 15 degrees and 210 degrees, between 15 degrees and 180 degrees, between 15 degrees and 150 degrees, between 15 degrees and 120 degrees, between 15 and 90 degrees, between 15 degrees and 60 degrees, between 15 degrees and 45 degrees, between 30 degrees and 90 degrees, between 90 degrees and 180 degrees, or any other suitable range. In some embodiments, the degree of curvature of each anchor 106 can be about degrees, about 30 degrees, about 45 degrees, about 60 degrees, about 90 degrees, about 120 degrees, about 150 degrees, about 180 degrees, or any other suitable degree.

FIGS. 4A-4D depict another embodiment of the SI joint implant system 100. The embodiment of FIGS. 4A-4D may include any of the same or similar features or functions as any of the other embodiments described herein and vice versa. As shown in FIGS. 4A-4D, in certain embodiments, the anchors 106 can extend distally to the distal end 105 of the primary implant 102. For example, the distal end of the anchors 106 can be coplanar with the distal end 105 of the primary implant 102.

FIGS. 5A-5D depict another embodiment of the SI joint implant system 100. The embodiment of FIGS. 5A-5D may include any of the same or similar features or functions as any of the other embodiments described herein and vice versa. In certain embodiments, the implant system 100 can include a fastener or attachment mechanism 110. The fastener or attachment mechanism 110 can couple the primary implant 102 and the secondary implant 104. This can be important when performing minimally invasive surgery and working through dense tissue. The secondary implant 104 can include an opening 114 configured to receive the fastener or attachment mechanism 110. The primary implant 102 can receive the fastener or attachment mechanism 110, for example, within the channel 160. As shown in FIGS. 5A-5D, the fastener or attachment mechanism 110 can be threaded fastener having a plurality of external threads 116. The primary implant 102 and/or the secondary implant 104 can include plurality of internal threads 118. For example, the internal threads 118 may extend at least partially or entirely along the length of the channel 160.

FIGS. 6A-6D depict another embodiment of the SI joint implant system 100. The embodiment of FIGS. 6A-6D may include any of the same or similar features or functions as any of the other embodiments described herein and vice versa.

FIGS. 7A-7D depict another embodiment of the SI joint implant system 100. The embodiment of FIGS. 7A-7D may include any of the same or similar features or functions as any of the other embodiments described herein and vice versa.

As shown in FIGS. 7A-7D, in certain embodiments, the secondary implant 104 can include a body or anchor ring 124. One or more anchors 106 can extend from the anchor ring 124. In certain embodiments, the one or more anchors 106 can be coupled to the anchor ring 124 by one or more arms 146.

As shown in FIGS. 7A-7D, in certain embodiments, the primary implant 102 may include tabs 108 that act as a guide for the secondary implant 104. The tabs 108 are attached to the primary implant 102 and may be broken off where the tabs 108 connect to the primary implant 102 (for example, at a frangible joint). In some embodiments, the tabs 108 may form a tulip configuration. The tabs 108 can act as a guide for the secondary implant 104. For example, the tabs 108 may define carve-outs or recesses 109 between the tabs 108 configured to receive the arms 146 of the secondary implant 104.

The tabs 108 can also allow for a fastener or attachment mechanism (such as a screw, for example a set screw (e.g., a grub screw), or a threaded nut) to connect the primary implant 102 and secondary implant 104. As described herein, this can be important when performing minimally invasive surgery and working through dense tissue.

In certain embodiments, after the secondary implant 104 is positioned within the recesses 109, the attachment mechanism 110 can engage the tabs 108 above the secondary implant 104 to secure the secondary implant 104 within the tabs 108 and to the primary implant 102.

In certain embodiments, the tabs 108 can provide for alignment to prevent or reduce cross-threading or failure to engage the threads when trying to connect the primary implant 102 and secondary implant 104. The tabs 108 may have internal threads 122 that capture threads 123 of the attachment mechanism 110 and allow the secondary implant 104 to be pulled into the primary implant 102. This may be useful if the secondary implant 104 doesn't sit perfectly into the primary implant 102. The recesses 109 can be positioned on one side or both sides of the threads 122 to allow the secondary implant 104 to slide down without hitting the threads 122.

The tabs 108 may be attached to the primary implant 102 permanently and can be configured to break or snap off due to forces applied by a user when desired. In other embodiments, the tabs may be assembled to primary implant 102 prior to insertion into the SI joint and then removed once the attachment mechanism 110 is properly inserted to anchor the primary implant 102 to the secondary implant 104. Breaking off or removal of the tabs 108 may provide a lower profile of the implant system 100 above the SI joint. In some embodiments, the implant system 100 can be flush or countersunk with the SI joint.

FIGS. 8A-8D depict another embodiment of the SI joint implant system 100. The embodiment of FIGS. 8A-8D may include any of the same or similar features or functions as any of the other embodiments described herein and vice versa.

As shown in FIGS. 8A-8D, in some embodiments, the secondary implant 104 may be adjustable so that the anchors 106 can be positioned at different lateral distances from primary implant 102. The anchors 106 can open to a position in which the lateral distance is greater and close to a distance where the lateral distance is smaller. In some embodiments, an implant 104 with adjustable anchor distances can be used, for example, to pull the ilium and sacrum together for compression (e.g., by drawing the anchors 106 towards the primary implant and/or towards one another). This force can prevent joint distraction and allow for compression on the primary implant 102. Pulling the ilium and sacrum together for compression can permit bone to implant contact if the SI joint is wide or hypermobile.

The secondary implant 104 may be comprised of one or multiple parts. The adjustable (for example, opening and/or closing) mechanism may be ratcheting, worm gear, spindle or any other mechanism that can open or close allowing for compression and distraction. An example of an adjustable secondary implant 10 is shown in FIGS. 8A-8D. As shown in FIGS. 8A-8D, the implant 10 includes two anchors 106 as separate pieces. The attachment mechanism 110 can be in the form of a gear wheel having teeth 125 configured to engage complementary teeth 127 on each of the anchors 106. The teeth 127 may be positioned along the arms 146 of the secondary implant 104. The attachment mechanism 110 can be adjusted (e.g., via rotation of the attachment mechanism) to pull the ilium and sacrum together.

In some embodiments, the primary implant 102 can include carve-outs or channels 113 on one or both sides to receive the arms 146 of the secondary implant 104 therethrough. The channels 113 may extend radially about the primary implant 102 and allow for rotation of portions of the secondary implant 104 relative to the implant 102. In certain embodiments, the channels 113 may restrict axial movement (e.g., proximal and distal movement) of the implant 104. When the arms 146 extend through the channels 113 and couple with the attachment mechanism 110, the secondary implant 104 may be secured to the primary implant 102.

In some alternative embodiments, the mechanism 110 of FIGS. 8A-8D does not attach the primary implant 102 to the secondary implant 104, but is only used to adjust the positioning of the two anchors 106, for example, to pull the ilium and sacrum together.

FIGS. 9A-9D depict another embodiment of the SI joint implant system 100. The embodiment of FIGS. 9A-9D may include any of the same or similar features or functions as any of the other embodiments described herein and vice versa.

FIGS. 10A-10D depict another embodiment of the SI joint implant system 100. The embodiment of FIGS. 10A-10D may include any of the same or similar features or functions as any of the other embodiments described herein and vice versa. As shown in FIGS. 10A-D, the edge 112 may converge to a sharp distal point generally inwards from the anterior and posterior directions (e.g., into and out of the page with reference to FIG. 10C), which may facilitate driving of the anchors 106 into bone, alternatively or in addition to converging generally laterally inwards.

FIGS. 11A-11D depict another embodiment of the SI joint implant system 100. The embodiment of FIGS. 10A-10D may include any of the same or similar features or functions as any of the other embodiments described herein and vice versa. In some embodiments, the edge 112 may converge to a blunted or curved distal end generally inwards from the anterior and posterior direction, alternatively or in addition to converging generally laterally inwards to a sharp distal end.

Figure 32:
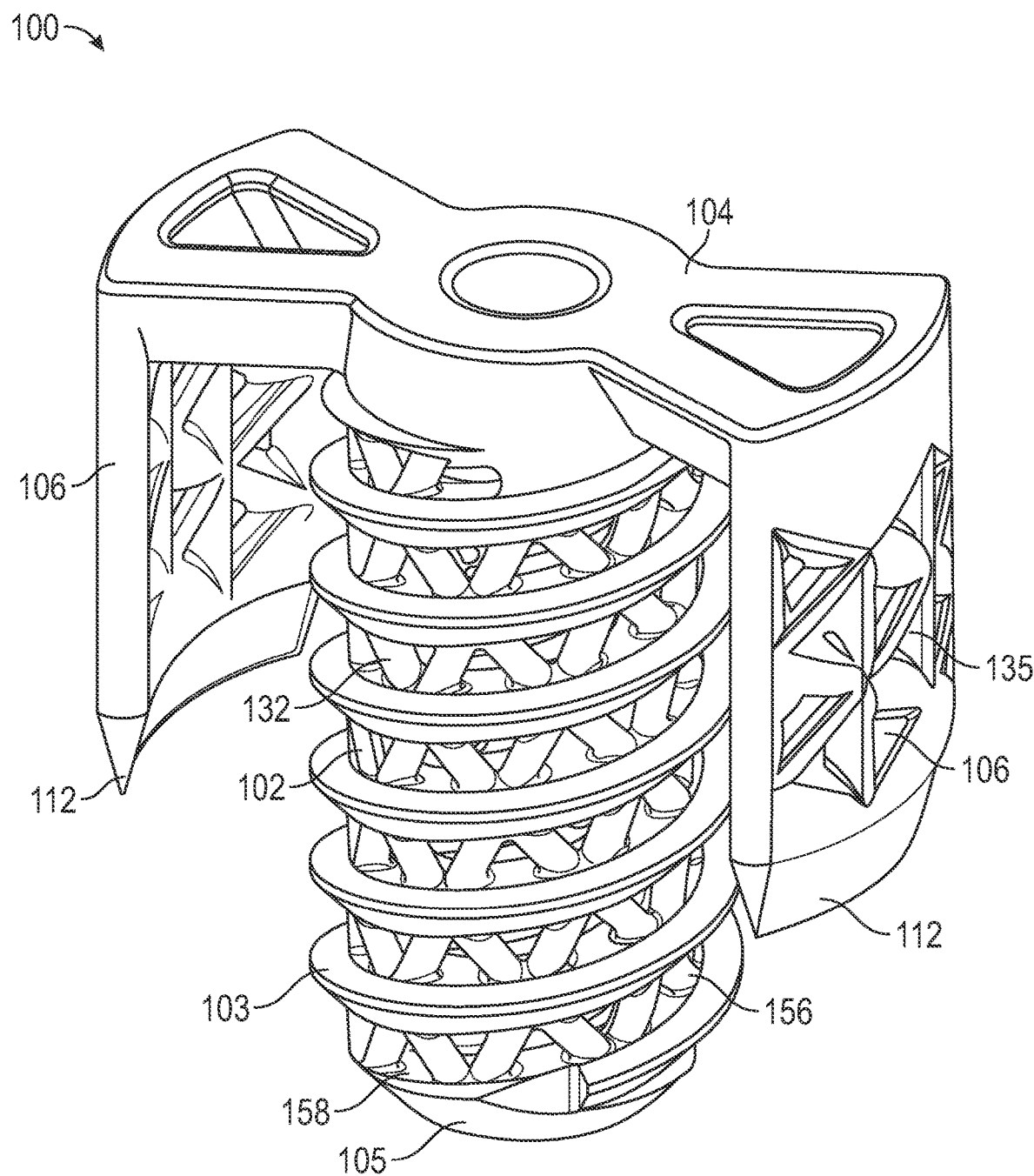
FIG. 32 illustrates a perspective view of an alternative embodiment of a joint implant.
Figure 33B:
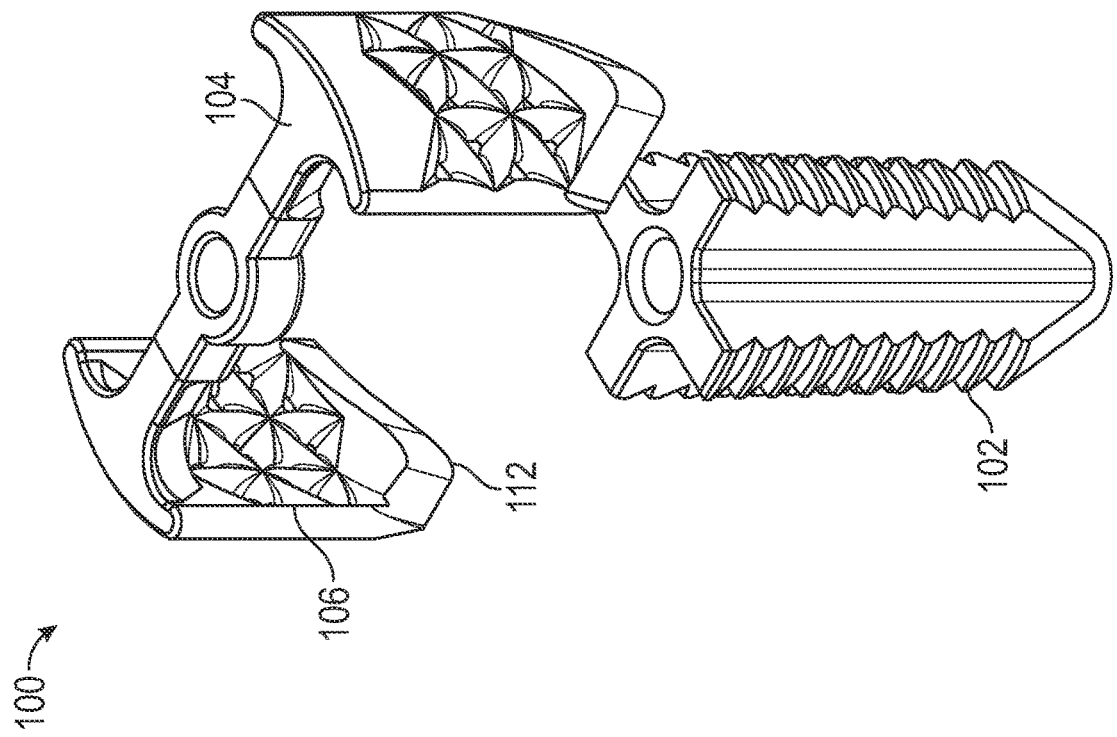
FIG. 33B illustrates an exploded view of the embodiment of the joint implant of FIG. 33A.
Figure 33A:
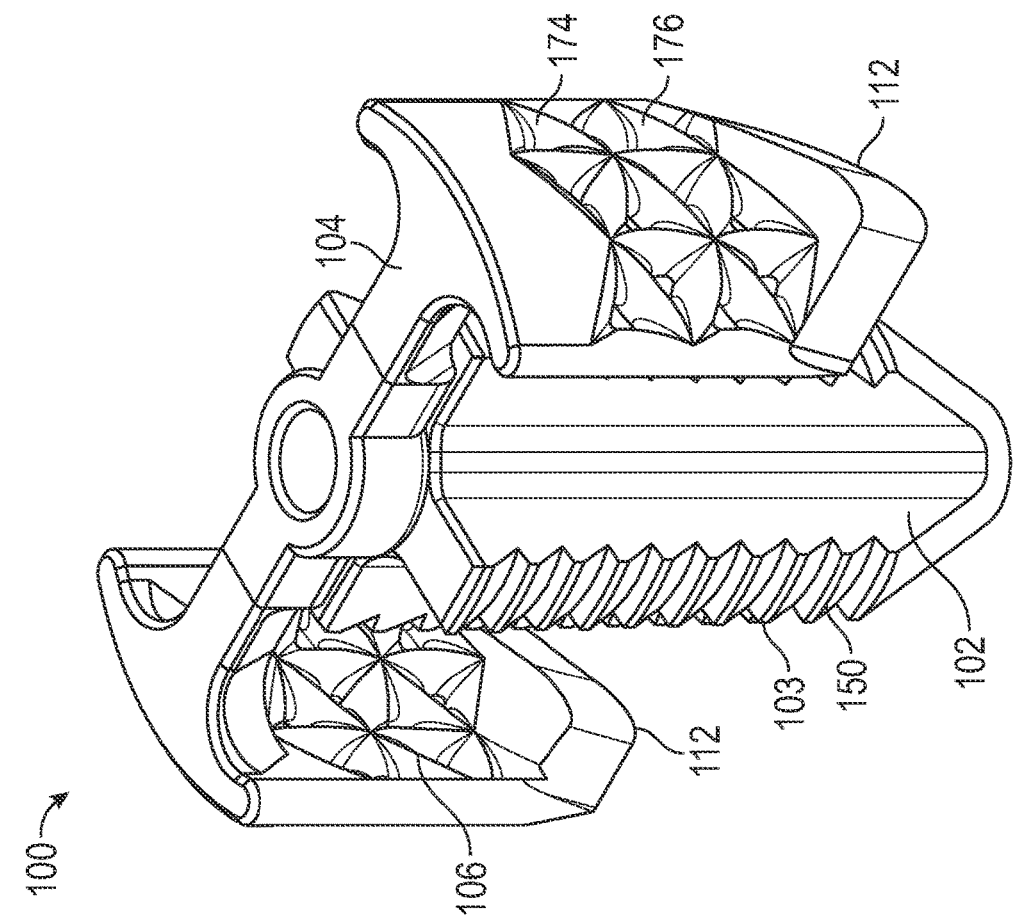
FIG. 33A illustrates a perspective view of an alternative embodiment of a joint implant.
Figure 33D:
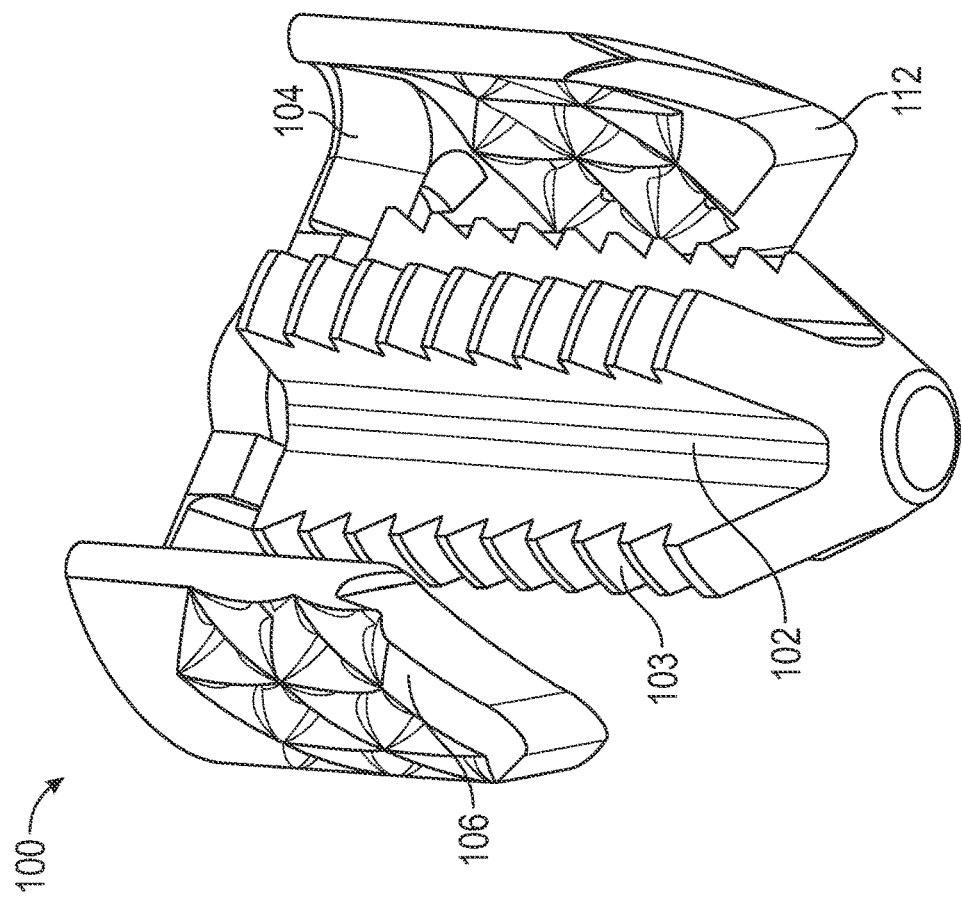
FIG. 33D illustrates a perspective view of the embodiment of the joint implant of FIG. 33A.
Figure 33C:
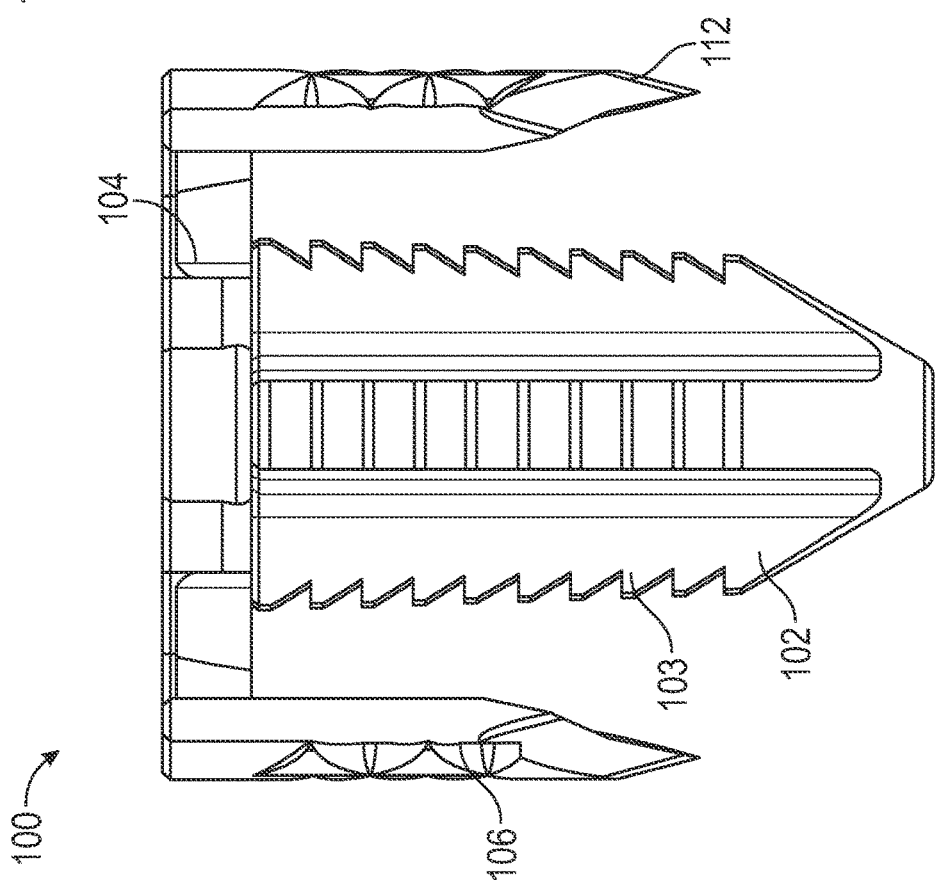
FIG. 33C illustrates a side view of the embodiment of the joint implant of FIG. 33A.

FIG. 32 depicts another embodiment of the SI joint implant system. The embodiment of FIG. 32 may include any of the same or similar features or functions as any of the other embodiments described herein and vice versa. As shown in FIG. 32, in some embodiments, the primary implant 102 and secondary implant 104 can be formed together as a single-piece.

FIGS. 33A-33D depict another embodiment of the SI joint implant system 100. The embodiment of FIGS. 33A-33D may include any of the same or similar features or functions as any of the other embodiments described herein and vice versa.

FIGS. 33A-33D show an embodiment of the implant system 100 in which the primary implant 102 includes engagement features 103 in the form of barbs instead of threads. In such embodiments, the primary implant 102 can be implanted by malleting a proximal end 101 of the primary implant 102. The secondary implant 104 can then be coupled to the primary implant 102. In some embodiments, the secondary implant 104 can be coupled to the primary implant 102 before placing the primary implant 102, and the implant system 100 can be placed in a single step by malleting a proximal end 101 of the secondary implant 104 while the secondary implant 104 is coupled to the primary implant.

As described herein, in certain embodiments, the secondary implant may contain a blade or sharp edge at the distal leading edge 112 to cut bone. In certain embodiments, the secondary implant 104 can be impacted directly into the bone without using a cutting tool such as a broach. Alternatively, for example, if the bone is too dense, a broach or other cutting device may be used prior to placement of the secondary implant 104. In certain embodiments, the secondary implant 104 may be inserted with an impactor or other device that creates enough blunt force to drive the secondary implant 104 into the bone.

Figure 34:
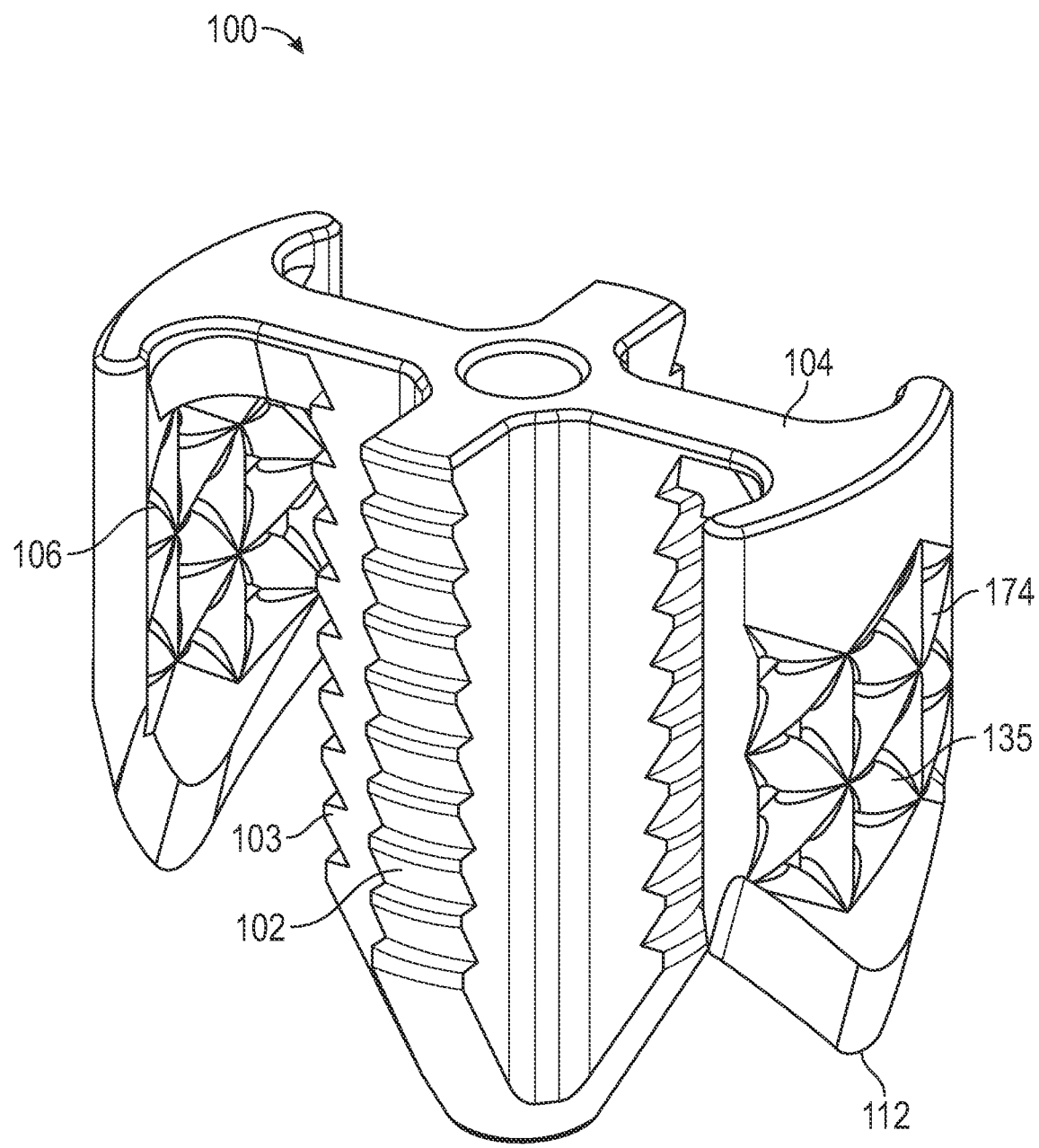
FIG. 34 illustrates a perspective view of an alternative embodiment of a joint implant.
Figure 35B:
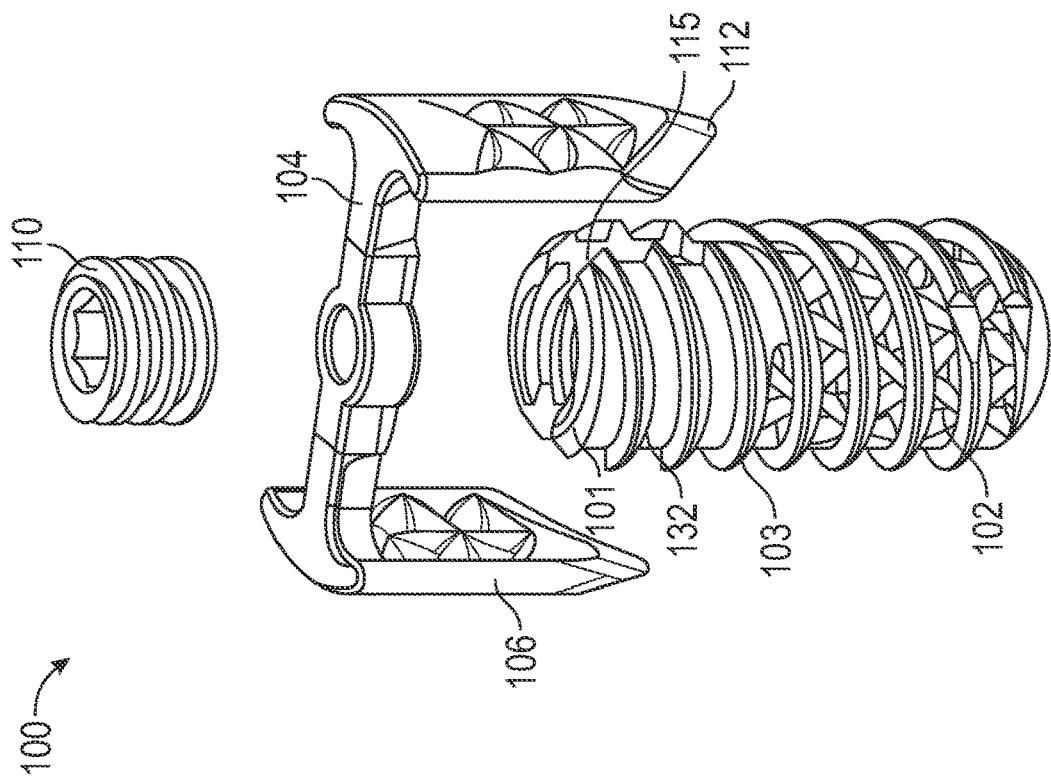
FIG. 35B illustrates an exploded view of the embodiment of the joint implant of FIG. 35A.
Figure 35A:
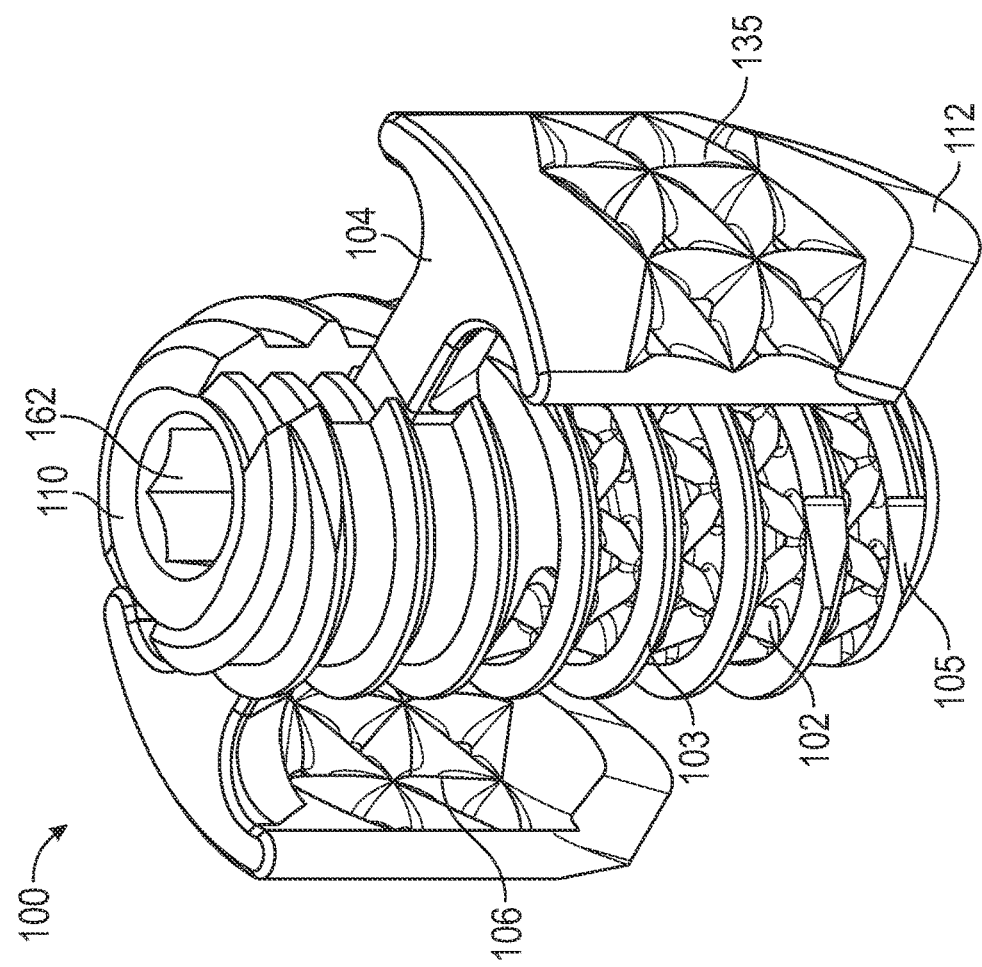
FIG. 35A illustrates a perspective view of an alternative embodiment of a joint implant.
Figure 35C:
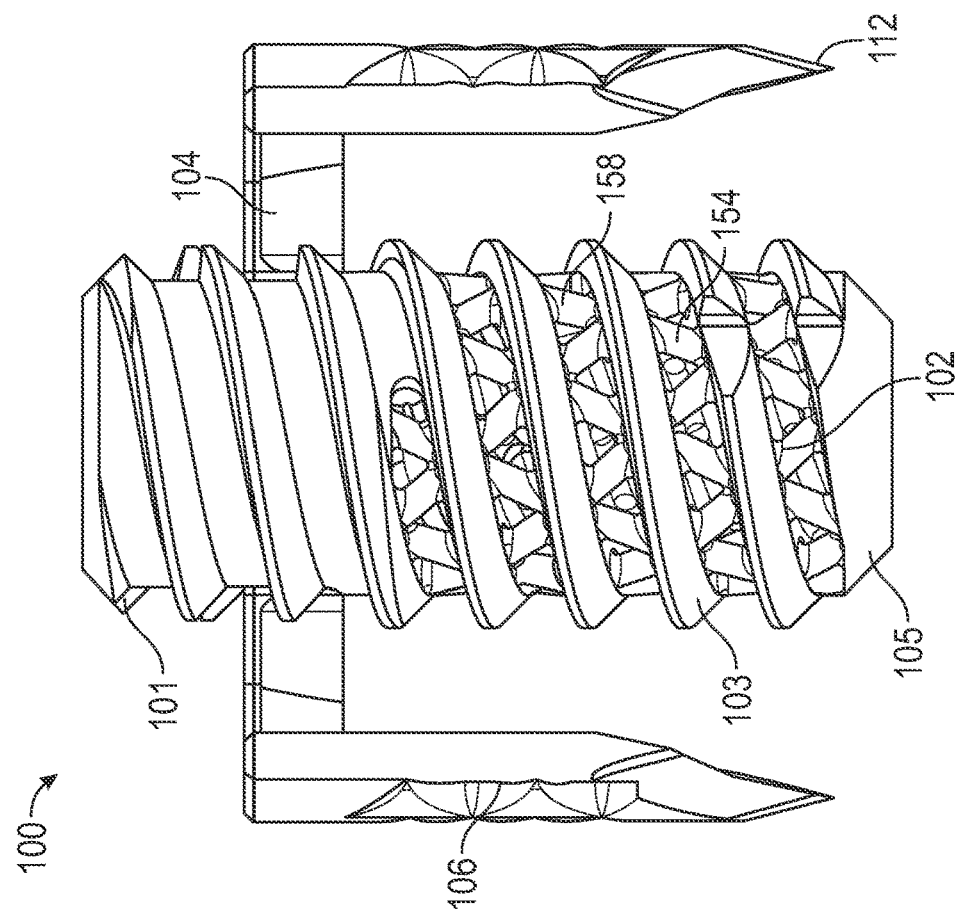
FIG. 35C illustrates a perspective view of the embodiment of the joint implant of FIG. 35A.
Figure 35D:
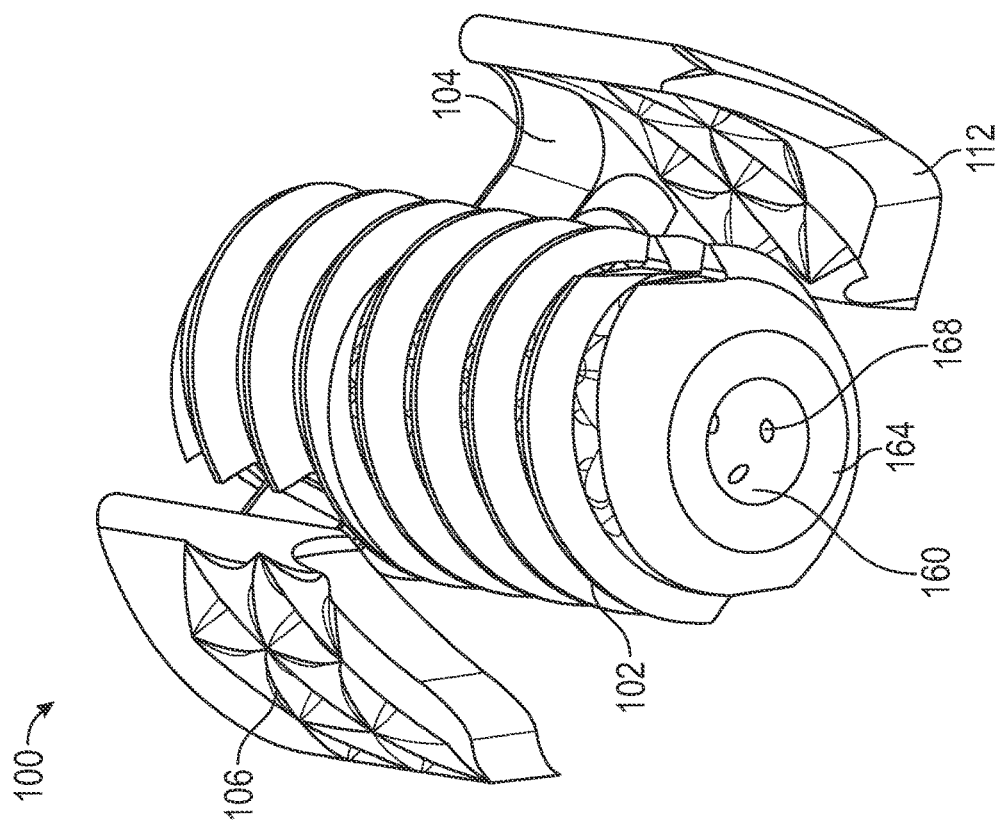
FIG. 35D illustrates a side view of the embodiment of the joint implant of FIG. 35A.
Figure 36A:
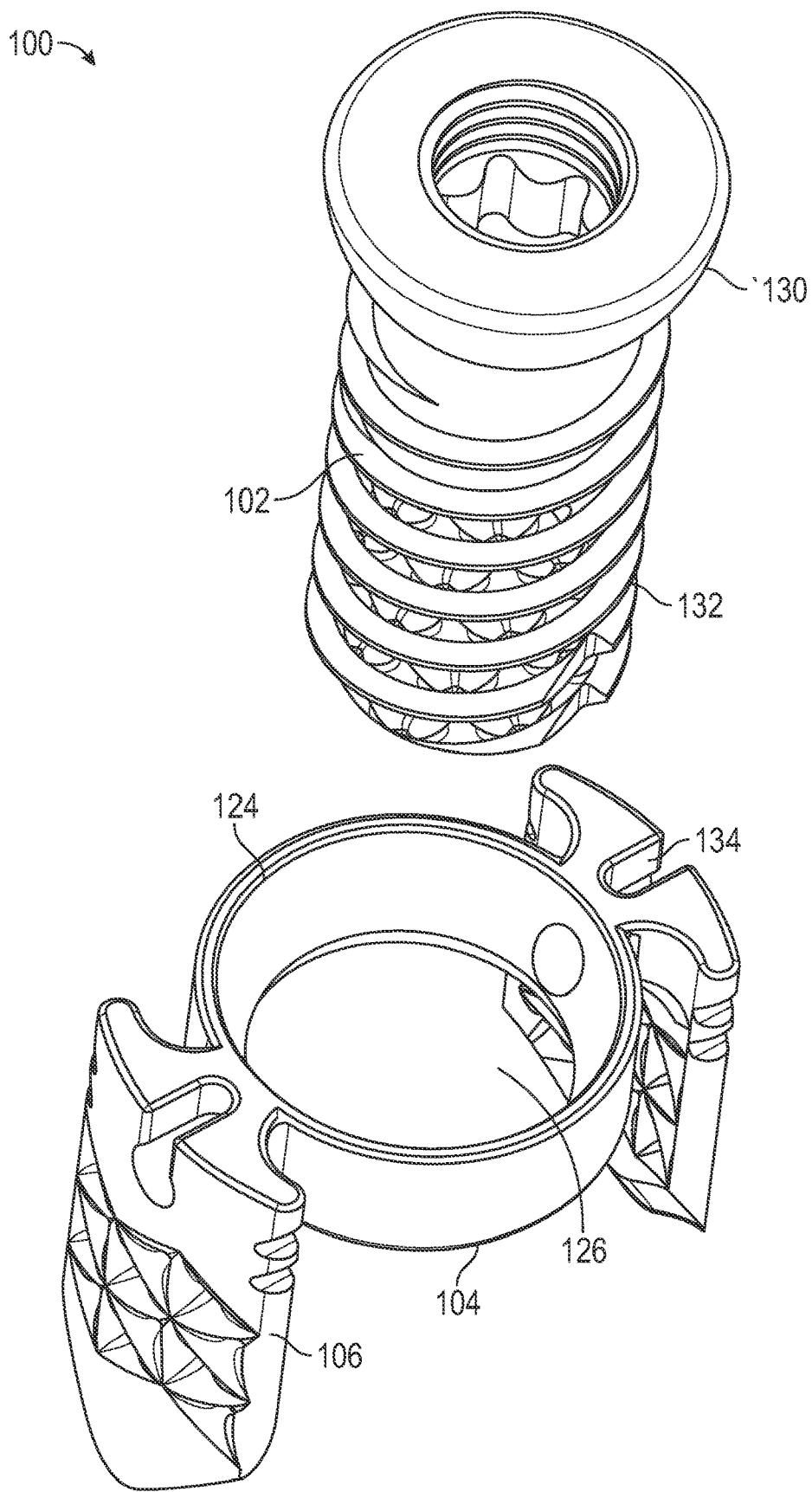
FIG. 36A illustrates a perspective view of an alternative embodiment of a joint implant.
Figure 36B:
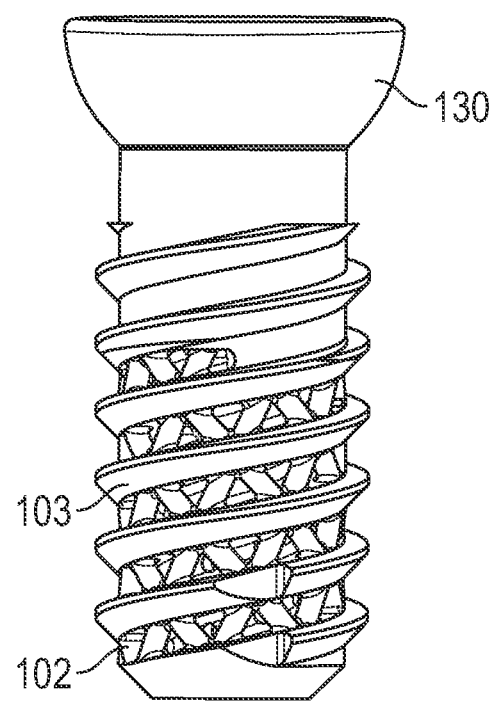
FIG. 36B illustrates a side view of an alternative embodiment of the joint implant of FIG. 36A.
Figure 36B:
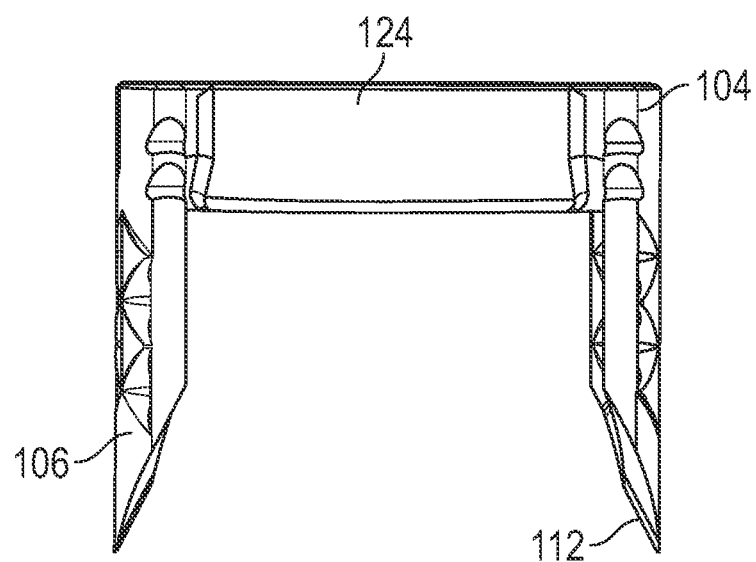
Figure 36C:
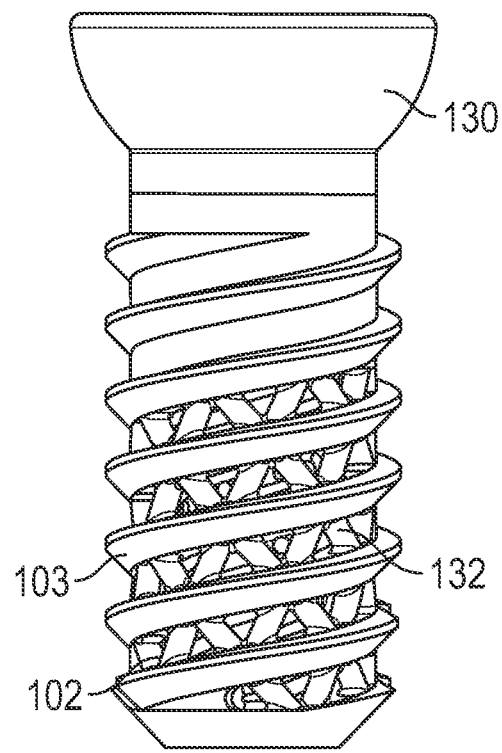
FIG. 36C illustrates a side view of an alternative embodiment of the joint implant of FIG. 36A.
Figure 36C:
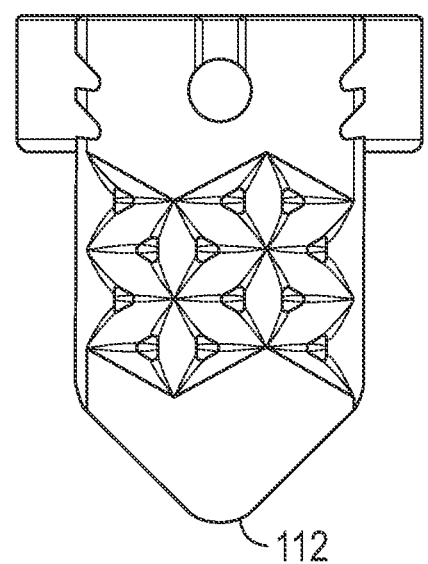
Figure 36E:
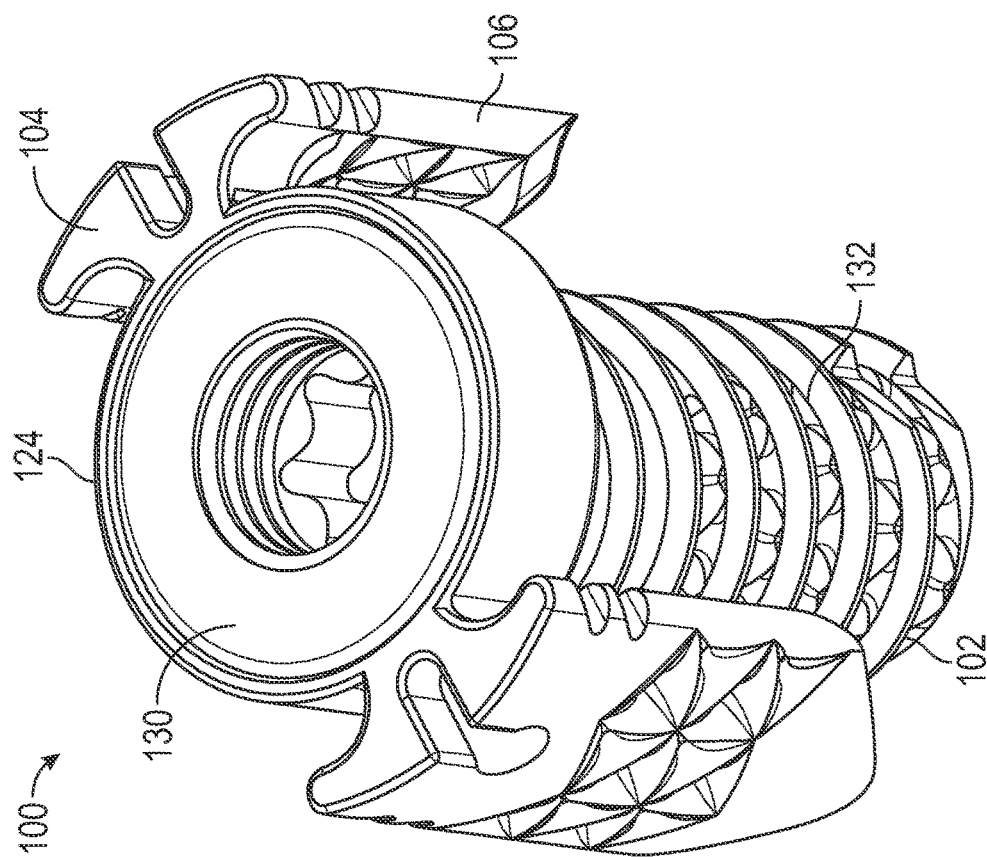
FIG. 36E illustrates a perspective view of an alternative embodiment of the joint implant of FIG. 36A.
Figure 36D:
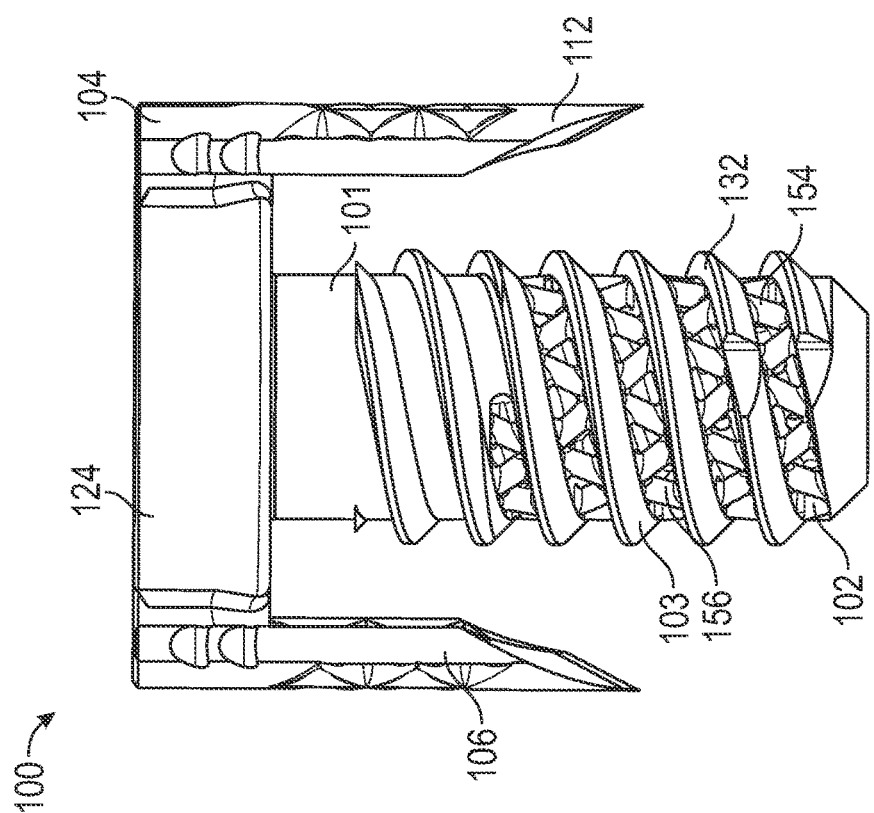
FIG. 36D illustrates a side view of an alternative embodiment of the joint implant of FIG. 36A.
Figure 36G:
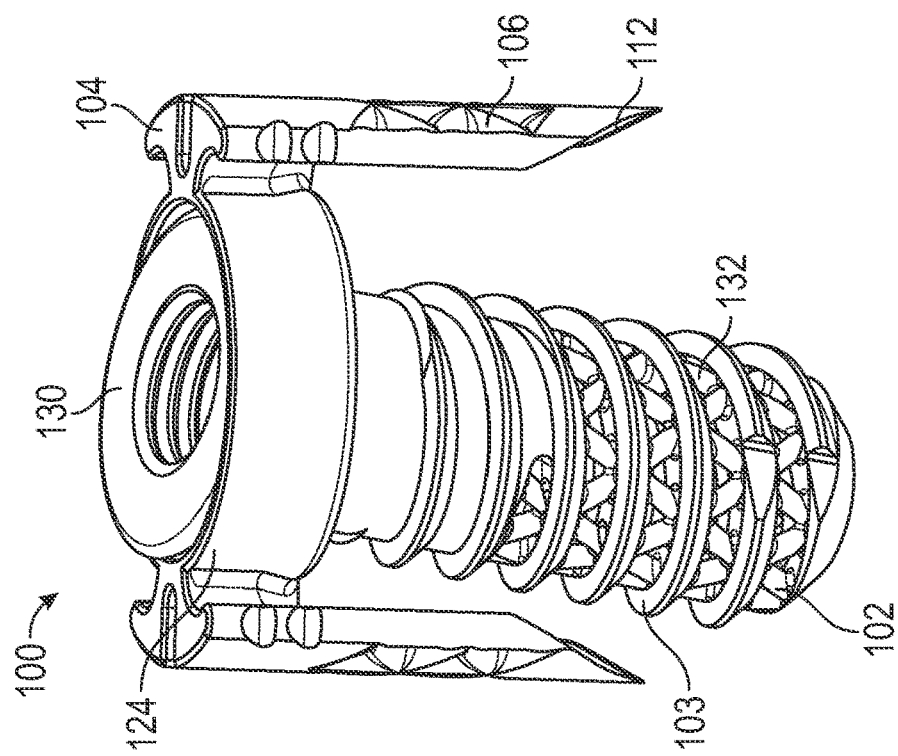
FIG. 36G illustrates a perspective view of an alternative embodiment of the joint implant of FIG. 36A.
Figure 36F:
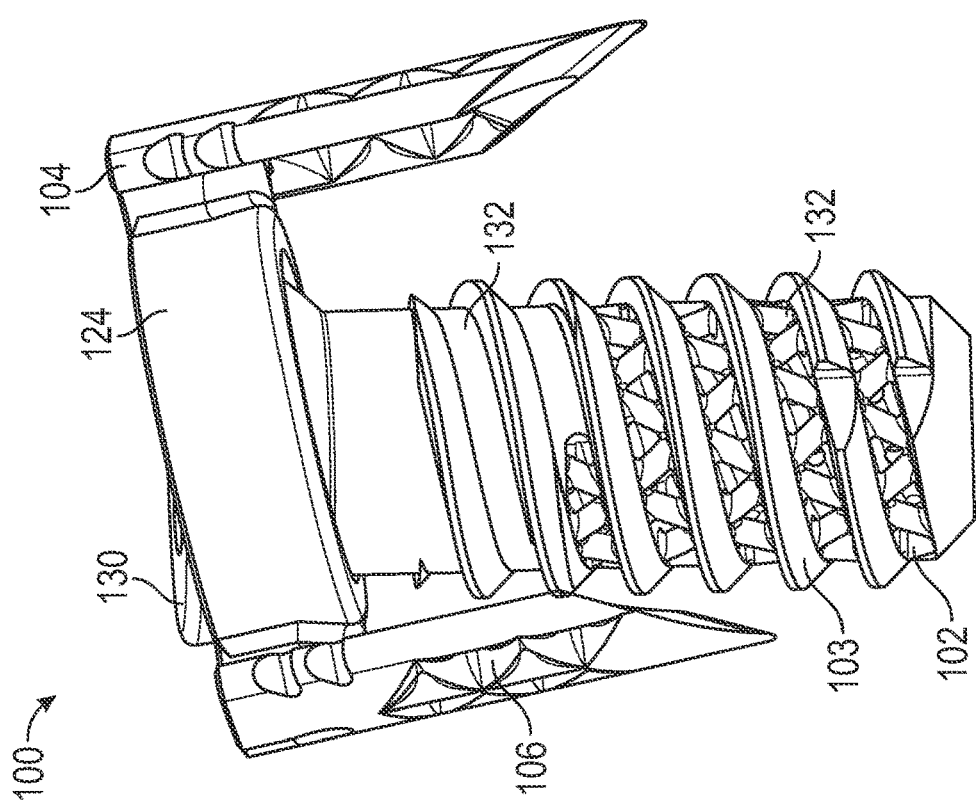
FIG. 36F illustrates a perspective view of an alternative embodiment of the joint implant of FIG. 36A.

FIG. 34 depicts another embodiment of the SI joint implant system. The embodiment of FIG. 34 may include any of the same or similar features or functions as any of the other embodiments described herein and vice versa. FIG. 34 depicts an embodiment of the implant system 100 in which the primary implant 102 and secondary implant 104 are formed as a single piece. The embodiment of FIG. 34 includes barbs 150.

FIGS. 35A-35D depict another embodiment of the SI joint implant system 100. The embodiment of FIGS. 35A-35D may include any of the same or similar features or functions as any of the other embodiments described herein and vice versa.

FIGS. 35A-35D depict an embodiment of the system 100 in which the primary implant 102 includes engagement features 103 in the form of threads extending along an entirety of the length of the shank 132. In other words, the threads can extend from a proximal end 101 of the primary implant 102 to the distal end 105. Threads extending along the entirety of the length of the shank 132 can promote countersinking of the entire primary implant 102 within the SI joint and can provide improved back out prevention in comparison to implants in which the threads only partially extend along the length of the implant, for example, by increasing bone purchase.

As shown in FIGS. 35A-35D, in some embodiments, the primary implant 102 can include recesses 115 extending distally form the proximal end 101. The recesses 115 may include any of the same or similar features or functions of the recesses 109 formed by the tabs 108, but may extend at least partially through the portion of the shank 132 having engagement features 103 thereon.

FIGS. 36A-36G depict another embodiment of the SI joint implant system 100. The embodiment of FIGS. 36A-36G may include any of the same or similar features or functions as any of the other embodiments described herein and vice versa.

As shown in FIGS. 36A-36G, the secondary implant 104 can include a plurality of anchors 106, as described herein, and an anchor body or anchor ring 124 defining a central opening 126. As shown, the anchors 106 can extend laterally form the ring 124. The ring 124 can be sized, shaped, and/or otherwise configured so that the central opening 126 is sized, shaped, and or otherwise configured to receive the primary implant 102 therethrough. In certain embodiments, the primary implant 102 can include a head 130 and a shank 132. The ring 124 can be sized, shaped, and/or otherwise configured so that an inner diameter thereof corresponds to an outer diameter of the head 130.

In certain embodiments, the head 130 and/or another portion of the primary implant 102 can be sized, shaped, and/or otherwise configured to prevent backout of the anchor after implantation through the central opening 126. For example, the head 130 can be sized, shaped, and/or otherwise configured to block, prevent, or restrict proximal movement of a portion of at least a portion of the ring 124 when positioned within the opening 126.

In other embodiments, the primary implant 102 may be headless. In other words, in some embodiments, the primary implant 102 does not include a separate head having a different diameter than the shank 132. Instead, the proximal end 101 of the primary implant can have the same diameter, a similar diameter, or a smaller diameter than the shank 132 of the primary implant 102 to facilitate countersinking of the implant 102.

FIGS. 54A-54G depict another embodiment of the SI joint implant system 100. The embodiment of FIGS. 54A-54G may include any of the same or similar features or functions as any of the other embodiments described herein and vice versa.

FIGS. 54A-54G depict an embodiment of the implant system 100 in which the primary implant 102 has threads 140 that can thread into complementary threads 142 of the secondary implant 104. The primary implant 102 can be advanced until it bottoms out in the secondary implant 104, preventing it from going further down into the SI joint. The complementary threads can allow for a positive stop and prevent over-inserting of the implant 102. This also prevents stripping of the implant 102 in the bone.

In the embodiment of FIGS. 54A-54G, a proximal end of the anchors 106 of the secondary implant are positioned below a proximal end of the primary implant 102. The positioning of the anchors 106 below the proximal end of the primary implant 102 can allow the anchors 106 to be countersunk within the bone of the ilium and sacrum and prevent the anchors 106 from being proud when implanted, for example, if the ilium and sacrum are uneven.

Figure 55:
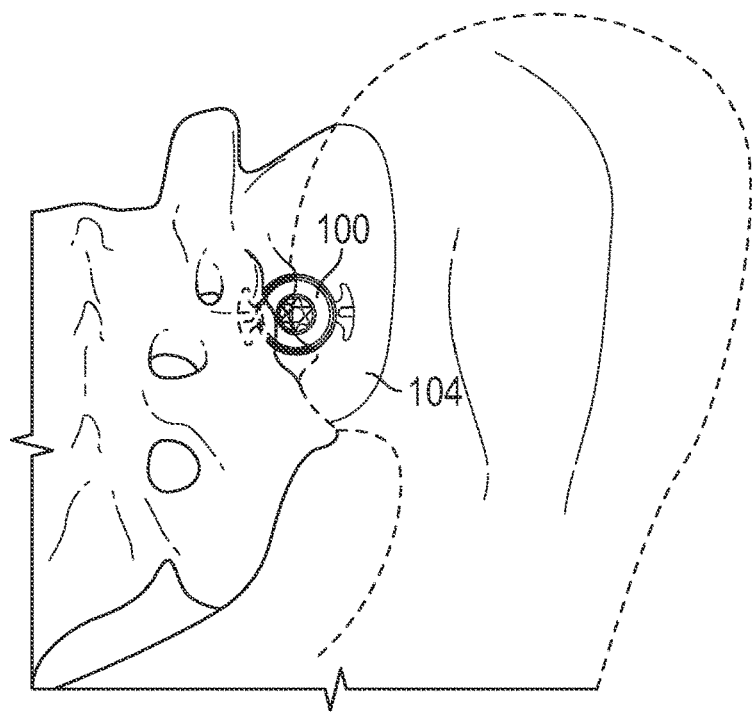
FIG. 55 illustrates a top view of an embodiment of the implant within the SI joint.
Figure 56:
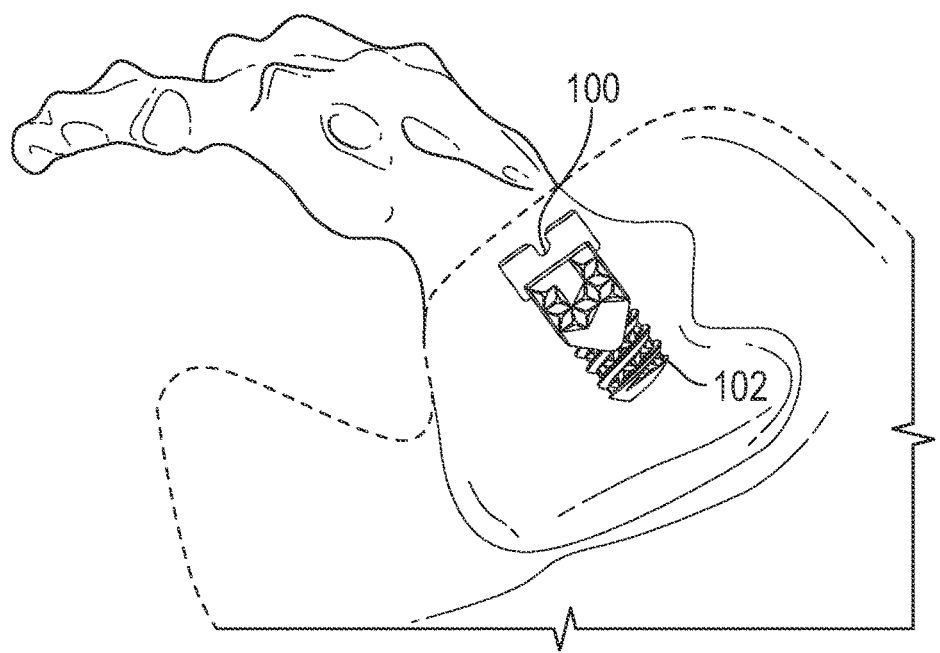
FIG. 56 illustrates a side view of an embodiment of the implant within the SI joint.
Figure 57:
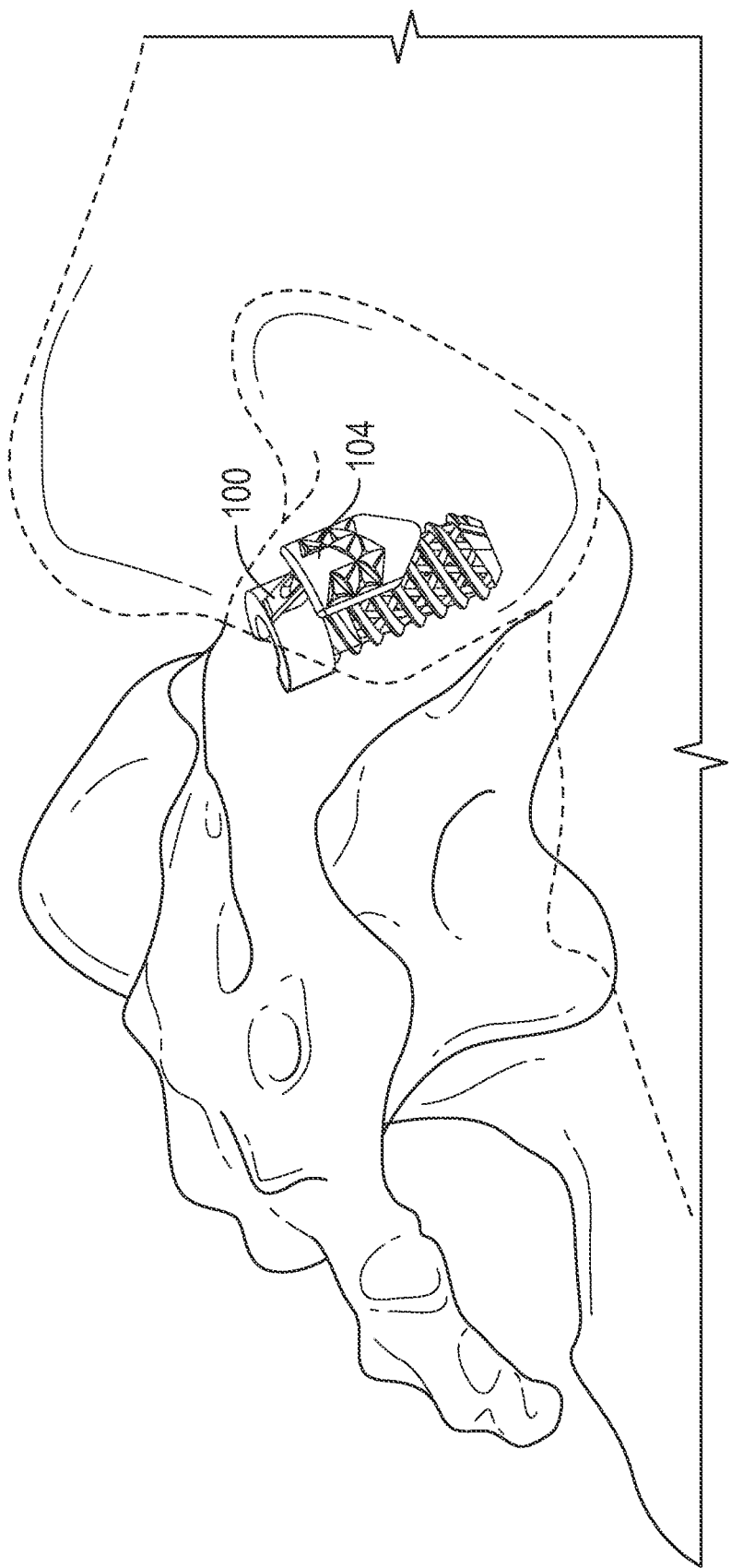
FIG. 57 illustrates an alternative perspective view of an embodiment of the implant within the SI joint.
Figure 58A:
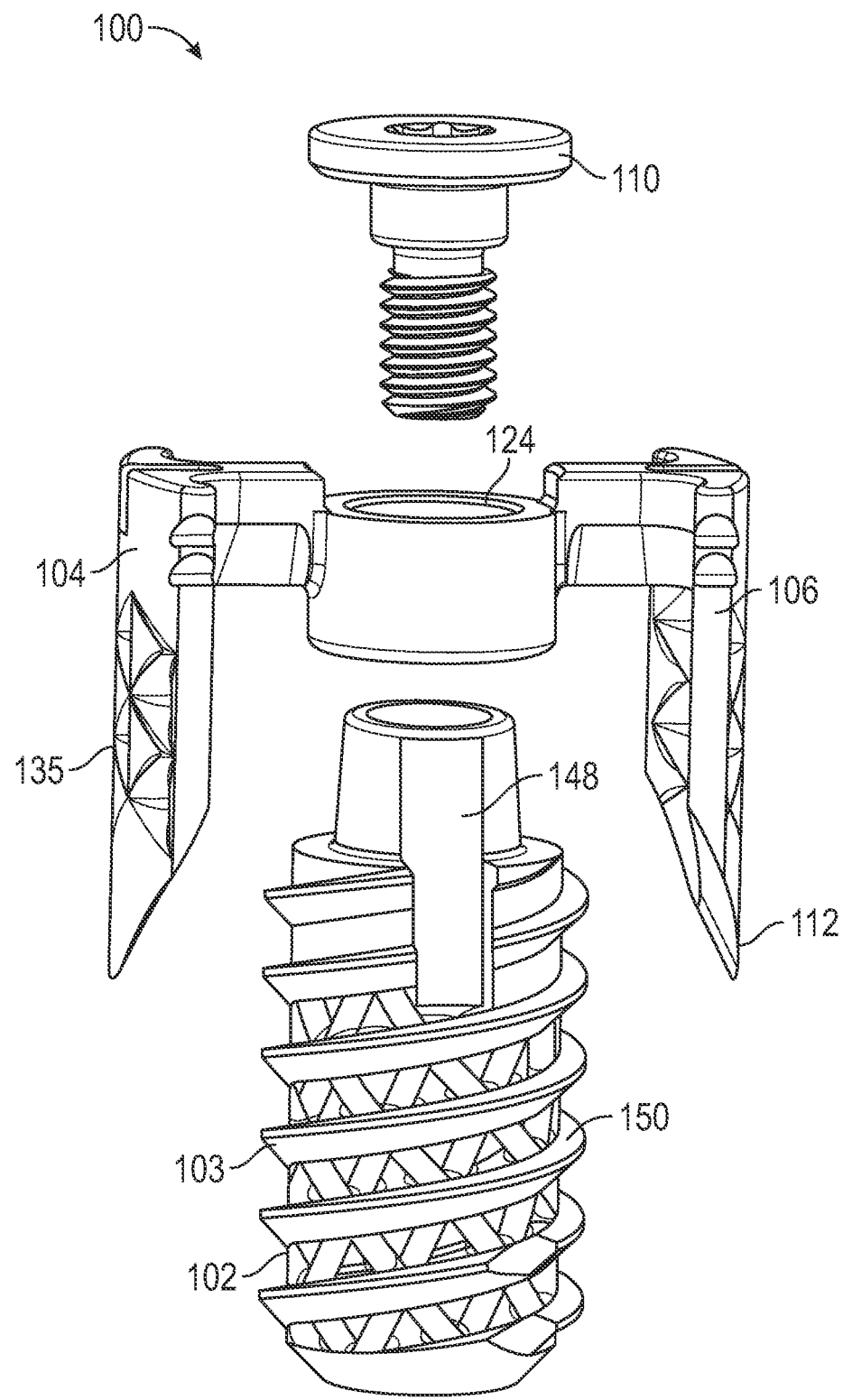
FIG. 58A illustrates an exploded view of an embodiment of the joint implant.
Figure 58B:
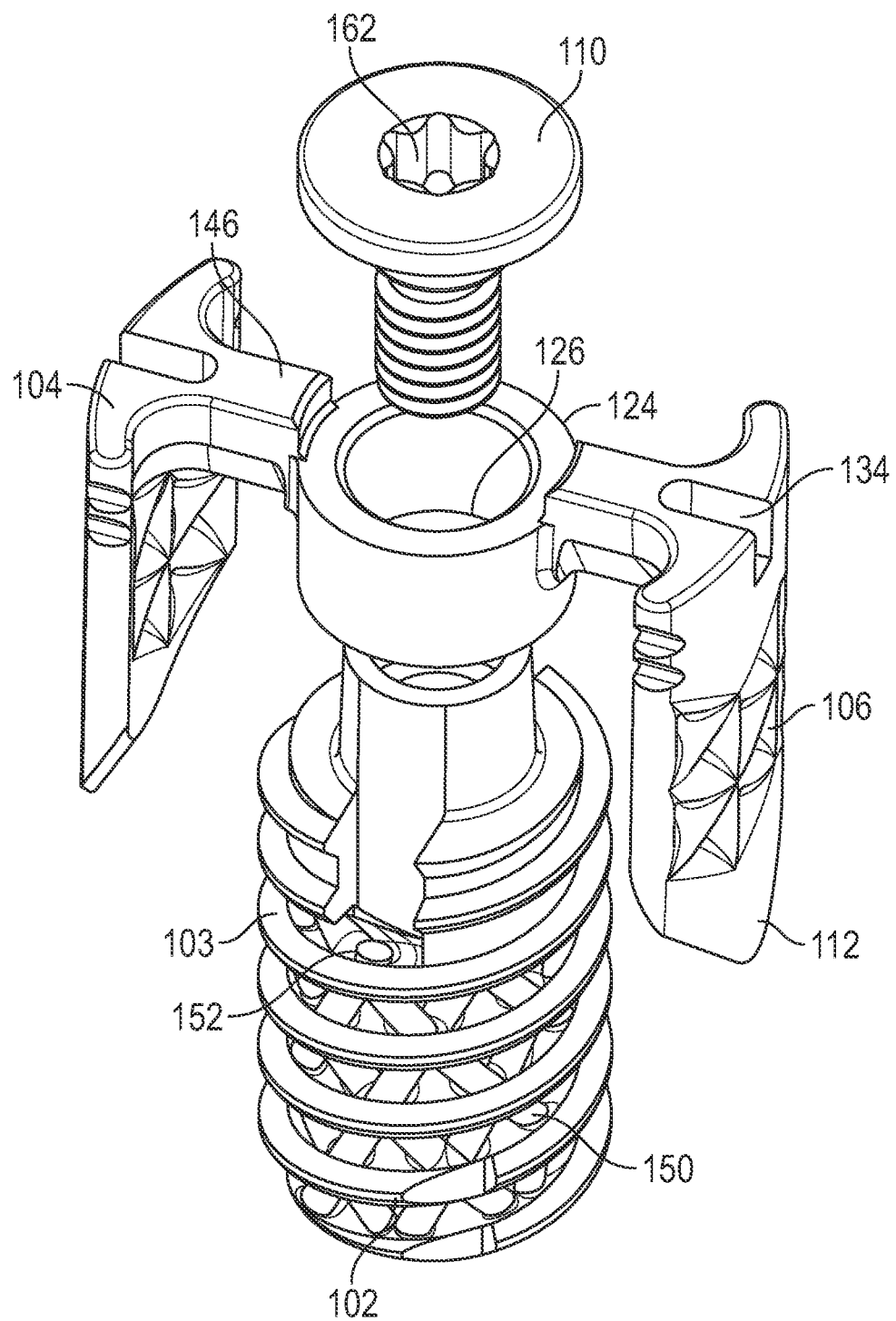
FIG. 58B illustrates an alternative exploded view of the joint implant from FIG. 58A.
Figure 58D:
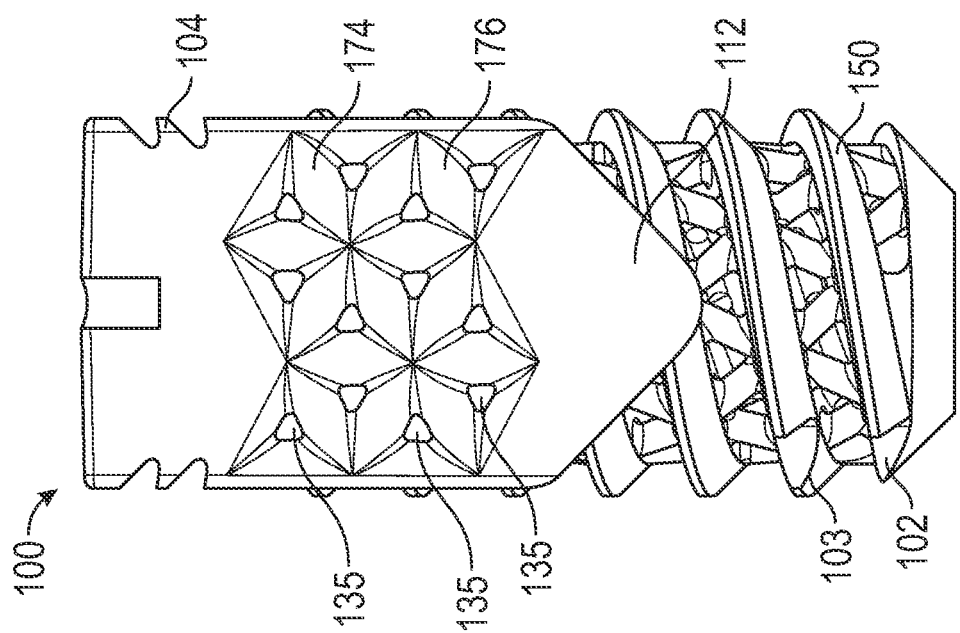
FIG. 58D illustrates an alternative side view of an embodiment of the joint implant from FIG. 58C.
Figure 58C:
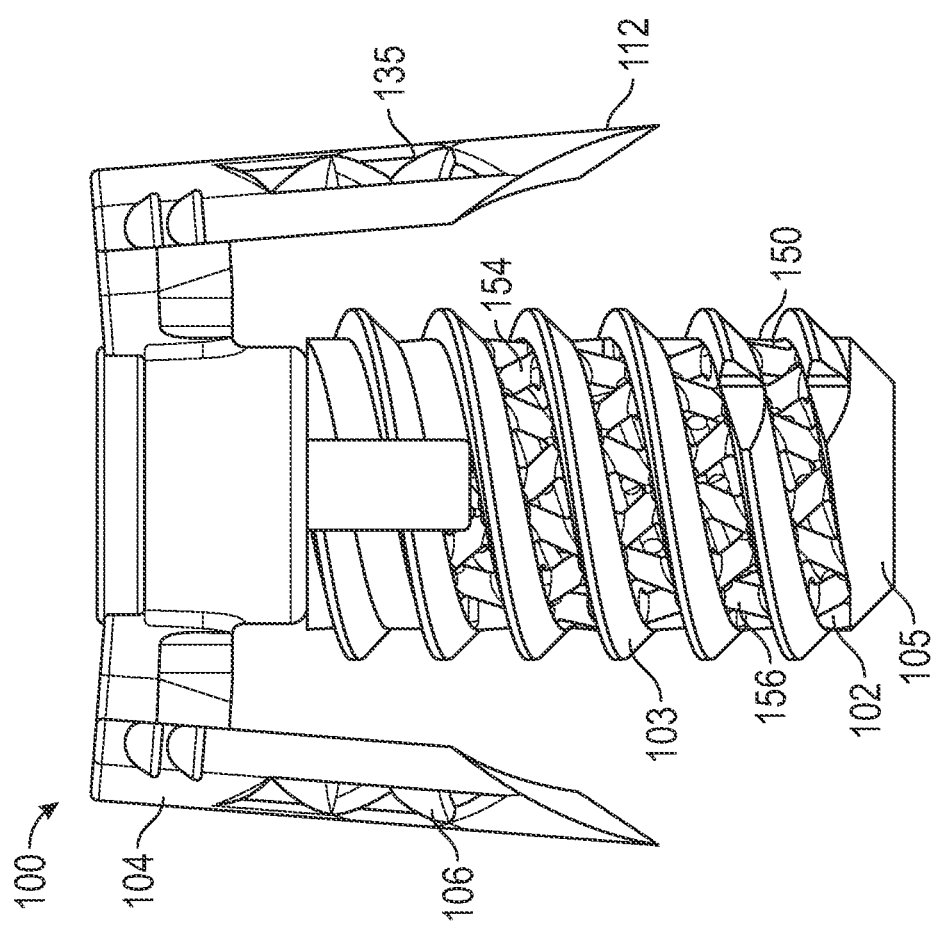
FIG. 58C illustrates a side view of an embodiment of the joint implant from FIG. 58A.
Figure 58F:
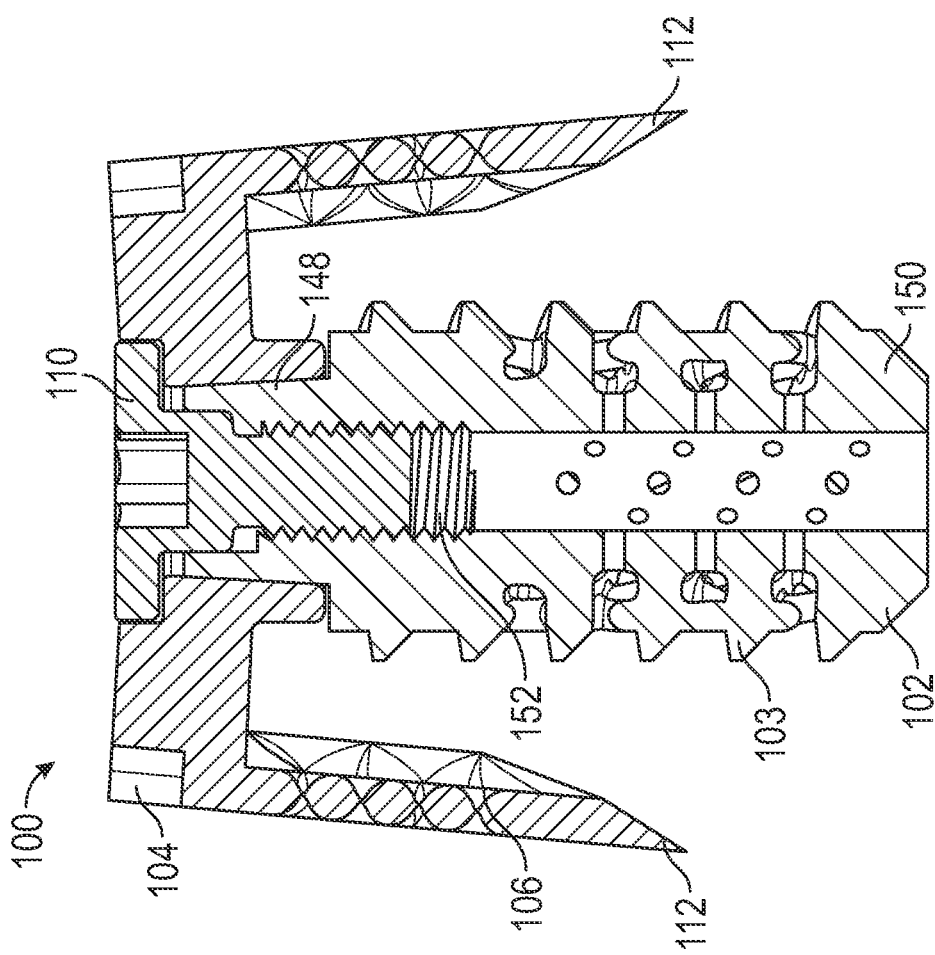
Figure 58E:
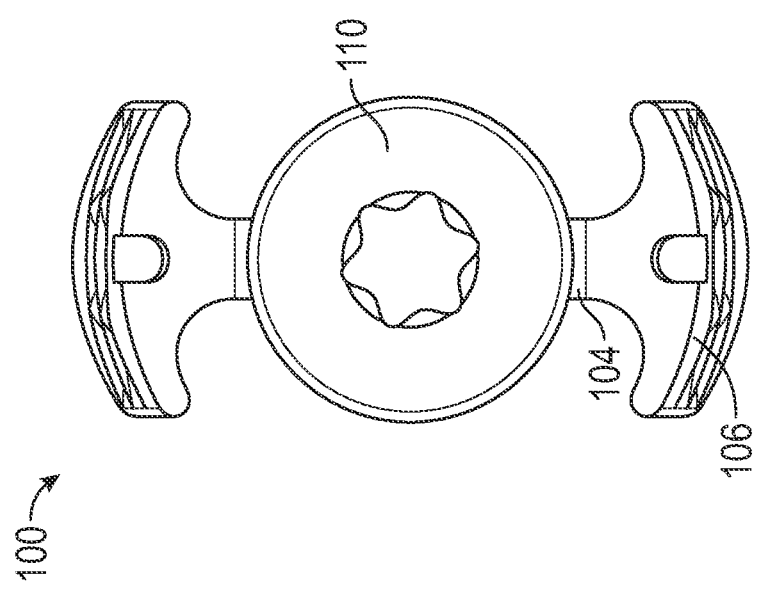
Figure 59B:
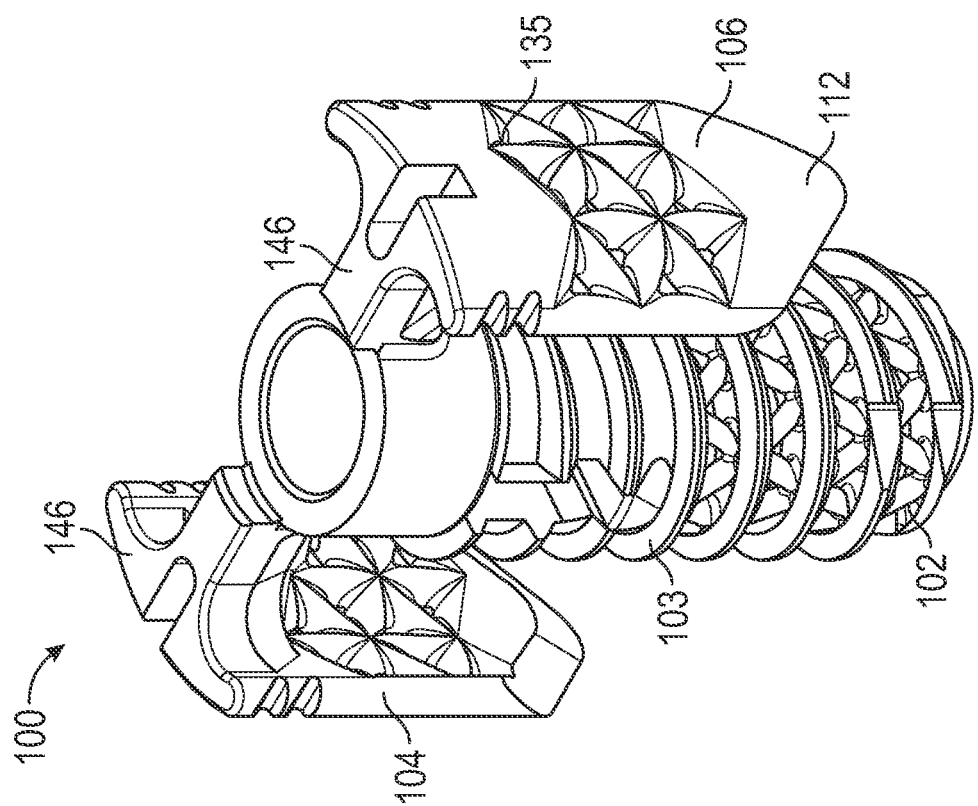
Figure 59A:
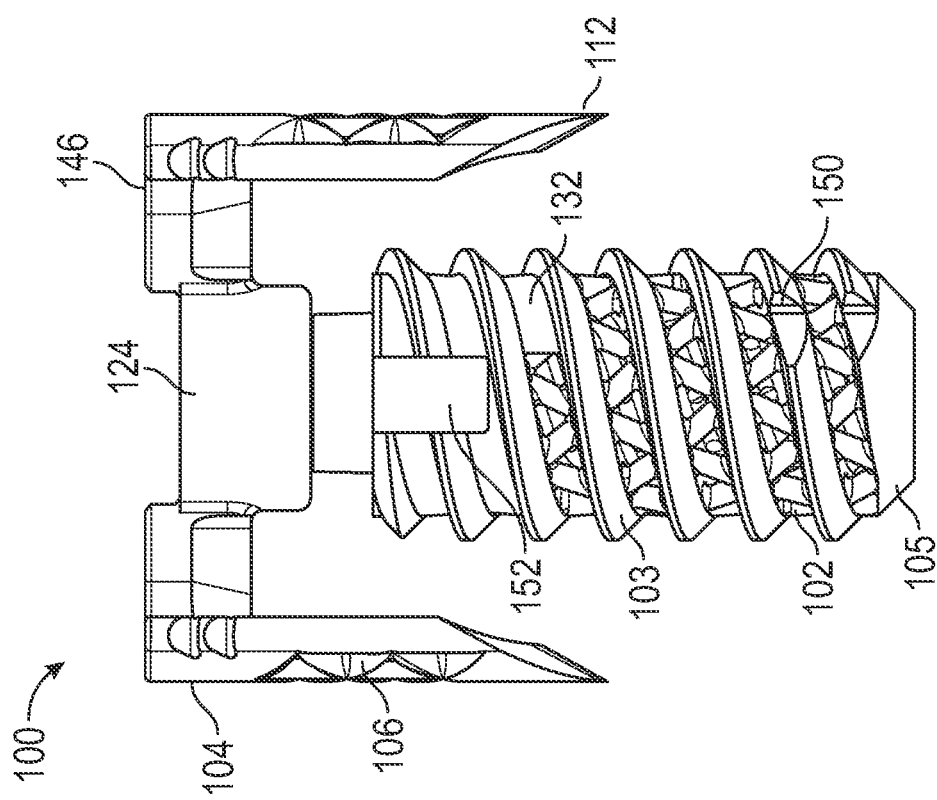
Figure 59D:
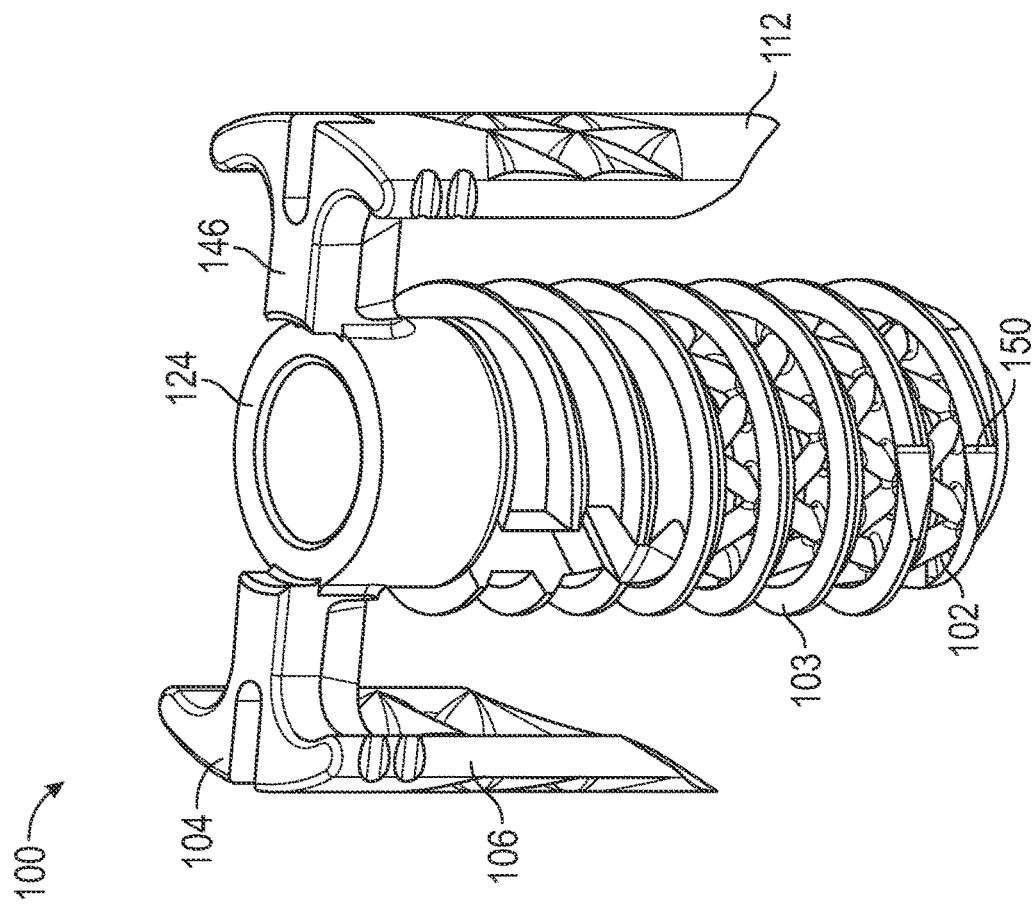
Figure 59C:
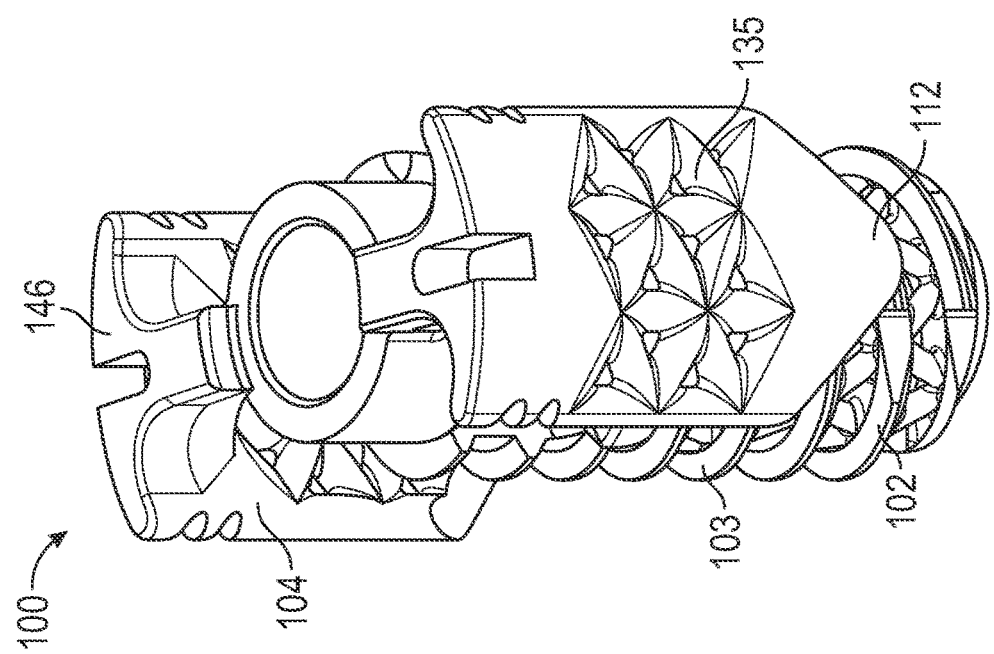

FIGS. 55, 56, and 57 show the implant of FIGS. 54A-54G implanted within the body.

FIGS. 38A-58F depict another embodiment of the SI joint implant system 100. The embodiment of FIGS. 58A-58F may include any of the same or similar features or functions as any of the other embodiments described herein and vice versa.

FIGS. 58A-58F depict another embodiment of an implant system 100 having a primary implant 102, a secondary implant 104, and a fastener or attachment mechanism 110. In certain embodiments, the primary implant 102 of FIGS. 58A-58F can be implanted prior to the secondary implant 104. In the embodiment of FIGS. 58A-58F, the secondary implant includes a body or anchor ring 124. One or more anchors 106 can extend from the anchor ring 124. In certain embodiments, the one or more anchors 106 can be coupled to the anchor ring 124 by one or more arms 146.

The primary implant 102 can include a proximal head or proximal end 148. As shown in FIGS. 58A-58F, in some embodiments, the proximal head or end 148 is an unthreaded portion of the primary implant 102. The ring 124 can define an opening 126 shaped, sized, or otherwise configured to receive the proximal end 148 of the primary implant 102. In certain embodiments, the ring 124 can be advanced over the proximal end 148 of the primary implant, for example, in a proximal to distal direction.

As shown in FIGS. 58A-58F, the primary implant 102 can include a threaded section 150, which may be below the proximal end 148 in some embodiments. In certain embodiments, the primary implant 102 can include a groove cut or recess 152 within the threaded section 150. The groove cut or recess 152 can be a mating feature configured to receive a complementary mating feature, such as a protrusion or tab, of an implant driver or inserter for advancing the primary implant 102 to a desired depth.

The fastener or attachment mechanism 110 can secure the secondary implant 104 to the primary implant 102. In certain embodiments, the attachment mechanism 110 can be in the form of a threaded fastener that can mate with corresponding interior threads within the primary implant 102. As shown in FIGS. 58A-58F, a head of the threaded fastener 110 can have a larger diameter than the opening 126 of the anchor ring 124. The fastener 110 can be coupled with the primary implant 102 after the anchor ring 124 of the secondary implant 104 is positioned over the proximal end 148 of the primary implant 102 to secure the secondary implant 104 to the primary implant 102. For example, the head of the threaded fastener 110 can prevent distal to proximal movement of the secondary implant 104 relative to the primary implant 102.

In the absence of the attachment mechanism 110, the secondary implant 104 can couple to the primary implant 102 so that it can be rotated or oriented at any angle, for example, about longitudinal axis of the primary implant. As described with respect to other embodiments herein, the primary implant 102 can be countersunk within the SI joint. After the primary implant 102 is countersunk, the secondary implant 104 can be rotated or oriented at any angle, for example, about the longitudinal axis of the primary implant 102, to maximize contact between the anchors 106 and the ilium and sacrum for greater bone purchase.

The primary implant 102 and secondary implant 104 can be mated through a male/female design or any other design that allows the primary implant and secondary implant to move independently until secured in place by the attachment mechanism 110, which may be a fastener, such as a screw, or any other suitable locking means. As shown in the embodiment of FIGS. 58A-58F, the primary implant 102 and secondary implant 104 can rotate freely relative to one another until secured together.

FIGS. 59A-59D depict another embodiment of the SI joint implant system 100. The embodiment of FIGS. 59A-59D may include any of the same or similar features or functions as any of the other embodiments described herein and vice versa.

FIGS. 59A-D depict another embodiment of the implant system 100 in which the secondary implant 104 can rotate relative to the primary implant when coupled thereto.

Figure 60:
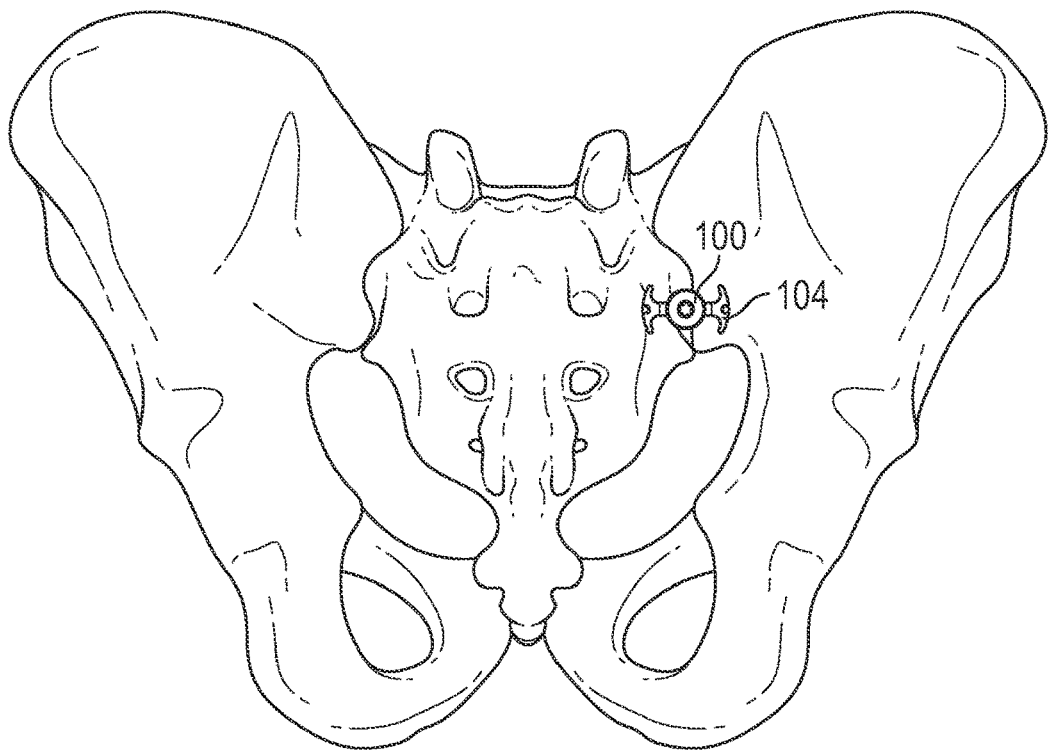
Figure 61:
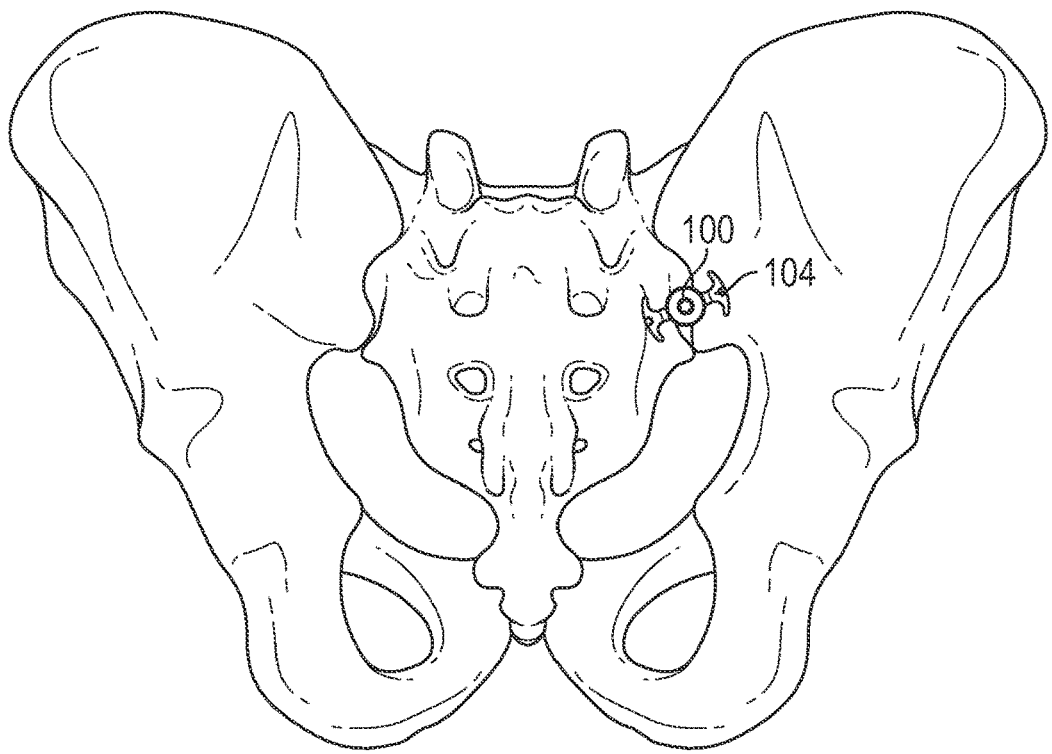
Figure 62:
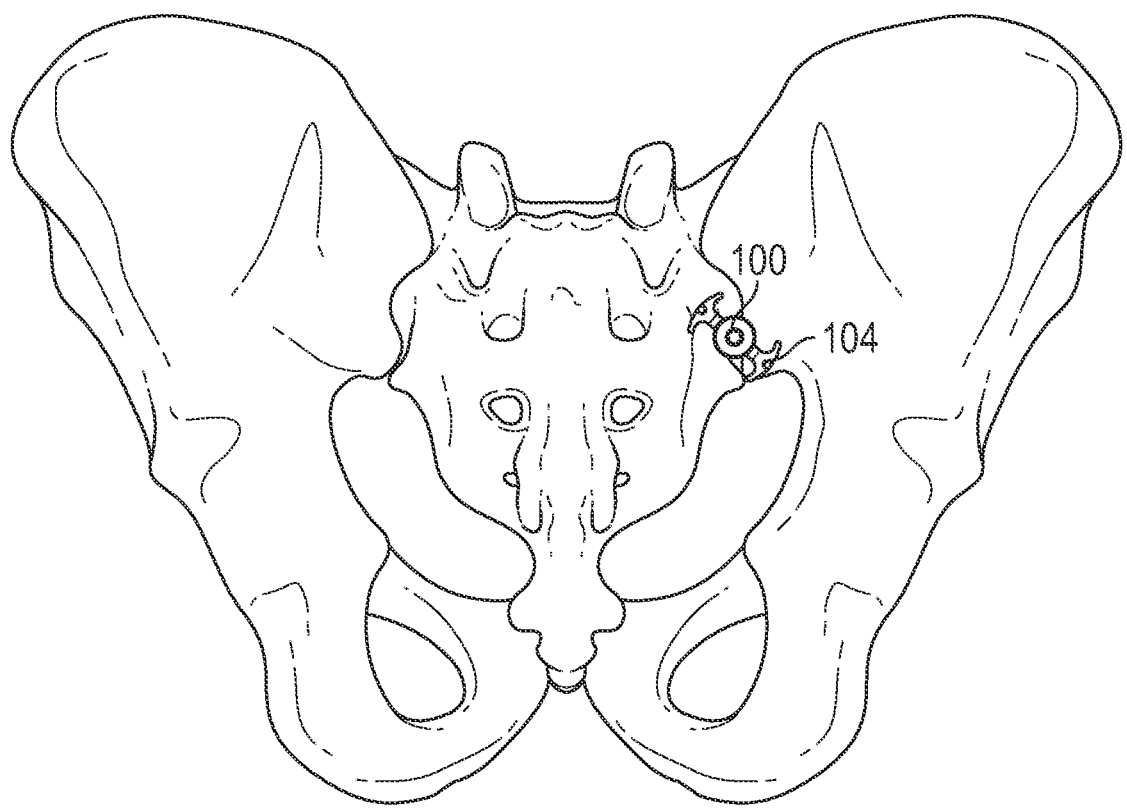

FIGS. 60, 61, and 62 show the embodiment of the implant system 100 of FIGS. 59A-59D implanted within the body with the secondary implant 104 rotated at different positions relative to the primary implant 102.

FIGS. 63A-63B depict another embodiment of the SI joint implant system 100. The embodiment of FIGS. 63A-63B may include any of the same or similar features or functions as any of the other embodiments described herein and vice versa.

In certain embodiments, the secondary implant 104 can be angled or tapered from a distal end to the proximal end by an angle θ so that when the secondary implant is driven into the sacrum and ilium, it compresses the bone and in turn the SI joint. The angle θ can range from 1° to 20° depending on the amount of compression desired. For example, an embodiment of an implant 104 having a 6° taper is shown in FIGS. 63A and 63B. A width $X_1$ at the proximal end of the implant 104 can be between 19 mm and 23 mm, between 20 mm and 22 mm, about 19 mm, about 20 mm, about 21 mm, about 22 mm, about 23 mm, or any other suitable width. A width $X_2$ at the distal end of the implant 104 can be between 21.5 mm and 25.5 mm, between 22.5 mm and 24.5 mm, about 21.5 mm, about 22.5 mm, about 23.5 mm, about 24.5 mm, about 25.5 mm, or any other suitable width. In the embodiment of FIGS. 63A and 63B, a width difference between the proximal end and the distal end is 2.5 mm, which can provide about 1.25 mm of compression per side after fully inserted. The distal portion of the secondary implant 104 can be beveled or tapered to help guide the secondary implant 104. The distal portion can guide the secondary implant 104 away from the SI joint or towards the SI joint to allow for compression of bone on the primary implant 102.

FIGS. 70A-70C depict another embodiment of the SI joint implant system 100. The embodiment of FIGS. 70A-70C may include any of the same or similar features or functions as any of the other embodiments described herein and vice versa.

FIGS. 70A-70C depict another embodiment of the implant system 100 in which a primary implant portion and secondary implant portion are formed (for example, integrally formed) as a single-piece. Anchors are attached to a center-piece. The anchors can resist compression and distraction forces once implanted. As shown, in some embodiments, the center-piece does not include any threads. The implant system 100 includes barbs, which can prevent back out after the implant system 100 is implanted. The implant system 100 can be maleated into position within the SI joint. Due to the single-piece design, both the primary implant portion and secondary implant portion are implanted at the same time. The embodiment of FIGS. 70A-70C may require less instrumentation and implant components and reduce time in the operating room.

FIGS. 71A-71B depict another embodiment of the SI joint implant system 100. The embodiment of FIGS. 71A-71B may include any of the same or similar features or functions as any of the other embodiments described herein and vice versa.

FIGS. 71A-71B depict another embodiment of the implant system 100. The implant system 100 of FIGS. 71A-71B is similar to the implant system 100 of FIGS. 70A-70C, but is greater in length between a proximal end and a distal end.

FIGS. 72A-72F depict another embodiment of the SI joint implant system 100. The embodiment of FIGS. 72A-72F may include any of the same or similar features or functions as any of the other embodiments described herein and vice versa.

FIGS. 72A-72F depict another embodiment of the implant system 100 having a primary implant 102 and a secondary implant 104. The primary implant 102 includes engagement features 103 in the form of threads extending proximally from a distal end 105 towards a head 130 of the primary implant 102. The primary implant 102 also includes a smooth or threadless shank section of the shank 166 positioned proximally of the threads. The threads can extend between the smooth shank section and the distal end 105. In certain embodiments, a primary implant 102 having threads along the entire length of the primary implant 102 can lead to the threads applying counterforces to threads of the secondary implant 104, which may pull or otherwise dislodge the anchors out of the bone. A smooth or threadless shank section near the head 130 of the primary implant proximal to the threads can prevent or reduce the counterforces that can cause dislodgement of the anchors 106. For example, as the primary implant 102 is threaded down into the SI joint, the secondary implant 104 can be relieved from counter forces as it comes off the thread of the primary implant. As the primary implant 102 continues to be threaded within the SI joint, it can pull the secondary implant 104 which can pull the anchors 106 tight into the ilium and sacrum. In other embodiments, the engagement features 103 (e.g., threads) may extend over an entire length of the shank 166.

In certain embodiments, the implant system 100 can be implanted using a posterior method. In certain embodiments, the implant system 100 can be implanted through an incision made directly over the posterior SI joint from the PIIS (Posterior Inferior Iliac Spine) to the PSIS (Posterior Superior Iliac Spine). In certain embodiments, the incision may be made over the midline of the sacrum. In certain embodiments, the incision can allow access to each joint through one incision in a less invasive approach. In certain embodiments, the tissue is mobilized from the midline incision to access the SI joint for unilateral (accessing one SI joint) or bilateral (accessing both SI joints) implantation. This can help gain access to the SI joints through the midline incision. In certain embodiments, this method can prevent the need to make two separate incisions over each SI joint. In certain embodiments, the incision may be made directly over the SI joint on each side or both sides.

In certain embodiments, after the incision is made, a guidewire or rod (see FIG. 13) can be placed posteriorly into the SI joint. In certain embodiments, the guidewire or rod can be placed in the joint line between the first and second sacral foramens. This can ensure that when drilling and implantation occurs the foramen are intact and nerve injury is avoided. Positioning of the guidewire or rod in the joint line between the first and second sacral foramens can also facilitate placement of the implant system to sit flush or countersunk within the SI joint. If the implant system is placed higher, it may not sit flush or countersunk because of the PSIS prominence. Lower placement can increase the risk of nerve injury due to neighboring sciatic notch harboring nerves.

In certain embodiments, if a guidewire or rod isn't used, a more robust instrument such as a joint locator, paddle, spatula or other instrument may be used to enter the SI joint. In certain embodiments, a series of sequential dilation may be used over the guidewire or joint locator, paddle, spatula, etc. The dilators may be circular, oval, square, rectangular or any other suitable three-dimensional shape to retract tissue for drilling or implanting. In certain embodiments, after dilation occurs, a drill guide may be placed within the SI joint. The drill guide may have two tangs or more tangs to prevent migration of the drill guide. The tangs may enter the SI joint and/or grip the bone on the sacrum and ilium. After the drill guide is docked in the desired location, a drill bit or broach may be used to create a defect that matches the SI fusion implant 100. A drill may be used freehand or placed over a guidewire (cannulated drill bit) to guide the drill bit to the desired location. After drilling has occurred the drill bit may be removed. In certain embodiments, a wisp or tissue collector may be inserted down the drill guide to remove excess cartilage or other tissue that may contain chondrocytes which compete with osteocytes for bone formation. The wisp or tissue collector may be re-usable or disposable. Once the joint defect has been created the implant may be inserted.

In certain embodiments, a driver or inserter can be used to insert the primary implant 102 into the pre-determined size void created. In certain embodiments, the primary implant 102 may be countersunk within the joint for better fixation and to pack bone graft over the implant 102 or may sit flush, for example, if desired due to shallow patient anatomy preventing the countersinking method. In certain embodiments, primary implant 102 placed within the joint can resist shearing forces of the sacrum. In certain embodiments, after the primary implant 102 is placed within the SI joint, the secondary implant 104 can be anchored to the top of the primary implant 102 or otherwise coupled or positioned against the top of the primary implant 102. The secondary implant 104 can be placed in both the ilium and sacrum and can act as a tension band. The secondary implant 104 can resist forces that compress and distract the sacroiliac joint. In combination, the primary implant 102 and secondary implant 104 can act as one system to achieve multiple points of fixation and resist multiple forces. The primary and secondary implants can be placed in one step or two steps. If a system 100 having a screw or screw-like primary implant 102 (e.g., an implant having threads) and a separate secondary implant 104 is used, they can be placed in two separate steps. For example, the primary implant 102 can first be screwed into the SI joint, and then the secondary implant 104 can be secured to the primary implant 102. If another shape is used in the primary implant 102 (for example, an implant having other engagement features 103, such as fins, barbs, teeth, or blades) the implant may be placed in one step in some embodiments, for example as shown respect to FIGS. 33A-33D. In certain embodiments, a tool or instrument may be used to align the secondary implant 104 to the primary implant 102 when inside the patient.

Figure 12A:
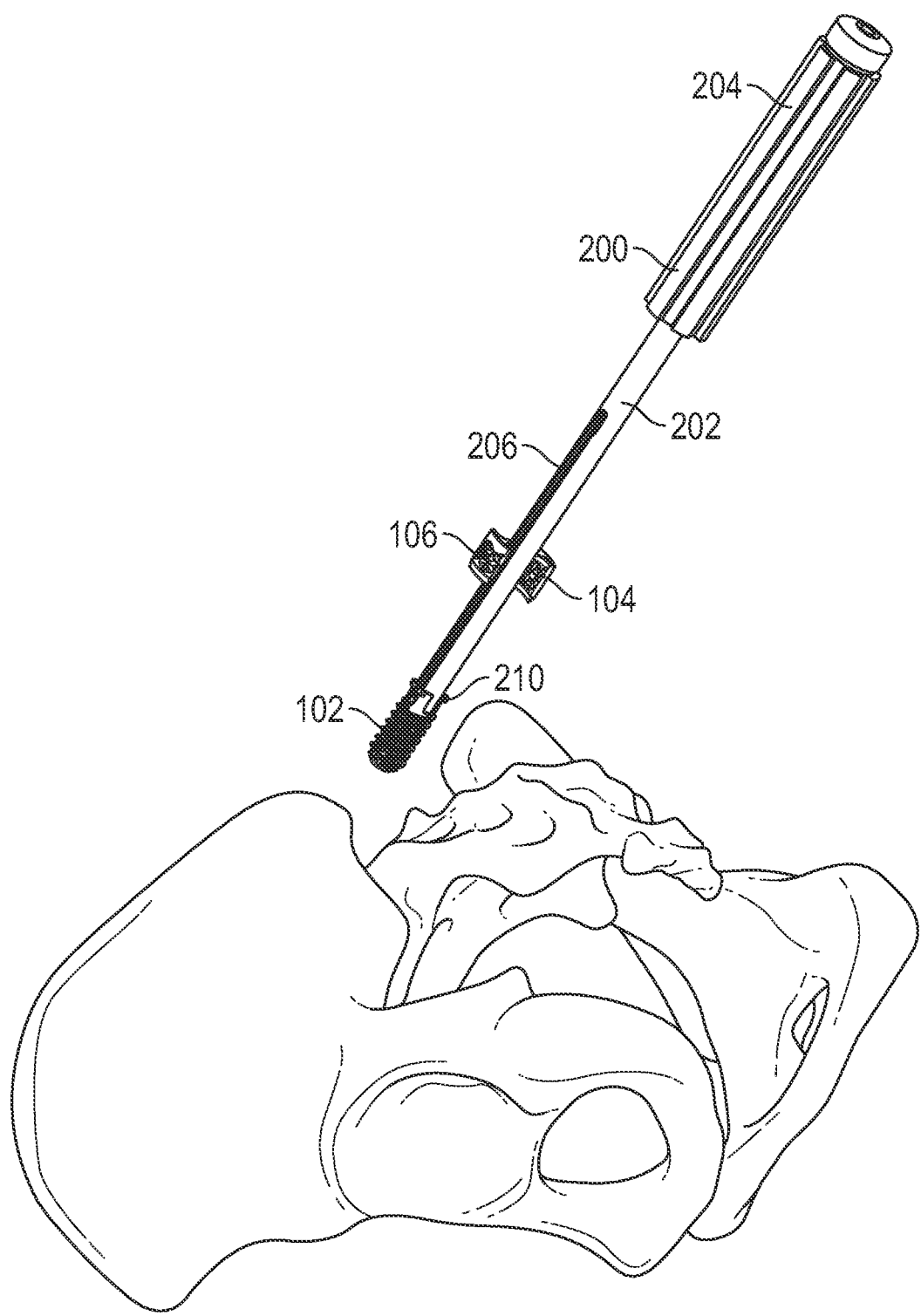
FIG. 12A illustrates a perspective view showing an embodiment of a driver coupled with an implant system by the SI joint.

FIG. 12A depicts an embodiment of a driver or inserter 200 that can be used in a method of implanting the implant system 100, as described above. The inserter 200 can include a shaft 202. The inserter 200 can include a handle 204 connected to the shaft 202. The inserter 200 can have one or more slots 206 that extend at least partially down the shaft 202. For example, the slots 206 can extend proximally from a distal portion or distal end 203 of the shaft 202 at least partially towards handle 204.

In certain embodiments, the shaft 202 can engage the primary implant 102 with a threaded rod 212 (as shown, for example, in FIG. 13) that can extend through the center of the shaft 202, for example through a lumen of the shaft 202, and enter the center of primary implant 102. The threaded rod 212 can include proximal threads 214 configured to mate with complementary internal threads within the lumen of the shaft 202. The threaded rod 212 can include distal threads 216 configured to mate with internal threads of the primary implant 102. The inserter 200 has a mating portion 210 at the distal portion or distal end 203 that engages the primary implant 102 to facilitate advancement of the primary implant 102 in the SI joint using the inserter 200. The threaded rod 212 can keep the primary implant 102 and inserter 200 held together during advancement of the primary implant 102 using the inserter 200.

The slots 206 can allow for the anchors 106 to extend laterally beyond the shaft 202 so that the secondary implant 104 can be positioned within a lumen of the shaft 202 above primary implant 102. After the primary implant 102 is coupled to the mating portion 210 of the inserter 200, the secondary implant 104 may be advanced along the slots 206 to couple with or otherwise contact the primary implant 102. In certain embodiments, the slots 206 may be shaped and/or positioned to align the secondary implant 104 with the primary implant 102.

Figure 12B:
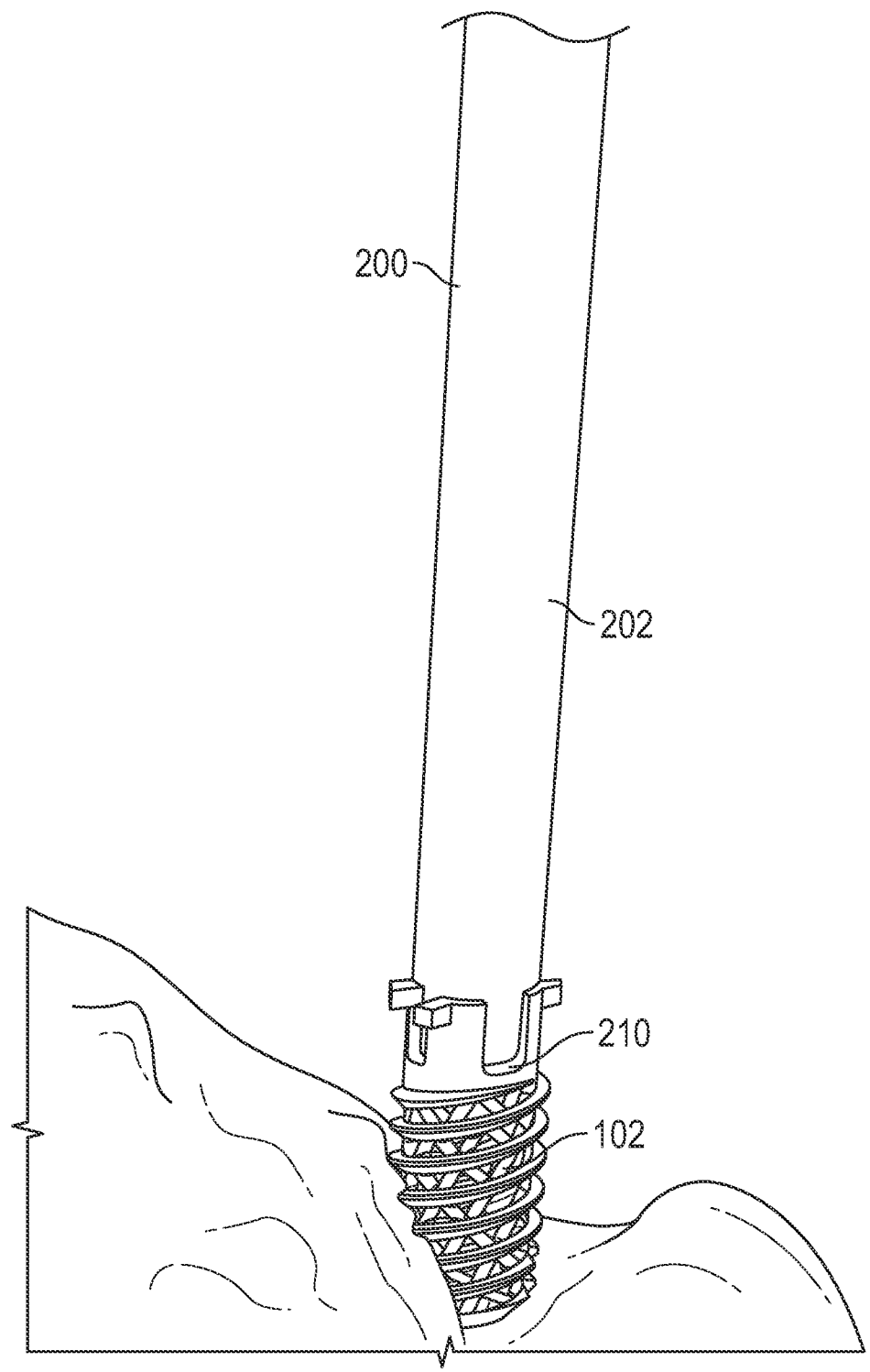
FIG. 12B illustrates a perspective view showing an embodiment of a driver coupled with an implant system within the SI joint.
Figure 12C:
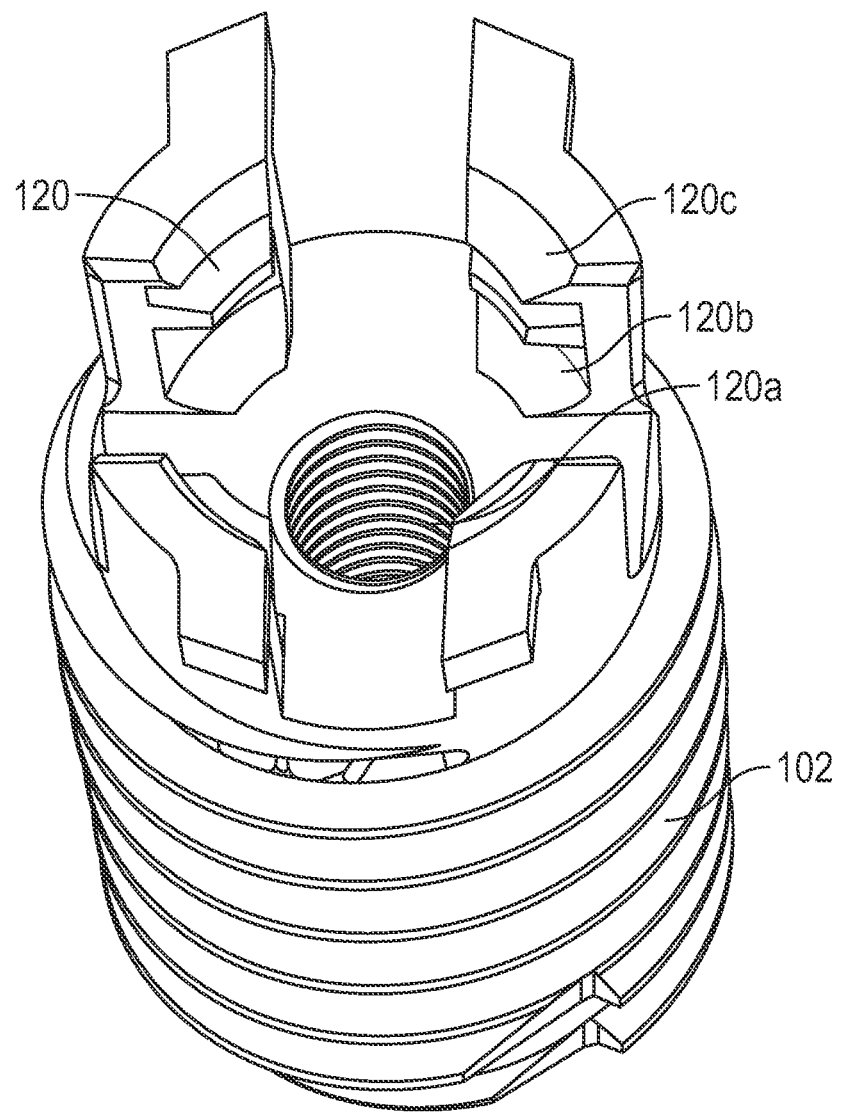
FIG. 12C illustrates a perspective view of an embodiment of the implant as pictured in FIG. 12A.
Figure 12D:
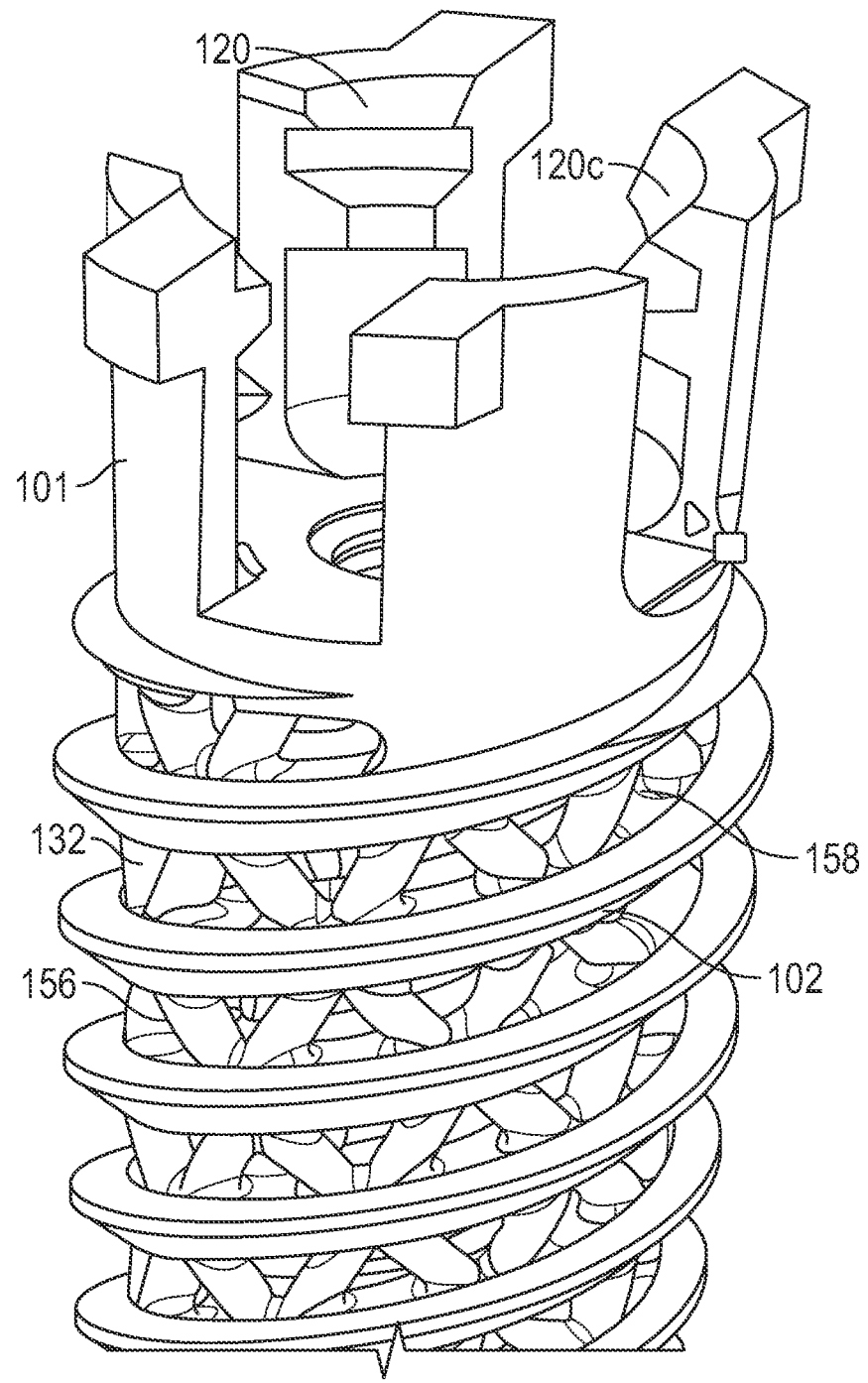
FIG. 12D illustrates a perspective view of an embodiment of the implant as pictured in FIG. 12A.

FIG. 12B illustrates shows the connection between the mating portion 210 and an embodiment of the primary implant 102. FIGS. 12C and 12D show the primary implant 102 of FIG. 12B. The embodiment of the primary implant 102 of FIGS. 12A-12D may include any of the same or similar features or functions as any of the other embodiments described herein and vice versa.

In certain embodiments, the primary implant 102 can include one or more engagement features 120. The engagement features 120 can include one or more grooves, rows, slots, etc. In certain embodiments, the inserter 200 can engage one or more of the engagement features 120 so that the inserter 200 stays engaged to the primary implant 102 during advancement of the primary implant into the SI joint.

In certain embodiments, the secondary implant 104 can be configured to engage one or more of the engagement features 120 to couple with the primary implant 102. For example, the secondary implant 104 may include corresponding engagement features that engagement features 120.

As described herein, n certain embodiments, the secondary implant 104 can be received by the primary implant 102, and an attachment mechanism 110 can couple the primary implant 102 and the secondary implant 104. In certain embodiments, the attachment mechanism 110 can engage one or more of the engagement features 120. For example, in certain embodiments, the primary implant 102 can include engagement features 120a for engaging the threaded rod 212. In certain embodiments, the primary implant 102 can include engagement features 120b for engaging the mating portion 210. In certain embodiments, the primary implant can include engagement features 120c for engaging the attachment mechanism 110.

In certain embodiments in which a threaded rod 212 is used, the threaded rod 212 can be removed from the primary implant 102 and inserter 200 to disengage the inserter 200 from the primary implant 102.

Figure 13:
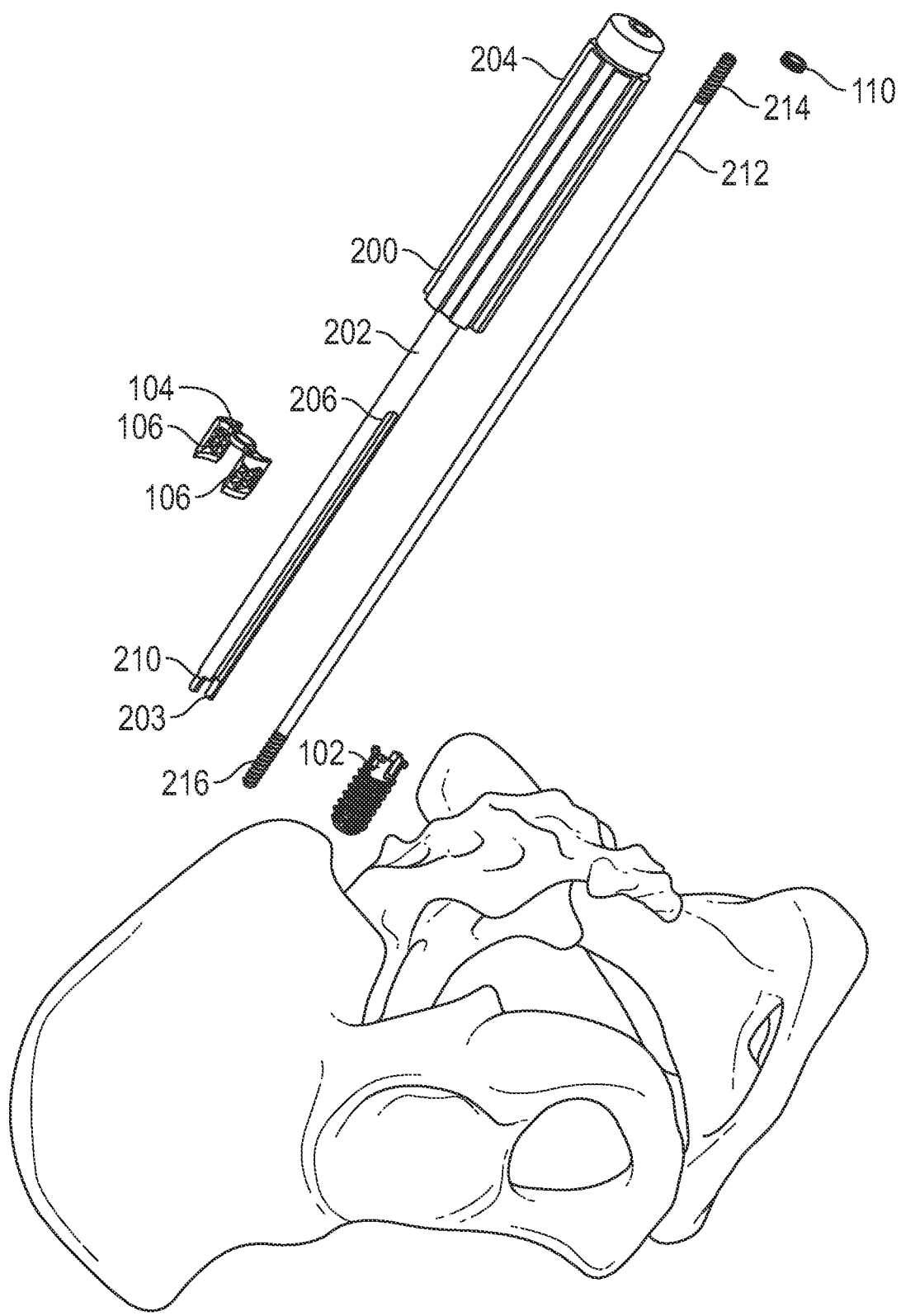
FIG. 13 illustrates a perspective view showing an embodiment of a driver, rod, and implant of an implant system for an SI joint.

FIG. 13 is an exploded view that shows the inserter 200, the threaded rod 212, the primary implant 102, the secondary implant 104, and the attachment mechanism 110.

Figure 14:
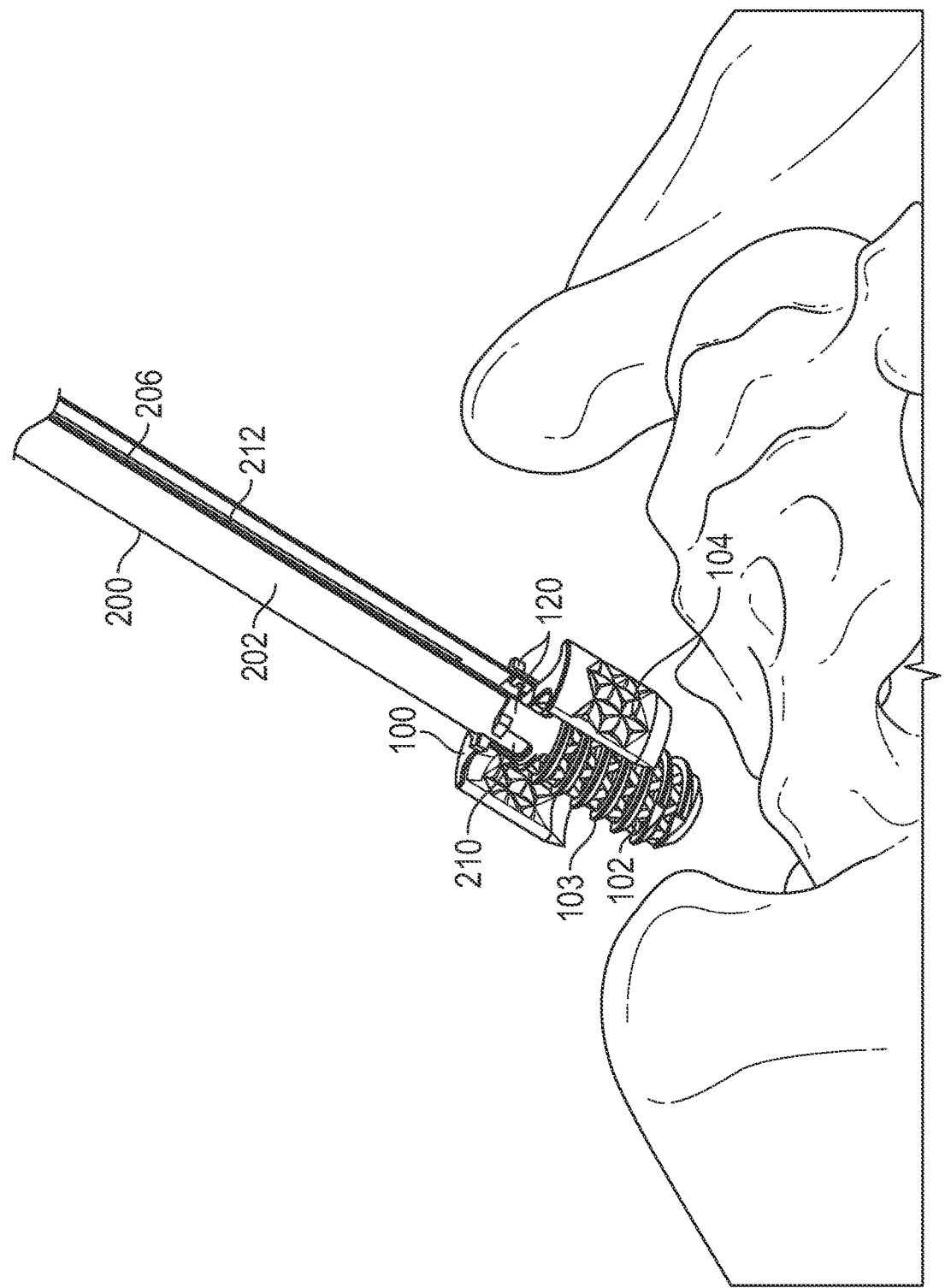
FIG. 14 illustrates a perspective view showing an embodiment of a driver, rod, and implant system by the SI joint.

FIG. 14 shows the primary implant 102, the secondary implant 104 and the inserter 200 held together although not inserted into bone.

Figure 27:
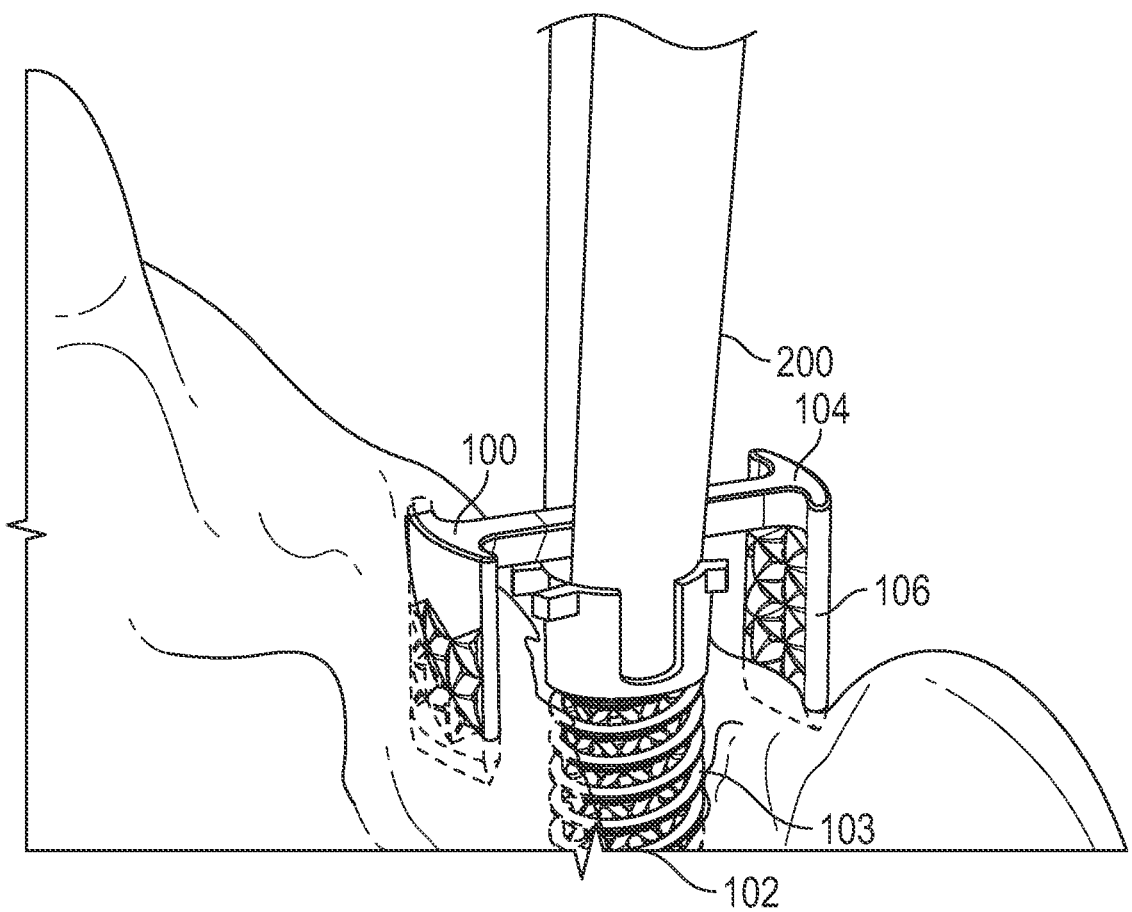
FIG. 27 illustrates a perspective view of an embodiment of the implant system inserted into the SI joint.
Figure 28:
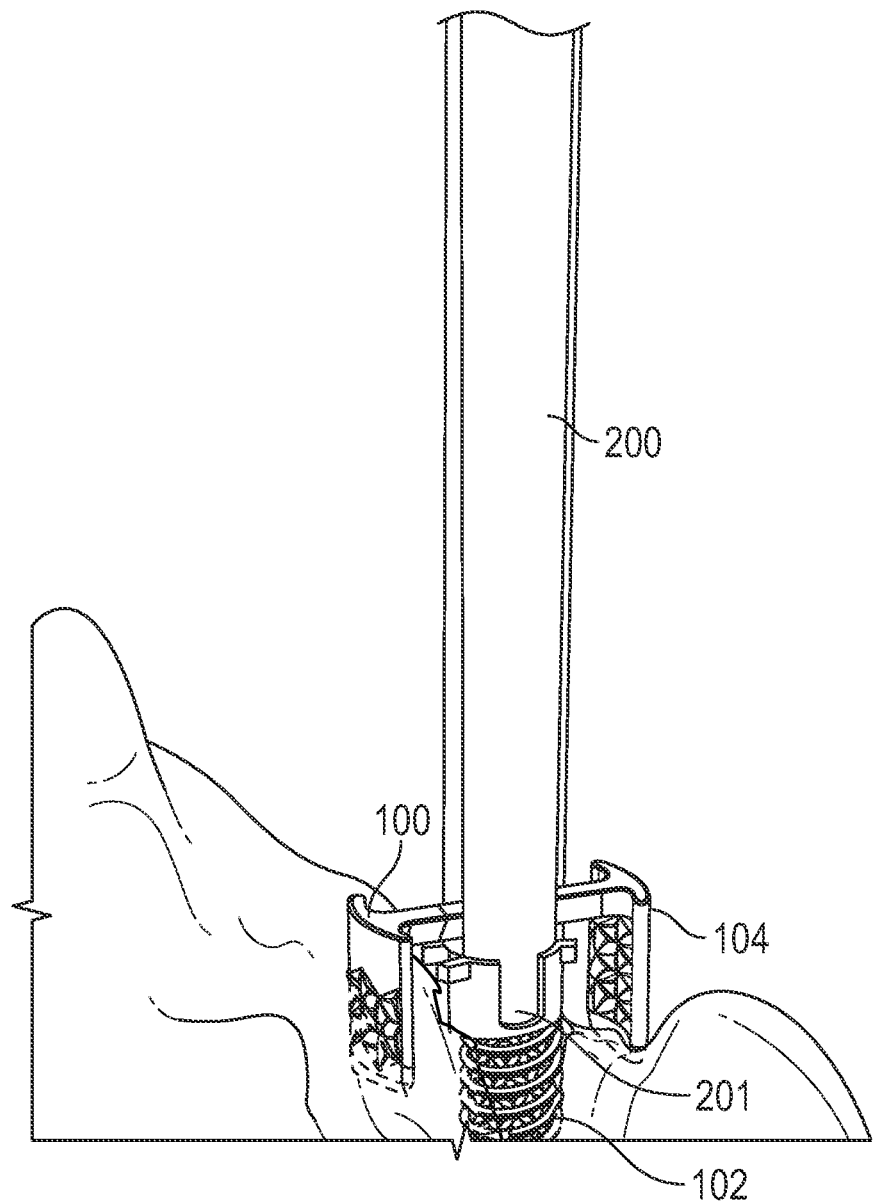
FIG. 28 illustrates a perspective view of an embodiment of the implant system inserted into the SI joint.

FIGS. 27 and 28 show the primary implant 102 and secondary implant 104 imbedded in bone together with the inserter 200 coupled to the implants. The primary implant 102 and secondary implant 104 may be proud of the SI joint, as shown in FIGS. 27 and 28, or may be countersunk to allow bone to grow over the implants.

Figure 15:
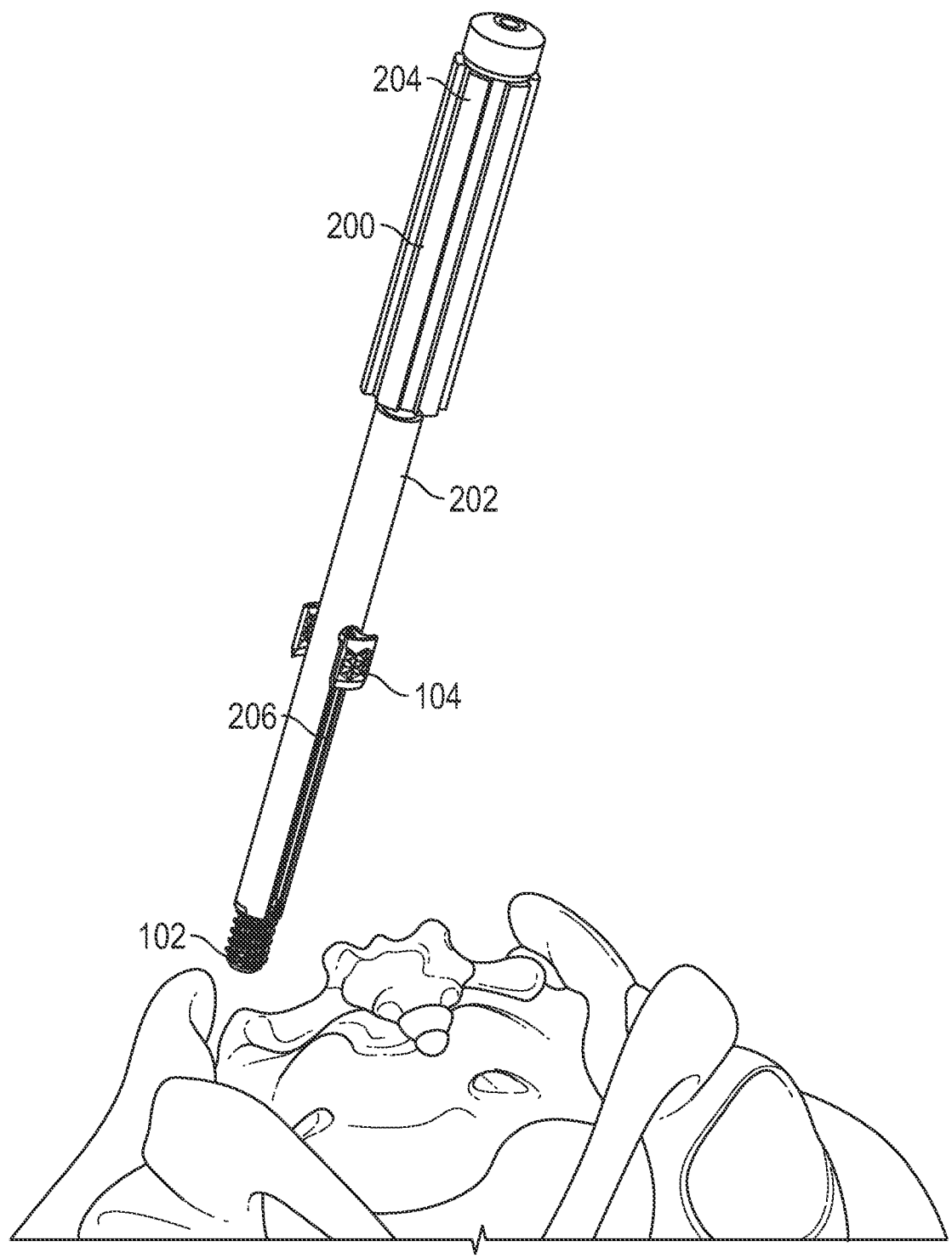
FIG. 15 illustrates a perspective view showing an embodiment of a driver coupled with an implant system for insertion into the SI joint.
Figure 16:
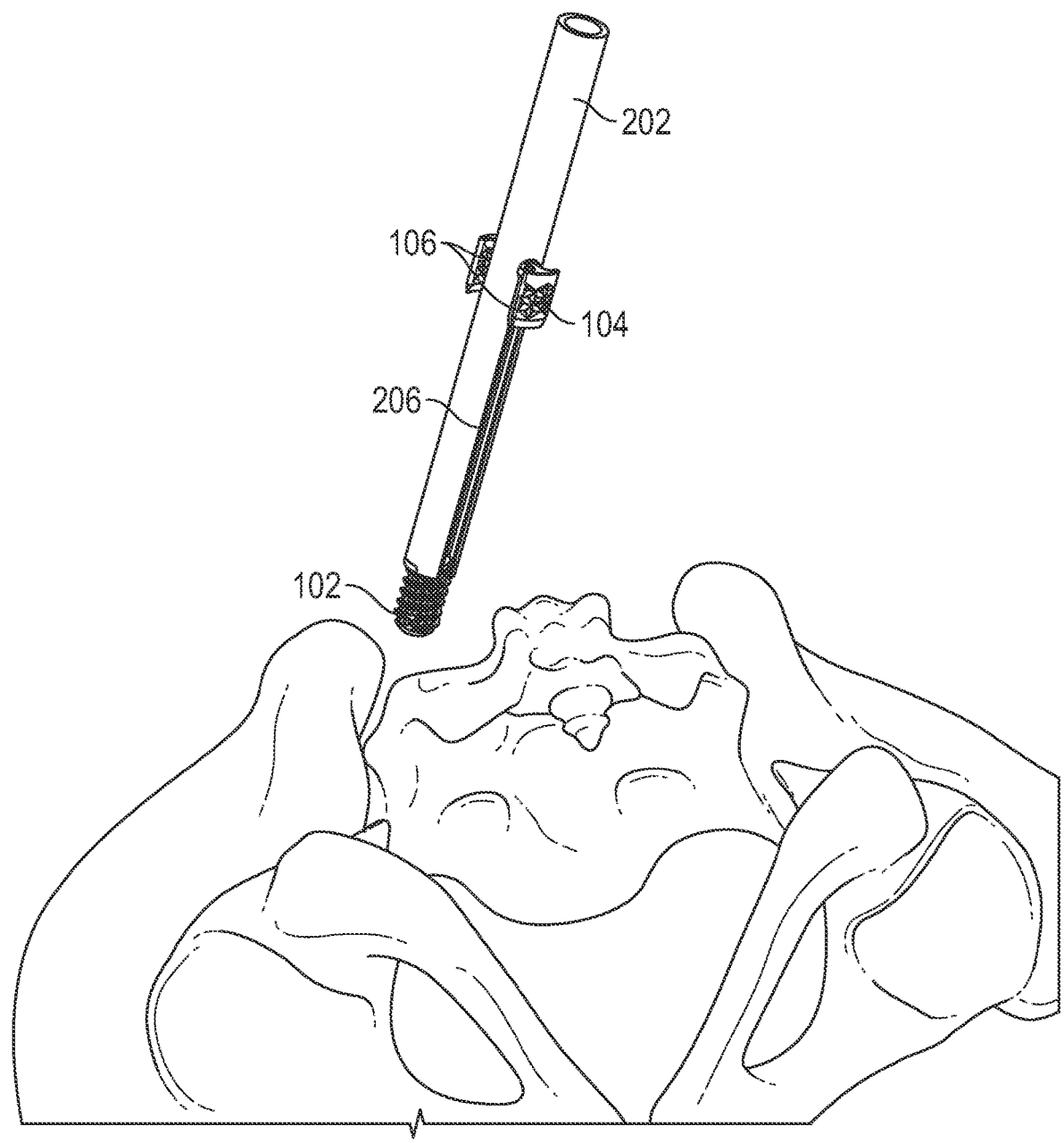
FIG. 16 illustrates a perspective view of another embodiment of the implant system for insertion into the SI joint.
Figure 17:
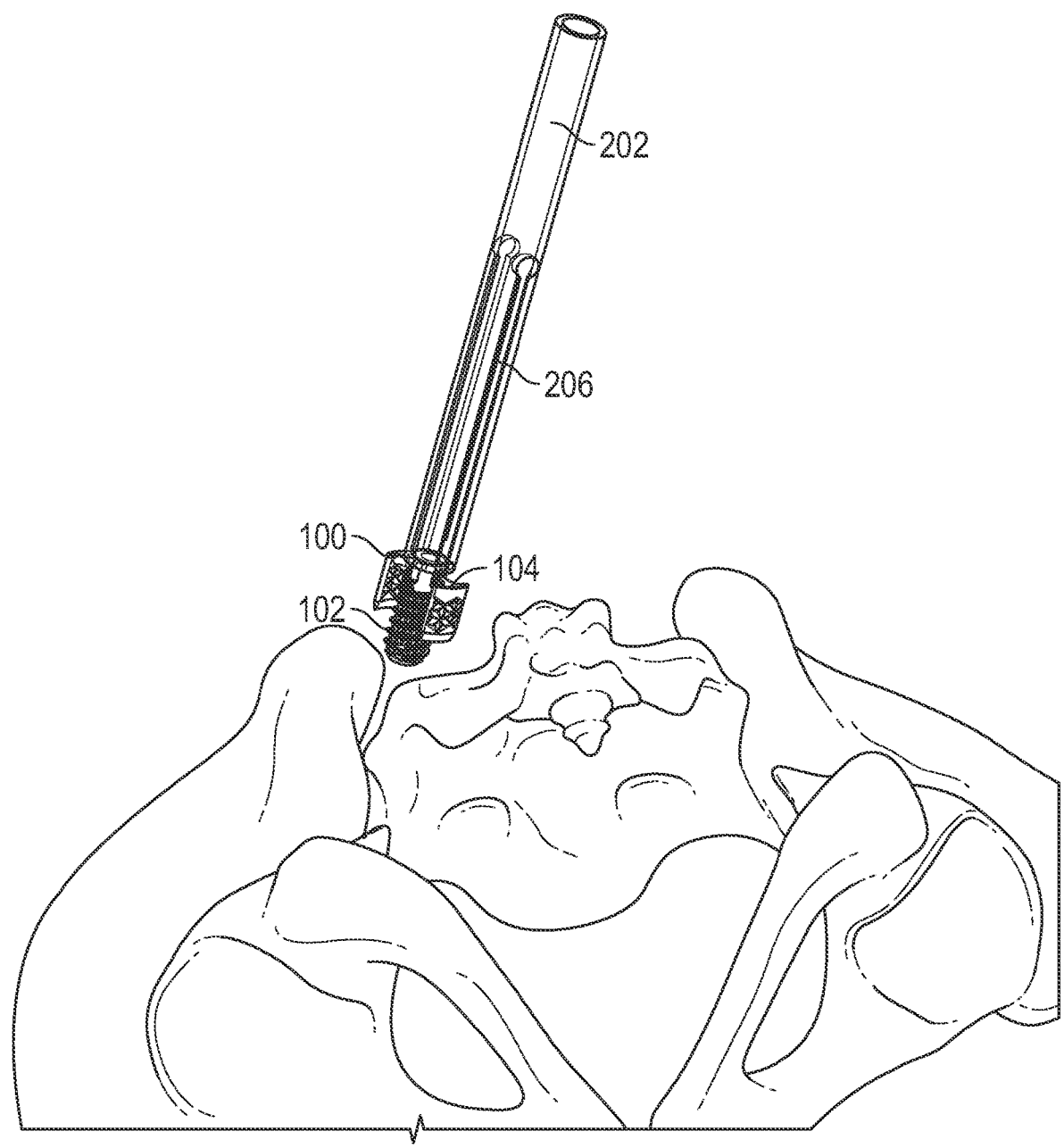
FIG. 17 illustrates a perspective view of another embodiment of the implant system for insertion into the SI joint.
Figure 19:
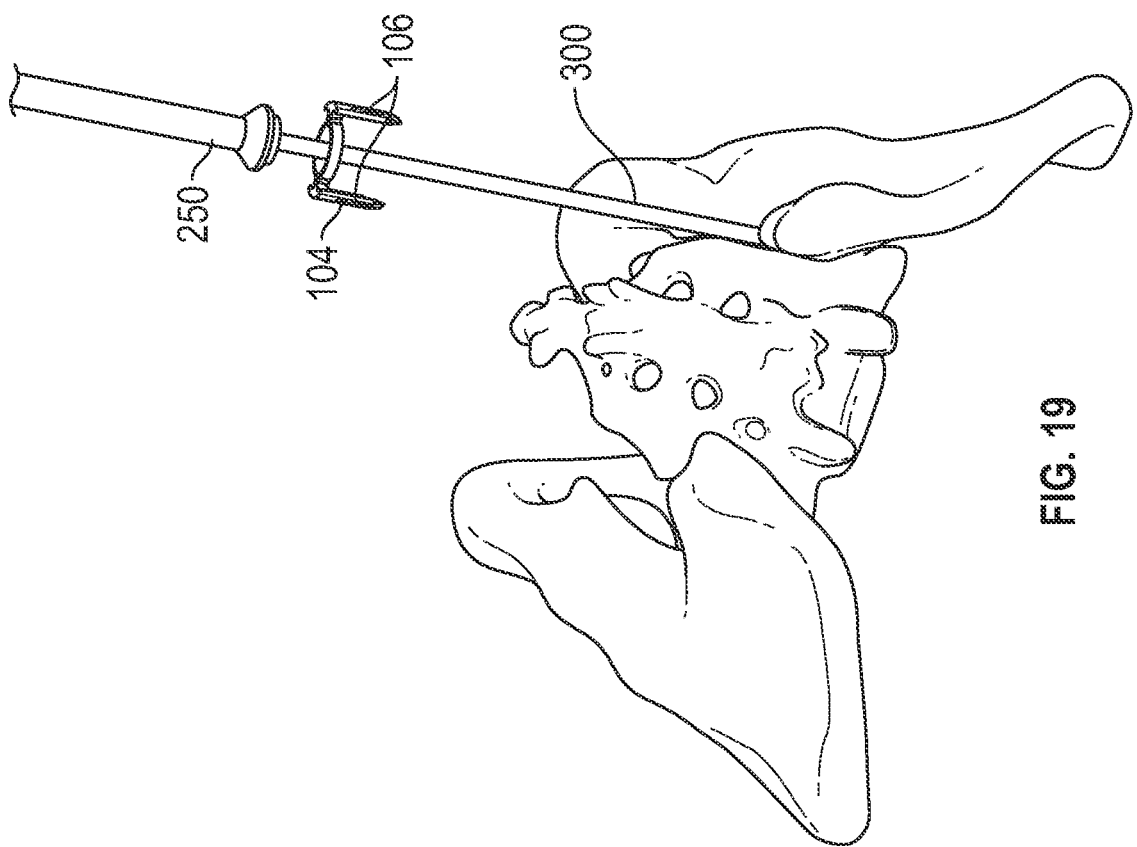
FIG. 19 illustrates a perspective view of another embodiment using a guidewire and driver in the implant system for insertion into the SI joint.
Figure 18:
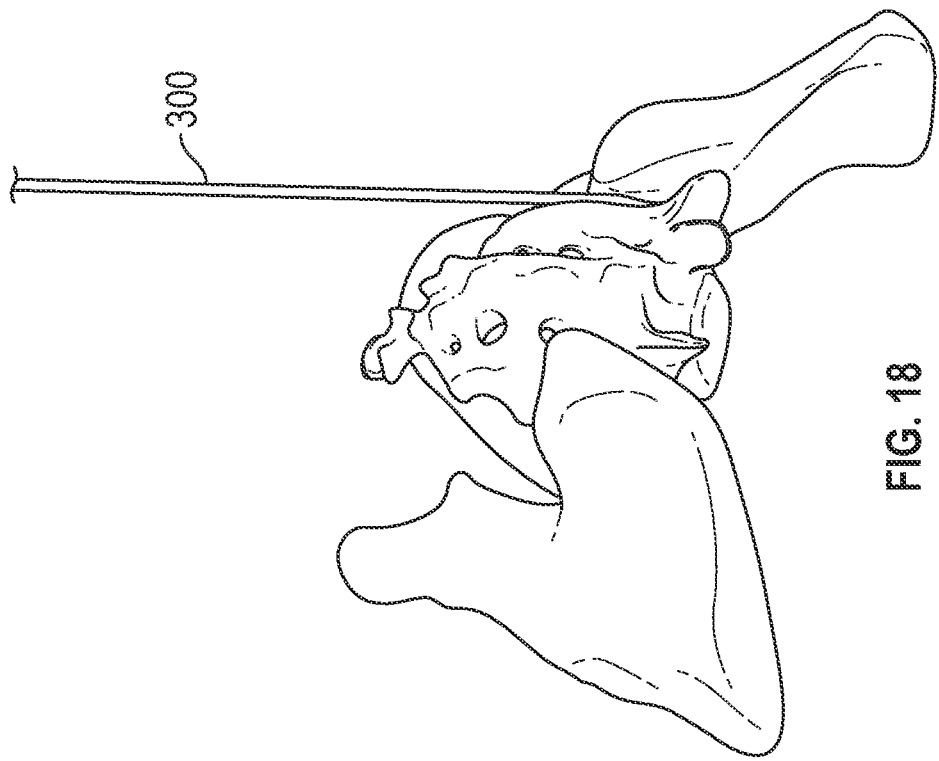
FIG. 18 illustrates a perspective view of another embodiment using a guidewire in the implant system for insertion into the SI joint.
Figure 20:
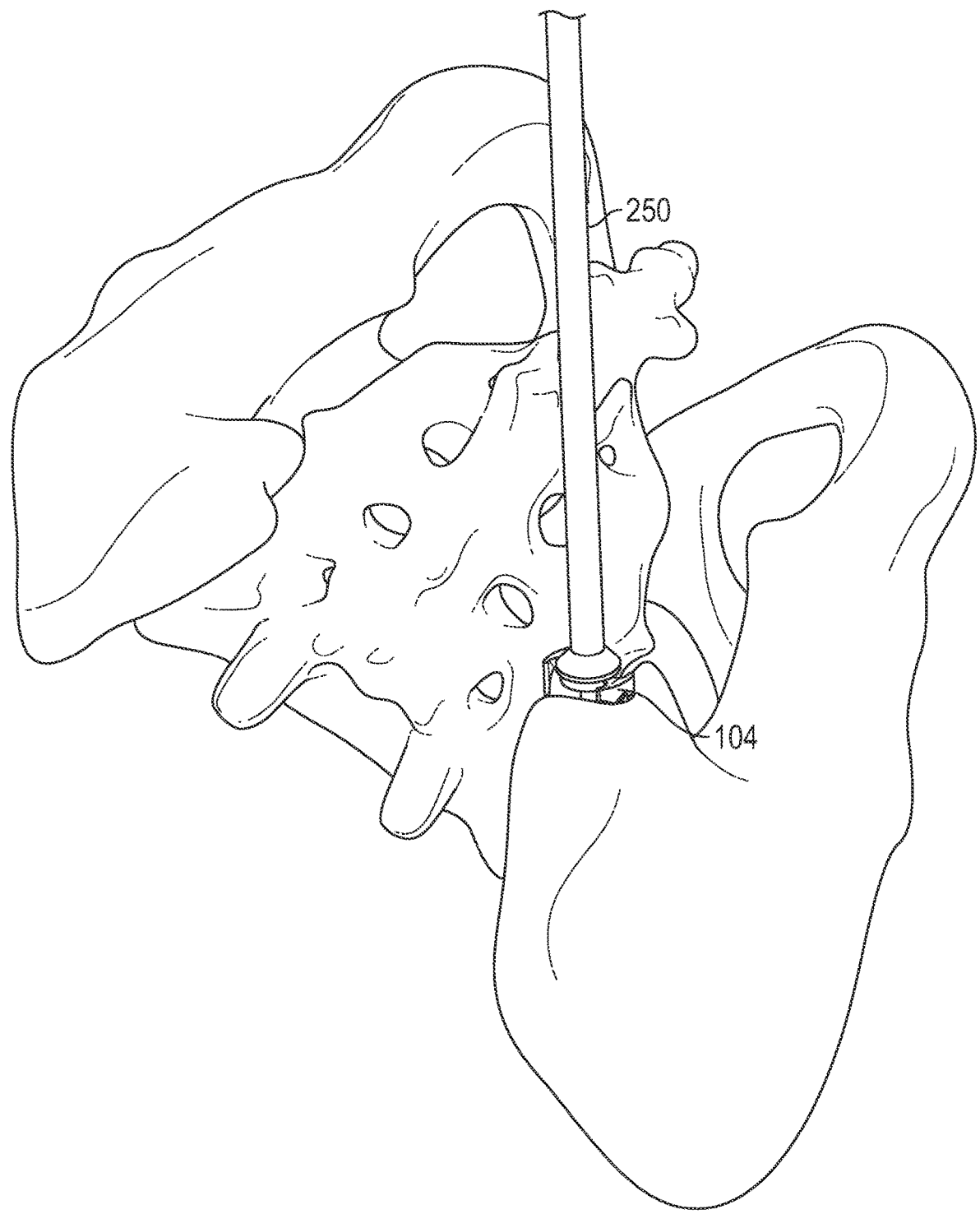
FIG. 20 illustrates a perspective view of an embodiment of the implant system using a driver and guidewire with an implant in the SI joint.
Figure 21:
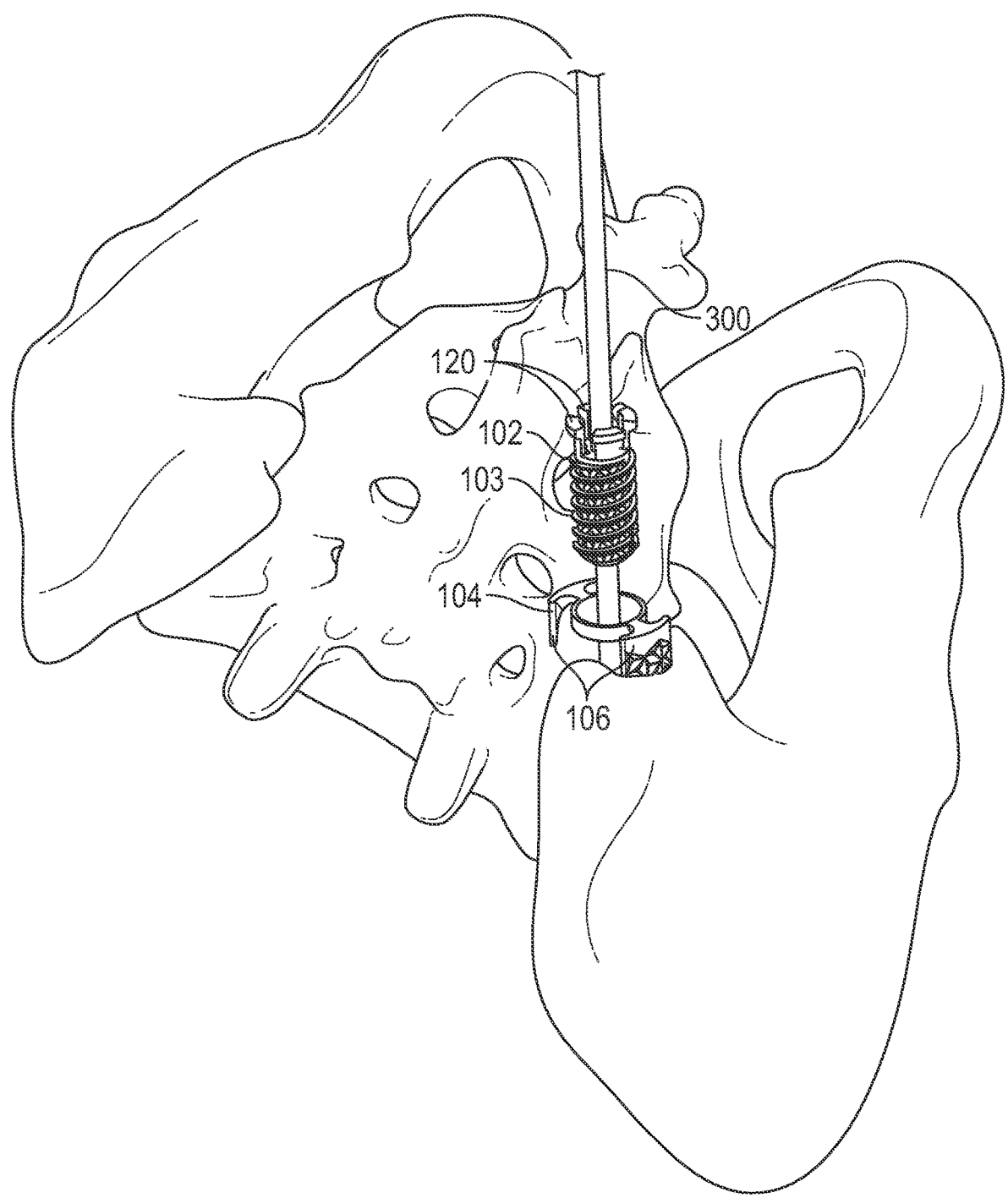
FIG. 21 illustrates a perspective view of an embodiment of the implant system inserted into the SI joint.
Figure 22:
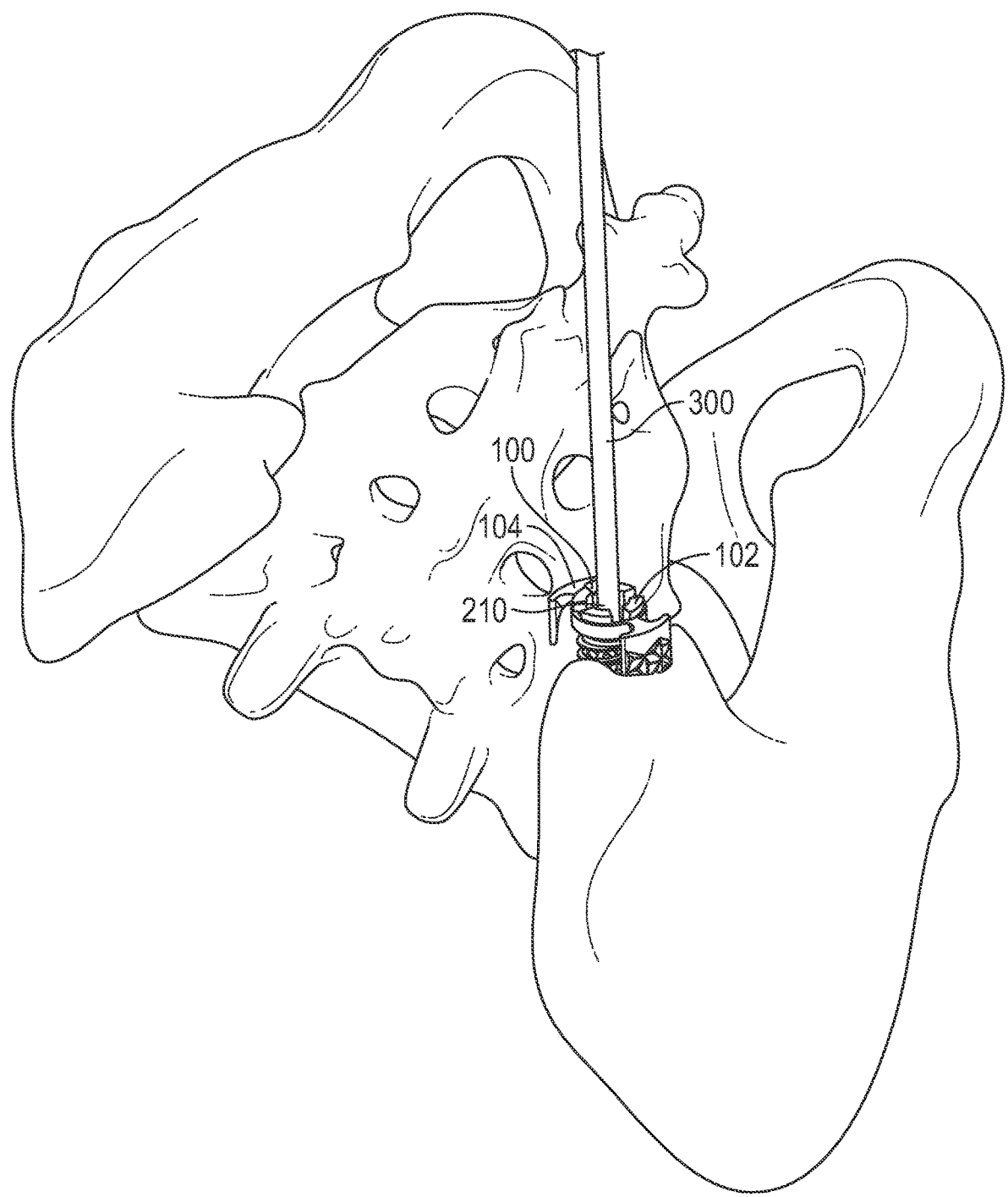
FIG. 22 illustrates a perspective view of an embodiment of the implant system during insertion into the SI joint.
Figure 23:
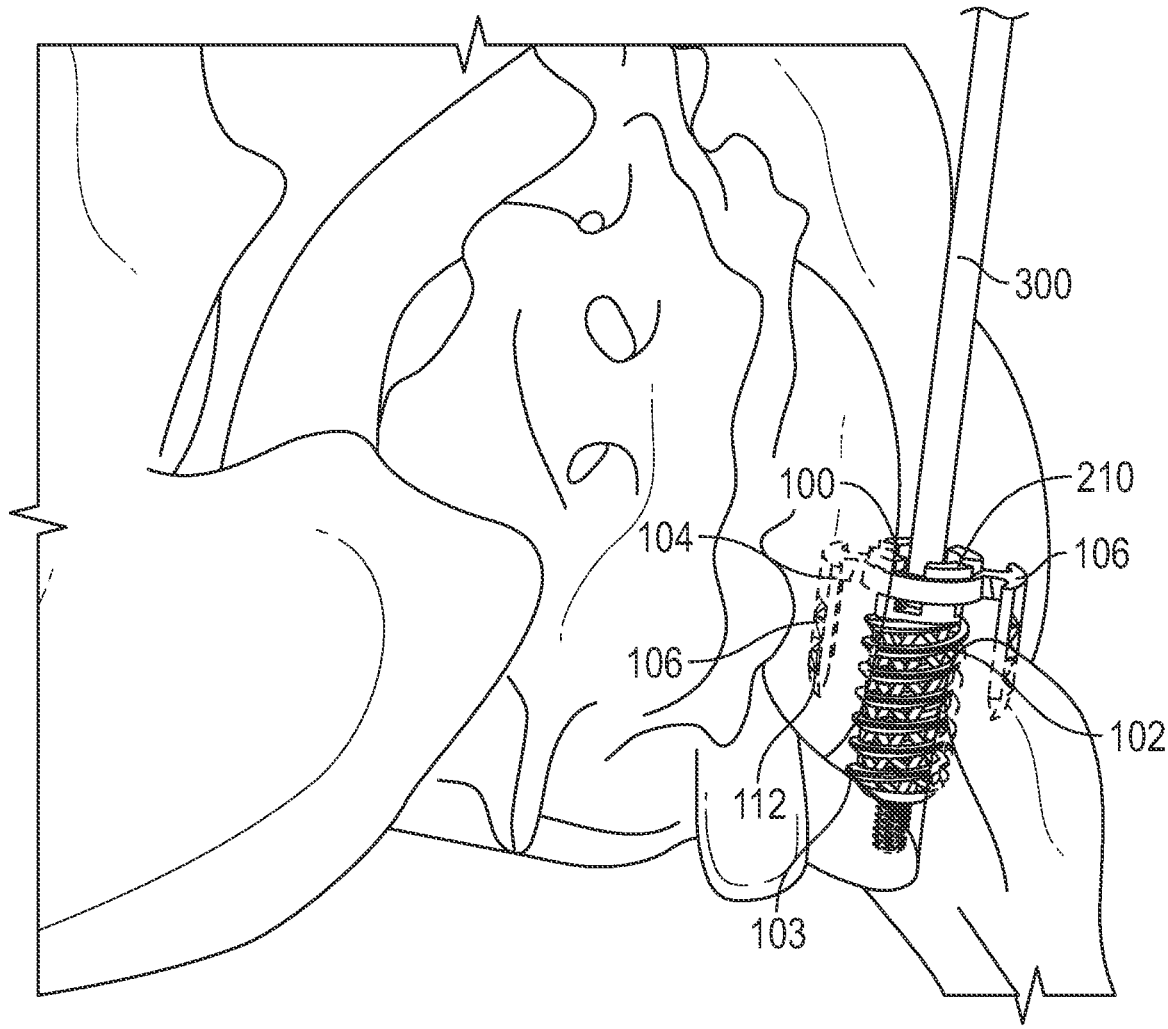
FIG. 23 illustrates a perspective view of an embodiment of the implant system during insertion into the SI joint.
Figure 24:
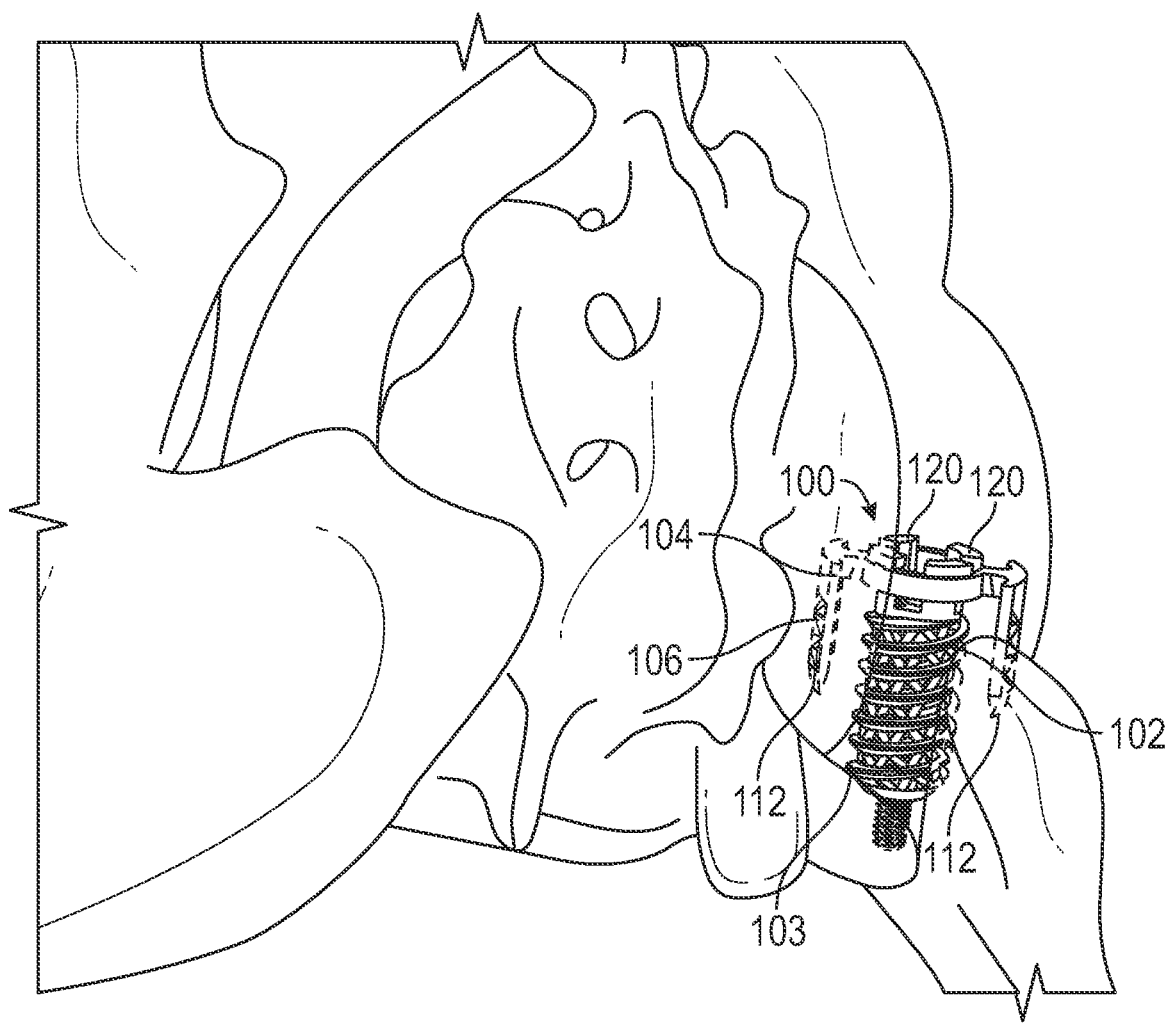
FIG. 24 illustrates a perspective view of an embodiment of the implant in the SI joint.

FIGS. 15, 16, and 17, show another version of an inserter 200 that is connected to the primary implant like a tower mechanism. The tower mechanism clips on or cinches onto the primary implant 102. The secondary implant 104 can then be driven into the bone. The tower mechanism can be released once the primary implant 102 and secondary implant 104 are inserted. A shaft 202 can grip an outer head of the primary implant 102 while a threaded rod, such as threaded rod 212 keeps the inserter 200 attached to the primary implant.

Figure 30:
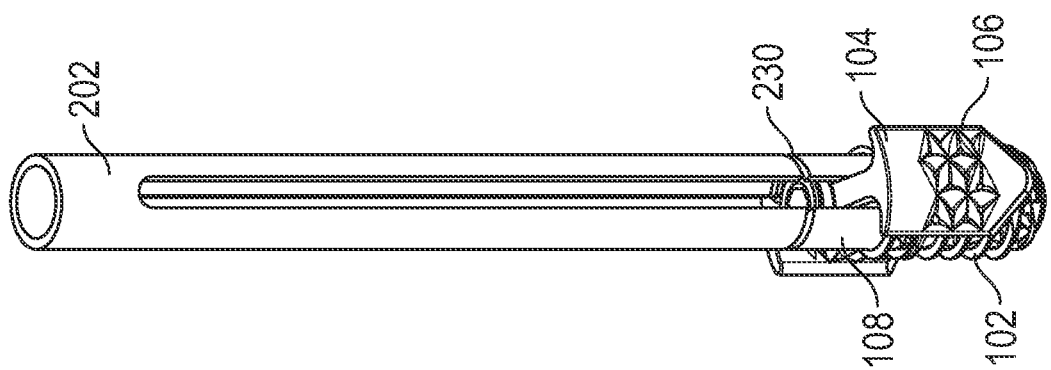
FIG. 30 illustrates a perspective view of an implant having extended tabs.
Figure 29:
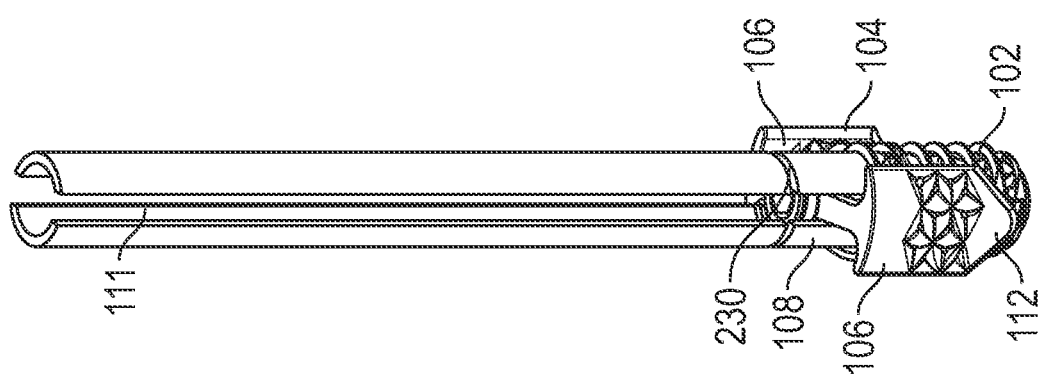
FIG. 29 illustrates a perspective view of an implant having extended tabs.

FIGS. 29 and 30 show alternative embodiments of the implant system 100 having extended tabs 108 of the primary implant including a frangible joint or break off point 230. A superior portion of the extended tabs 108 can be broken off from the tabs after the implant system 100 is positioned within the SI joint. The extended tabs 108 can serve as an inserter and minimize instrumentation required to implant the implant system. The extended tabs 108 may act as a dilator for a working channel 111 for delivery of the secondary implant, the connection mechanism 110, and/or any other components of the implant system 100. In some embodiments, a broach or punch can be placed through the channel 111 prior to the secondary implant to create a pathway for the secondary implant, for example, if bone is dense or hard. In certain embodiments, a set screw can be placed down the channel. In certain embodiments, the extended tabs can provide a channel for packing bone graft over the implant system 100. In some embodiments, the implant system 100 can be implanted within the SI joint (and countersunk in some embodiments), and bone graft can be packed over the implant system 100 through the channel formed by the extended tabs 108. After the bone graft is introduced, the extended tabs can be broken at the frangible joint or break off point 230 and the superior portion of the extended tabs can be removed.

Figure 31:
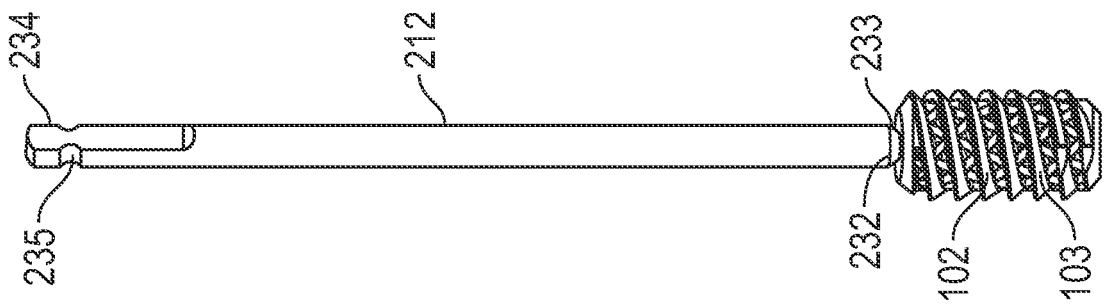
FIG. 31 illustrates a perspective view of an implant coupled to a rod.

FIG. 31 depicts an alternative embodiment of a rod 212 in which the rod 212 is coupled to the primary implant 102 by a frangible joint or break off point 232. As shown in FIG. 31, the rod 212 can have a distal end 233 and a proximal end 234, wherein the proximal end contains notches 235 for connecting to handles or for gripping. The frangible joint or break off point 232 can be formed by a sharp angle at the distal end 233 of the rod 212. The frangible joint or break off point 232 can be broken in response to bending or application of torque on the rod 212.

FIGS. 18, 19, 20, 21, 22, 23, and 24 depict an embodiment of a method of implanting an embodiment of an implant system 100 in which no fastener or attachment mechanism 110 is used to keep the primary implant 102 and secondary implant 104 together. In certain embodiments, the primary implant 102 has threads or anti backout features preventing it and the secondary implant 104 from expulsing. In certain embodiments, a guidewire or rod 300 can be used to locate the SI joint. After the SI joint is located, the secondary implant 104 can be inserted first into the ilium and sacrum, as shown, for example, in FIGS. 19 and 20. For example, an inserter or driver 250 can be used to insert the secondary implant 104. After the secondary implant 104 is inserted, a drill bit with or without a surface reamer can be used to drill or ream into the SI joint to form a pilot hole for the primary implant 102. The drill bit can be removed and the primary implant 102 can be inserted over the rod or guidewire 300, as shown for example, in FIG. 21. The primary implant 102 can be advanced until the primary implant 102 bottoms out on the secondary implant 104 preventing it from going further down the SI joint, as shown, for example, in FIGS. 22 and 23. After the implant 102 is inserted into the SI joint, the guidewire or rod 300 can be removed, as shown, for example, in FIG. 24.

In certain embodiments, a head of the primary implant 102 can have a fixed or variable orientation with respect to the secondary implant 104. In certain embodiments, the head of the primary implant 102 can rotate, for example, to make up for needed trajectory change.

Figure 26:
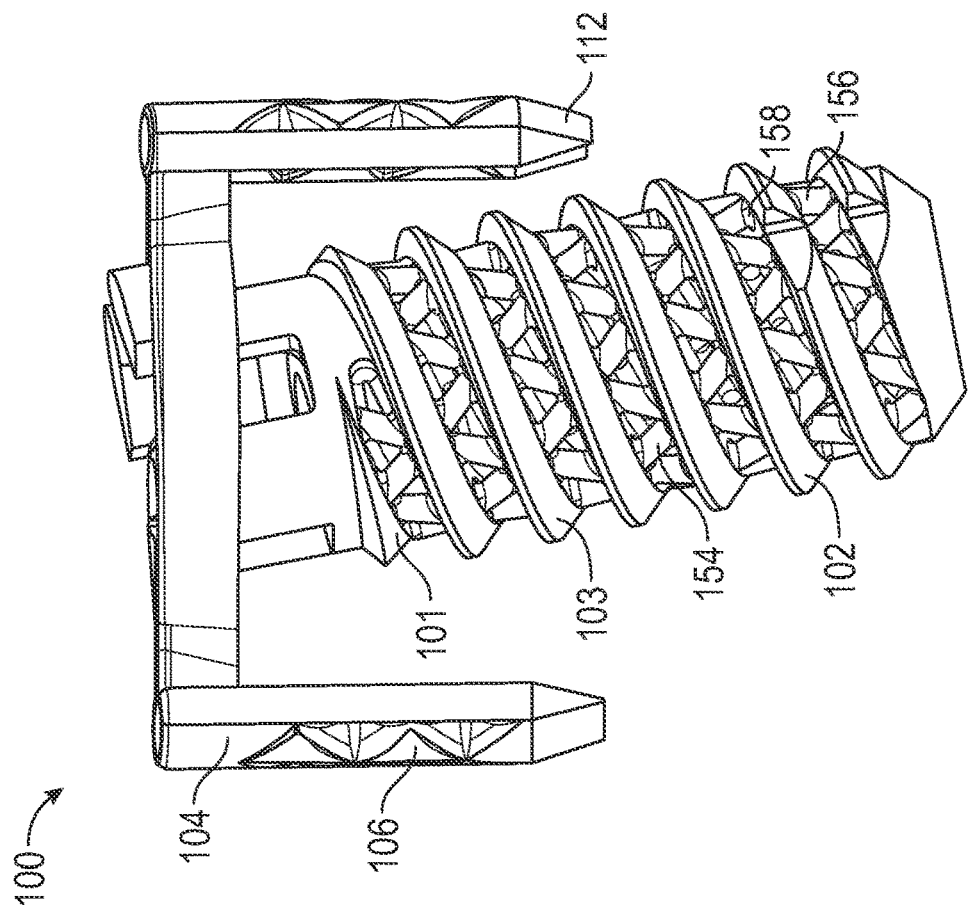
FIG. 26 illustrates a front view of an alternative rotating embodiment of the implant.
Figure 25:
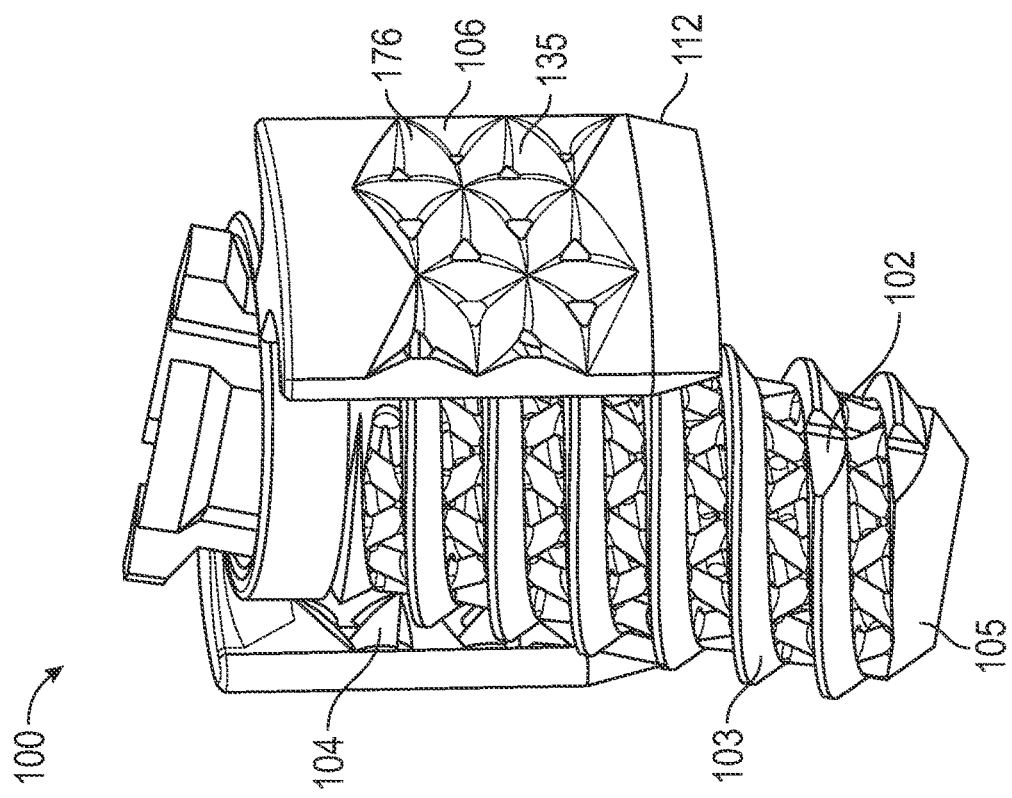
FIG. 25 illustrates a front view of an alternative rotating embodiment of the implant.

FIGS. 25 and 26 depict another embodiment of the SI joint implant system 100. The embodiment of FIGS. 25 and 26 may include any of the same or similar features or functions as any of the other embodiments described herein and vice versa. FIGS. 25 and 26 depict another embodiment of the implant system 100 in which the primary implant 102 can be received within the secondary implant 104.

FIGS. 25 and 26 show examples of rotation of the head of the primary implant 102 relative to the secondary implant 104. If the trajectory of the primary implant 102 is changed it can still seat properly in the secondary implant 104. In certain embodiments, the primary implant 102 and secondary implant 104 can have engagement features that allow the two implants to lock together. For example, the primary implant 102 and secondary implant 104 can be locked together using threads, snaps, grooves, etc.

Similarly, in certain embodiments, the secondary implant 104 of FIGS. 36A-36G can be implanted prior to the primary implant 102.

In certain embodiments, the implant system 100, as shown in FIGS. 36A-36G, can be placed using a posterior method below the posterior superior iliac spine (PSIS) to prevent instruments and the implants from being hung up during placement. The PSIS overhangs the SI joint and can be difficult for physicians to navigate. In certain embodiments, one implant system 100 can be placed in the SI joint below the PSIS. In certain embodiments, such as in a patient with weak or soft bone, a second implant system 100 can be placed above the PSIS for increased fixation.

A method for implanting the system 100, for example, as shown in FIGS. 36A-36G, is described with respect to FIGS. 37-53. Although the method is described with respect to the embodiment shown in FIGS. 36A-36G, it may be used with or modified for use with any of the other embodiments described herein. Additionally, any of the steps may be modified based on surgeon preference or anatomical variation.

As described above, the implant system 100 can be implanted using a posterior method through an incision. The incision can be approximately 1 inch in length. In certain embodiments, the incision can be made in a horizontal direction. In certain embodiments, a vertical incision may be insufficient for passage of the instruments described herein.

Figure 37B:
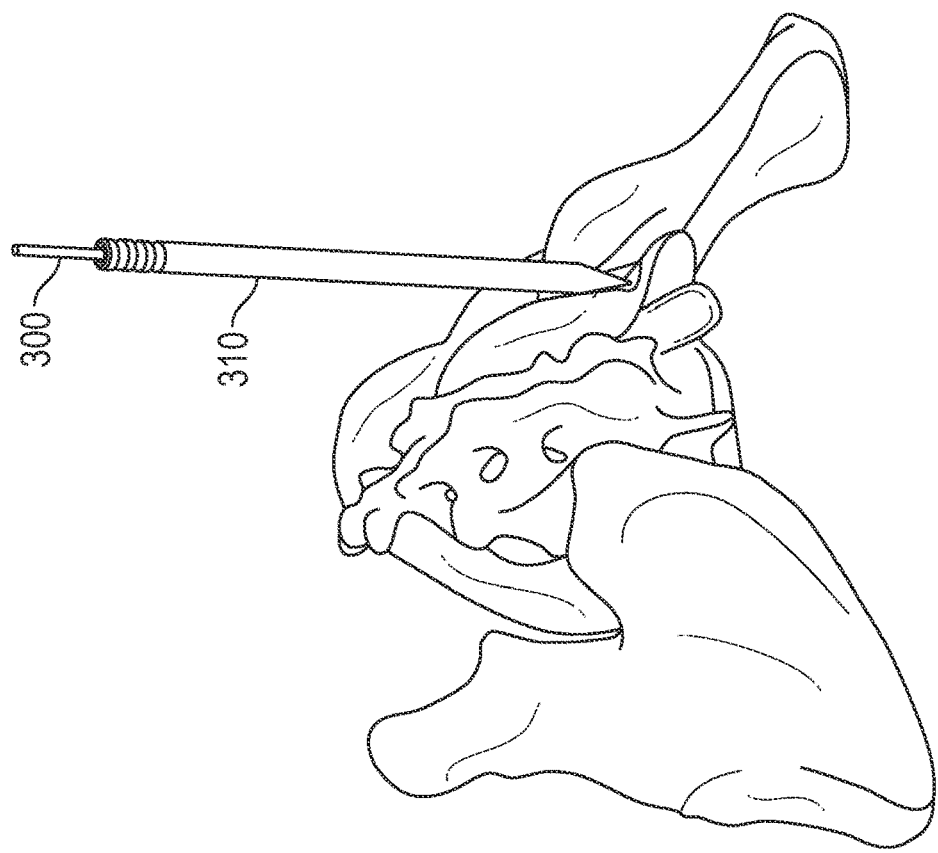
FIG. 37B illustrates a perspective view of a guidewire and SI joint locator as part of an implant system inserted into the SI joint.
Figure 37A:
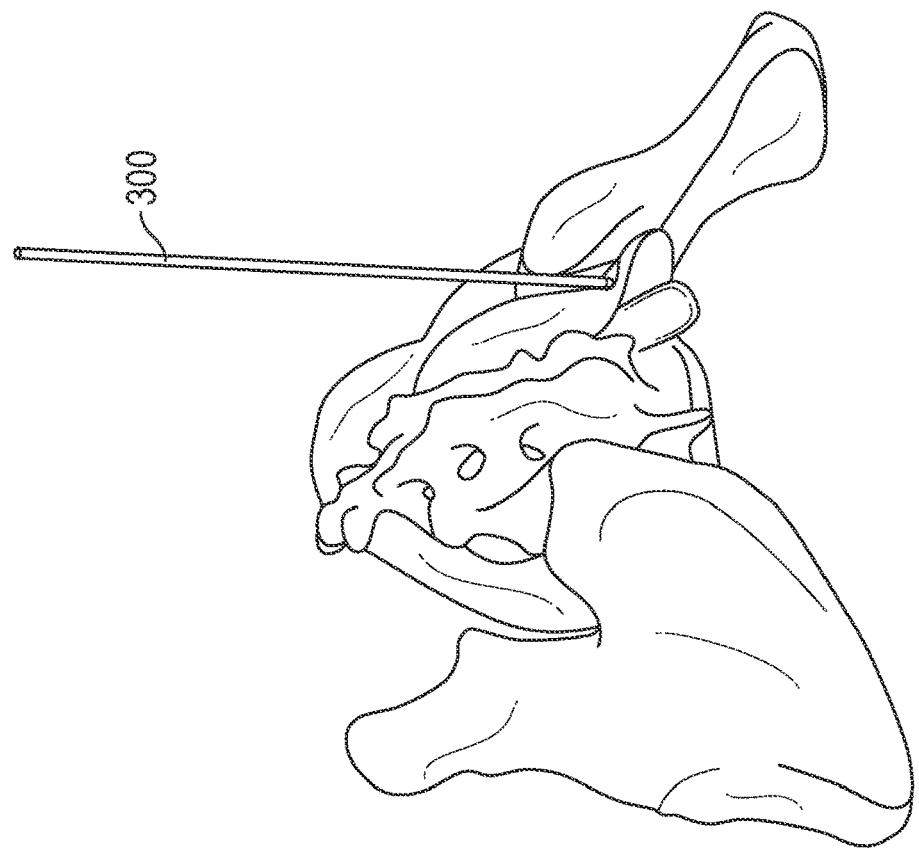
FIG. 37A illustrates a perspective view of a guidewire as part of an implant system inserted into the SI joint.

As shown in FIG. 37A, in certain embodiments, a guidewire or rod 300 can be placed into the SI joint through the incision. The guidewire 300 may be placed using fluoroscopic anterior-posterior, lateral, and/or pelvic inlet views. The fluoroscopic views may be used in any order. Any of the views may be omitted if desired. The guidewire 300 can be placed using a posterior approach. The guidewire 300 can be traversed down the SI joint to ensure that the implant system 100 is placed properly and has proper fixation.

Figure 39:
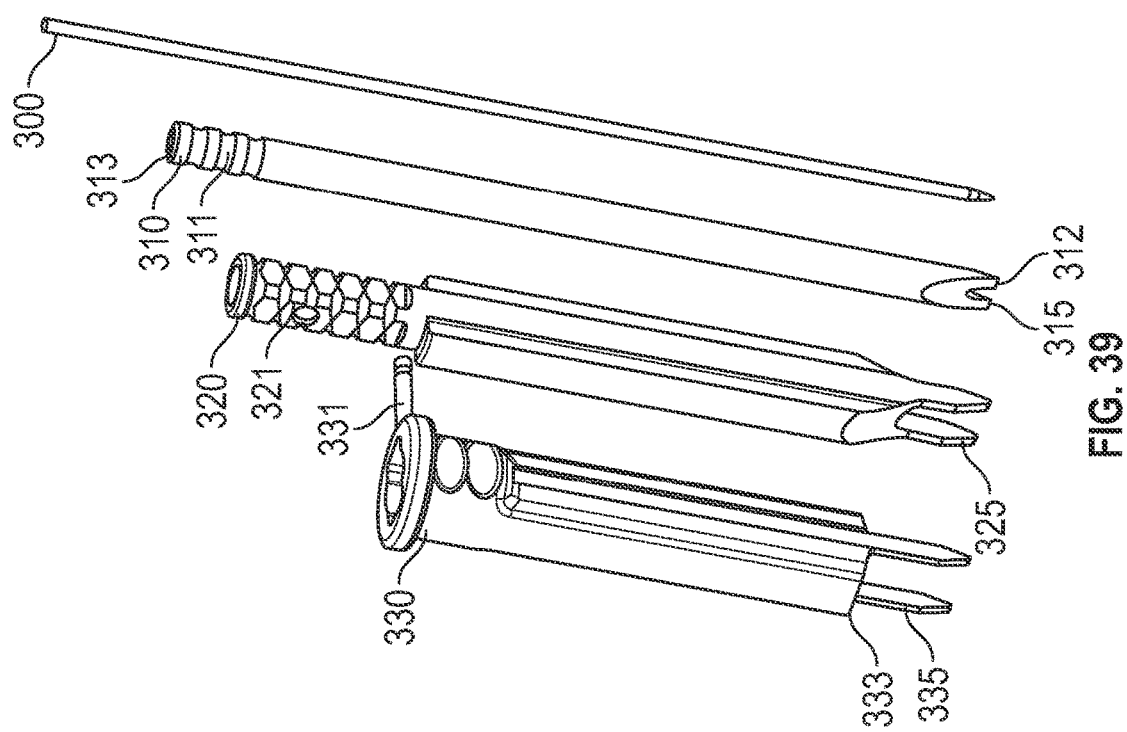
FIG. 39 illustrates the guidewire, SI joint locator, dilator, and guide as part of an implant system.

After the guidewire 300 is placed within the SI joint, an SI joint locator 310 can be placed over the guidewire 300 and into the SI joint, as shown in FIG. 37B. In some procedures, the guidewire may be omitted, and the SI joint locator 310 may be placed within the SI joint as an initial step. This may be beneficial if the SI joint is tight and prevents proper placement of the guidewire 300. The SI joint locator 310 may have a proximal end 313 and a distal end 312, wherein the distal end 312 is inserted into the joint. The SI joint locator may have ridges or a grip 311 on the distal end 312. A lumen runs through the SI joint locator so the guidewire 300 may extend therethrough. The SI locator 310 may include teeth or tangs 315 that may anchor within the SI joint, as seen in FIG. 39.

Figure 38B:
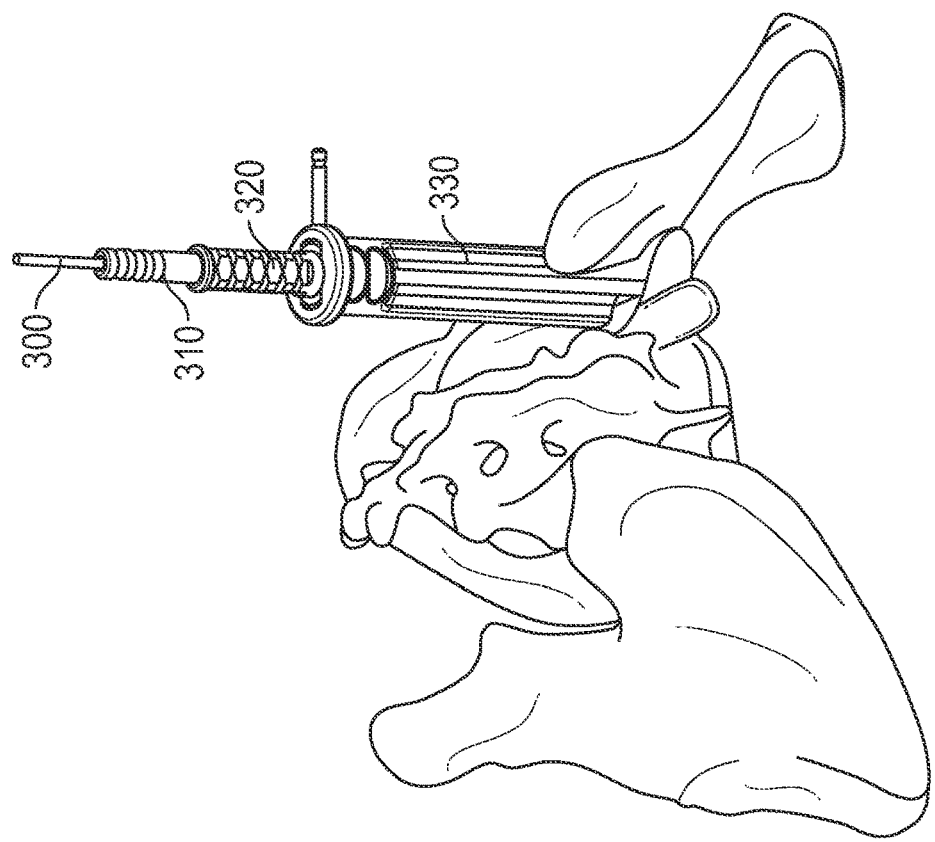
FIG. 38B illustrates a perspective view of a guidewire, SI joint locator, dilator, and guide as part of an implant system inserted into the SI joint.
Figure 38A:
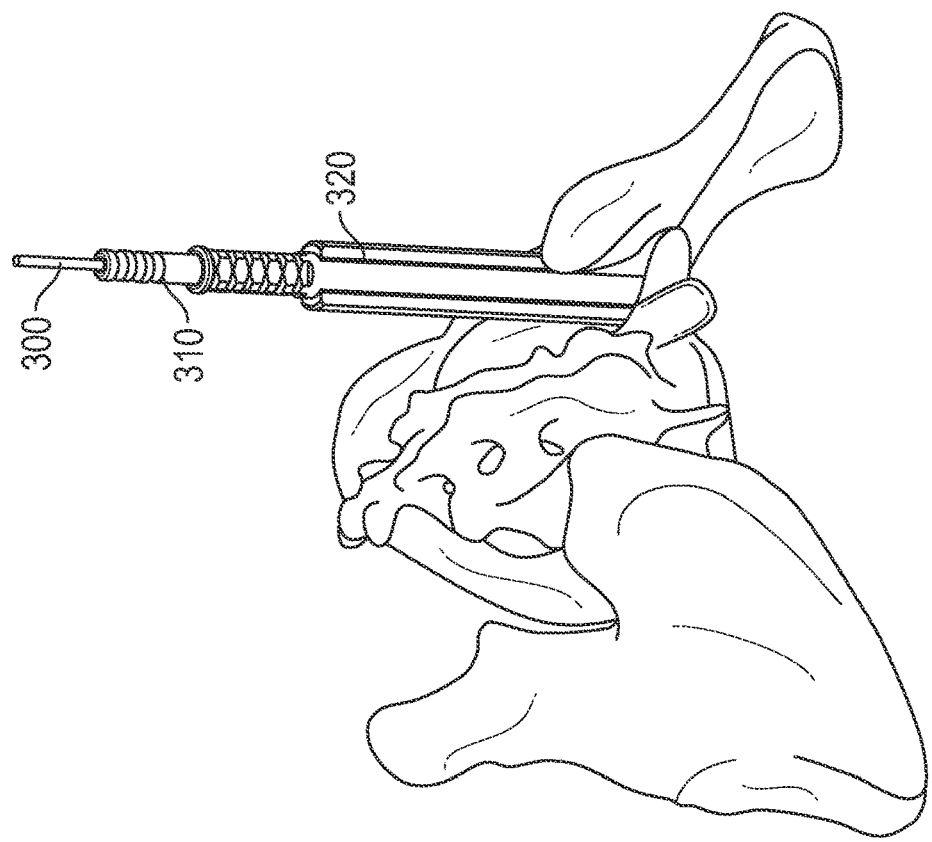
FIG. 38A illustrates a perspective view of a guidewire, SI joint locator, and a dilator as part of an implant system inserted into the SI joint.

As shown in FIG. 38A, in some embodiments, after the joint locator 310 is placed, one or more dilators 320 (for example, a single dilator or a plurality of dilators in series) may be used to dilate the tissue. The one or more dilators 320 can include teeth or tangs 325 that may anchor within the SI joint. The one or more dilators may also include handles or grips 321.

In some embodiments, the one or more dilators 320 can dilate the tissue to provide a path for a guide 330, for example, as shown in FIG. 38B. The guide 330 may act as a drill guide. In some embodiments, the guide 330 may act as a guide for one or more other instructions and/or as a guide for the secondary implant 104 and/or primary implant 102. In some embodiments, the guide 330 may be the largest dilator of the one or more dilators. Each of the dilators 320 have a central lumen to allow the dilator to be placed over smaller sized dilators or the SI joint locator 310 already placed within the joint.

Figure 40:
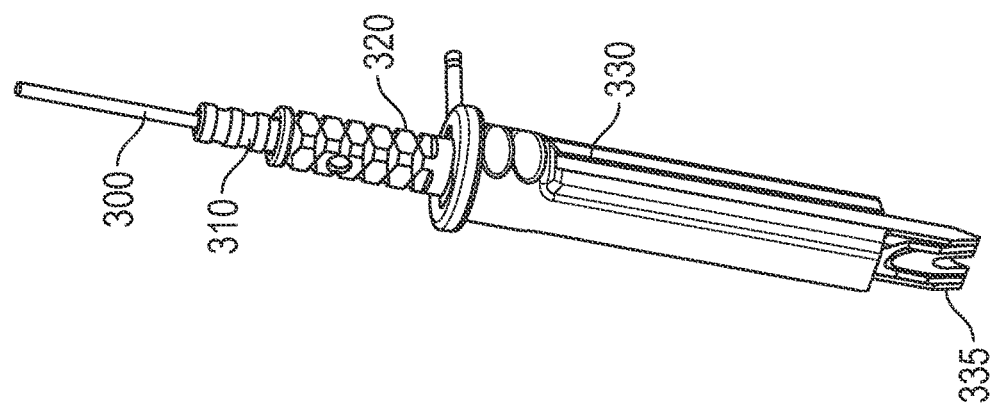
FIG. 40 illustrates a perspective view of the guidewire, SI joint locator, dilator, and guide fit together as part of an implant system.

After the one or more dilators 320 are inserted, the guide 330 can be placed within the SI joint. The guide 330 can include teeth or tangs 335 that anchor into the SI joint. The teeth or tangs may be parallel or perpendicular to the joint, for example, depending on user preference. As shown in FIGS. 39 and 40, two or more teeth or tangs 335 can be located at a base of the guide 330 to allow for anchoring and prevent slipping during drilling, broaching, bone punching and/or inserting implants. As described herein, the SI joint locator 310 and/or one or more dilators 320 may also include teeth or tangs. The guide 330 can also include a handle 331 that can be gripped during use.

Figure 41:
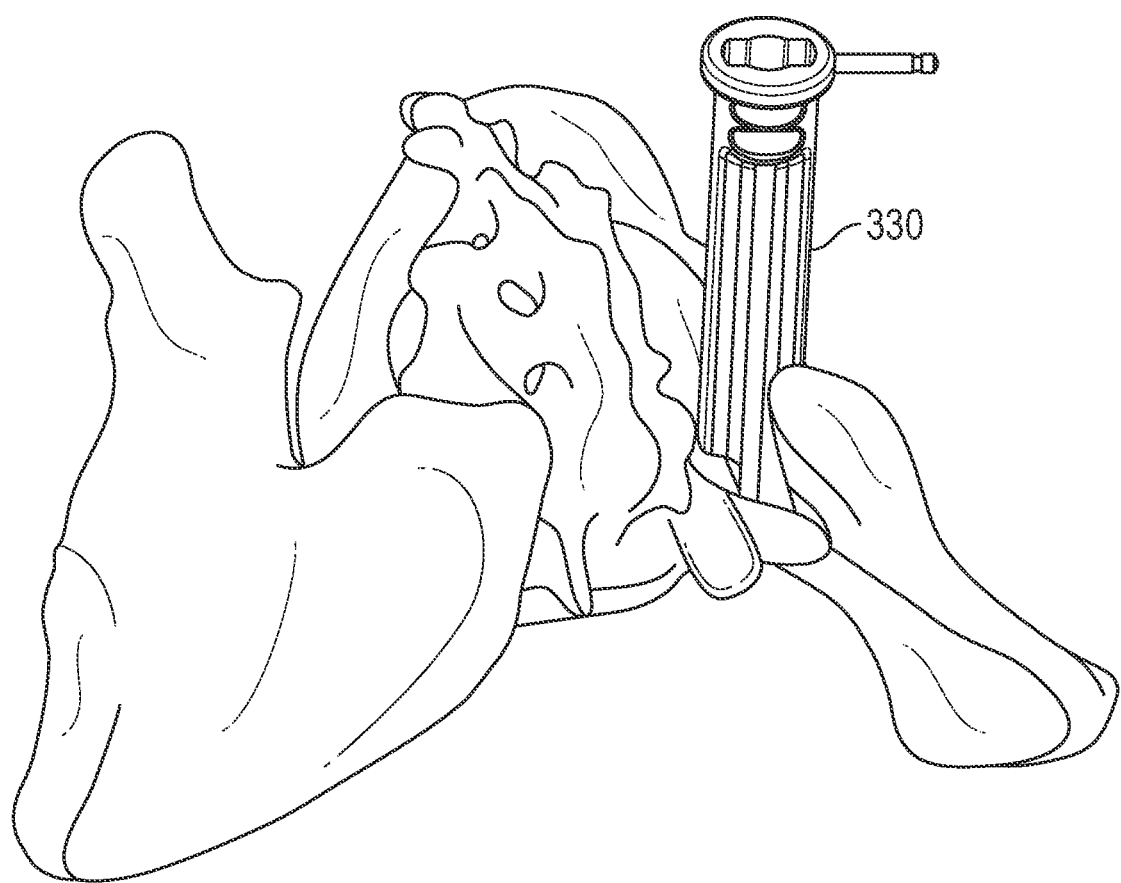
FIG. 41 illustrates a perspective view of the guide as part of the implant system in the SI joint.

Once the guide 330 is positioned within the SI joint, the guidewire 300, SI joint locator 310, and one or more dilators 320 can be removed from the guide 330 as shown, for example, as shown in FIG. 41. In some embodiments, the shape and/or dimensions of the guide 330 can be the same at the portions of a distal end 333 that contact the ilium and the sacrum. In other embodiments, the distal end 333 can have a different shape and/or dimensions on the ilium and sacral sides to match the anatomy of the patient, for example, a longer sacral side or ilium side. The distal end 333 or distal surface of the guide 330 can be shaped, dimensioned, or otherwise configured to sit flush within the SI joint on both the sacral side and ilium side, for example, to allow a drill bit and/or implant inserters to provide accurate depths for accurate implant insertion and prevent the implants from sitting proud of the SI joint or being countersunk too deep.

Figure 43:
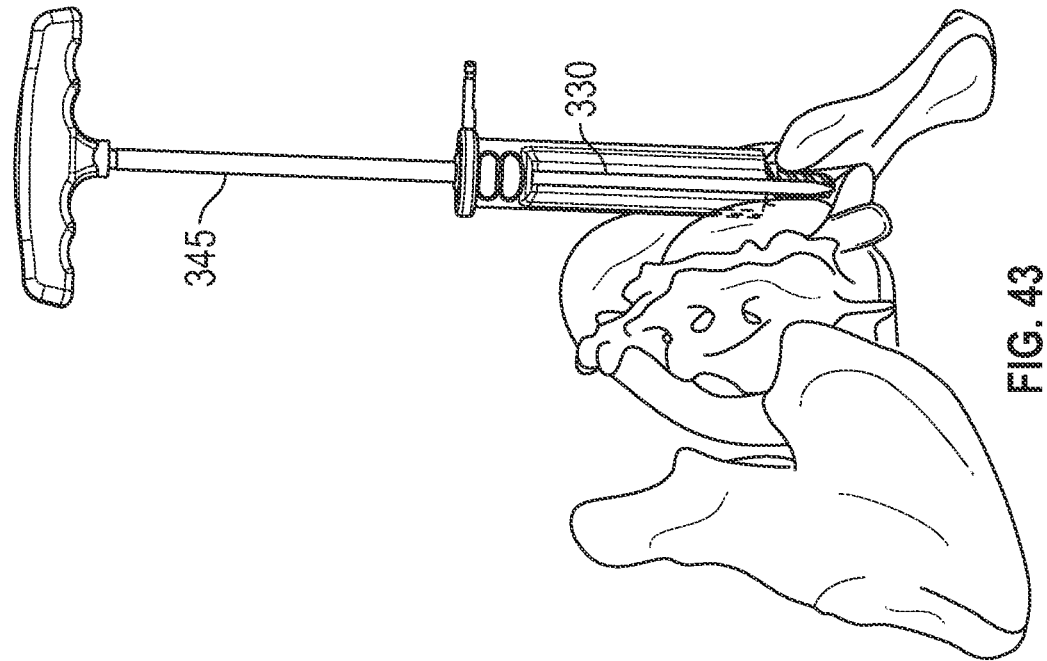
FIG. 43 illustrates a perspective view of a handle, drill tool, and implant as part of an alternative embodiment of an implant system inserted into the SI joint.
Figure 42:
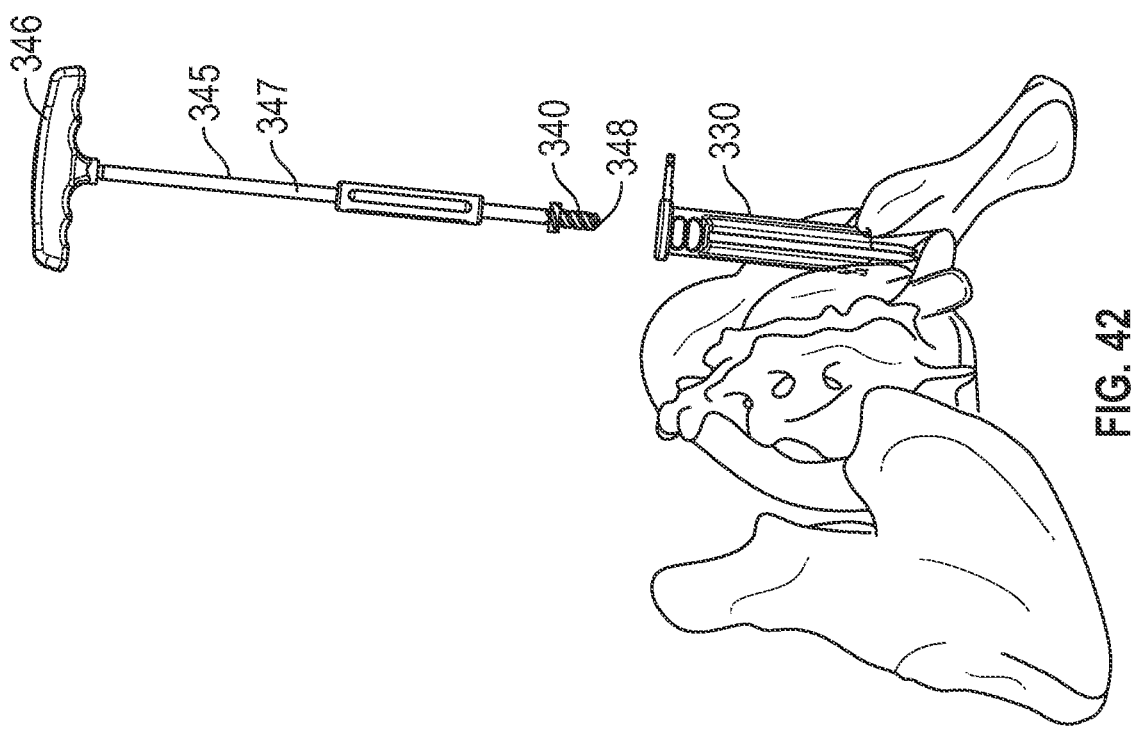
FIG. 42 illustrates a perspective view of a handle, drill tool, and implant as part of an embodiment of an implant system inserted into the SI joint.
Figure 44:
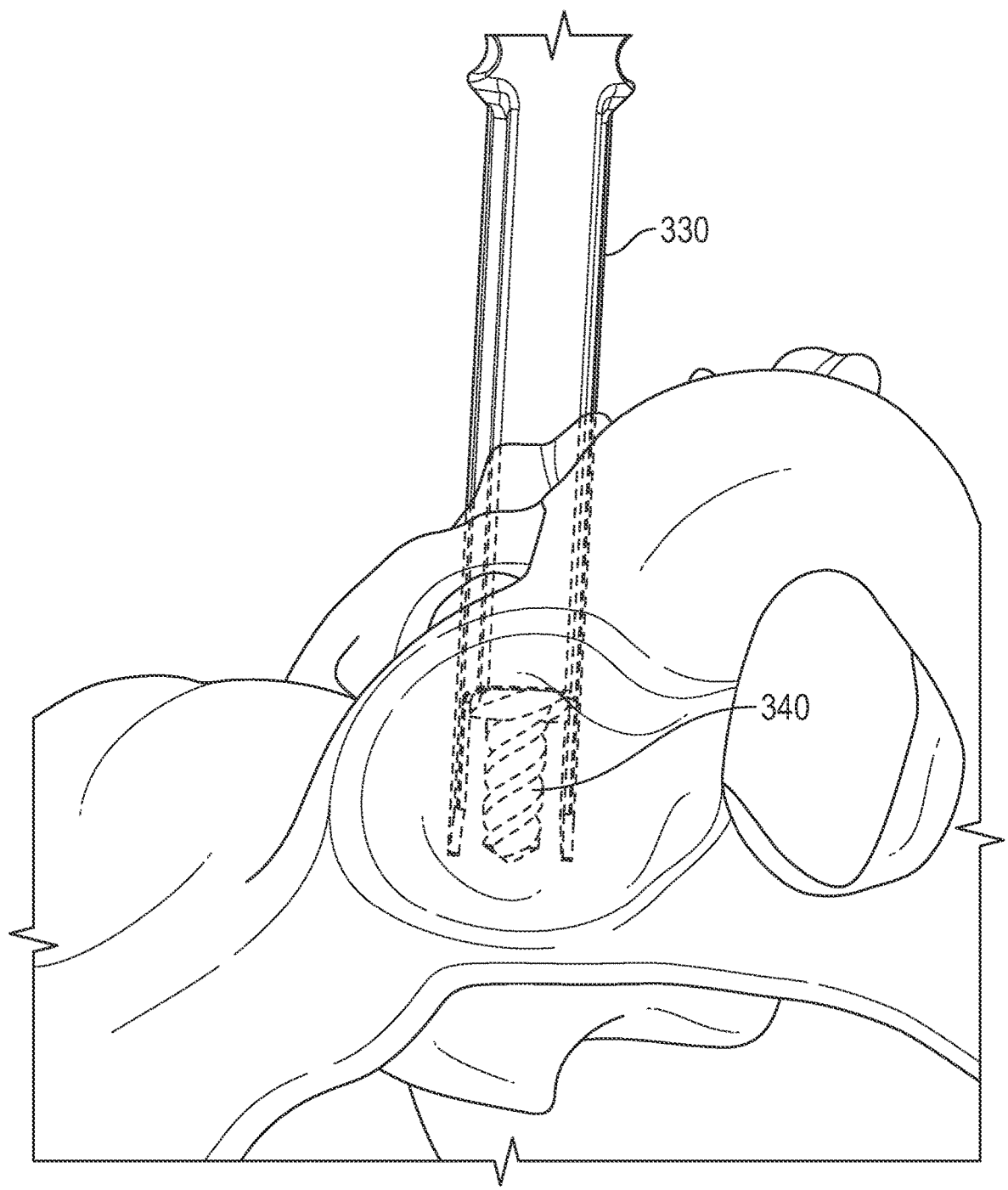
FIG. 44 illustrates a side view of a drill bit and a guide as part of an implant system in an embodiment.

After the guidewire 300, SI joint locator 310, and one or more dilators 320 are removed, a drill bit 340 of a drill tool 345 may be placed down the guide 330 to create a pilot hole for the primary implant 102, as shown in FIGS. 42-44. The drill tool 345 includes a handle 346 connected to a shaft 347 leading to a distal end 348. The guide 330 can be variable to allow for the drill bit to be angled so that a user can change trajectory. Alternatively, the guide 330 may be fixed so as to allow little or no variability in drill angle or position when inserted within the SI joint. The drill bit may be cannulated or non-cannulated.

In an alternative embodiment, an all-in-one inserter may be used. FIGS. 75A-75D illustrate an embodiment of an all-in-one inserter 420 system. The all-in-one inserter 420 saves time, makes insertion less cumbersome, and prevents cross threading or mal-insertion of the two implants. With the all-in-one inserter 420, the secondary implant 104 is tightened to the end of an inserter body 421. The primary implant 102 is threaded onto the end of a driver 422. The top of the inserter body 421 may be maleated to position the secondary implant 104. The secondary implant 104 may be bridged across the SI joint into the ilium and sacrum. Once the secondary implant 104 is flush or counter-sunk into the joint, the driver 422 coupled to the primary implant 102 is placed down the inserter body 421 to thread the primary implant 102 through the secondary implant 104.

In some embodiments, shown in FIG. 75D, there may be a nut 423 positioned on threading 424 at the top of the driver 422. The threading 424 may contain an immovable stopper 425 at the top to prevent the nut 423 from completely unthreading from the driver 422. This is to prevent the nut 423 from disengaging and getting lost during the cleaning process. When the driver 422 is positioned within the inserter body 421 and the nut 423 is threaded down towards the driver 422, shown in FIG. 75C, the driver 422 and inserter body 421 are tightened together, and the secondary implant 104 is tightened against the inserter body 421. In some embodiments, there may be more than one nut on the threading.

FIGS. 75A and 75B illustrate an all-in-one inserter 420 system with an attached handle 331 which may be used for threading the primary implant 102 into position. The handle can be twisted to insert the primary implant 102 into the joint. Once the primary implant 102 is threaded down, the all-in-one inserter 420 may be released from both implants by threading the nut 423 away from the driver 422, as shown in FIGS. 75A and 75B. Once the nut is threaded up, the driver can then be unscrewed from the primary implant. The user may use a ratcheting handle or non-ratcheting handle to thread the primary implant down.

Figure 45:
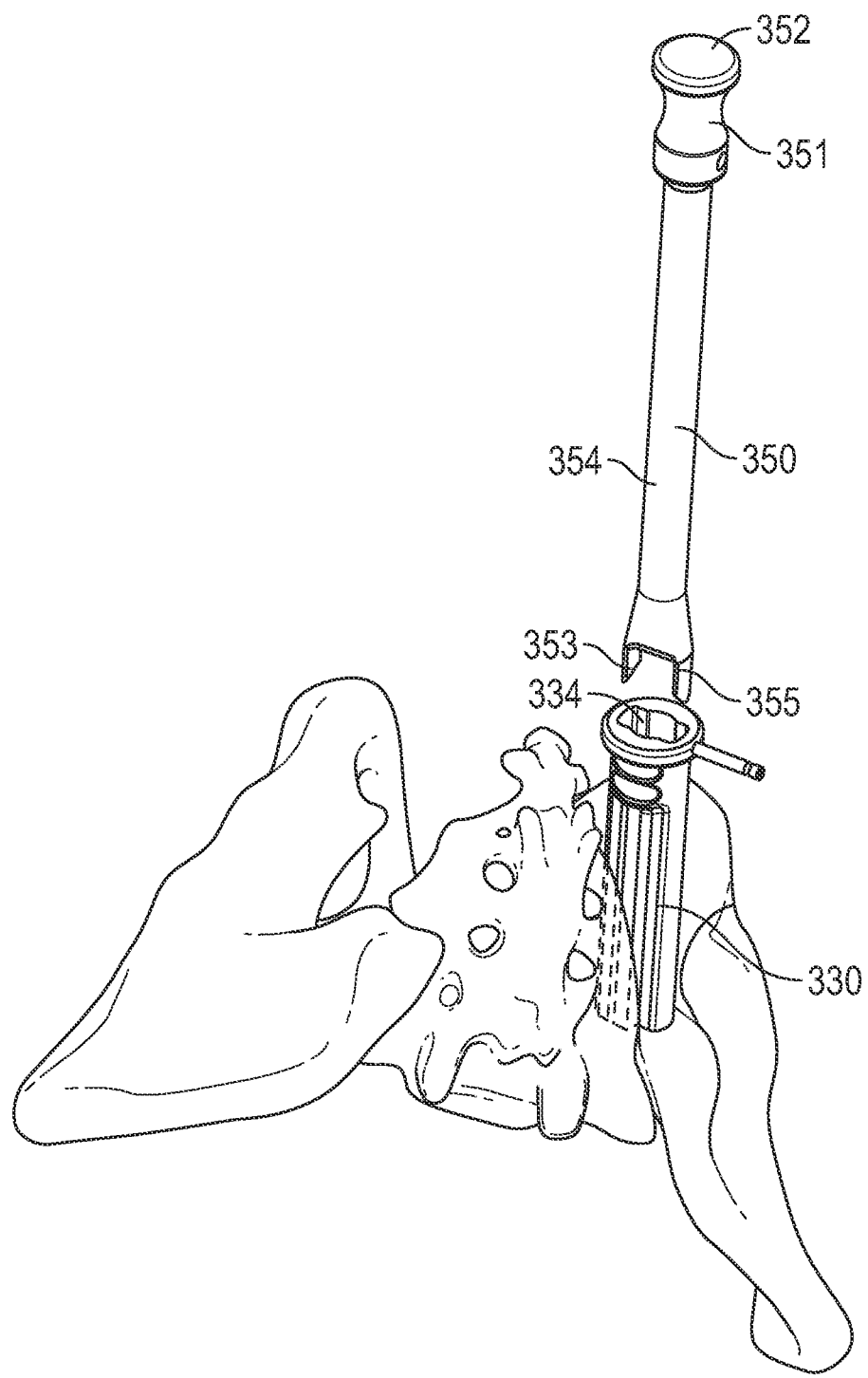
FIG. 45 illustrates a perspective view of a guide and bone punch as part of an embodiment of an implant system inserted into the SI joint.
Figure 46:
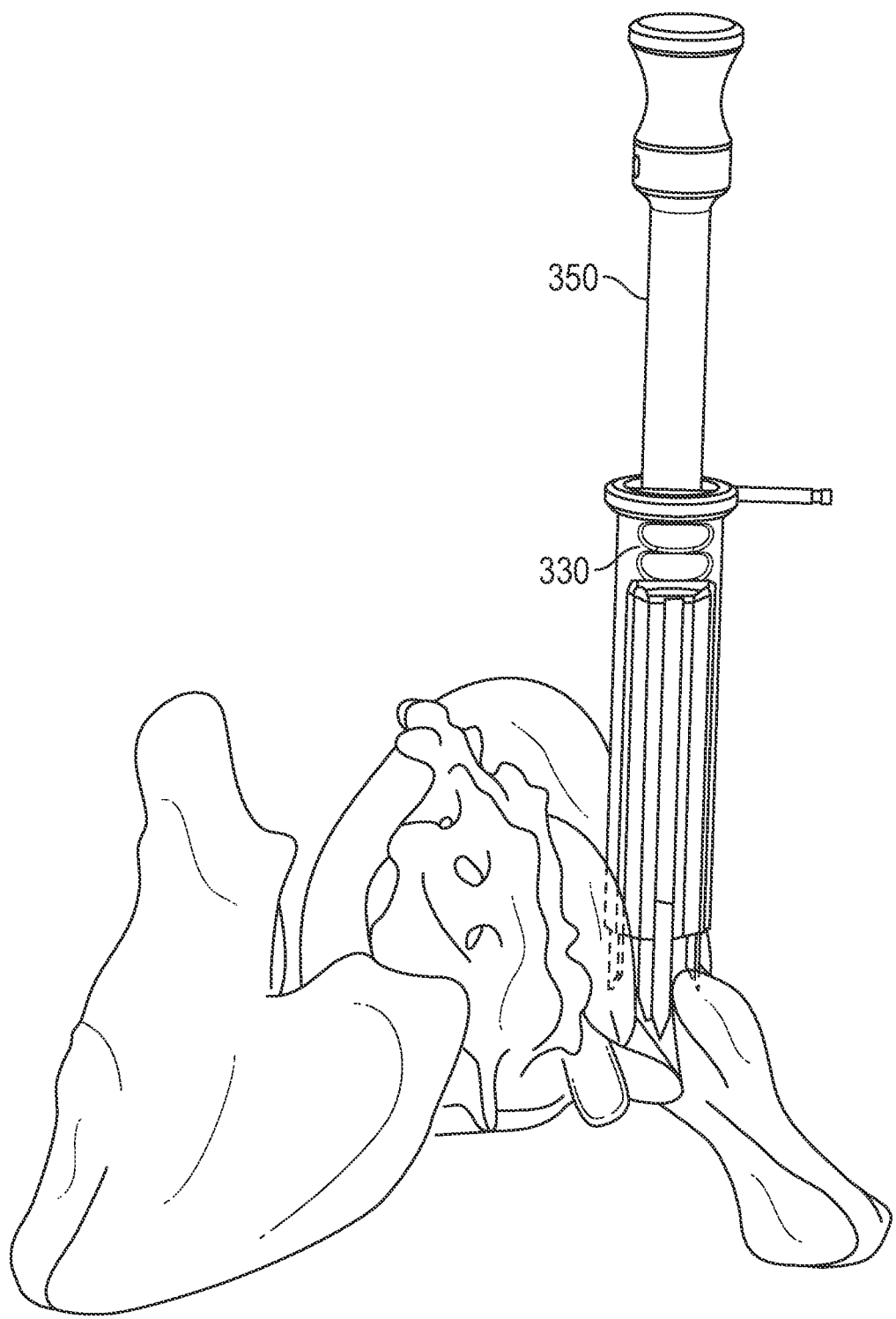
FIG. 46 illustrates a perspective view of a guide and bone punch as part of an alternative embodiment of an implant system inserted into the SI joint.

As shown in FIGS. 45 and 46, after the pilot hole is created with the drill bit 340, a bone punch 350 may inserted through the guide 330 and used to create a path for the secondary implant 104 or anchors. In some embodiments, the guide 330 may provide a pre-set trajectory for the punch to prevent variability in punch placement. The bone punch 350 includes a handle 351 at its proximal end 352, protrusions 355 at its distal end 353 for punching into bone, and a shaft 354 extending therebetween. The guide 330 may contain channels or slots 334 that receive the protrusions 355. These slots 334 can be shaped and dimensioned to prevent rotational movement of the protrusions 355 within the guide 330, for example, to maintain a pre-set trajectory of the bone punch as it is advanced through the guide 330.

Figure 47A:
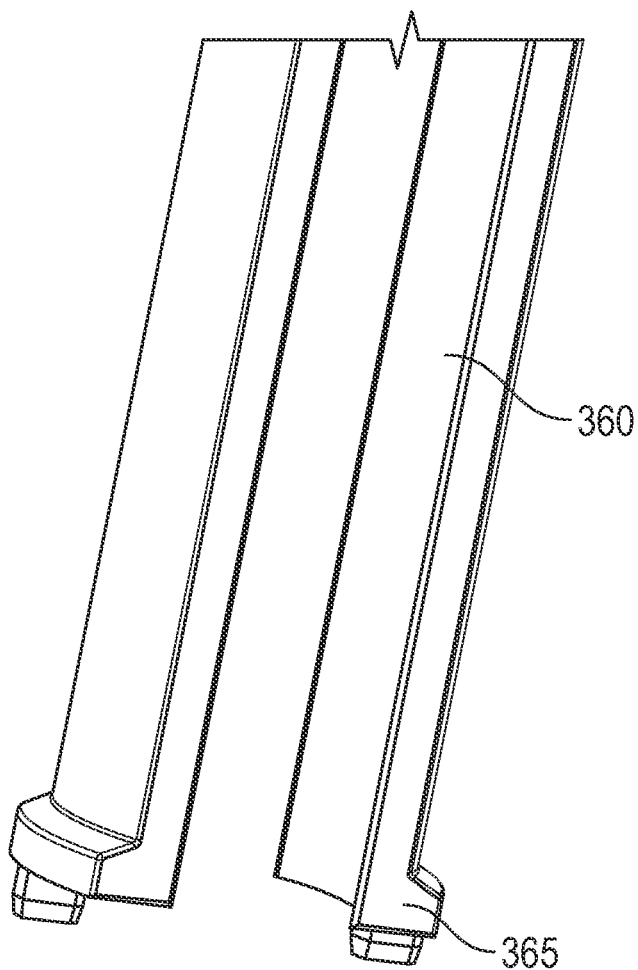
FIG. 47A illustrates an enlarged perspective view of an end of an implant inserter and implant of an implant system.
Figure 47A:
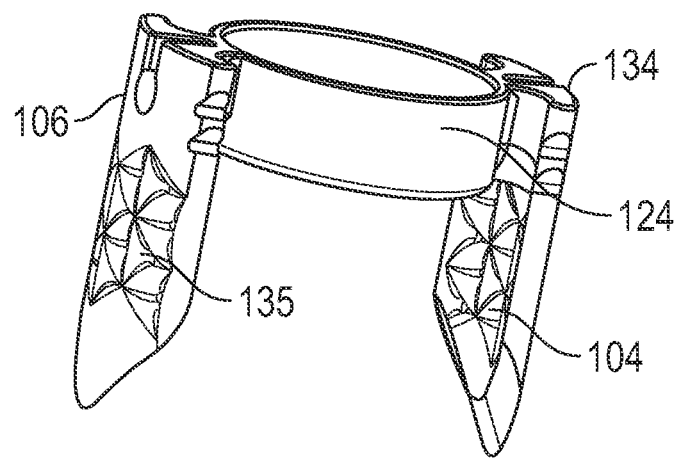
Figure 47C:
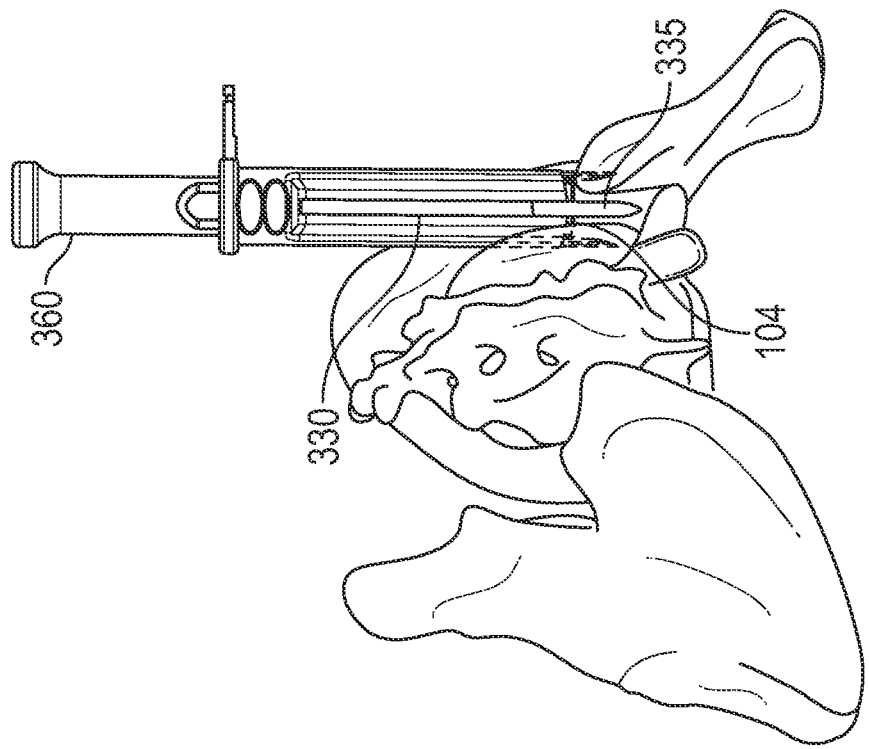
FIG. 47C illustrates a perspective view of an implant inserter inserted into a guide within the SI joint.
Figure 47B:
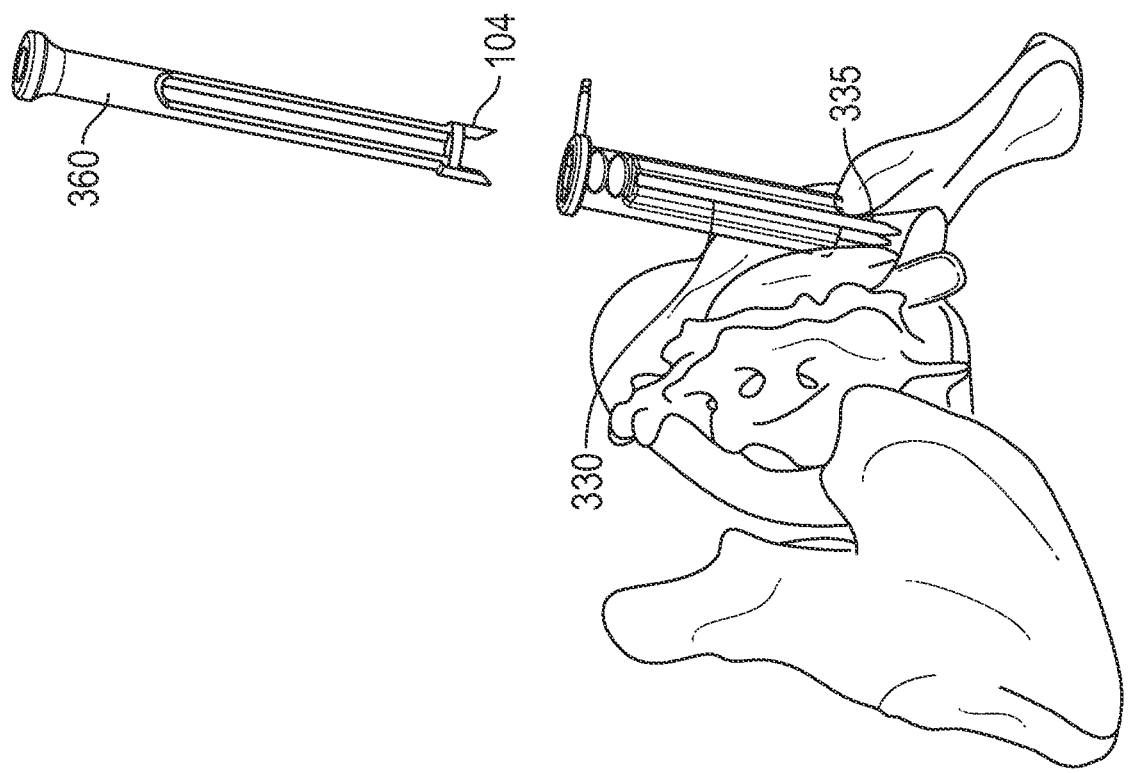
FIG. 47B illustrates a perspective view of a guide and an implant inserter as part of an embodiment of an implant system inserted into the SI joint.
Figure 48:
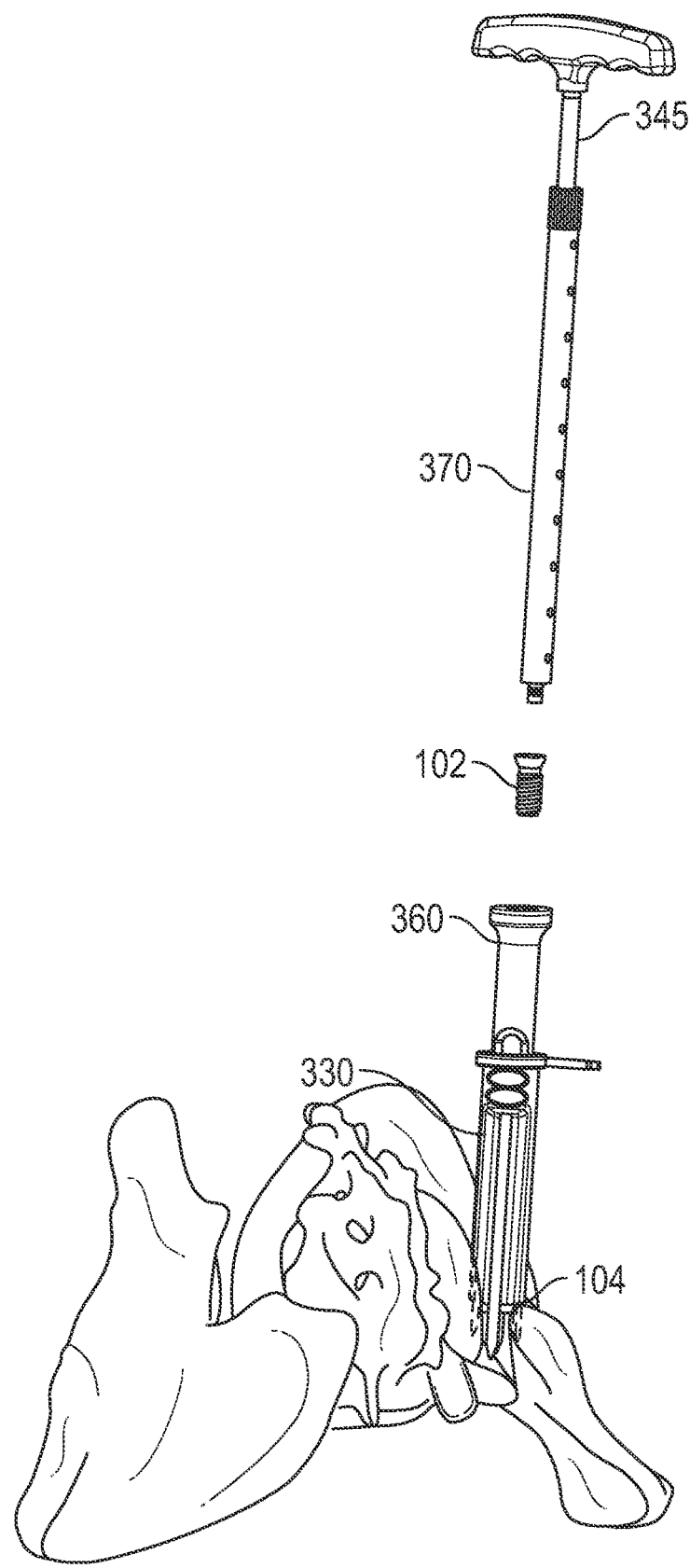
FIG. 48 illustrates a perspective view of a handle, guide, and inserter of an embodiment of an implant system.
Figure 49:
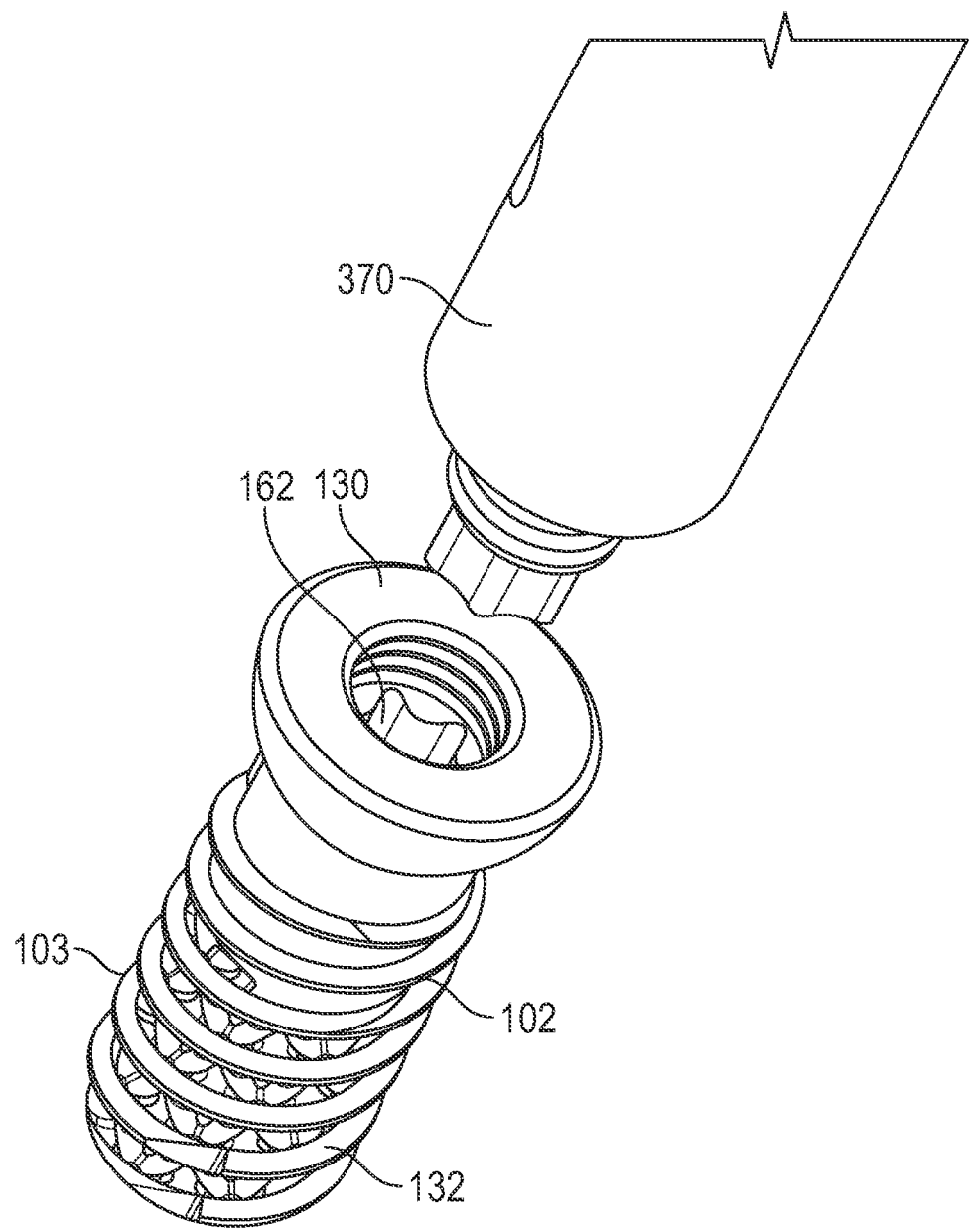
FIG. 49 illustrates an enlarged perspective view of an embodiment of the end of inserter next to an implant.
Figure 51:
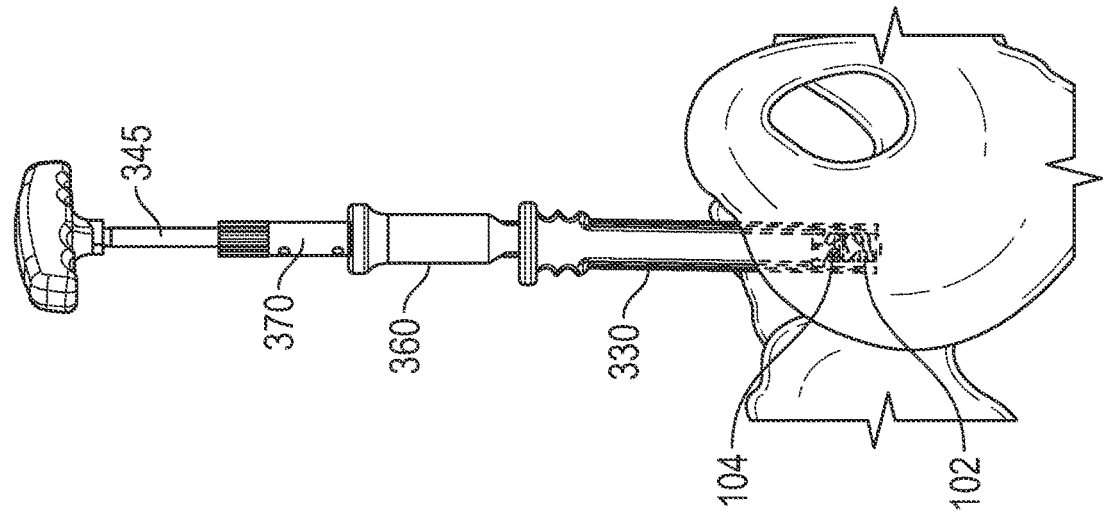
FIG. 51 illustrates an alternative perspective view of one embodiment of an implant tool including a drill tool, implant inserter, dilator, and guide as part of an implant system.
Figure 50:
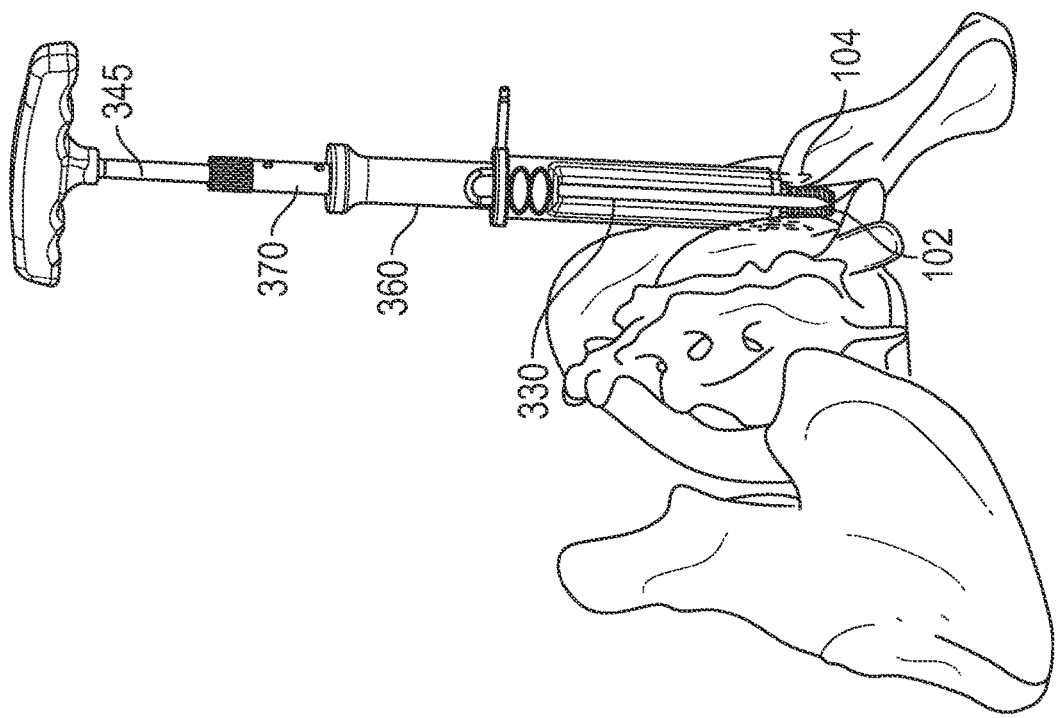
FIG. 50 illustrates a perspective view of one embodiment of an implant tool including a drill tool, implant inserter, dilator, and guide as part of an implant system.

Following use of the bone punch 350, the secondary implant 104 can be inserted through the guide 330. The secondary implant 104 can be inserted using an implant inserter 360, as shown in FIGS. 47A-47C. For some patients, for example if the bone is sufficiently soft, use of the bone punch instrument may be omitted. In such embodiments, the anchors or secondary implant 104 can be inserted using the implant inserter 360 without use of a bone punch.

As shown in FIG. 47A, the implant inserter 360 can include mating features 365 (for example, mating tabs or protrusions) configured to engage corresponding mating features 134 of the secondary implant 104. The mating features 134 can be in the form of one or more recesses or slots. The mating features 134 can be positioned within the ring 124 or within the anchors 106. For example, as shown in FIG. 47A, each of the anchors 106 includes a mating feature 134 in the form of a slot or recess configured to receive a complementary mating feature 365 of the implant inserter 360 in the form of a tab or protrusion. Additionally, the implant inserter 360 may have a handle or a grip that may be rubber or silicone to facilitate gripping by the surgeon.

In some embodiments, these slots 334 of the guide 330 can be configured to receive the anchors 106 of the secondary implant 104, for example, to maintain a pre-set trajectory of the anchors 106 as they are advanced through the drill guide to a surgical location (e.g., into the path created by the bone punch 350). The slots 334 can be shaped and dimensioned to prevent rotational movement of the protrusions 355 within the guide 330

The anchors 106 may be driven into the ilium and sacrum to allow for stabilization and transfixing the SI joint from a posterior approach. In certain embodiments, one of the anchors 106 can be driven in each side of the ilium and sacrum. In certain embodiments, the anchors 106 may include windows or openings 135 for bone ingrowth and/or barbs to prevent the anchors from backing out. The secondary implant 104 can be driven until it is countersunk such that the implant 104 is not proud of the SI joint.

After the implant 104 is positioned at the desired location relative to the SI joint (e.g., countersunk such that it is not proud of the SI joint), the screw or primary implant 102 can be inserted into the SI joint through the opening 126 of the ring 124. For example, as shown in FIGS. 48-51, the primary implant 102 can be inserted using an implant inserter 370. The implant inserter 370 may contain mating hardware at the distal end to couple with the primary implant 102. In some embodiments, the primary implant 102 can be inserted through a lumen 361 within the implant inserter 360 while the implant inserter 360 is positioned within the guide 330.

In certain embodiments, the ring 124 may allow for polyaxial movement of the primary implant 102 to allow for different angles of the primary implant 102 relative to the ring 124. In other embodiments, the position of the implant 102 can be fixed to prevent any movement between the primary implant 102 and the anchors 106.

The implant inserter 370 can be used to drive the implant 102 through the opening 126 of the ring 124 until the implant 102 locks or stops. For example, the implant 102 can include threads on a collar that can thread into the ring 124 that allow for a positive stop and prevent over-inserting of the implant 102. This may also prevent stripping of the implant 102 in the bone.

Figure 53:
FIG. 53 illustrates an alternative view of an embodiment of the implant system within the SI joint.
Figure 52:
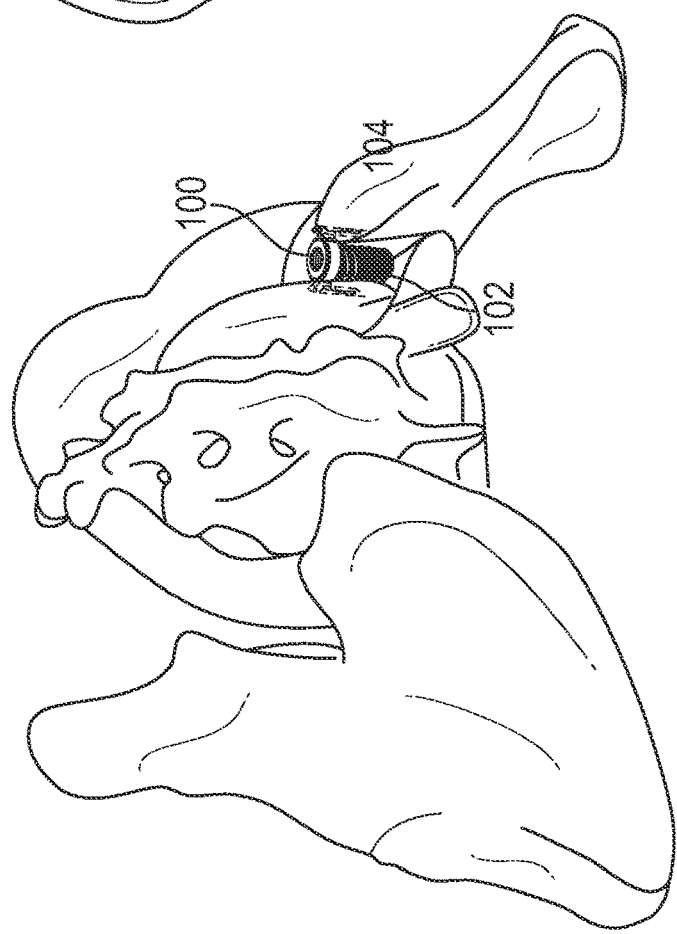
FIG. 52 illustrates a perspective view of an embodiment of the implant system within the SI joint.
Figure 54B:
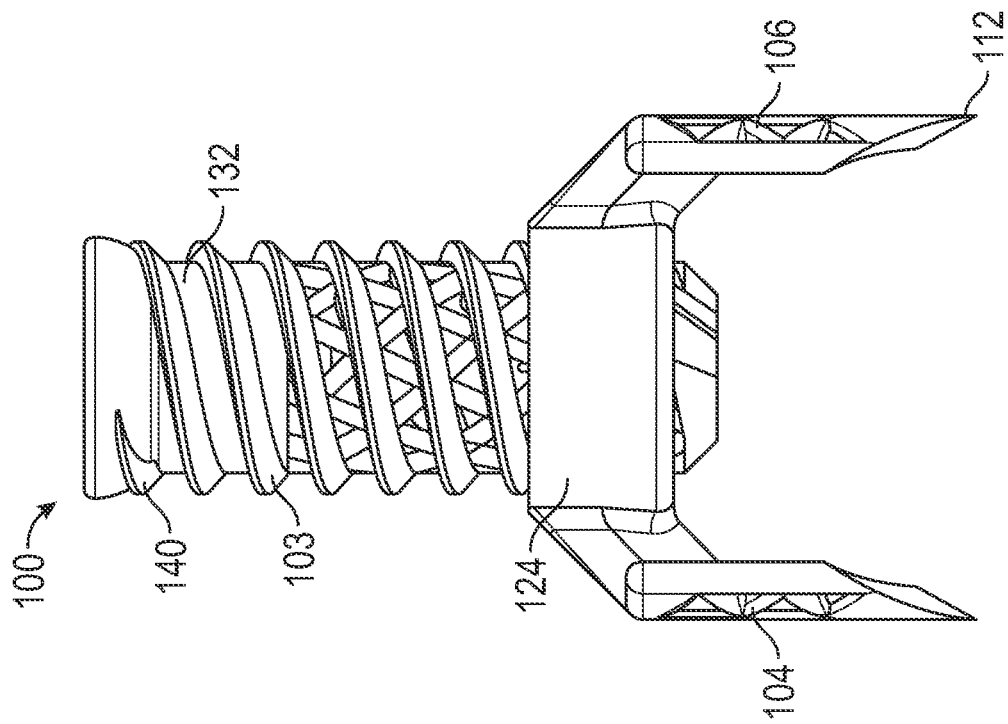
FIG. 54B illustrates a side view of an alternative configuration of the joint implant from FIG. 54A.
Figure 54A:
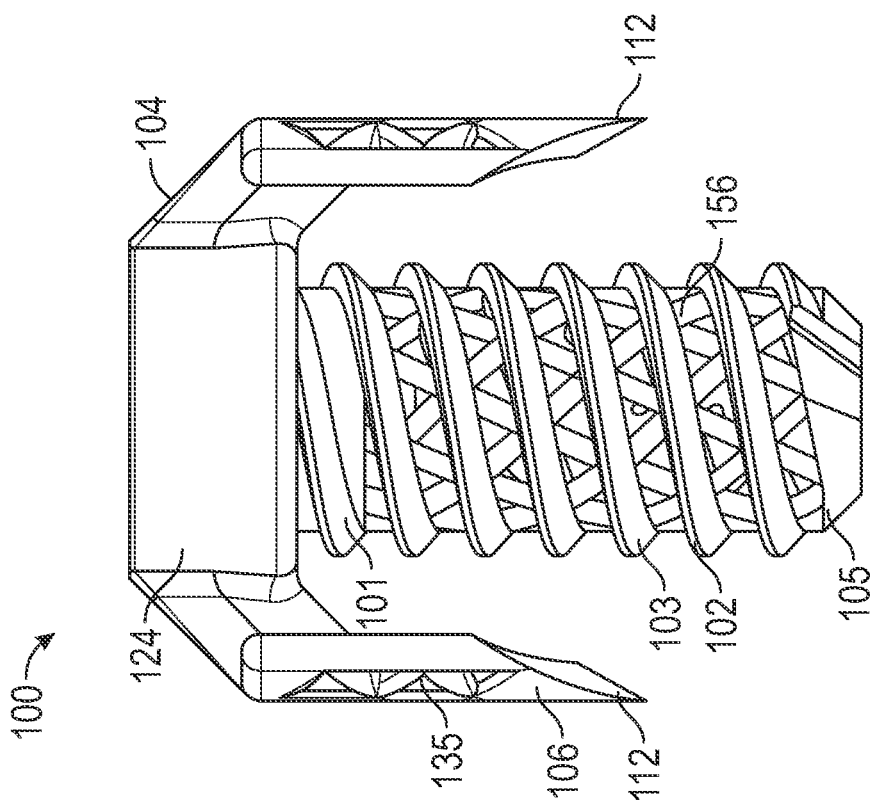
FIG. 54A illustrates a side view of an embodiment of a joint implant.
Figures 54C, 54D:
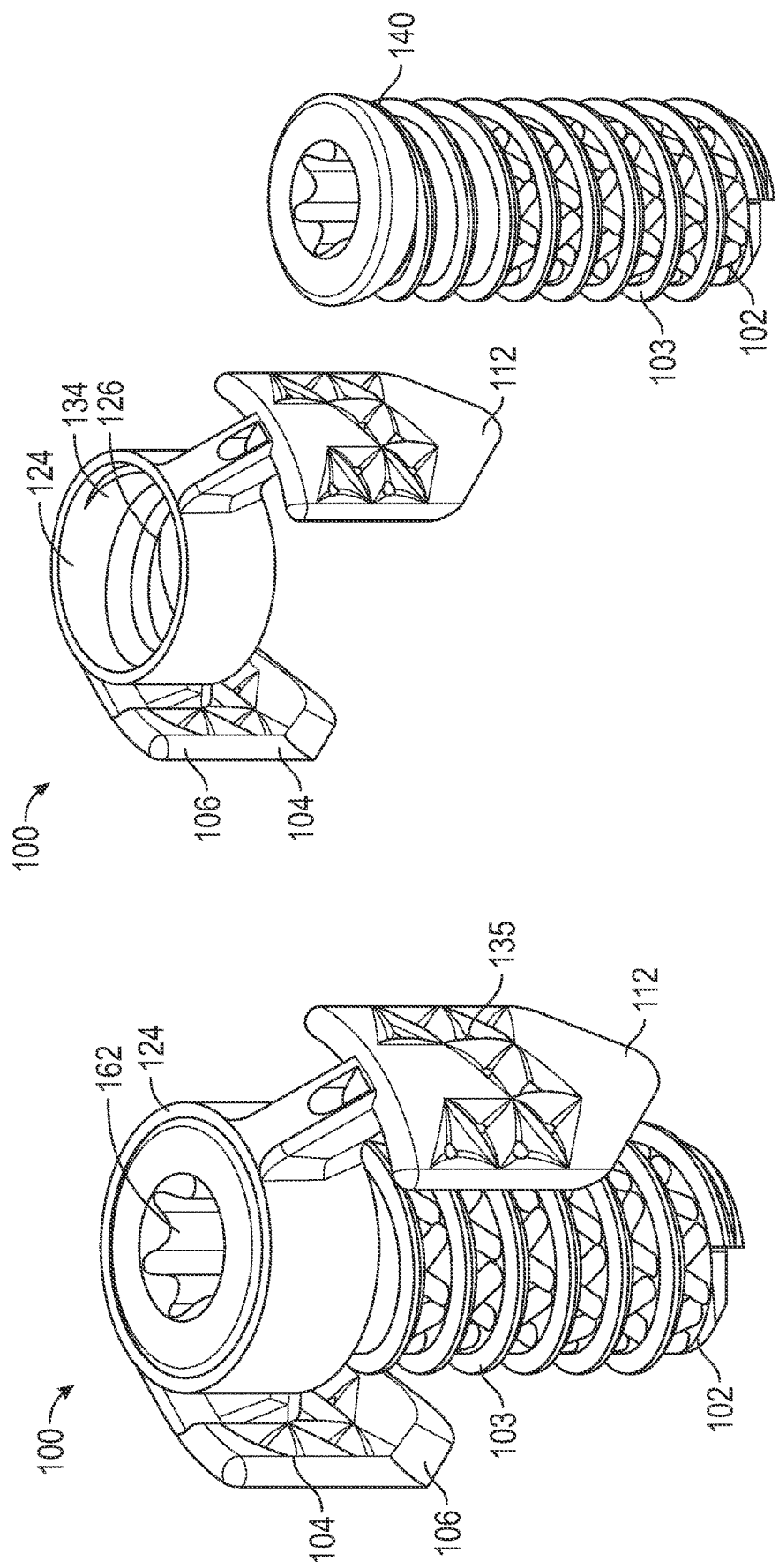
FIG. 54C illustrates a perspective view of the joint implant from FIG. 54A.
FIG. 54D illustrates an exploded view of the joint implant from FIG. 54D.
Figure 54E:
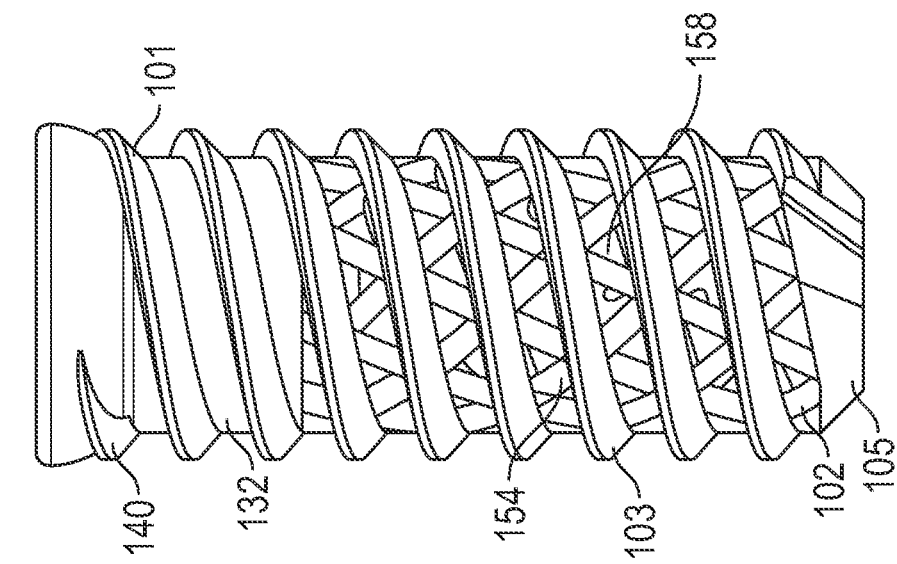
FIG. 54E illustrates a side view of the components of the joint implant from FIG. 54D.
Figure 54E:
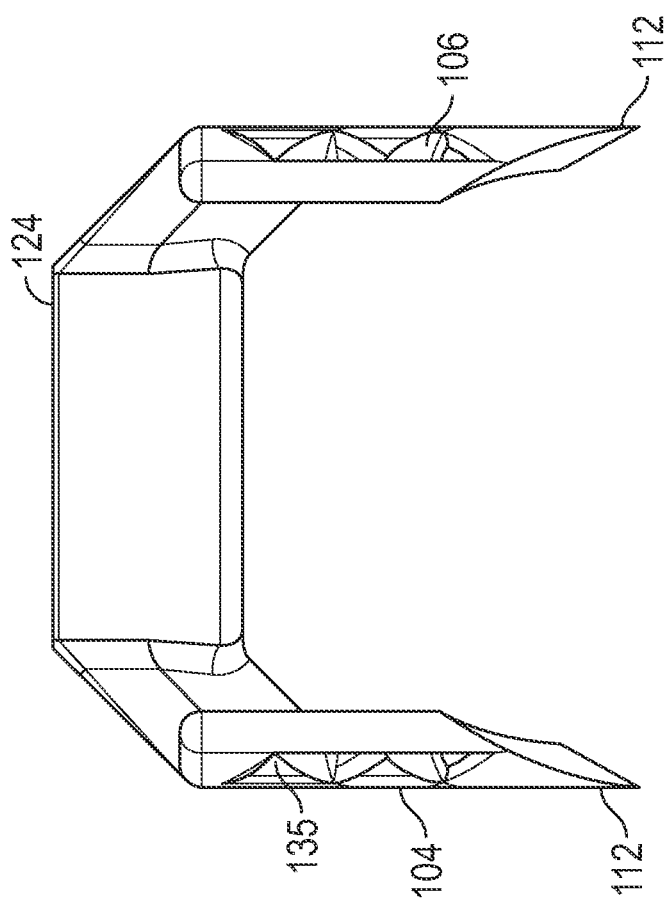
Figure 54G:
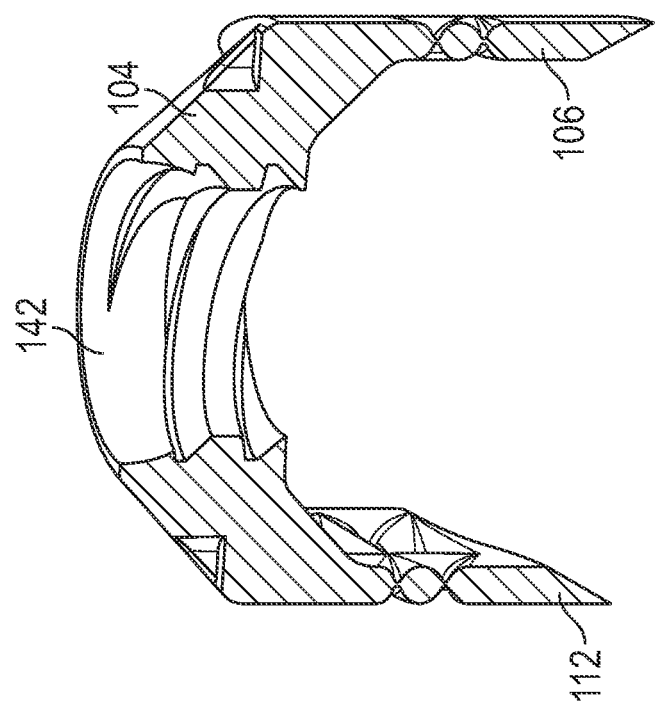
FIG. 54G illustrates a cross sectional view of the secondary implant from FIG. 54D.
Figure 54F:
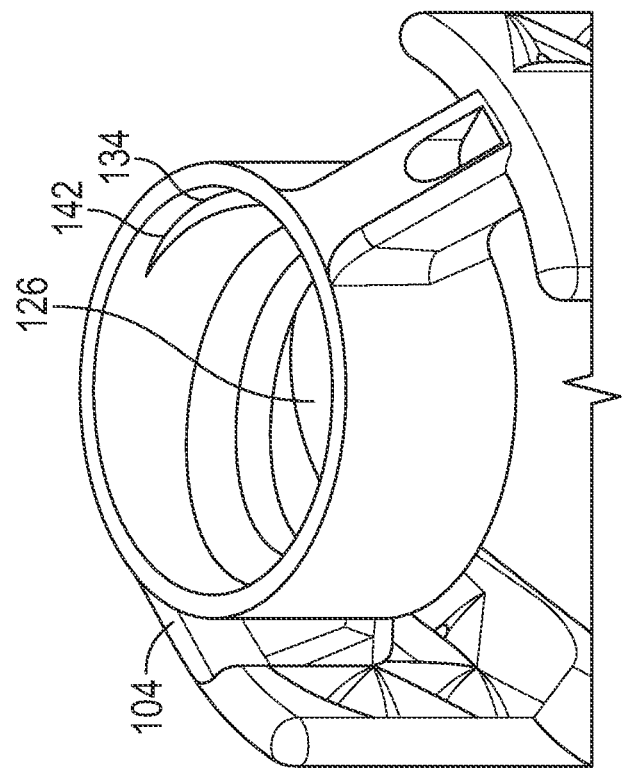
FIG. 54F illustrates an enlarged perspective view of the secondary implant from FIG. 54D.

After the primary implant 102 is in place, the implant inserter 370, implant inserter 360, and guide 330 can be removed. The primary implant 102 can be provided in a variety of lengths between 20 mm to 45 mm. Primary implants 102 of different lengths may be used interchangeably with the secondary implants 104. In some embodiments, a primary implant 102 having a greater length can allow for more purchase into the SI joint. FIGS. 52 and 53 depict the primary implant 102 and secondary implant 104 after implantation.

In certain embodiments, one or more of the primary implant 102, secondary implant 104, guidewire 300, joint locator 310, one or more dilators 320, guide 330, drill tool 345, bone punch 350, implant inserter 360, and implant inserter 370 can be provided in a kit. In some embodiments, one or more of the instruments used to implant the primary implant 102 and secondary implant 104, such as the guidewire 300, joint locator 310, one or more dilators 320, guide 330, drill tool 345, bone punch 350, implant inserter 360, and implant inserter 370, can be provided in a kit. The instruments may be disposable and can be provided in a kit of pre-packaged sterile disposable instruments. The pre-packaged sterile disposable instruments can reduce costs associated with autoclaves and prevent the risk of cross-contamination from blood if the same instruments are used to perform multiple surgeries. Shipping a tray of sterile instruments can be costly due to weight and size of the trays. In some embodiments, the implants 102 and 104 and the instruments used for implantation can be placed in one sterile tray together or in separate trays separating implants and instruments. In some embodiments, the instruments and implants 102 and 104 can be provided in autoclavable trays if desired, for example, to meet surgeon desires of durability and handling. Some physicians may prefer metal instruments that are heavier and more durable. In such embodiments, the implants and instruments may be placed in one tray that can be sterilized together.

Another method for implanting the SI joint implant system 100, for example, the embodiments of the SI joint implant system 100 as shown in FIG. 58A-58F, 59A-59D, or 63A-63B, is described with respect to FIGS. 64A-69C. Although the method is described with respect to the embodiments shown in FIG. 58A-58F, 59A-59D, or 63A-63B, it may be used with or modified for use with any of the other embodiments described herein. Additionally, any of the steps may be modified based on surgeon preference or anatomical variation. Further any of the instruments in the method of FIGS. 64A-69C may be provided in a kit as described with respect to the instruments described with respect to FIGS. 37-53 (for example, as pre-packaged sterile disposable instruments or instruments in an autoclavable tray).

As shown in FIGS. 64A and 64B, one or more of a guidewire 300, a joint locator 310, one or more dilators 320, and a guide 330 may be inserted into the SI joint as described herein. The guide 330 can include a handle 332. The handle 332 may be removably coupled to the guide 330.

In some embodiments, the one or more dilators 320 can include a series of dilators (for example, two or more dilators, up to five dilators, or any other suitable number of dilators). In some embodiments, guide 330 may be the largest dilator of the one or more dilators. The one or more dilators 320 and/or drill guide 330 can include slots 334 that guide the secondary implant 104 along a desired trajectory. The SI joint locator, one or more dilators 320, and/or drill guide 330 can include teeth or tangs to anchor into the SI joint, as described herein.

As shown in FIGS. 65A and 65B, the guidewire 300, SI joint locator 310, and one or more dilators 320 can be removed, and a drill bit 340 of a drill tool 345 may be placed down the guide 330 to create a pilot hole for the primary implant 102.

As shown in FIGS. 66A-66D, the primary implant 102 can be coupled to an implant inserter 370. The implant inserter 370 can include a handle 372, a shaft 374 coupled to the handle 372, and a threaded rod 376. The shaft 374 can include one or more mating features, such as tabs or protrusions 378 that can couple with the groove cuts or recesses 152 of the primary implant 102. The engagement of the tabs or protrusions 378 with the groove cuts or recesses 152 can facilitate driving of the primary implant into the SI joint. The threaded rod 376 can be positioned partially within the shaft. A threaded distal end 380 of the threaded rod 376 can extend out of the distal end of the shaft and couple with interior threads of the primary implant 102 to secure the primary implant to the implant inserter 370.

As shown in FIGS. 67A-67B, the primary implant 102 can be driven into the SI joint through the guide 330 using the implant inserter 370. After the primary implant 102 is in position, the handle 372 and shaft 374 can be decoupled from the threaded rod 376 and removed while the threaded rod 376 remains coupled to the primary implant 102. In certain embodiments, the handle 372 and shaft 374 can be decoupled from the rod 376 via a rod and spring mechanism as shown in FIG. 67C. As shown in FIG. 67C, the rod and spring mechanism can include a rod 382 that can be actuated to decouple the handle 372 and shaft 374 from the rod 376. The rod and spring mechanism can include a spring configured to bias the rod 382 to a locked configuration in which removal of the handle 372 and shaft 374 from the rod 376 is prevented.

As shown in FIG. 68A, the secondary implant 104 can be coupled to an implant inserter 360. The inserter 360 can include mating features 365 (for example, mating tabs or protrusions) configured to engage corresponding mating features 134 of the secondary implant 104. After the implant inserter 360 is coupled to the implant 104, the inserter 360 can be used to insert the implant 104 over the threaded rod 376, as shown in FIG. 68B, and over the proximal end 148 of the primary implant 102. As shown in FIG. 68B, the guide 330 includes slots 334 that can receive the anchors 106 of the secondary implant 104 and guide the secondary implant 104 along a desired trajectory.

The anchor ring 124 can be guided along the threaded rod 376 with the threaded rod 376 extending through the central opening 126. The secondary implant 104 can then be driven into the bone. In some embodiments, the secondary implant can be driven into the bone using a mallet, as shown in FIG. 68C.

After the secondary implant is driven into bone, a handle can be attached to the threaded rod 376 and used to remove the threaded rod 376, as shown in FIG. 69A. The attachment mechanism 110 can then then be inserted through a lumen of the implant inserter 360 using an implant inserter 390 and into engagement with the interior threads of the primary implant 102 to secure the secondary implant 104 and primary implant 102 together, as shown in FIGS. 69B and 69C.

After the primary implant 102 and secondary implant 104 are secured together in place, the guide 330, implant inserter 360 and implant inserter 390 can be removed.

FIGS. 73A-73E depict an embodiment of a rasp 400. The rasp 400 extends between a proximal end 402 and a distal end 404. The rasp 400 can include a rasping tip 406 having rasping surfaces 408a and 408b extending from opposing generally rectangular surfaces 410a and 410b. In certain embodiments, the surface 410a and the surface 410b can be a top surface and a bottom surface, respectively, of the rasping tip 406. The rasping tip 406 can include generally flat side surfaces 412a and 412b. The distal end 404 can be a pointed or wedge shaped distal end of the rasping tip 406.

The distal end 404 and rasping tip 406 can be dimensioned, shaped, or otherwise configured to be inserted into a SI joint. In certain embodiments, the rasp 400 can be used to decorticate bone within a SI joint. In certain embodiments, the rasp 400 can be used to decorticate bone in the SI joint prior to forming a pilot hole with a drill bit and/or implanting a primary implant 102. The rasping tip 406 can be dimensioned to be wider than a drill bit 502 of a drill 500 used in a procedure for implanting an SI joint implant system 100. The rasping surface 408a and/or the rasping surface 408b can have a width X4 that is wider than a width X3 of the drill bit 502 or any other drill bit described herein. For example, in certain embodiments, the width X4 can be about 16 mm and the width X3 can be about 10 mm. In certain embodiments, the width X4 can be between 5 mm and 7 mm and the width X3 can be between 3.5 mm and 4.5 mm. The rasping surface 408a and/or the rasping surface 408b may also be wider than the primary implant 102. A rasping surface 408a and/or rasping surface 408b that is wider than the drill bit and/or implant can create an area of decortication in the SI joint around (e.g., laterally beyond a cross-sectional area of) the primary implant 102 to promote bone fusion.

In certain embodiments, a rasp 400 may be used with a drill guide 330. FIGS. 74A-74D illustrate the rasp 400 and drill guide 330 in different configurations. A user may first take a rasp 400, as seen in FIG. 74A, and drive it down through the joint until notches 403 on opposite sides of the rasp match up with the posterior SI joint margin. The notches 403 are located on the distal end 404 of the rasp 400, proximal to the rasping surface, and help with countersinking the insertion instruments to the correct depth. The correct depth of the rasp 400 may be seen on fluoro imaging. Once the rasp 400 is driven to the correct depth within the SI joint, the drill guide 330 is placed over the rasp 400 and driven down until the notches 403 are covered and can no longer be seen on fluoro imaging. FIG. 74B shows the drill guide 330 being placed over the rasp 400 but is not yet into position since the notches 403 are still visible. FIGS. 74C and 74D illustrate the drill guide 330 positioned all the way over the rasp 400 so that the notches on the distal end 404 are no longer visible.

In some embodiments, the drill guide 330 may be shaped with a symmetrical V 336 toward the distal end, before the tip, to improve insertion into the joint between the ilium and sacrum. The symmetrical V is illustrated in FIG. 74A. In alternative embodiments, the drill guide, as well as other insertion instruments, may have an asymmetrical V shape 337 at the end to accommodate the different size and shape of the ilium and sacrum; this is illustrated on the rasp in FIG. 73C. The asymmetrical V shape 337 may help align the instruments to ensure they do not move around in the joint.

Although use of the devices has been described with respect to an example SI joint procedure, the devices described herein can also be used in other procedures or other orthopedic applications to provide stabilization across joints.

Additional details regarding implants, inserters, rasps, bone graft delivery devices and systems, and related accessories that may be used in the embodiments described herein are described in U.S. patent application patent Ser. No. 11,116,647, issued Sep. 14, 2021, and in U.S. patent application Ser. No. 17/882,337, filed Aug. 5, 2022, each of which is incorporated by reference herein in its entirety and for all purposes.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible.

What is claimed is:

1. A sacroiliac joint implant system, comprising:
a primary implant configured to be received in a sacroiliac joint of a patient, the primary implant comprising:
a cylindrical body comprising a head and a shank extending distally from the head, the body extending from a proximal end to a distal end; and
a plurality of threads extending from the shank of the body to provide fixation of the primary implant within the sacroiliac joint; and
a secondary implant configured to couple with the primary implant, the secondary implant comprising:
a ring configured to receive the head of the primary implant;
a plurality of arms extending laterally from the ring;
a first anchoring element configured to anchor within a sacrum of the patient, the first anchoring element extending at an angle from a first arm of the plurality of arms; and
a second anchoring element configured to anchor within an ilium of the patient, the second anchoring element extending at an angle from a second arm of the plurality of arms;
wherein the primary implant further comprises:
a longitudinal interior channel configured to receive bone graft material; and
a plurality of truss elements, the plurality of truss elements forming a plurality of openings exposed to an exterior of the primary implant and sized and configured to facilitate bone ingrowth;
wherein each of the first and second anchoring elements comprises a curved wedge having:
a plurality of openings sized and configured to facilitate bone ingrowth;
a plurality of truss elements, the plurality of truss elements forming the plurality of openings; and
a leading edge configured to cut bone.

2. The system of claim 1, wherein the ring is configured to couple with the head of the primary implant to facilitate polyaxial movement of the primary implant relative to the secondary implant.

3. The system of claim 1, wherein the plurality of openings of the primary implant extend between the channel and the exterior of the primary implant.

4. The system of claim 1, wherein the plurality of openings of the primary implant are positioned about the primary implant so that at least some of the plurality of openings are positioned to contact the bone of the sacrum and at least some of the plurality of openings are positioned to contact the bone of the ilium regardless of an orientation of the primary implant when the primary implant is received in the sacroiliac joint of the patient.

5. The system of claim 1, wherein the head of the primary implant is shaped to restrict proximal movement of at least a portion of the ring when positioned within an opening defined by the ring.

6. The system of claim 1, wherein the shank of the primary implant comprises a smooth shank section proximal to the plurality of threads.

7. The system of claim 6, wherein the body of the primary implant comprises a tapered distal end.

8. The system of claim 1, wherein the first anchoring element and the second anchoring element are integrally formed with one another.

9. The system of claim 1, wherein the ring, the plurality of arms, the first anchoring element, and the second anchoring element are integrally formed.

10. The system of claim 1, wherein the leading edge tapers to a sharp distal point.

11. The system of claim 1, wherein the secondary implant tapers from a proximal end to a distal end to compress the sacroiliac joint when the first anchoring element is driven into the sacrum and the second anchoring element is driven into the ilium.

12. The system of claim 1, wherein the curved wedge of each of the first anchoring element and the second anchoring element comprises a beveled distal end.

\* \* \* \* \*